US011034772B2

(12) United States Patent
Oostindie et al.

(10) Patent No.: US 11,034,772 B2
(45) Date of Patent: Jun. 15, 2021

(54) BISPECIFIC ANTI-CD37 ANTIBODIES, MONOCLONAL ANTI-CD37 ANTIBODIES AND METHODS OF USE THEREOF

(71) Applicant: GENMAB HOLDING B.V., Utrecht (NL)

(72) Inventors: Simone Oostindie, Utrecht (NL); Frank Beurskens, Utrecht (NL); Esther Breij, Utrecht (NL); Edward Van Den Brink, Utrecht (NL); Andreas Hollenstein, Utrecht (NL); Marije Overdijk, Utrecht (NL); Margaret Lindorfer, Keswick, VA (US); Ronald Taylor, Keswick, VA (US); Paul Parren, Odijk (NL); Hilma Van Der Horst, Utrecht (NL); Martine E. D. Chamuleau, Amsterdam (NL); Tuna Mutis, Amsterdam (NL)

(73) Assignee: GENMAB HOLDING B.V., Utrecht (NL)

( * ) Notice: Subject to any disclaimer, the term of this patent is extended or adjusted under 35 U.S.C. 154(b) by 0 days.

(21) Appl. No.: 17/066,190

(22) Filed: Oct. 8, 2020

(65) Prior Publication Data

US 2021/0024647 A1    Jan. 28, 2021

Related U.S. Application Data

(60) Division of application No. 16/872,140, filed on May 11, 2020, which is a continuation of application No. 16/498,104, filed as application No. PCT/EP2018/058479 on Apr. 3, 2018.

(60) Provisional application No. 62/479,712, filed on Mar. 31, 2017.

(30) Foreign Application Priority Data

Mar. 27, 2018    (WO) .................. PCT/EP2018/057836

(51) Int. Cl.
| C07K 16/28 | (2006.01) |
| A61P 35/00 | (2006.01) |
| A61K 49/00 | (2006.01) |
| G01N 33/68 | (2006.01) |
| A61K 39/00 | (2006.01) |

(52) U.S. Cl.
CPC .......... C07K 16/2896 (2013.01); A61K 49/00 (2013.01); A61P 35/00 (2018.01); C07K 16/2887 (2013.01); G01N 33/68 (2013.01); A61K 2039/505 (2013.01); A61K 2039/545 (2013.01); C07K 2317/21 (2013.01); C07K 2317/24 (2013.01); C07K 2317/31 (2013.01); C07K 2317/526 (2013.01); C07K 2317/565 (2013.01); C07K 2317/732 (2013.01); C07K 2317/734 (2013.01); C07K 2317/94 (2013.01); G01N 2333/70596 (2013.01)

(58) Field of Classification Search
CPC ............ C07K 16/2896; C07K 2317/21; C07K 2317/24; C07K 2317/31; C07K 2317/526; C07K 2317/565; C07K 2317/732; C07K 2317/734; C07K 2317/94; C07K 2317/34; C07K 2317/72; C07K 2317/92; A61P 35/00; A61K 49/00; A61K 2039/505; A61K 2039/545; A61K 2039/507; G01N 2333/70596
See application file for complete search history.

(56) References Cited

U.S. PATENT DOCUMENTS

| 8,765,917 | B2 | 7/2014 | Deckert et al. |
| 9,150,663 | B2 | 10/2015 | Labrijn et al. |
| 10,344,050 | B2 | 7/2019 | Gramer et al. |
| 10,597,464 | B2 | 3/2020 | Labrijn et al. |
| 10,759,867 | B2 | 9/2020 | Parren et al. |
| 2008/0227198 | A1 | 9/2008 | Hariharan et al. |
| 2013/0039913 | A1 | 2/2013 | Labrijn et al. |
| 2014/0242075 | A1 | 8/2014 | Parren et al. |
| 2014/0303356 | A1 | 10/2014 | Gramer et al. |
| 2015/0353636 | A1 | 12/2015 | Parren et al. |
| 2016/0046727 | A1 | 2/2016 | Labrijn et al. |
| 2017/0233497 | A1 | 8/2017 | Labrijn et al. |
| 2020/0048304 | A1 | 2/2020 | Gramer et al. |
| 2020/0262932 | A1 | 8/2020 | Labrijn et al. |

(Continued)

FOREIGN PATENT DOCUMENTS

| EP | 2241577 A1 | 10/2010 |
| WO | 2007/014278 A2 | 2/2007 |

(Continued)

OTHER PUBLICATIONS

U.S. Appl. No. 16/872,140, filed May 11, 2020, Simone Oostindie.

(Continued)

*Primary Examiner* — Phuong Huynh
(74) *Attorney, Agent, or Firm* — Nelson Mullins Riley & Scarborough LLP; Jane E. Remillard, Esq.; Christopher L. Frank

(57) ABSTRACT

CD37-specific bispecific antibody molecules binding to different epitopes of the human CD37 antigen which bispecific antibody molecules have enhanced Fc-Fc interactions upon binding to CD37 on the cell surface. The invention also relates to the monoclonal parental antibodies from which the first or the second binding region of the bispecific antibody molecules is obtained. The invention also relates to pharmaceutical compositions containing these molecules and the treatment of cancer and other diseases using these compositions.

20 Claims, 41 Drawing Sheets

Specification includes a Sequence Listing.

(56) References Cited

U.S. PATENT DOCUMENTS

| | | | | |
|---|---|---|---|---|
| 2020/0270359 A1* | 8/2020 | Oostindie | .............. | G01N 33/68 |
| 2020/0291124 A1* | 9/2020 | Oostindie | .............. | G01N 33/68 |

FOREIGN PATENT DOCUMENTS

| | | |
|---|---|---|
| WO | 2007/146968 A2 | 12/2007 |
| WO | 2009/126944 A1 | 10/2009 |
| WO | 2011/112978 A1 | 9/2011 |
| WO | 2011/131746 A2 | 10/2011 |
| WO | 2012/007576 A1 | 1/2012 |
| WO | 2012/135740 A2 | 10/2012 |
| WO | 2014/108198 A1 | 7/2014 |

OTHER PUBLICATIONS

U.S. Appl. No. 16/498,104, filed Sep. 26, 2019, Simone Oostindie.
U.S. Appl. No. 16/777,053, filed Jan. 30, 2020, Aran Frank Labrijn.
U.S. Appl. No. 15/414,122, filed Jan. 24, 2017, Aran Frank Labrijn.
U.S. Appl. No. 14/830,336, filed Aug. 19, 2015, Aran Frank Labrijn.
U.S. Appl. No. 13/642,253, filed Oct. 24, 2012, Aran Frank Labrijn.
U.S. Appl. No. 16/921,154, filed Jul. 6, 2020, Paul Parren.
U.S. Appl. No. 14/130,543, filed May 5, 2014, Paul Parren.
U.S. Appl. No. 16/426,647, filed May 30, 2019, Michael Gramer.
U.S. Appl. No. 14/353,962, filed Apr. 24, 2014, Michael Gramer.
U.S. Appl. No. 14/760,135, filed Jul. 9, 2015, Paul Parren.
U.S. Appl. No. 16/498,104, Aug. 4, 2020.
U.S. Appl. No. 13/642,253, May 22, 2015.
U.S. Appl. No. 13/642,253, Jan. 22, 2015.
U.S. Appl. No. 13/642,253, Sep. 11, 2014.
U.S. Appl. No. 13/642,253, Apr. 23, 2014.
U.S. Appl. No. 14/830,336, Oct. 27, 2016.
U.S. Appl. No. 14/830,336, Jun. 23, 2016.
U.S. Appl. No. 15/414,122, Jan. 27, 2020.
U.S. Appl. No. 15/414,122, Dec. 13, 2019.
U.S. Appl. No. 15/414,122, Apr. 9, 2019.
U.S. Appl. No. 15/414,122, Sep. 13, 2018.
U.S. Appl. No. 15/414,122, Apr. 20, 2018.
U.S. Appl. No. 14/353,962, Mar. 1, 2019.
U.S. Appl. No. 14/353,962, Jul. 20, 2018.
U.S. Appl. No. 14/353,962, Nov. 6, 2017.
U.S. Appl. No. 14/353,962, May 30, 2017.
U.S. Appl. No. 14/353,962, Sep. 13, 2016.
U.S. Appl. No. 14/353,962, Mar. 23, 2016.
U.S. Appl. No. 14/353,962, Sep. 23, 2015.
U.S. Appl. No. 14/130,543, Apr. 7, 2020.
U.S. Appl. No. 14/130,543, Aug. 23, 2019.
U.S. Appl. No. 14/130,543, Jan. 11, 2019.
U.S. Appl. No. 14/130,543, May 23, 2018.
U.S. Appl. No. 14/130,543, Jun. 23, 2017.
U.S. Appl. No. 14/130,543, Mar. 9, 2017.
U.S. Appl. No. 14/130,543, Nov. 18, 2016.
U.S. Appl. No. 14/130,543, Jul. 29, 2016.
U.S. Appl. No. 14/760,135, Jul. 10, 2019.
U.S. Appl. No. 14/760,135, Sep. 13, 2018.
U.S. Appl. No. 14/760,135, Jan. 24, 2018.
U.S. Appl. No. 14/760,135, Oct. 5, 2017.
Maecker et al., "The tetraspanin superfamily: molecular facilitators," FASEB J. 11:428-442 (1997).
Robak et al., "Anti-CD37 antibodies for chronic lymphocytic leukemia," Expert Opin. Biol. Ther. 14(5):651-661 (2014).
Schwartz-Albiez et al., "The B cell-associated CD37 antigen (gp40-52). Structure and subcellular expression of an extensively glycosylated glycoprotein," J. Immunol. 140:905-914 (1988).
Brinkmann, U. et al., "The making of bispecitic antibodies," MABS vol. 9(2):182-212 (2017).
Brown, M. et al. "Tolerance to single, but not multiple, amino acid replacements in antibody V-H CDR2: A means of minimizing B cell wastage from somatic hypermutatuion?" The Journal of Immunology, vol. 156(9):3285-3291 (1996).
Dahle, J. et al., "Evaluating Antigen Targeting and Anti-tumor Activity of a New Anti-CD37 Radioimmunoconjugate Against Non-Hodgkin's Lymphoma," Anticancer Res., vol. 33: 85-96 (2013).
Deckert, J. et al., "A novel anti-CD37 antibody-drug conjugate with multiple anti-tumor mechanisms for the treatment of B-cell malignancies," Blood, vol. 122(20):3500-3510 (2013).
Gershoni, J.M., et al. "Epitope mapping—The first step in developing epitope-based vaccines" BIOD, Adis international Ltd, vol. 21(3):145-156 (2007).
Heider, K.H., et al., "A novel Fc-engineered monoclonal antibody to CD37 with enhanced ADCC and high proapoptotic activity for treatment of B-cell malignancies," Blood, vol. 118: 4159-4168 (2011).
Pereira, D. et al., "AGS67E, an Anti-CD37 Monomethyl Auristatin E Antibody-Drug Conjugate as a Potential Therapeutic for B/T-Cell Malignancies and AML:A New Role for CD37 in AML," Mol Cancer Ther., vol. 14(7): 1650-1660 (2015).
Zhao, X. et al., "Targeting CD37-positive lymphoid malignancies with a novel engineered small modular immunopharmaceutical," Blood, vol. 110 (7): 2569-2577 (2007).
Rudikoff, S. et al., "Single amino acid substitution altering antigen-binding specificity," PNAS, vol. 79(6):1979-1983 (1982).
Wu, H. et al., "Humanization of a murine monoclonal antibody by simultaneous optimization of framework and CDR residues," J. Md. Biol., vol. 294: 151-162 (1999).

* cited by examiner

FIG. 8

| Probing Ab (labeled) \ Primary binding Ab (unlabeled) | IgG1-37.3-E430G | IgG1-G28.1-E430G | IgG1-004-H5L2-E430G | IgG1-005-H1L2-E430G | IgG1-010-H5L2-E430G | IgG1-016-H5L2-E430G |
|---|---|---|---|---|---|---|
| IgG1-37.3-E430G | □ | □ | □ | ■ | ■ | □ |
| IgG1-G28.1-E430G | □ | □ | □ | ■ | ■ | □ |
| IgG1-004-H5L2-E430G | □ | □ | □ | ■ | ■ | □ |
| IgG1-005-H1L2-E430G | □ | ■ | ■ | ■ | □ | ■ |
| IgG1-010-H5L2-E430G | □ | ■ | ■ | □ | □ | ■ |
| IgG1-016-H5L2-E430G | □ | □ | □ | ■ | ■ | □ |

● Newly diagnosed
□ Relapsed/refractory

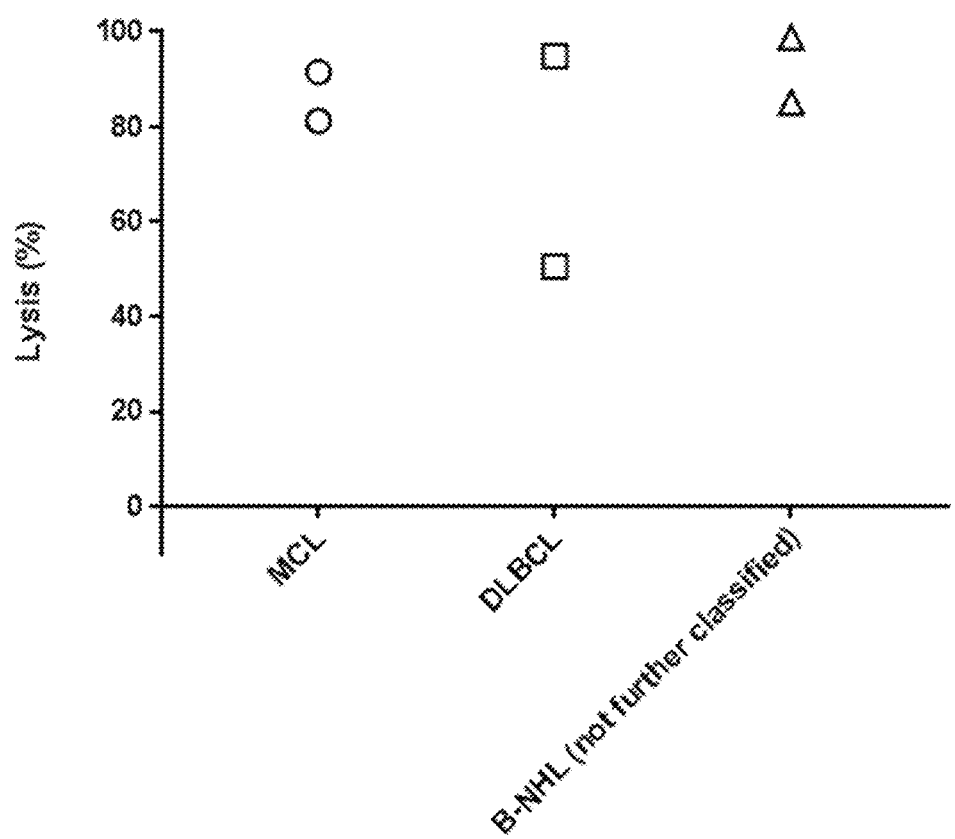

BISPECIFIC ANTI-CD37 ANTIBODIES, MONOCLONAL ANTI-CD37 ANTIBODIES AND METHODS OF USE THEREOF

RELATED APPLICATIONS

This application is a divisional of U.S. patent application Ser. No. 16/872,140, filed May 11, 2020, which is a continuation of U.S. patent application Ser. No. 16/498,104, filed Sep. 26, 2019, which is a 35 U.S.C. 371 national stage filing of International Application No. PCT/EP2018/058479, filed Apr. 3, 2018, which claims priority to International Application No. PCT/EP2018/057836, filed Mar. 27, 2018, and U.S. Provisional Application No. 62/479,712, filed Mar. 31, 2017. The contents of the aforementioned applications are hereby incorporated by reference.

SEQUENCE LISTING

The instant application contains a Sequence Listing which has been submitted electronically in ASCII format and is hereby incorporated by reference in its entirety. Said ASCII copy, created on Oct. 8, 2020, is named GMI_162USCNDV_Sequence_Listing.txt and is 109,337 bytes in size.

FIELD OF THE INVENTION

The present invention relates to bispecific antibodies that specifically bind the human CD37 antigen. The invention relates in particular to CD37-specific bispecific antibody molecules binding to different epitopes of the human CD37 antigen where the bispecific antibody molecules have enhanced Fc-Fc interactions upon binding to CD37 on the cell surface and thus have enhanced effector functions. The invention also relates to new monoclonal parental antibodies from which the first or the second antigen binding region of the bispecific antibody molecules is obtained. The invention also relates to pharmaceutical compositions containing these molecules and the treatment of cancer and other diseases using these compositions.

BACKGROUND OF THE INVENTION

Leukocyte antigen CD37 ("CD37"), also known as GP52-40, tetraspanin-26, or TSPAN26, is a transmembrane protein of the tetraspanin superfamily (Maecker et al., FASEB J. 1997; 11:428-442). In normal physiology, CD37 is expressed on B cells during the pre-B to peripheral mature B-cell stages but is reportedly absent on plasma cells (Link et al., J Pathol. 1987; 152:12-21). The CD37 antigen is only weakly expressed on T-cells and myeloid cells such as monocytes, macrophages, dendritic cells and granulocytes (Schwartz-Albiez et al., J. Immunol 1988; 140(3):905-914). CD37 is broadly expressed on malignant cells in a variety of B-cell leukemias and lymphomas, including non-Hodgkin's lymphoma (NHL) and chronic lymphoid leukemia (CLL) (Moore et al. J Immunol. 1986; 137(9):3013).

Several antibody-based CD37-targeting agents are being evaluated as potential therapeutics for B-cell malignancies and other malignancies. These include, for example, radio-immuno-conjugates such as Betalutin®, antibody-drug conjugates such as IMGN529 and AGS-67E, and reformatted or Fc-engineered antibodies such as otlertuzumab and BI 836826 (Robak and Robak, Expert Opin Biol Ther 2014; 14(5):651-61). Anti-CD37 antibodies have been proposed for use as therapeutic agents in the formats described above and other formats (see, e.g., WO 2012/135740, WO 2012/007576, WO 2011/112978, WO 2009/126944, WO 2011/112978 and EP 2 241 577).

Betalutin is a mouse anti-CD37 antibody, lilotomab (formerly HH1/tetulomab), conjugated to 177-lutetium. Betalutin internalizes rapidly, inhibits B cell growth in vitro and prolongs survival in an i.v. Daudi-SCID model (Dahle et al 2013, Anticancer Res 33: 85-96).

IMGN529 is an ADC consisting of the K7153A antibody conjugated to the maytansinoid DM1 via an SMCC linker. The K7153 antibody is reported to induce apoptosis on CD37 expressing Ramos cells in the absence of cross-linking. It also induced CDC and ADCC in Burkitt's lymphoma cell lines, though the ability to induce CDC was much less compared to rituximab (Deckert et al, Blood 2013; 122(20):3500-10). These Fc-mediated effector functions of K7153A are retained in the DM-1 conjugated antibody.

Agensys is developing AGS-67E, a human anti-CD37 IgG2 mAb conjugated to monomethyl auristatin E. AGS67E induces potent cytotoxicity and apoptosis (Pereira et al, Mol Cancer Ther 2015; 14(7): 1650-1660).

Otlertuzumab (originally known as TRU-016) is a SMIP (small modular immuno pharmaceutical; SMIPS are disulfide-linked dimers of single-chain proteins comprised of one antigen binding VH/VL, a connecting hinge region, and an Fc (fragment, crystallizable) region (CH2-CH3)). Its mechanisms of action are induction of apoptosis and ADCC, but not CDC (Zhao et al 2007, Blood 110 (7), 2569-2577).

mAb37.1/BI 836826 is a chimeric antibody that is engineered for high-affinity binding to FcγRIIIa (CD16a)(Heider et al 2011, Blood 118: 4159-4168). It has pro-apoptotic activity independent of IgG Fc crosslinking, although the pro-apoptotic activity is increased by cross-linking. It shows potent ADCC of CD37+ B cell lines and primary CLL cells.

Despite these and other advances in the art, however, there is still a need for improved anti-CD37 antibodies for the treatment of cancer and other diseases.

Accordingly, it is an object of the present invention to provide anti-CD37 antibodies which may be useful in the treatment of cancer and/or other diseases. It is an object of the present invention to provide anti-CD37 antibodies which are improved with respect to CDC of human cells by human complement compared to the prior art antibodies. It is a further object to provide a bispecific antibody having binding arms obtained from two parental antibodies which bind to different epitopes on CD37 and which bispecific antibody has increased CDC and/or ADCC compared to a combination of the two parental monoclonal antibodies binding said different epitopes, and/or to either parental monoclonal antibody by itself. It is a further object to provide new monoclonal antibodies binding different epitopes on CD37 in particular it is an object to provide anti-CD37 antibodies binding new epitopes of CD37. It is a further object of the present invention to provide new monoclonal antibodies binding different epitopes on CD37 which monoclonal antibodies may serve as parental antibodies for the bispecific antibodies of the invention. It is a further object to provide bispecific antibodies which bind to two different epitopes on CD37 and which bispecific antibodies have enhanced Fc-Fc interaction upon binding to CD37 on the plasma membrane compared to a bispecific antibody of the same isotype and having identical binding arms as the bispecific antibody of the invention.

SUMMARY OF THE INVENTION

The inventors of the present invention surprisingly found that a bispecific antibody having binding specificity against two different epitopes on CD37 and having a mutation increasing the Fc-Fc interaction upon binding to CD37 on the plasma membrane was more potent in inducing CDC than a combination of two anti-CD37 antibodies each having a binding specificity towards one of the two different epitopes on CD37 and having the same mutation enhancing the Fc-Fc interaction, or either antibody having the same mutation enhancing the Fc-Fc interaction by itself. In addition, a bispecific antibody having binding specificity against two different epitopes on CD37 and having a mutation increasing the Fc-Fc interactions was more potent in inducing ADCC than a combination of two anti-CD37 antibodies each having a binding specificity towards one of the two different epitopes on CD37 and having the same mutation enhancing the Fc-Fc interaction.

Accordingly, the invention relates to novel bispecific antibodies binding to human CD37 which have advantageous properties in terms of their antigen-binding characteristics, their ability to induce CDC and ADCC, their Fc-Fc interaction upon binding to membrane-bound targets, their cytotoxic effect on CD37-expressing cells and other properties, as described herein.

Accordingly, in a first aspect the present invention relates to a bispecific antibody comprising a first and second antigen binding region binding to human CD37 having the sequence of SEQ ID NO: 62, and a first and second Fc region of a human immunoglobulin, wherein the first and second antigen binding regions bind different epitopes on CD37 and wherein the first and second Fc regions comprises one or more amino acid mutations which mutation(s) enhances the Fc-Fc interaction between the bispecific antibodies upon binding to membrane-bound CD37 compared to the Fc-Fc interaction between bispecific antibodies not having said mutation(s).

Thus, in one aspect a bispecific antibody comprising a first and second antigen binding region binding to human CD37 having the sequence of SEQ ID NO: 62, and a first and second Fc region of a human immunoglobulin, wherein the first and second antigen binding regions bind different epitopes on CD37 and wherein the first and second Fc regions comprise one or more amino acid mutations which mutation(s) enhances the Fc-Fc interaction between bispecific antibodies upon binding to membrane-bound target compared to the Fc-Fc interaction between bispecific antibodies not having said mutation(s).

In a second aspect the invention relates to an anti-CD37 antibody binding to the same epitope on human CD37 as an anti-CD37 antibody which antibody comprises:
(i) a VH region comprising a CDR1 sequence set forth in SEQ ID NO: 16, a CDR2 sequence set forth in SEQ ID NO: 17 and a CDR3 sequence set forth in SEQ ID NO: 18, and a VL region comprising a CDR1 sequence set forth in SEQ ID NO: 20, and CDR2 sequence: KAS, and CDR3 sequence set forth in SEQ ID NO: 21[010]; or
(ii) a VH region comprising a CDR1 sequence set forth in SEQ ID NO: 9, a CDR2 sequence set forth in SEQ ID NO:10 and a CDR3 sequence set forth in SEQ ID NO: 11, and a VL region comprising a CDR1 sequence set forth in SEQ ID NO: 113, and CDR2 sequence: AAS, and CDR3 sequence set forth in SEQ ID NO: 14[005].

In a third aspect the invention relates to an anti-CD37 antibody which binds to human CD37 which antibody comprises:
(i) a VH region comprising a CDR1 sequence set forth in SEQ ID NO: 23, a CDR2 sequence set forth in SEQ ID NO: 24 and a CDR3 sequence set forth in SEQ ID NO: 25, and a VL region comprising a CDR1 sequence set forth in SEQ ID NO: 27, and CDR2 sequence: YAS, and CDR3 sequence set forth in SEQ ID NO: 28; [016] or
(ii) a VH region comprising a CDR1 sequence set forth in SEQ ID NO: 2, a CDR2 sequence set forth in SEQ ID NO: 3 and a CDR3 sequence set forth in SEQ ID NO: 4, and a VL region comprising a CDR1 sequence set forth in SEQ ID NO: 6, and CDR2 sequence: EAS, and CDR3 sequence set forth in SEQ ID NO: 7. [004]

In a fourth aspect the invention relates to a pharmaceutical composition comprising the bispecific antibody or the antibody of the invention and a pharmaceutically acceptable carrier.

In a fifth aspect the invention relates to the bispecific antibody or the antibody or the composition of the invention for use as a medicament. In specific aspects they are for use in the treatment of cancer or an autoimmune disease or inflammatory disorders and in particular for use in the treatment of B-cell malignancies.

In other aspects the invention relates to methods of treatment, to combination treatments, to nucleic acid sequences encoding the antibodies of the invention, to vectors and host cells expressing such and to methods of detecting presence or a CD37 antigen or cells expressing CD37 antigens in a sample or in a subject.

BRIEF DESCRIPTION OF THE DRAWINGS

(FIG. 7A) Binding competition between IgG1-37.3-E430G, IgG1-G28.1-E430G, IgG1-004-H5L2-E430G, IgG1-005-H1L2-E430G, IgG1-010-H5L2-E430G and IgG1-016-H5L2-E434G was determined by flow cytometry. Raji cells were incubated with unlabeled antibodies for primary binding and subsequently with Alexa Fluor 488 labeled probing antibodies. Loss of binding of the A488-labeled probing antibodies after pre-incubation with an unlabeled antibody, compared to binding of the A488-labeled antibody alone, indicates binding competition between the A488-labeled and the unlabeled antibody. Data shown are duplicate values of Molecules of Equivalent Soluble Fluorochrome (MESF), for one representative experiment. (FIGS. 7B-7G) The capacity to induce CDC on Raji cells of IgG1-004-H5L2, of IgG1-005-H1L2, IgG1-010-H5L2, IgG1-016-H5L2 and IgG1-37.3, with or without E430G mutation, and combinations of these was determined in vitro. Data shown are % lysis determined by measurement of the percentage of dead cells (corresponding to PI-positive cells) by flow cytometry.

FIG. 8: Schematic overview of binding competition between CD37 antibodies. Binding competition between IgG1-37.3-E430G, IgG1-G28.1-E430G, IgG1-004-H5L2-E430G, IgG1-005-H1L2-E430G, IgG1-010-H5L2-E430G and IgG1-016-H5L2-E4340G to Raji cells was determined by flow cytometry, using unlabeled antibodies for primary binding and Alexa Fluor 488 labeled probing antibodies for detecting subsequent binding of a competing antibody. Color indication: black; simultaneous binding, white; competition for binding, grey; cognate antibody.

(FIG. 10A) The capacity to induce CDC on Daudi cells of IgG1-G28.1, IgG1-G28.1-E430G, IgG1-37.3 and IgG1-37.3-E430G was determined in vitro. Data shown are % lysis determined by measurement of the percentage of dead cells (corresponding to PI-positive cells) by flow cytometry. (FIGS. 10B and 10C) The capacity to induce CDC on Daudi cells of (FIG. 10A) IgG1-010-H5L2-K409R-E430G, IgG1-010-H5L2-E345R-K409R, IgG1-010-H5L2-E345K-K409R, IgG1-010-H5L2-K409R-E430S, IgG1-010-H5L2-RRGY and (FIG. 10B) IgG1-016-H5L2-LC90S-F405L-E430G, IgG1-016-H5L2-E345K-F405L, IgG1-016-H5L2-F405L-E430S and IgG1-016-H5L2-E345R-F405L was determined in vitro. Data shown are % lysis (maximum killing, at an antibody concentration of 10 μg/mL) determined by measurement of the percentage of dead cells (corresponding to PI-positive cells) by flow cytometry, for one representative experiment. Error bars indicate the variation within the experiment (performed in duplicate).

(FIG. 12A) The capacity to induce CDC on Daudi cells of bsIgG1-016-H5L2-LC90S-F405L-E430Gx005-H1L2-K409R-E430G, IgG1-005-H1L2-E430G, IgG1-016-H5L2-E430G, a combination of IgG1-005-H1L2-K409R-E430G plus IgG1-016-H5L2-F405L-E430G, bsIgG1-b12-F405L-E430Gx005-H1L2-K409R-E430G and bsIgG1-016-H5L2-LC90S-F405L-E430Gxb12-K409R-E430G, and (FIG. 12B) bsIgG1-016-H5L2-LC90S-F405L-E430Gx010-H5L2-K409R-E430G, IgG1-010-H5L2-E430G, IgG1-016-H5L2-E430G, a combination of IgG1-010-H5L2-E430G plus IgG1-016-H5L2-E430G, bsIgG1-016-H5L2-LC90S-F405L-E430Gxb12-K409R-E430G and bsIgG1-b12-F405L-E430Gx010-H5L2-K409R-E430G was determined in vitro. Data shown are % lysis determined by measurement of the percentage of dead cells (corresponding to PI-positive cells) by flow cytometry. (FIG. 12C) The capacity to induce OCI-Ly-7 cells of the CD37 bispecific antibody bsIgG1-016-H5L2-LC90S-F405L-E430Gx010-H5L2-K409R-E430G, the CD37 monospecific bivalent (monoclonal) antibodies IgG1-010-H5L2-E430G, IgG1-016-H5L2-E430G, a combination of IgG1-010-H5L2-E430G plus IgG1-016-H5L2-E430G, the monovalent CD37 antibodies bsIgG1-016-H5L2-LC90S-F405L-E430Gxb12-K409R-E430G, bsIgG1-b12-F405L-E430Gx010-H5L2-K409R-E430G and a combination of bsIgG1-016-H5L2-LC90S-F405L-E430Gxb12-K409R-E430G plus bsIgG1-b12-F405L-E430Gx010-H5L2-K409R-E430G was determined in vitro. Data shown are % lysis determined by measurement of the percentage of dead cells (corresponding to PI-positive cells) by flow cytometry. (FIG. 12D) EC50 values of CDC induction by bsIgG1-016-H5L2-LC90S-F405L-E430Gxb12-K409R-E430G plus bsIgG1-b12-F405L-E430Gx010-H5L2-K409R-E430G and IgG1-010-H5L2-E430G plus IgG1-016-H5L2-E430G, as determined in 2 independent experiments. (FIG. 12E) EC50 values of CDC induction by bsIgG1-016-H5L2-LC90S-F405L-E430Gx010-H5L2-K409R-E430G and IgG1-010-H5L2-E430G plus IgG1-016-H5L2-E430G, as determined in 3 independent experiments.

Figure 14A:
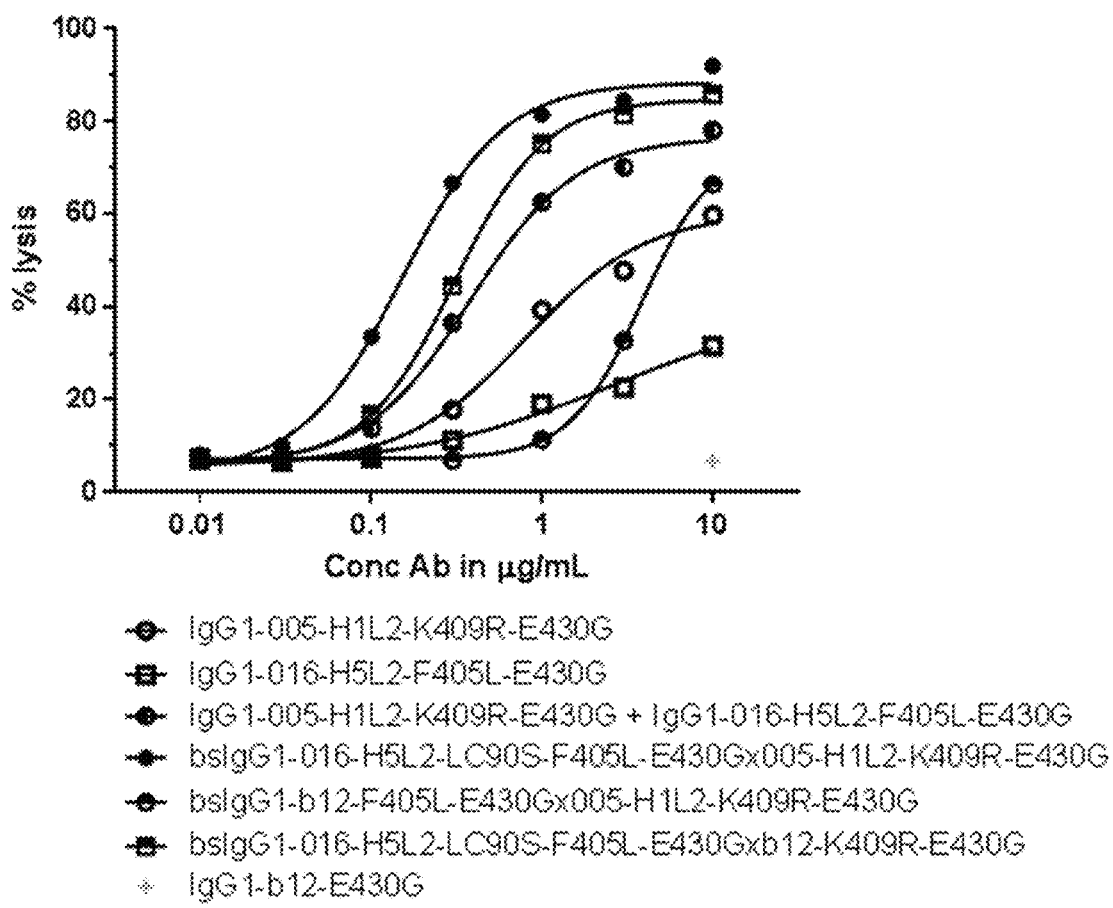
Figure 14B:
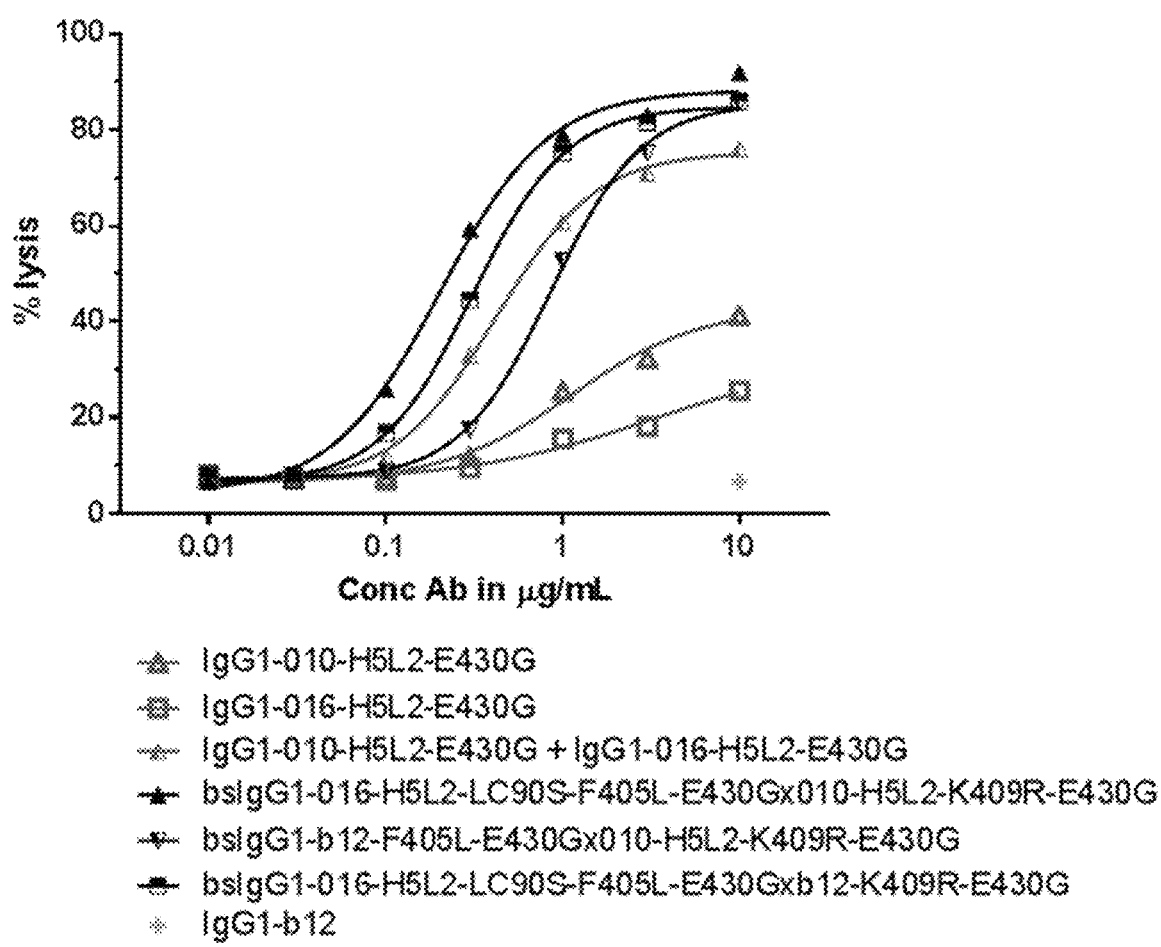

FIGS. 14A and 14B: CDC mediated by bispecific CD37 antibodies with an Fc-Fc interaction enhancing mutation, (combinations of) CD37 antibodies with an Fc-Fc interaction enhancing mutation, and monovalent binding CD37 antibodies with an Fc-Fc interaction enhancing mutation on primary CLL tumor cells. The capacity to induce CDC on primary CLL tumor cells (Patient: VM-BM0091 Newly Diagnosed/Untreated (BM=bone marrow derived)) of (FIG. 14A) bsIgG1-016-H5L2-LC90S-F405L-E430Gx005-H1L2-K409R-E430G, IgG1-005-H1L2-K409R-E430G, IgG1-016-H5L2-F405L-E430G, a combination of IgG1-005-H1L2-K409R-E430G plus IgG1-016-H5L2-F405L-E430G, bsIgG1-b12-F405L-E430Gx005-H1L2-K409R-E430G and bsIgG1-016-H5L2-LC90S-F405L-E430Gxb12-K409R-E430G, and (FIG. 14B) bsIgG1-016-H5L2-LC90S-F405L-E430Gx010-H5L2-K409R-E430G, IgG1-010-H5L2-E430G, IgG1-016-H5L2-E430G, a combination of IgG1-010-H5L2-E430G plus IgG1-016-H5L2-E430G, bsIgG1-016-H5L2-LC90S-F405L-E430Gxb12-K409R-E430G and bsIgG1-b12-F405L-E430Gx010-H5L2-K409R-E430G was determined in vitro. Data shown are % lysis determined by measurement of the percentage of dead cells (corresponding to PI-positive cells) by flow cytometry.

Figure 15:
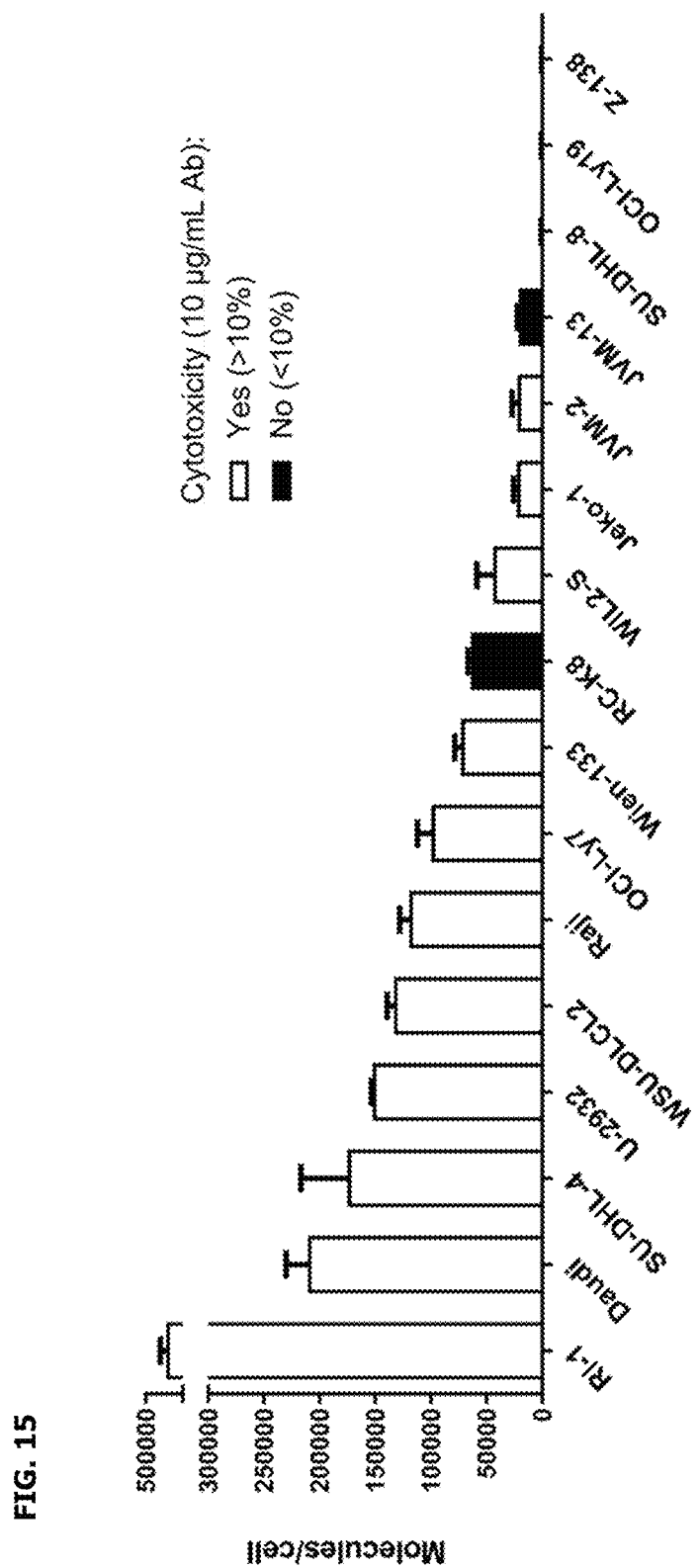

FIG. 15: CDC mediated by a bispecific CD37 antibody with an Fc-Fc interaction enhancing mutation on B cell lymphoma cell lines. The capacity of bsIgG1-016-H5L2-LC90S-F405L-E430Gx010-H5L2-K409R-E430G, at a concentration of 10 µg/mL, to induce CDC on a range of B cell lymphoma cell lines was determined in vitro. Expression levels of CD37 were determined by quantitative flow cytometry, and are shown as molecules/cell, average±SD of 2 experiments. White bars indicate susceptible to CDC (>10% lysis, average of 2 experiments) mediated by bsIgG1-016-H5L2-LC90S-F405L-E430Gx010-H5L2-K409R-E430G, black bars indicate unsusceptible to CDC (<10% lysis, average of 2 experiments) mediated by bsIgG1-016-H5L2-LC90S-F405L-E430Gx010-H5L2-K409R-E430G.

Figure 16A:
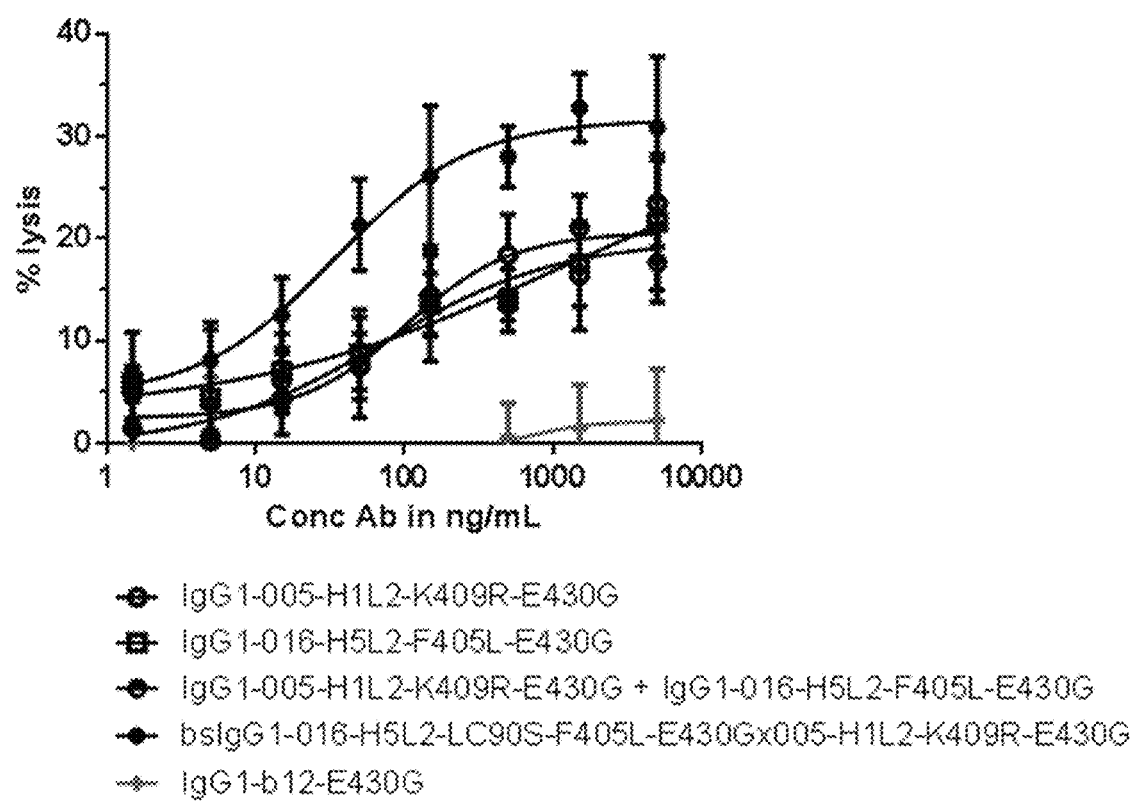
Figure 16B:
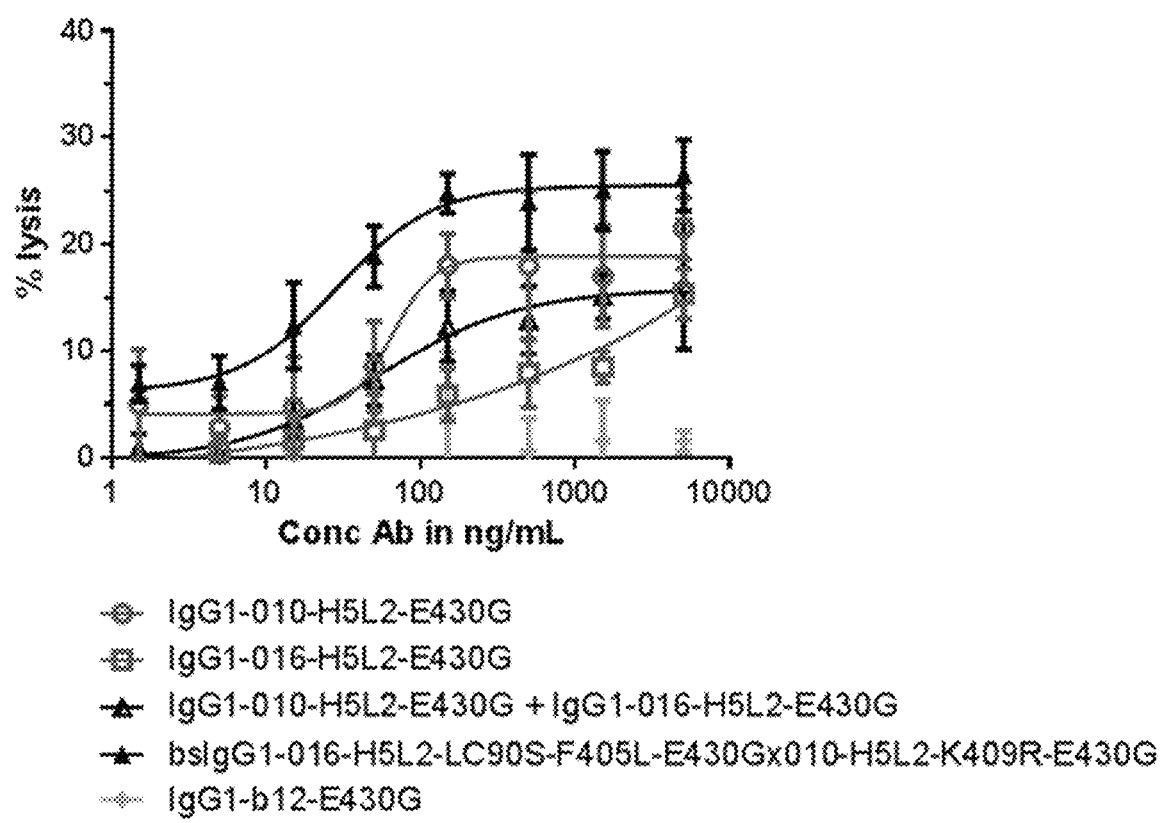
Figure 16C:
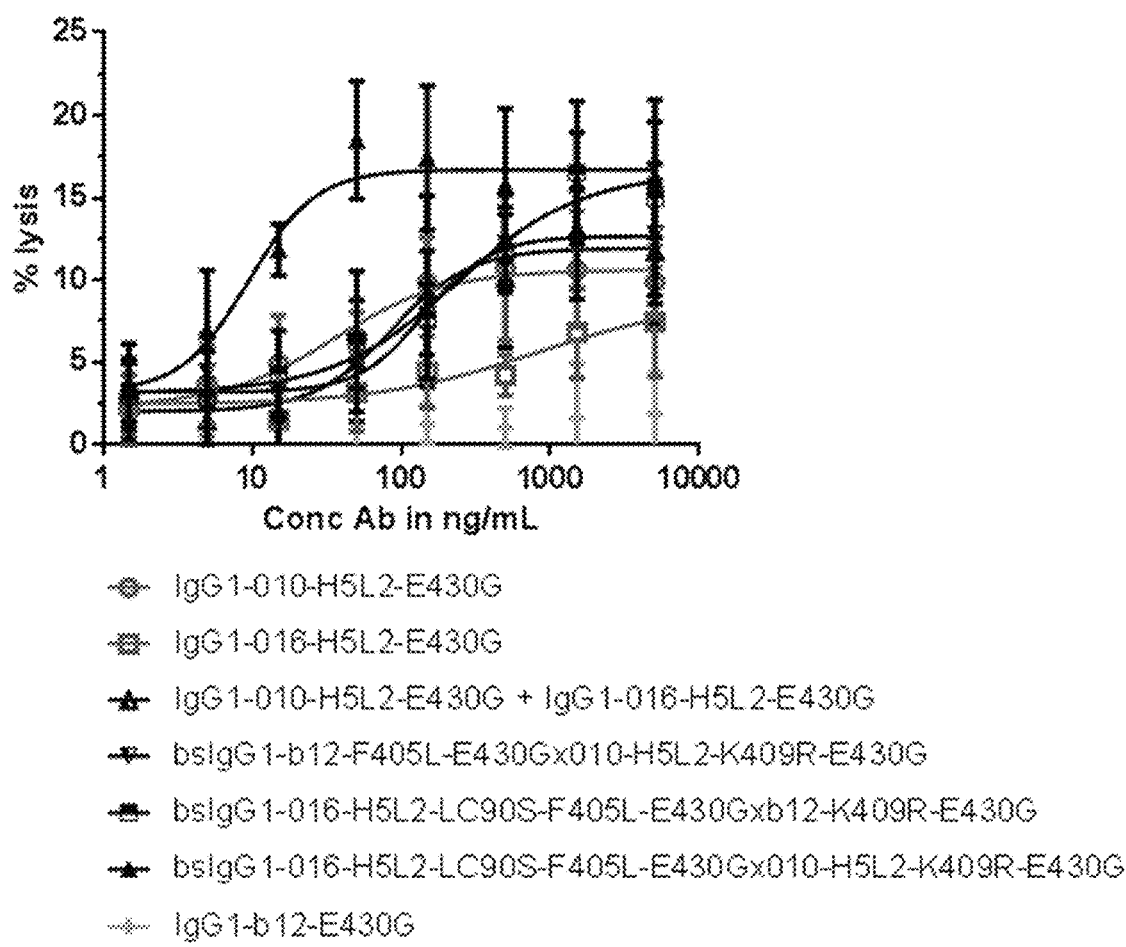
Figure 17A:
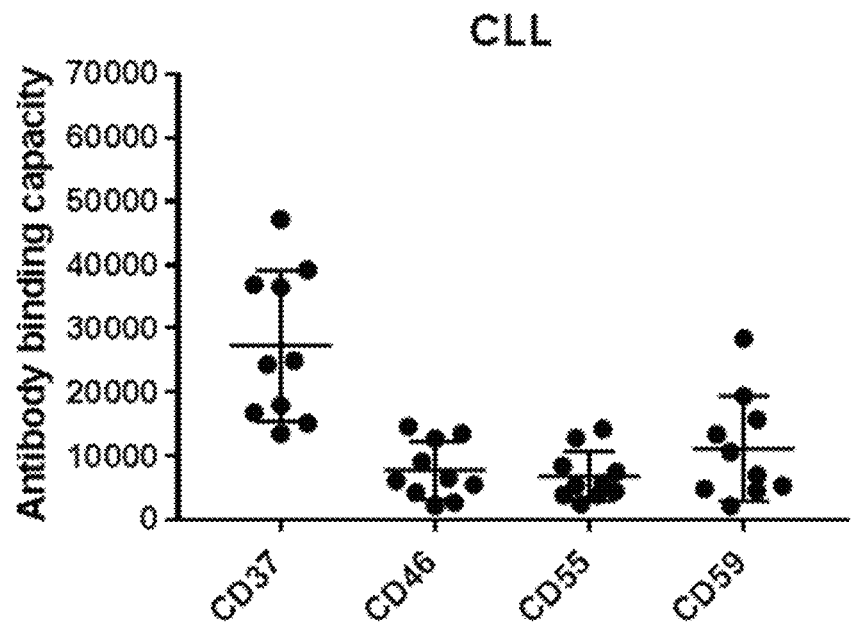
Figure 17B:
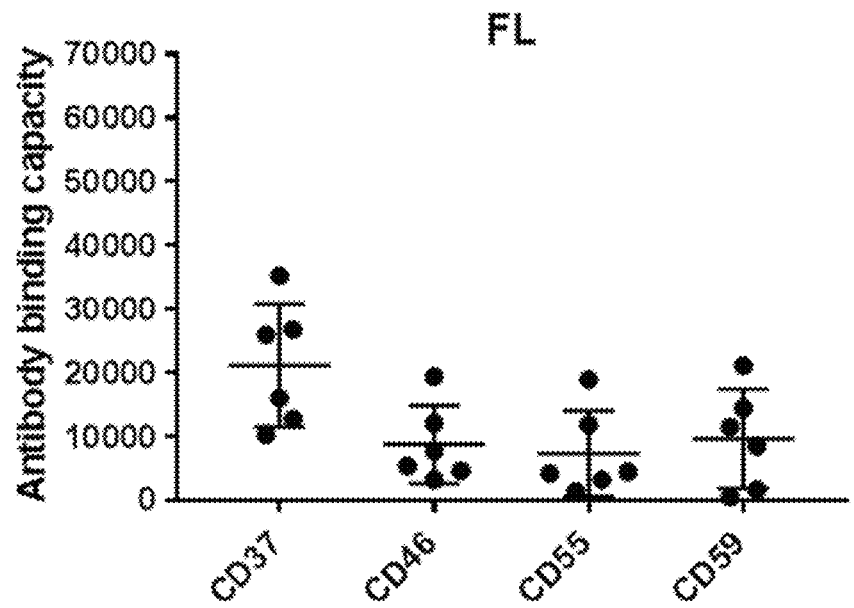
Figure 17C:
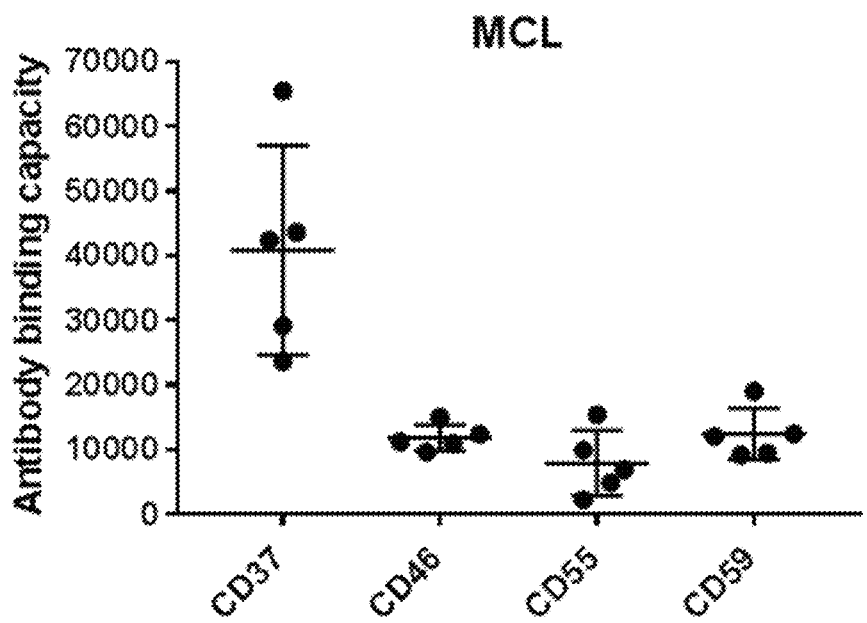
Figure 17D:
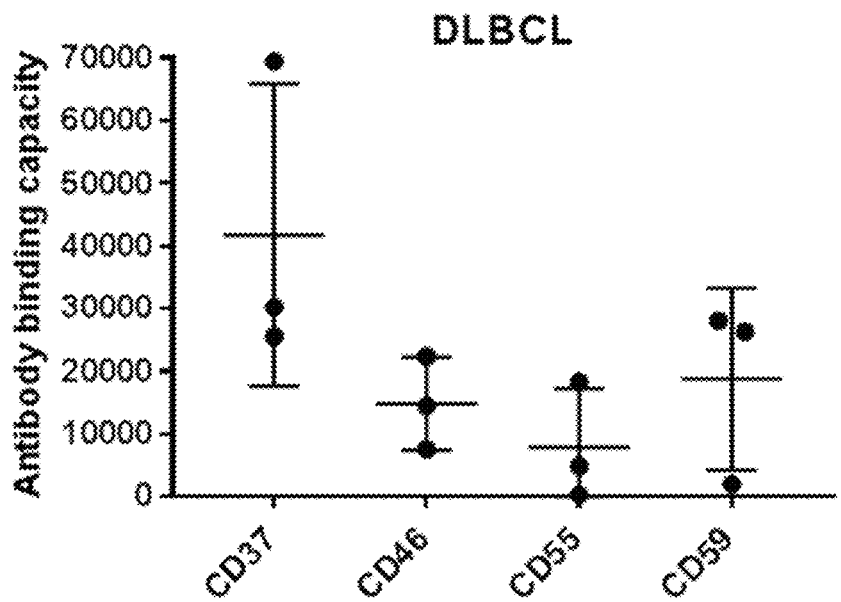

FIGS. 16A-16C: ADCC mediated by bispecific CD37 antibodies with an Fc-Fc interaction enhancing mutation, (combinations of) CD37 antibodies with an Fc-Fc interaction enhancing mutation, and monovalent binding CD37 antibodies with an Fc-Fc interaction enhancing mutation on Daudi and Raji cells. The capacity to induce ADCC of (FIG. 16A) bsIgG1-016-H5L2-LC90S-F405L-E430Gx005-H1L2-K409R-E430G, IgG1-005-H1L2-K409R-E430G, IgG1-016-H5L2-F405L-E430G and a combination of IgG1-005-H1L2-K409R-E430G plus IgG1-016-H5L2-F405L-E430G on Daudi cells, and (FIG. 16B) bsIgG1-016-H5L2-LC90S-F405L-E430Gx010-H5L2-K409R-E430G, IgG1-010-H5L2-E430G, IgG1-016-H5L2-E430G and a combination of IgG1-010-H5L2-E430G plus IgG1-016-H5L2-E430G on Daudi cells, and (FIG. 16C) bsIgG1-016-H5L2-LC90S-F405L-E430Gx010-H5L2-K409R-E430G, IgG1-010-H5L2-E430G, IgG1-016-H5L2-E430G, a combination of IgG1-010-H5L2-E430G plus IgG1-016-H5L2-E430G, bsIgG1-016-H5L2-LC90S-F405L-E430Gxb12-K409R-E430G and bsIgG1-b12-F405L-E430Gx010-H5L2-K409R-E430G on Raji cells was determined in vitro using a chromium release assay. Data shown are % specific lysis; error bars indicate variation within the assay, with 5 replicates (FIG. 16A, FIG. 16B) or 6 replicates (FIG. 16C) per data point.

FIGS. 17A-17D: Quantitative determination of CD37, CD46, CD55 and CD59 expression levels on (FIG. 17A) CLL, (FIG. 17B) FL, (FIG. 17C) MCL or (FIG. 17D) DLBCL tumor cells. Expression levels on tumor cells were determined by flow cytometry. Antigen quantity is shown as antibody binding capacity.

Figure 18A:
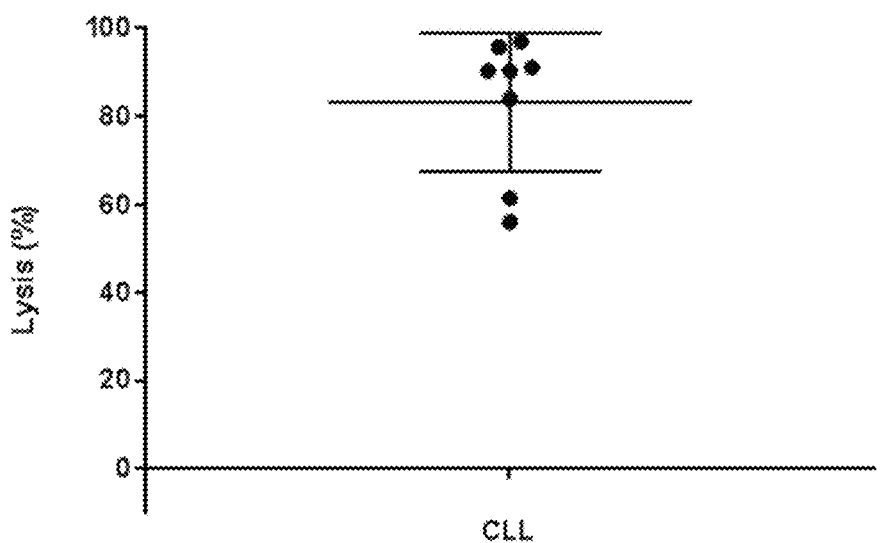
Figure 18B:
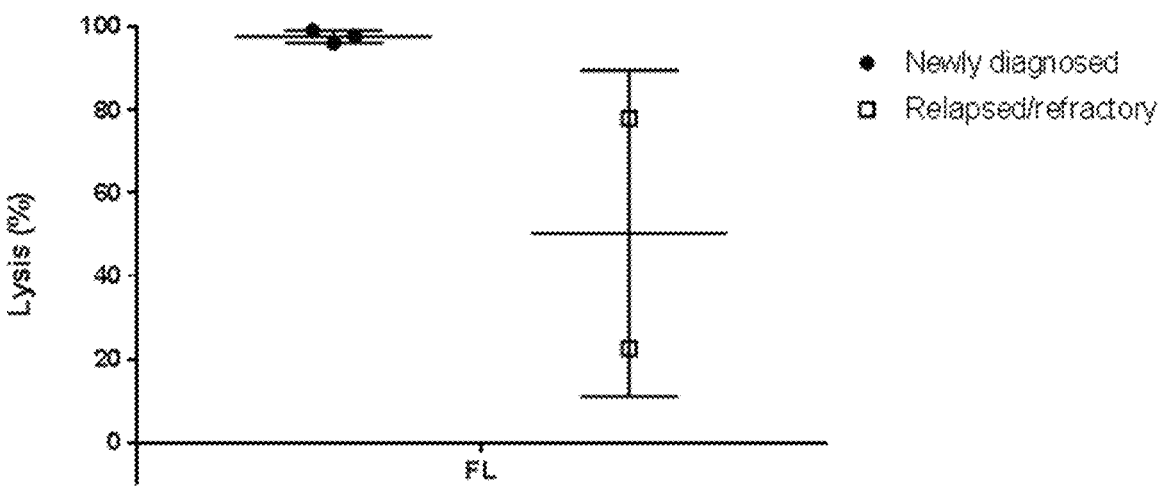

FIGS. 18A-18C: CDC mediated by a bispecific CD37 antibody with an Fc-Fc interaction enhancing mutation on primary tumor cells of patients with CLL, FL, MCL, DLBCL or B-NHL (not further specified). The capacity of bsIgG1-016-H5L2-LC90S-F405Lx010-H5L2-K409R-E430G to induce CDC on tumor cells derived from patients with (FIG. 18A) CLL, (FIG. 18B) FL and (FIG. 18C) MCL, DLBCL or B-NHL (not further specified) was determined by flow cytometry. CDC induction is presented as the percentage lysis determined by the fraction of 7-AAD positive tumor cells, using 100 µg/mL (FIGS. 18A and 18B) or 10 µg/mL (FIG. 18C) of bsIgG1-016-H5L2-LC90S-F405Lx010-H5L2-K409R-E430G.

Figure 19A:
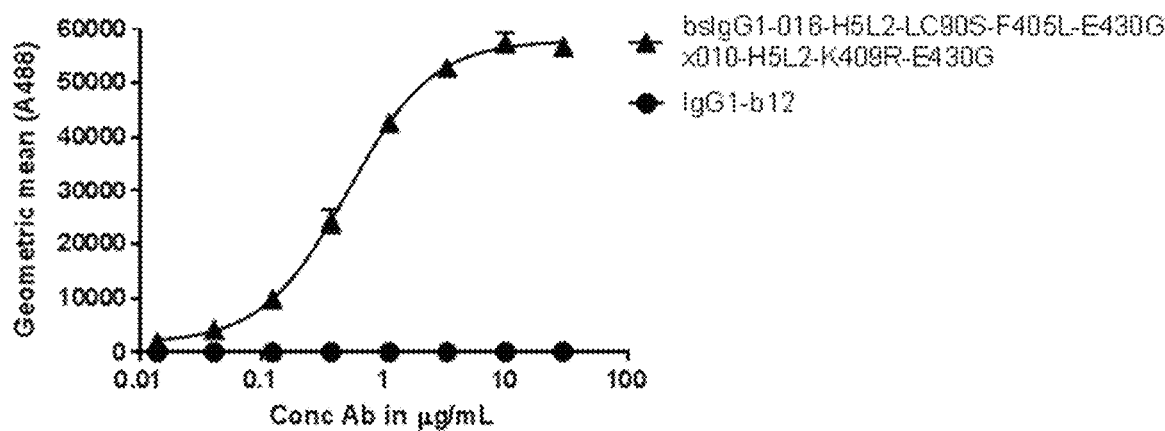
Figure 19B:
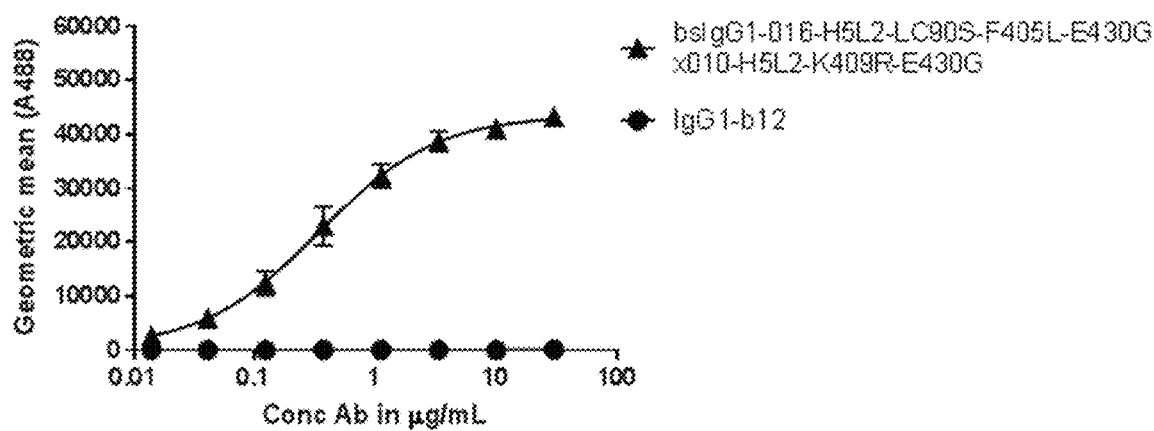

FIGS. 19A and 19B: Binding of a bispecific CD37 antibody with an Fc-Fc interaction enhancing mutation to B cells in human or cynomolgus monkey blood. Binding of Alexa-488 labeled bsIgG1-016-H5L2-LC90S-F405L-E430Gx010-H5L2-K409R-E430G to B cells in (FIG. 19A) human or (FIG. 19B) cynomolgus monkey blood was determined by flow cytometry. Alexa-488 labeled IgG1-b12 was used as a negative control antibody. Data are shown as geometric mean A488 fluorescence intensity values, for one representative donor/animal. Error bars show variation within the experiment (duplicate measurements).

Figure 20A:
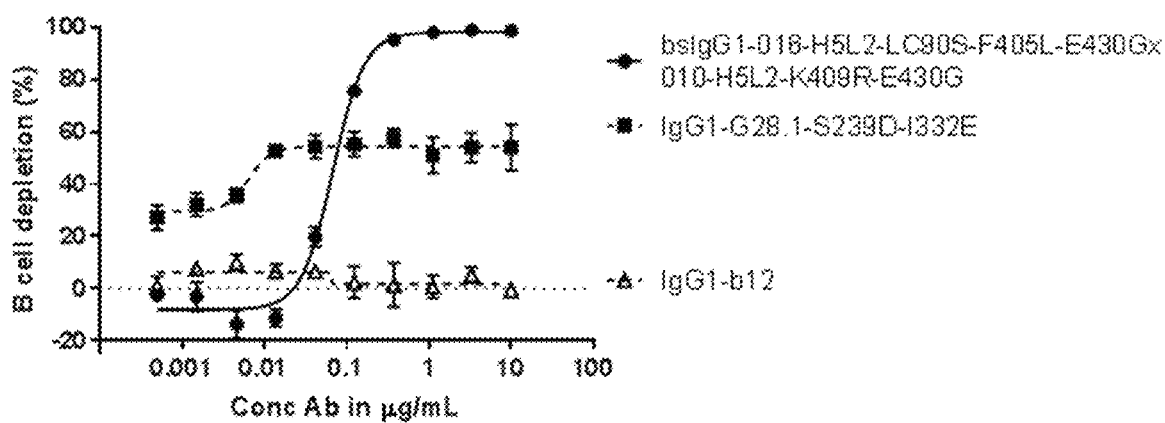
Figure 20B:
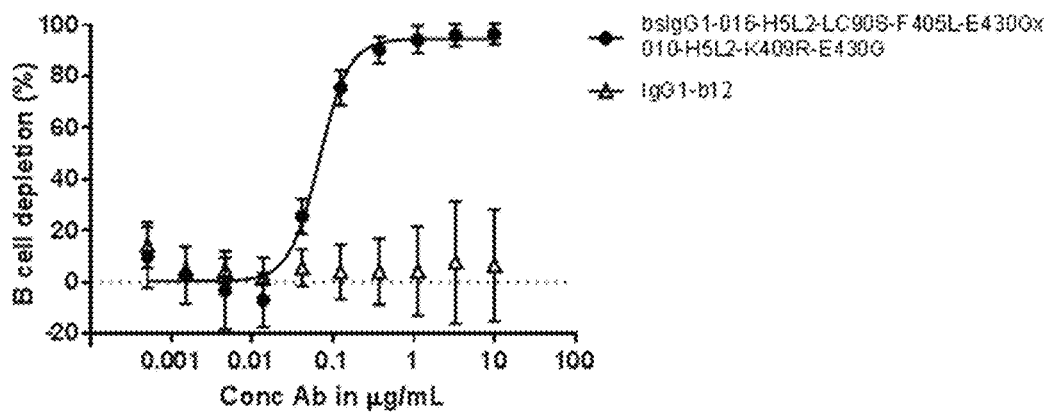

FIGS. 20A and 20B: Cytotoxicity of a bispecific CD37 antibody with an Fc-Fc interaction enhancing mutation and an FcγR-interaction enhanced monoclonal CD37 specific antibody to B cells in human or cynomolgus monkey blood. (FIG. 20A) Cytotoxicity of bsIgG1-016-H5L2-LC90S-F405L-E430Gx010-H5L2-K409R-E430G and IgG1-CD37-B2-S239D-1332E to B cells in human blood and (FIG. 20B) of bsIgG1-016-H5L2-LC90S-F405L-E430Gx010-H5L2-K409R-E430G to B cells in cynomolgus monkey blood was determined in a whole blood cytotoxicity assay. IgG1-b12 was used as a negative control antibody. Data are shown as % B cell depletion for one representative donor/animal. Error bars show variation within the experiment (duplicate measurements).

FIGS. 21A-21D: CDC mediated by a bispecific CD37 antibody with an Fc-Fc interaction enhancing mutation, a CD20-specific antibody or a combination thereof. (FIGS. 21A-21D) The capacity to induce CDC on tumor cells derived from 2 CLL patients of bsIgG1-016-H5L2-LC90S-F405L-E430Gx010-H5L2-K409R-E430G, ofatumumab or a combination thereof, at indicated concentrations, was determined ex vivo. Data are shown as the % of viable B cells.

Figure 22A:
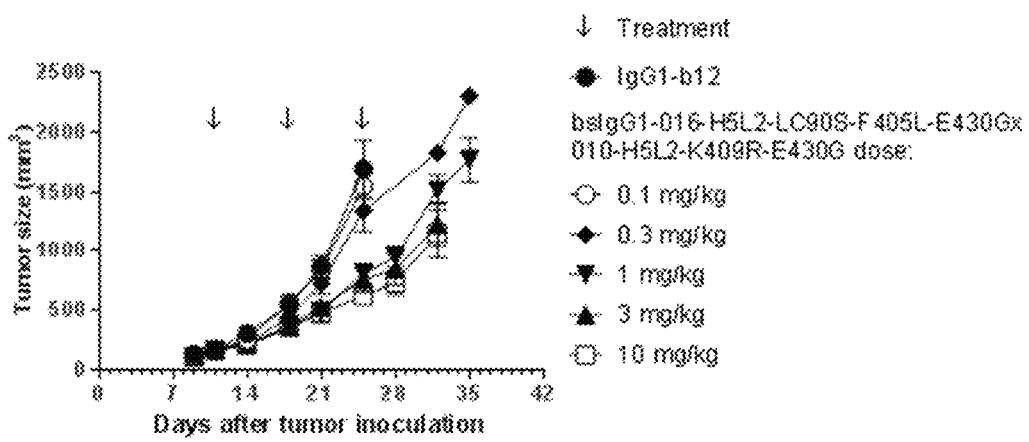
Figure 22B:
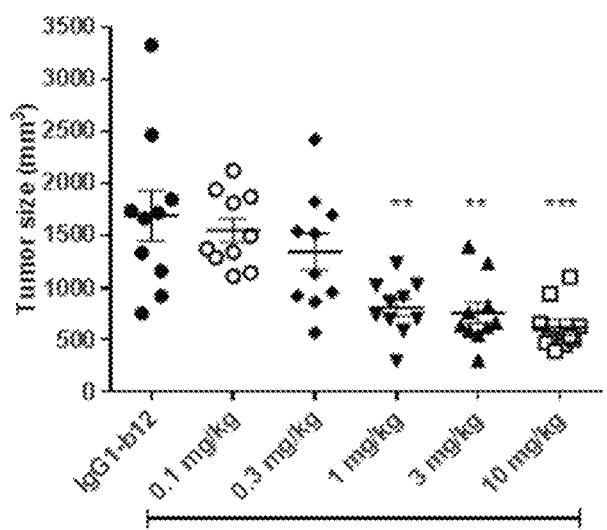

FIGS. 22A and 22B: Dose-effect relationship for 3 weekly doses of bsIgG1-016-H5L2-LC90S-F405L-E430Gx010-H5L2-K409R-E430G in the JVM-3 model. (FIG. 22A) Tumor growth of JVM-3 xenografts after treatment with different doses of bsIgG1-016-H5L2-LC90S-F405L-E430Gx010-H5L2-K409R-E430G or isotype control antibody (IgG1-b12). Mean and SEM of each group (n=10) is shown per time point. (FIG. 22B) Tumor size per mouse at day 25. Mean and SEM are indicated per treatment group. Differences were analyzed by Mann Whitney test. Statistically significant differences were indicated as follows: : $p<0.01$; *: $p<0.001$.

Figure 23A:
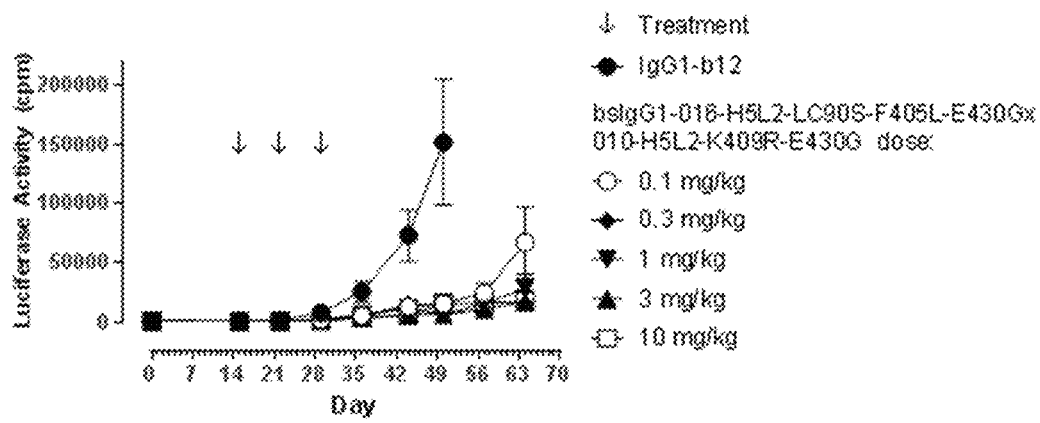
Figure 23B:
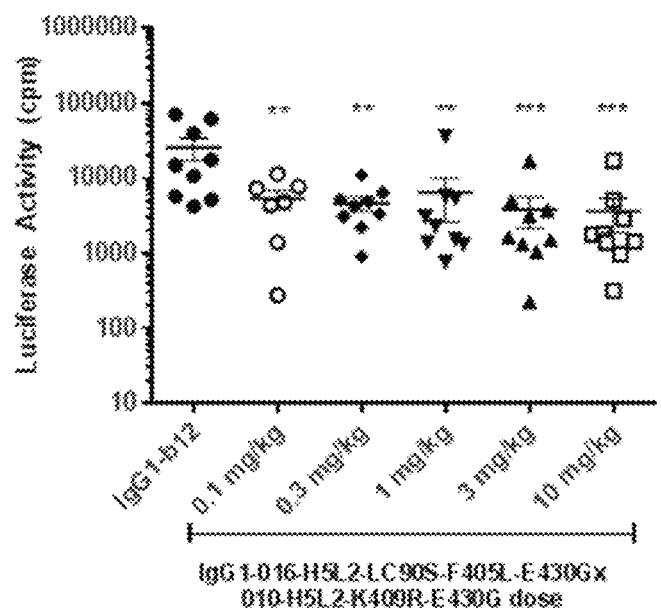

FIGS. 23A and 23B: Dose-effect relationship for 3 weekly doses of bsIgG1-016-H5L2-LC90S-F405L-E430Gx010-H5L2-K409R-E430G in the Daudi-luc model. (FIG. 23A) Tumor growth (measured by luciferase activity, bioluminescence) of Daudi-luc xenografts after treatment with different doses of bsIgG1-016-H5L2-LC90S-F405L-E430Gx010-H5L2-K409R-E430G or isotype control antibody (IgG1-b12). Mean and SEM of each group (n=9) is shown per time point. (FIG. 23B) Luciferase activity per mouse at day 36. Mean and SEM are indicated per treatment group. Differences were analyzed by One Way Anova, Uncorrected Fisher's LSD. Statistically significant differences were indicated as follows: : p<0.01; *: p<0.001.

FIGS. 24A-24D: Plasma concentrations of bsIgG1-016-H5L2-LC90S-F405L-E430Gx010-H5L2-K409R-E430G and IgG1-b12 following intravenous injection in SCID mice.

SCID mice were injected with a single i.v. dose of (FIGS. 24A and 24B) 100 μg (5 mg/kg) or (FIGS. 24C and 24D) 500 μg (25 mg/kg) of bsIgG1-016-H5L2-LC90S-F405L-E430Gx010-H5L2-K409R-E430G or IgG1-b12.

Figure 25:
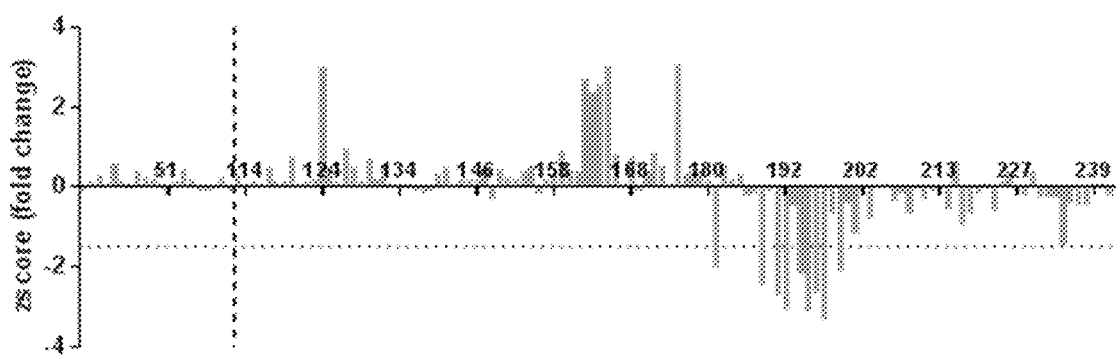
Figure 25:
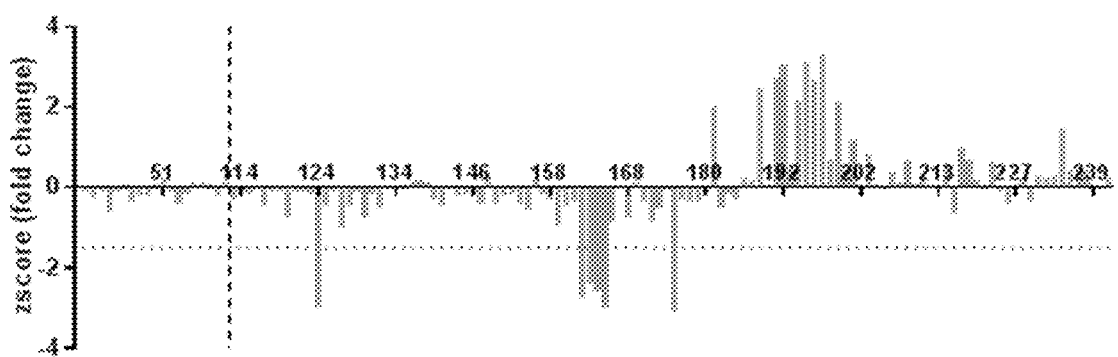
Figure 26A:
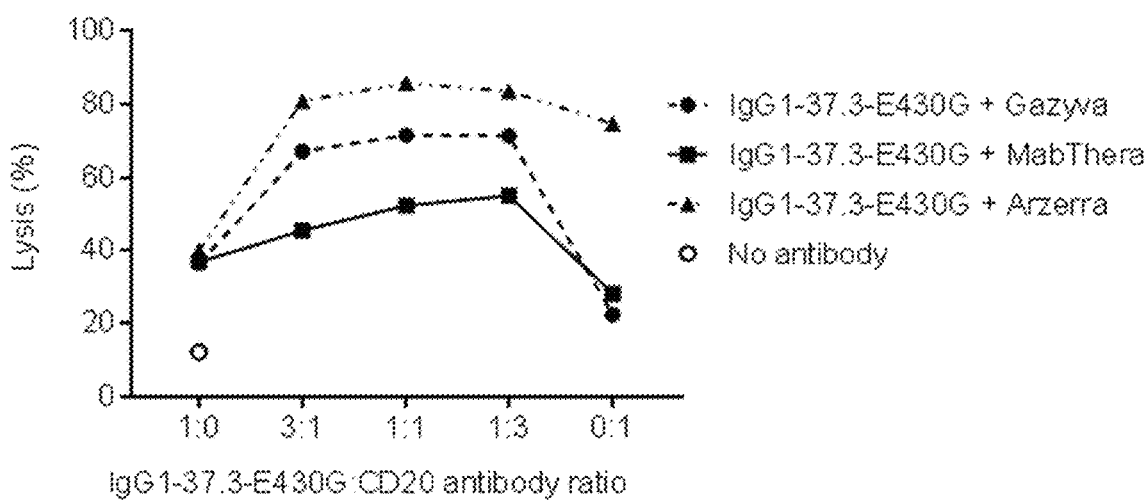
Figure 26B:
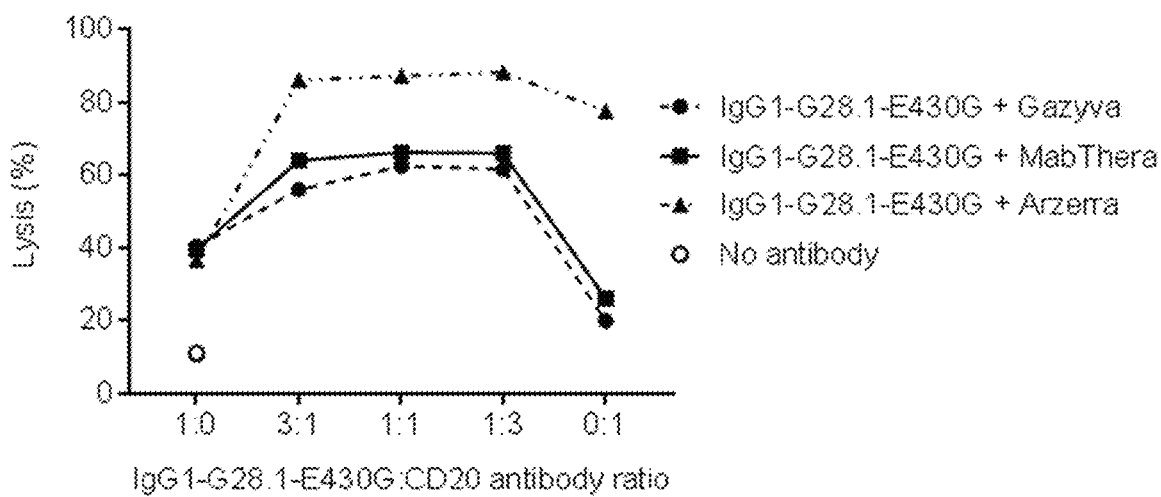
Figure 26C:
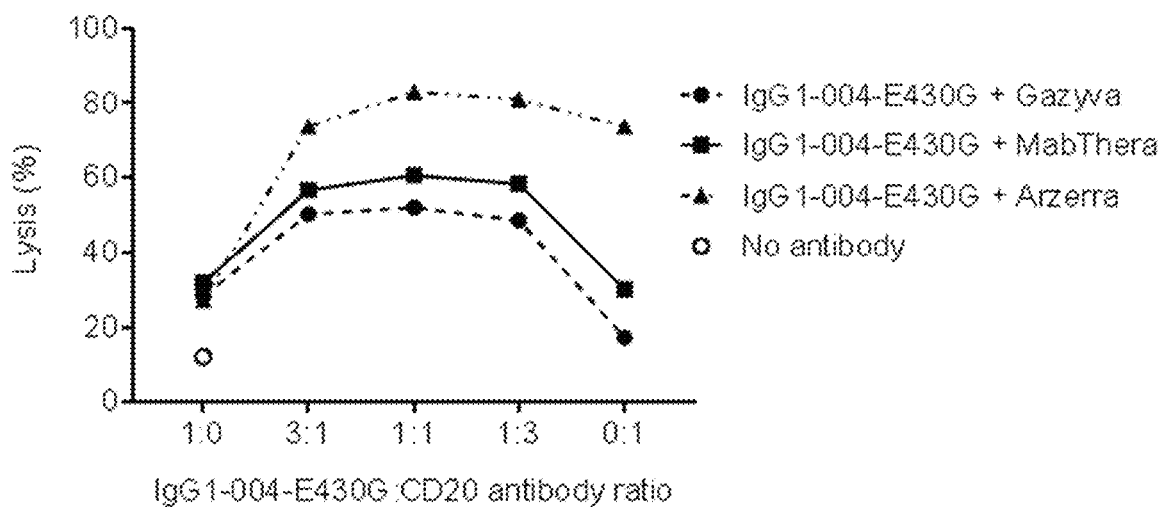
Figure 26D:
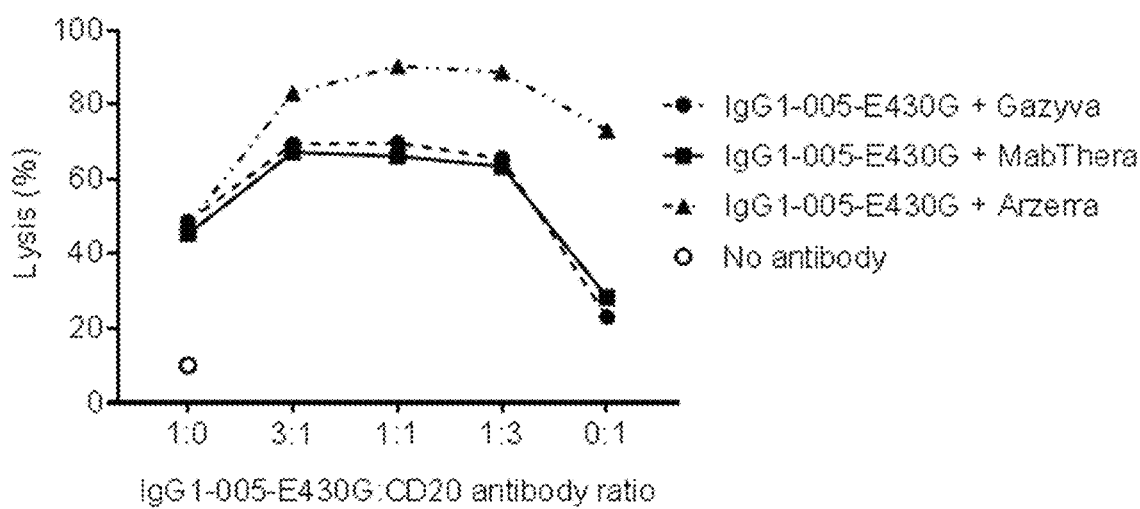
Figure 26E:
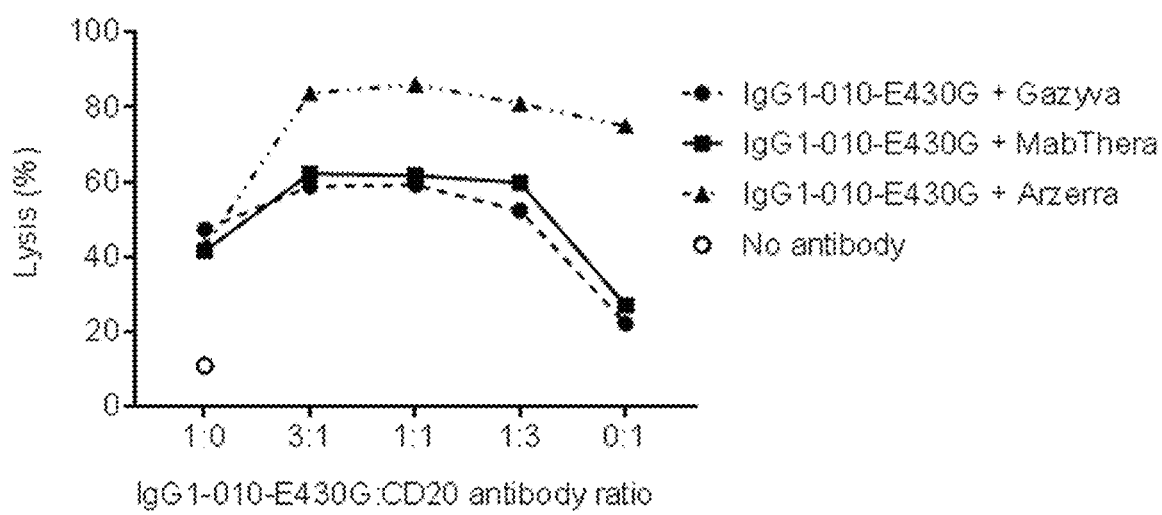
Figure 26F:
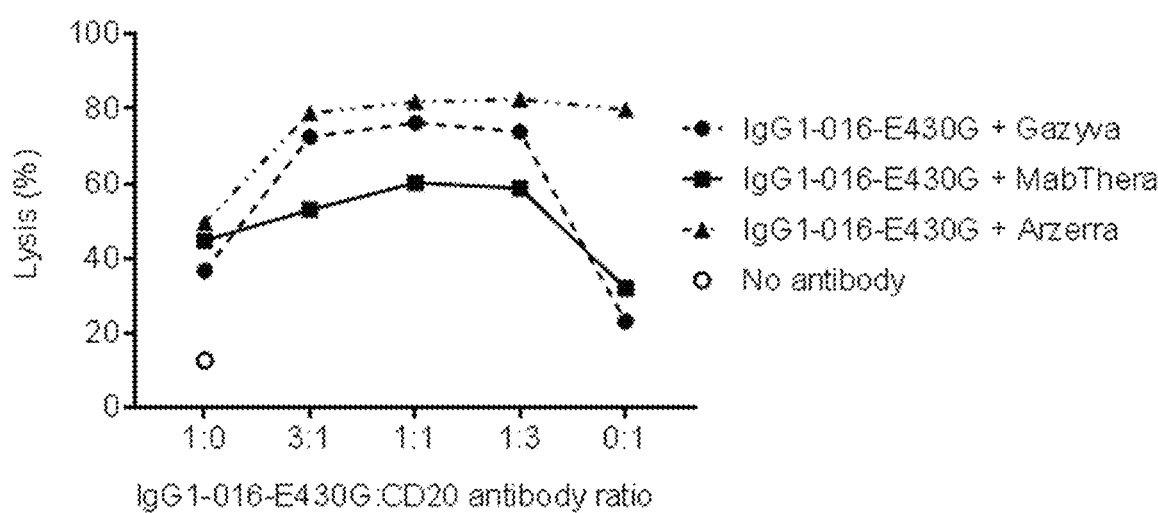

FIG. 25. Analysis of binding of CD37 antibodies to CD37 variants with alanine mutations in the extracellular domains. Zscore (fold change) was defined as (normalized gMFI[aa position]−μ)/σ, where μ and σ are the mean and standard deviation (SD) of the normalized gMFI of all mutants. Residues where the where the zscore was lower than −1.5 (indicated by the dotted line) were considered 'loss of binding mutants'. Number above the x-axis refer to amino acid positions. Note that x-axis is non-continuous: the left part (until the striped line) of the axis represents aa residues in the small extracellular loop of human CD37 which are not alanines or cysteines; the right part of the axis represents aa residues in the large extracellular loop of human CD37 which are not alanines or cysteines. The dotted line indicates a zscore (fold change) of −1.5.

FIGS. 26A-26F CDC mediated by mixtures of CD37 antibodies with an Fc-Fc interaction enhancing mutation plus clinically established CD20 antibody products on Raji cells. CDC-mediated killing of Raji cells (% lysis expressed as the PI-positive cell fraction as determined by flow cytometry) for antibody concentration dilution series of 1:0, 3:1, 1:1, 3:1 and 0:1 antibody mixtures (10 μg/mL final concentration) of CD37 antibodies with an Fc-Fc interaction enhancing mutation plus standard of care CD20 antibody products MabThera (rituximab), Arzerra (ofatumumab) and Gazyva (obinutuzumab, GA101): (FIG. 26A) mixtures with IgG1-37.3-E430G, (FIG. 26B) mixtures with IgG1-G28.1-E430G, (FIG. 26C) mixtures with IgG1-004-E430G, (FIG. 26D) mixtures with IgG1-005-E430G, (FIG. 26E) mixtures with IgG1-010-E430G and (FIG. 26F) mixtures with IgG1-016-E430G.

DETAILED DESCRIPTION OF THE INVENTION

Definitions

The term "CD37", as used herein, refers to Leukocyte Antigen CD37, also known as GP52-40, tetraspanin-26, and TSPAN26, which is a heavily glycosylated transmembrane protein with four transmembrane domains (TMs) and one small and one large extracellular domain. Homo sapiens, i.e., human, CD37 protein is encoded by a nucleic acid sequence encoding the amino acid sequence shown in SEQ ID NO: 62 (human CD37 protein: UniprotKB/Swissprot P11049). In this amino acid sequence, residues 112 to 241 correspond to the large extracellular domain, residues 39 to 59 to the small extracellular domain, while the remaining residues correspond to transmembrane and cytoplasmic domains. Macaca fascicularis, i.e., cynomolgus monkey, CD37 protein is encoded by a nucleic acid sequence encoding the amino acid sequence shown in SEQ ID NO: 63 (cynomolgus CD37 protein: Genbank accession no. XP_005589942). Unless contradicted by context the term "CD37" means "human CD37". The term "CD37" includes any variants, isoforms and species homologs of CD37 which are naturally expressed by cells, including tumor cells, or are expressed on cells transfected with the CD37 gene or cDNA.

The term "human CD20" or "CD20" refers to human CD20 (UniProtKB/Swiss-Prot No P11836) and includes any variants, isoforms and species homologs of CD20 which are naturally expressed by cells, including tumor cells, or are expressed on cells transfected with the CD20 gene or cDNA. Species homologs include rhesus monkey CD20 (Macaca mulatta; UniProtKB/Swiss-Prot No H9YXP1) and cynomolgus monkey CD20 (Macaca fascicularis).

The term "antibody binding CD37", "anti-CD37 antibody", "CD37-binding antibody", "CD37-specific antibody", "CD37 antibody" which may be used interchangeably herein, refers to any antibody binding an epitope on the extracellular part of CD37.

The term "antibody" (Ab) in the context of the present invention refers to an immunoglobulin molecule, a fragment of an immunoglobulin molecule, or a derivative of either thereof, which has the ability to specifically bind to an antigen under typical physiological conditions with a half-life of significant periods of time, such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to recruit an effector activity). The variable regions of the heavy and light chains of the immunoglobulin molecule contain a binding domain that interacts with an antigen. The constant regions of the antibodies (Abs) may mediate the binding of the immunoglobulin to host tissues or factors, including various cells of the immune system (such as effector cells) and components of the complement system such as C1q, the first component in the classical pathway of complement activation. As indicated above, the term antibody herein, unless otherwise stated or clearly contradicted by context, includes fragments of an antibody that are antigen-binding fragments, i.e., retain the ability to specifically bind to the antigen. It has been shown that the antigen-binding function of an antibody may be performed by fragments of a full-length antibody. Examples of antigen-binding fragments encompassed within the term "antibody" include (i) a Fab' or Fab fragment, a monovalent fragment consisting of the $V_L$, $V_H$, $C_L$ and $C_H1$ domains, or a monovalent antibody as described in WO2007059782 (Genmab); (ii) F(ab')$_2$ fragments, bivalent fragments comprising two Fab fragments linked by a disulfide bridge at the hinge region; (iii) a Fd fragment consisting essentially of the $V_H$ and $C_H1$ domains; (iv) a Fv fragment consisting essentially of the $V_L$ and $V_H$ domains of a single arm of an antibody, (v) a dAb fragment (Ward et al., Nature 341, 544-546 (1989)), which consists essentially of a $V_H$ domain and also called domain antibodies (Holt et al; Trends Biotechnol. 2003 November; 21(11):484-90); (vi) camelid or nanobodies (Revets et al; Expert Opin Biol Ther. 2005 January; 5(1):111-24) and (vii) an isolated complementarity determining region (CDR). Furthermore, although the two domains of the Fv fragment, $V_L$ and $V_H$, are coded for by separate genes, they may be joined, using recombinant methods, by a synthetic linker that enables them to be made as a single protein chain in which the $V_L$ and $V_H$ regions pair to form monovalent molecules (known as single chain antibodies or single chain Fv (scFv), see for instance Bird et al., Science 242, 423-426 (1988) and Huston et al., PNAS USA 85, 5879-5883 (1988)). Such single chain antibodies are encompassed within the term antibody unless otherwise noted or clearly indicated by context. Although such fragments are generally included within the meaning of antibody, they collectively and each independently are unique features of the present invention, exhibiting different biological properties and utility. These and other useful antibody fragments in the context of the present invention, as well as bispecific formats of such fragments, are discussed further herein. For the bispecific antibodies of the invention such fragments are linked to an Fc domain. It also should be understood that the term antibody, unless specified otherwise, also includes polyclonal antibodies, monoclonal antibodies (mAbs), antibody-like polypeptides, such as chimeric antibodies and humanized antibodies, and antibody fragments retaining the ability to specifically bind to the antigen (antigen-binding fragments) provided by any known technique, such as enzymatic cleavage, peptide synthesis, and recombinant techniques. An antibody as generated can possess any isotype.

The term "bispecific antibody" refers to antibody having specificities for at least two different, typically non-overlapping, epitopes. Such epitopes may be on the same or different targets. For the present invention the epitopes are on the same target, namely CD37. Examples of different classes of bispecific antibodies comprising an Fc region include but are not limited to: asymmetric bispecific molecules, e.g., IgG-like molecules with complementary CH3 domains; and symmetric bispecific molecules, e.g., recombinant IgG-like dual targeting molecules wherein each antigen-binding region of the molecule binds at least two different epitopes.

Examples of bispecific molecules include but are not limited to Triomab® (Trion Pharma/Fresenius Biotech, WO/2002/020039), Knobs-into-Holes (Genentech, WO 1998/50431), CrossMAbs (Roche, WO 2009/080251, WO 2009/080252, WO 2009/080253), electrostatically-matched Fc-heterodimeric molecules (Amgen, EP1870459 and WO2009089004; Chugai, US201000155133; Oncomed, WO 2010/129304), LUZ-Y (Genentech), DIG-body, PIG-body and TIG-body (Pharmabcine), Strand Exchange Engineered Domain body (SEEDbody) (EMD Serono, WO2007110205), Bispecific IgG1 and IgG2 (Pfizer/Rinat, WO 2011/143545), Azymetric scaffold (Zymeworks/Merck, WO2012058768), mAb-Fv (Xencor, WO 2011/028952), XmAb (Xencor), Bivalent bispecific antibodies (Roche, WO 2009/080254), Bispecific IgG (Eli Lilly), DuoBody® molecules (Genmab A/S, WO 2011/131746), DuetMab (Medimmune, US2014/0348839), Biclonics (Merus, WO 2013/157953), NovImmune (KABodies, WO 2012/023053), FcAAdp (Regeneron, WO 2010/151792), (DT)-Ig (GSK/Domantis), Two-in-one Antibody or Dual Action Fabs (Genentech, Adimab), mAb2 (F-Star, WO 2008/003116), Zybody™ molecules (Zyngenia), CovX-body (CovX/Pfizer), FynomAbs (Covagen/Janssen Cilag), DutaMab (Dutalys/Roche), iMab (MedImmune), Dual Variable Domain (DVD)-Ig™ (Abbott), dual domain double head antibodies (Unilever; Sanofi Aventis, WO 2010/0226923), Ts2Ab (MedImmune/AZ), BsAb (Zymogenetics), HERCULES (Biogen Idec, U.S. Pat. No. 7,951,918), scFv-fusions (Genentech/Roche, Novartis, Immunomedics, Changzhou Adam Biotech Inc, CN 102250246), TvAb (Roche, WO2012/025525, WO2012/025530), ScFv/Fc Fusions, SCORPION (Emergent BioSolutions/Trubion, Zymogenetics/BMS), Interceptor (Emergent), Dual Affinity Retargeting Technology (Fc-DART™) (MacroGenics, WO2008/157379, WO2010/080538), BEAT (Glenmark), Di-Diabody (Imclone/Eli Lilly) and chemically crosslinked mAbs (Karmanos Cancer Center), and covalently fused mAbs (AIMM therapeutics).

The term "full-length antibody", as used herein, refers to an antibody (e.g., a parent or variant antibody) which contains all heavy and light chain constant and variable domains corresponding to those that are normally found in a wild-type antibody of that class or isotype.

The term "chimeric antibody" as used herein, refers to an antibody wherein the variable region is derived from a non-human species (e.g. derived from rodents) and the constant region is derived from a different species, such as human. Chimeric antibodies may be generated by antibody engineering. "Antibody engineering" is a term used generic for different kinds of modifications of antibodies, and which is a well-known process for the skilled person. In particular, a chimeric antibody may be generated by using standard DNA techniques as described in Sambrook et al., 1989, Molecular Cloning: A laboratory Manual, New York: Cold Spring Harbor Laboratory Press, Ch. 15. Thus, the chimeric antibody may be a genetically or an enzymatically engineered recombinant antibody. It is within the knowledge of the skilled person to generate a chimeric antibody, and thus, generation of the chimeric antibody according to the present invention may be performed by other methods than described herein. Chimeric monoclonal antibodies for therapeutic applications are developed to reduce antibody immunogenicity. They may typically contain non-human (e.g. murine) variable regions, which are specific for the antigen of interest, and human constant antibody heavy and light chain domains. The terms "variable region" or "variable domains" as used in the context of chimeric antibodies, refers to a region which comprises the CDRs and framework regions of both the heavy and light chains of the immunoglobulin.

The term "oligomer", as used herein, refers to a molecule that consists of more than one but a limited number of monomer units (e.g. antibodies) in contrast to a polymer that, at least in principle, consists of an unlimited number of monomers. Exemplary oligomers are dimers, trimers, tetramers, pentamers and hexamers. Likewise, "oligomerization" such as e.g. "hexamerization", as used herein, means that there is an increase in the distribution of antibodies and/or other dimeric proteins comprising target-binding regions according to the invention into oligomers, such as hexamers. The increased formation of oligomers such as hexamers is due to increased Fc-Fc interaction after binding to membrane-bound targets.

The term "antigen-binding region", "antigen binding region", "binding region" or antigen binding domain, as used herein, refers to a region of an antibody which is capable of binding to the antigen. This binding region is typically defined by the VH and VL domains of the antibody which may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). The antigen can be any molecule, such as a polypeptide, e.g. present on a cell, bacterium, or virion or in solution. The terms "antigen" and "target" may, unless contradicted by the context, be used interchangeably in the context of the present invention.

The term "target", as used herein, refers to a molecule to which the antigen binding region of the antibody binds. The target includes any antigen towards which the raised antibody is directed. The term "antigen" and "target" may in relation to an antibody be used interchangeably and constitute the same meaning and purpose with respect to any aspect or embodiment of the present invention.

The term "humanized antibody" as used herein, refers to a genetically engineered non-human antibody, which contains human antibody constant domains and non-human variable domains modified to contain a high level of sequence homology to human variable domains. This can be achieved by grafting of the six non-human antibody complementarity-determining regions (CDRs), which together form the antigen binding site, onto a homologous human acceptor framework region (FR) (see WO92/22653 and EP0629240). In order to fully reconstitute the binding affinity and specificity of the parental antibody, the substitution of framework residues from the parental antibody (i.e. the non-human antibody) into the human framework regions (back-mutations) may be required. Structural homology modeling may help to identify the amino acid residues in the framework regions that are important for the binding properties of the antibody. Thus, a humanized antibody may comprise non-human CDR sequences, primarily human framework regions optionally comprising one or more amino acid back-mutations to the non-human amino acid sequence, and fully human constant regions. Optionally, additional amino acid modifications, which are not necessarily back-mutations, may be applied to obtain a humanized antibody with preferred characteristics, such as affinity and biochemical properties.

Humanized antibodies can be generated using immunized rabbits, humanization of rabbit antibodies using germline humanization (CDR-grafting) technology, and, if necessary, by back-mutating residues which may be critical for the antibody binding properties, as identified in structural modeling, to rabbit residues. Screening for potential T cell epitopes can be applied.

The term "human antibody" as used herein, refers to antibodies having variable and constant regions derived from human germline immunoglobulin sequences. Human antibodies may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. Human monoclonal antibodies of the invention can be produced by a variety of techniques, including conventional monoclonal antibody methodology, e.g., the standard somatic cell hybridization technique of Kohler and Milstein, *Nature* 256: 495 (1975). Although somatic cell hybridization procedures are preferred, in principle, other techniques for producing monoclonal antibody can be employed, e.g., viral or oncogenic transformation of B-lymphocytes or phage display techniques using libraries of human antibody genes.

A suitable animal system for preparing hybridomas that secrete human monoclonal antibodies is the murine system. Hybridoma production in the mouse is a very well established procedure. Immunization protocols and techniques for isolation of immunized splenocytes for fusion are known in the art. Fusion partners (e.g., murine myeloma cells) and fusion procedures are also known.

Human monoclonal antibodies can be generated using e.g. transgenic or transchromosomal mice or rabbits carrying parts of the human immune system rather than the mouse or rabbit system.

The term "immunoglobulin" refers to a class of structurally related glycoproteins consisting of two pairs of polypeptide chains, one pair of light (L) low molecular weight chains and one pair of heavy (H) chains, all four interconnected by disulfide bonds. The structure of immunoglobulins has been well characterized. See for instance Fundamental Immunology Ch. 7 (Paul, W., ed., 2nd ed. Raven Press, N.Y. (1989)). Briefly, each heavy chain typically is comprised of a heavy chain variable region (abbreviated herein as $V_H$ or VH) and a heavy chain constant region (abbreviated herein as $C_H$ or $C_H$). The heavy chain constant region typically is comprised of three domains, $C_H1$, $C_H2$, and $C_H3$. Each light chain typically is comprised of a light chain variable region (abbreviated herein as $V_L$ or VL) and a light chain constant region (abbreviated herein as $C_L$ or CL). The light chain constant region typically is comprised of one domain, $C_L$. The $V_H$ and $V_L$ regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each $V_H$ and $V_L$ is typically composed of three CDRs and four FRs, arranged from amino-terminus to carboxy-terminus in the following order: FR1, CDR1, FR2, CDR2, FR3, CDR3, FR4 (see also Chothia and Lesk J. Mol. Biol. 196, 901-917 (1987)). Unless otherwise stated or contradicted by context, CDR sequences herein are identified according to IMGT rules (Brochet X., Nucl Acids Res. 2008; 36:W503-508 and Lefranc M P., Nucleic Acids Research 1999; 27:209-212; see also internet http address http://www.imgt.org/). Unless otherwise stated or contradicted by context, reference to amino acid positions in the constant regions in the present invention is according to the EU-numbering (Edelman et al., Proc Natl Acad Sci USA. 1969 May; 63(1):78-85; Kabat et al., Sequences of Proteins of Immunological Interest, Fifth Edition. 1991 NIH Publication No. 91-3242).

When used herein, unless contradicted by context, the term "Fab-arm" or "arm" refers to one heavy chain-light chain pair and is used interchangeably with "half molecules" herein. Accordingly, a "Fab-arm" comprises the variable regions of the heavy chain and light chain as well as the constant region of the light chain and the constant region of the heavy chain which comprises the CH1 region, the hinge, the CH2 region and the CH3 region of an immunoglobulin. The "CH1 region" refers e.g. to the region of a human IgG1 antibody corresponding to amino acids 118-215 according to the EU numbering. Thus, the Fab fragment comprises the binding region of an immunoglobulin.

The term "fragment crystallizable region", "Fc region", "Fc fragment" or "Fc domain", which may be used interchangeably herein, refers to an antibody region comprising, arranged from amino-terminus to carboxy-terminus, at least a hinge region, a CH2 domain and a CH3 domain. An Fc region of an IgG1 antibody can, for example, be generated by digestion of an IgG1 antibody with papain. The Fc region of an antibody may mediate the binding of the immunoglobulin to host tissues or factors, including various cells of the immune system (such as effector cells) and components of the complement system such as C1q, the first component in the classical pathway of complement activation. The term "hinge region", as used herein, is intended to refer to the hinge region of an immunoglobulin heavy chain. Thus, for example the hinge region of a human IgG1 antibody corresponds to amino acids 216-230 according to the EU numbering.

The term "core hinge" or "core hinge region" as used herein refers to the four amino acids corresponding to positions 226-229 of a human IgG1 antibody.

The term "CH2 region" or "CH2 domain", as used herein, is intended to refer the CH2 region of an immunoglobulin heavy chain. Thus, for example the CH2 region of a human IgG1 antibody corresponds to amino acids 231-340 according to the EU numbering. However, the CH2 region may also be any of the other isotypes or allotypes as described herein.

The term "CH3 region" or "CH3 domain" as used herein, is intended to refer to the CH3 region of an immunoglobulin heavy chain. Thus, for example the CH3 region of a human IgG1 antibody corresponds to amino acids 341-447 according to the EU numbering. However, the CH3 region may also be any of the other isotypes or allotypes as described herein.

As used herein, the term "isotype" refers to the immunoglobulin class (for instance IgG1, IgG2, IgG3, IgG4, IgD, IgA, IgE, or IgM) that is encoded by heavy chain constant region genes.

The term "monovalent antibody" means in the context of the present invention that an antibody molecule is capable of binding a single molecule of the antigen, and thus is not capable of antigen crosslinking.

A "CD37 antibody" or "anti-CD37 antibody" is an antibody as described above, which binds specifically to the antigen CD37.

A "CD37×CD37 antibody" or "anti-CD37×CD37 antibody" is a bispecific antibody, which comprises two different antigen-binding regions, one of which binds specifically to a first epitope on the antigen CD37 and a second which binds specifically to a different epitope on CD37.

In an embodiment, the bispecific antibody of the invention is isolated. An "isolated bispecific antibody," as used herein, is intended to refer to a bispecific antibody which is substantially free of other antibodies having different antigenic specificities (for instance an isolated bispecific antibody that specifically binds to CD37 is substantially free of monospecific antibodies that specifically bind to CD37).

The term "epitope" means a protein determinant capable of binding to an antigen-binding region of an antibody ("paratope"). Epitopes usually consist of surface groupings of molecules such as amino acids or sugar side chains and usually have specific three-dimensional structural characteristics, as well as specific charge characteristics. Conformational and nonconformational epitopes are distinguished in that the binding to the former but not the latter is lost in the presence of denaturing solvents. Epitope mapping techniques can determine "structural epitopes" or "functional epitopes". Structural epitopes are defined as those residues within a structure that are in direct contact with the antibody and can for example be assessed by structure based methods such as X-ray crystallography. A structural epitope may comprise amino acid residues directly involved in the binding of an antibody as well as other amino acid residues, which are not directly involved in the binding, such as amino acid residues which are effectively blocked or covered by antibody (in other words, the amino acid residue is within the footprint of the antibody). Functional epitope are defined as those residues that make energetic contributions to the antigen-antibody binding interaction and can for example be assessed by site-directed mutagenesis such as alanine scanning (Cunningham, B. C., & Wells, J. A. (1993) *Journal of Molecular Biology*; Clackson, T., & Wells, J. (1995) *Science*, 267(5196), 383-386). A functional epitope may comprise amino acid residues directly involved in the binding of an antibody as well as other amino acid residues which are not directly involved in the binding, such as amino acid residues which cause conformational changes to the location of residues involved in direct interactions (Greenspan, N. S., & Di Cera, E. (1999) *Nature Biotechnology*, 17(10), 936-937). In case of antibody-antigen interactions, the functional epitope may be used to distinguish antibody molecules between each other. A functional epitope may be determined by use of the method of alanine scanning as described in Example 17. Thus, amino acids in the protein may be substituted with alanines thereby generating a series of mutant proteins, binding of the antigen-binding region of the antibody to the mutant protein is reduced as compared to a wild type protein; reduced binding being determined as standardized log(fold change) (expressed as z-scores) in binding of said antibody being less than −1.5 as set forth in Example 17.

The term "monoclonal antibody" as used herein refers to a preparation of antibody molecules essentially of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be generated by a hybridoma which includes a B cell obtained from a transgenic or transchromosomal non-human animal, such as a transgenic mouse, having a genome comprising a human heavy chain transgene and a light chain transgene, fused to an immortalized cell.

As used herein, the term "binding" in the context of the binding of an antibody to a predetermined antigen typically is a binding with an affinity corresponding to a $K_D$ of about $10^{-6}$ M or less, e.g. $10^{-7}$ M or less, such as about $10^{-8}$ M or less, such as about $10^{-9}$ M or less, about $10^{-10}$ M or less, or about $10^{-11}$ M or even less when determined by for instance BioLayer Interferometry (BLI) technology in a Octet HTX instrument using the antibody as the ligand and the antigen as the analyte, and wherein the antibody binds to the predetermined antigen with an affinity corresponding to a $K_D$ that is at least ten-fold lower, such as at least 100-fold lower, for instance at least 1,000-fold lower, such as at least 10,000-fold lower, for instance at least 100,000-fold lower than its $K_D$ of binding to a non-specific antigen (e.g., BSA, casein) other than the predetermined antigen or a closely related antigen. The amount with which the $K_D$ of binding is lower is dependent on the $K_D$ of the antibody, so that when the $K_D$ of the antibody is very low, then the amount with which the $K_D$ of binding to the antigen is lower than the $K_D$ of binding to a non-specific antigen may be at least 10,000-fold (that is, the antibody is highly specific).

The term "$K_D$" (M), as used herein, refers to the dissociation equilibrium constant of a particular antibody-antigen interaction.

"Affinity", as used herein, and "$K_D$" are inversely related, that is, higher affinity is intended to refer to lower $K_D$, and lower affinity is intended to refer to higher $K_D$.

As used herein, an antibody which "competes" or "cross-competes" is used interchangeably with an antibody which "blocks" or "cross-blocks" with another antibody, i.e. a reference antibody, and means that the antibody and the reference antibody compete for binding to human CD37, e.g. as determined in the assay described in Examples 7 herein. In one embodiment the antibody binds with less than 50%, such as less than 20%, such as less than 15% of its maximum binding in the presence of the competing reference antibody.

As used herein, an antibody which "does not compete" or "does not cross-compete" or "does not block" with another antibody, i.e. a reference antibody, means that the antibody and the reference antibody do not compete for binding to human CD37, e.g. as determined in the assay described in Examples 7 herein. For some pairs of antibody and reference antibody, non-competition in the assay of Example 7 is only observed when one antibody is bound to an antigen on a cell and the other is used to compete, and not vice versa. The term "does not compete with" or "non-competition" or "non-blocking" when used herein is also intended to cover such combinations of antibodies. In one embodiment the antibody binds with at least 75%, such as least 80%, such as at least 85% of its maximum binding in the presence of the reference antibody.

The term "Fc-Fc interaction enhancing mutation", as used herein, refers to a mutation in IgG antibodies that strengthens Fc-Fc interactions between neighboring IgG antibodies that are bound to a cell surface target. This may result in enhanced oligomer formation such as e.g. hexamerization of the target-bound antibodies, while the antibody molecules remain monomeric in solution as described in WO 2013/004842; WO 2014/108198 both which are hereby incorporated by reference.

The term "Fc effector functions" or "Fc-mediated effector functions" as used herein, is intended to refer to functions that are a consequence of binding a polypeptide or antibody to its target, such as an antigen, on a cell membrane, and subsequent interaction of the IgG Fc domain with molecules of the innate immune system (e.g. soluble molecules or membrane-bound molecules). Examples of Fc effector functions include (i) C1q-binding, (ii) complement activation, (iii) complement-dependent cytotoxicity (CDC), (iv) antibody-dependent cell-mediated cytotoxicity (ADCC), (v) Fc-gamma receptor-binding, (vi) antibody-dependent cellular phagocytosis (ADCP), (vii) complement-dependent cellular cytotoxicity (CDCC), (viii) complement-enhanced cytotoxicity (ix) binding to complement receptor of an opsonized antibody mediated by the antibody, (x) opsonisation, and (xi) a combination of any of (i) to (x).

When used herein the term "heterodimeric interaction between the first and second CH3 regions" refers to the interaction between the first CH3 region of the first Fc-region and the second CH3 region of the second Fc-region in a first-CH3/second-CH3 heterodimeric protein. A bispecific antibody is an example of a heterodimeric protein.

When used herein the term "homodimeric interactions of the first and second CH3 regions" refers to the interaction between a first CH3 region and another first CH3 region in a first-CH3/first-CH3 homodimeric protein and the interaction between a second CH3 region and another second CH3 region in a second-CH3/second-CH3 homodimeric protein. A monoclonal antibody is an example of a homodimeric protein.

The term "reducing conditions" or "reducing environment" refers to a condition or an environment in which a substrate, such as e.g. a cysteine residue in the hinge region of an antibody, is more likely to become reduced than oxidized.

The present invention also provides bispecific antibodies comprising functional variants of the $V_L$ regions, $V_H$ regions, or one or more CDRs of the bispecific antibodies of the examples. A functional variant of a $V_L$, $V_H$, or CDR used in the context of a bispecific antibody still allows each arm of the bispecific antibody to retain at least a substantial proportion (at least about 50%, 60%, 70%, 80%, 90%, 95% or more) of the affinity and/or the specificity/selectivity of the parent bispecific antibody and in some cases such a bispecific antibody may be associated with greater affinity, selectivity and/or specificity than the parent bispecific antibody. Such functional variants typically retain significant sequence identity to the parent bispecific antibody. The percent identity between two sequences is a function of the number of identical positions shared by the sequences (i.e., % homology=# of identical positions/total # of positions× 100), taking into account the number of gaps, and the length of each gap, which need to be introduced for optimal alignment of the two sequences. The percent identity between two nucleotide or amino acid sequences may e.g. be determined using the algorithm of E. Meyers and W. Miller, Comput. Appl. Biosci 4, 11-17 (1988) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch, J. Mol. Biol. 48, 444-453 (1970) algorithm.

Exemplary variants include those which differ from VH and/or VL and/or CDR regions of the parent bispecific antibody sequences mainly by conservative substitutions; for instance 10, such as 9, 8, 7, 6, 5, 4, 3, 2 or 1 of the substitutions in the variant are conservative amino acid residue replacements. Preferably, a variant contains at most 10 amino acid substitutions in the VH and/or VL region of the parent antibody, such as at most 9, 8, 7, 6, 5, 4, 3, 2 or at most 1 amino acid substitution. Preferably such substitutions are conservative substitutions especially so if the substitutions are in a CDR sequence.

In the context of the present invention, conservative substitutions may be defined by substitutions within the classes of amino acids reflected in the following table:

Amino Acid Residue Classes for Conservative Substitutions

| | |
|---|---|
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

In the context of the present invention, the following notations are, unless otherwise indicated, used to describe a mutation; i) substitution of an amino acid in a given position is written as e.g. K409R which means a substitution of a Lysine in position 409 with an Arginine; and ii) for specific variants the specific three or one letter codes are used, including the codes Xaa and X to indicate any amino acid residue. Thus, the substitution of Lysine with Arginine in position 409 is designated as: K409R, and the substitution of Lysine with any amino acid residue in position 409 is designated as K409X. In case of deletion of Lysine in position 409 it is indicated by K409*.

The term "recombinant host cell" (or simply "host cell"), as used herein, is intended to refer to a cell into which an expression vector has been introduced, e.g. an expression vector encoding an antibody of the invention. Recombinant host cells include, for example, transfectomas, such as CHO, CHO-S, HEK, HEK293, HEK-293F, Expi293F, PER.C6 or NS0 cells, and lymphocytic cells.

The term "treatment" refers to the administration of an effective amount of a therapeutically active bispecific antibody of the present invention with the purpose of easing, ameliorating, arresting or eradicating (curing) symptoms or disease states.

The term "effective amount" or "therapeutically effective amount" refers to an amount effective, at dosages and for periods of time necessary, to achieve a desired therapeutic result. A therapeutically effective amount of a bispecific antibody may vary according to factors such as the disease state, age, sex, and weight of the individual, and the ability of the bispecific antibody to elicit a desired response in the individual. A therapeutically effective amount is also one in which any toxic or detrimental effects of the antibody or antibody portion are outweighed by the therapeutically beneficial effects.

The term "anti-idiotypic antibody" refers to an antibody which recognizes unique determinants generally associated with the antigen-binding site of an antibody.

EMBODIMENTS OF THE INVENTION

In a first main embodiment the invention provides a bispecific antibody comprising a first and second antigen binding region binding to human CD37 having the sequence of SEQ ID NO: 62, and a first and second Fc region of a human immunoglobulin, wherein the first and second antigen binding regions bind different epitopes on CD37 and wherein the first and second Fc regions comprises one or more amino acid mutations which mutation(s) enhances the Fc-Fc interaction between the bispecific antibodies upon binding to membrane-bound targets compared to the Fc-Fc interaction between bispecific antibodies not having said mutation(s). Hereby a bispecific anti-CD37 antibody is provided which binds two different epitopes on CD37. Preferably the two epitopes are such that both binding arms can bind the same protein and thus such that each binding arm does not block binding of the other arm and/or does not compete for binding with the other binding arm of the bispecific molecule. Also, the bispecific antibody comprises a mutation that enhances the Fc-Fc interaction between two or more of the bispecific antibodies of the invention. This has the effect that the bispecific molecules form oligomers upon binding to CD37 expressed on the plasma membrane of the target cell. The Fc-Fc interaction is enhanced compared to a molecule that is identical except for the mutation. Preferably the mutation is in the Fc region of the bispecific molecule. In one embodiment it is a single amino acid substitution in the Fc region of the bispecific molecule. It is preferably a symmetric substitution meaning that both half molecules (parental antibodies) have the mutation. It is a further advantage of the present bispecific antibody that it has enhanced CDC and/or ADCC effector functions compared to an identical bispecific molecule not having the Fc-Fc interaction enhancing mutation. Surprisingly the bispecific molecule also has improved CDC and/or ADCC compared to a combination of the two parental monoclonal anti-CD37 antibodies which are mutated to have enhanced Fc-Fc interactions, and improved CDC and/or ADCC compared to either parental monoclonal anti-CD37 antibody which is mutated to have enhanced Fc-Fc interactions by itself. Thus, the bispecific antibody of the invention is more potent in inducing CDC and/or ADCC than a combination of an antibody having the first antigen binding region and a second antibody having the second antigen binding region and where both antibodies comprise the Fc-Fc interaction enhancing mutation, or compared to the single monoclonal anti-CD37 antibodies having the first or the second antigen binding regions and which comprise the Fc-Fc interaction enhancing mutation.

In an embodiment of the invention the first antigen binding region of the bispecific antibody is obtained from an antibody which competes for binding to human CD37 with a CD37 antibody comprising the CDR sequences:
  VH CDR1 sequence set forth in SEQ ID NO: 16,
  VH CDR2 sequence set forth in SEQ ID NO: 17,
  VH CDR3 sequence set forth in SEQ ID NO: 18,
  VL CDR1 sequence set forth in SEQ ID NO: 20,
  VL CDR2 sequence KAS, and
  VL CDR3 sequence set forth in SEQ ID NO: 21. [010]

Preferably competition for binding is determined according to example 7.

In another embodiment the first antigen binding region of the bispecific antibody binds to the same epitope on human CD37 as a CD37 antibody comprising the CDR sequences:
  VH CDR1 sequence set forth in SEQ ID NO: 16,
  VH CDR2 sequence set forth in SEQ ID NO: 17,
  VH CDR3 sequence set forth in SEQ ID NO: 18,
  VL CDR1 sequence set forth in SEQ ID NO: 20,
  VL CDR2 sequence KAS, and
  VL CDR3 sequence set forth in SEQ ID NO: 21. [010]

In a further embodiment of the invention the first antigen binding region of the bispecific antibody comprises the CDR sequences:
  VH CDR1 sequence set forth in SEQ ID NO: 16,
  VH CDR2 sequence set forth in SEQ ID NO: 17,
  VH CDR3 sequence set forth in SEQ ID NO: 18,
  VL CDR1 sequence set forth in SEQ ID NO: 20,
  VL CDR2 sequence KAS, and
  VL CDR3 sequence set forth in SEQ ID NO: 21. [010]

In a further embodiment of the invention the first antigen binding region of the bispecific antibody of the invention comprise the VH and VL sequences:
  (i) VH sequence set forth in SEQ ID NO: 15 and VL sequence set forth in SEQ ID NO: 19 or
  (ii) VH sequence having at least 90% identity, such as at least 95% identity, such as at least 98% identity, such as at least 99% identity and a VL sequence having at least 90% identity, such as at least 95% identity, such as at least 98% identity, such as at least 99% identity with the VH sequence and VL sequences of SEQ ID Nos 15 and 19.

In a further embodiment of the invention the first antigen binding region of the bispecific antibody is obtained from an antibody which competes for binding to human CD37 with a CD37 antibody comprising the CDR sequences:
  VH CDR1 sequence set forth in SEQ ID NO: 9,
  VH CDR2 sequence set forth in SEQ ID NO: 10,
  VH CDR3 sequence set forth in SEQ ID NO: 11,
  VL CDR1 sequence set forth in SEQ ID NO: 13,
  VL CDR2 sequence: AAS, and
  VL CDR3 sequence set forth in SEQ ID NO: 14. [005]

In a further embodiment of the invention the first antigen binding region of the bispecific antibody binds to the same epitope on human CD37 as a CD37 antibody comprising the CDR sequences:

VH CDR1 sequence set forth in SEQ ID NO: 9,
VH CDR2 sequence set forth in SEQ ID NO: 10,
VH CDR3 sequence set forth in SEQ ID NO: 11,
VL CDR1 sequence set forth in SEQ ID NO: 13,
VL CDR2 sequence: AAS, and
VL CDR3 sequence set forth in SEQ ID NO: 14. [005]

In one embodiment of the invention the first antigen binding region of the bispecific antibody has a functional epitope comprising one or more of the amino acids Y182, D189, T191, I192, D194, K195, V196, I197 and P199 of SEQ ID No: 62 (CD37).

In one embodiment of the invention said first antigen binding region binds to a functional epitope comprising one or more of the amino acids selected from the group consisting of: Y182, D189, T191, I192, D194, K195, V196, I197 and P199 of SEQ ID No: 62 (CD37).

In one embodiment of the invention the first antigen binding region of the bispecific antibody binds to a functional epitope on CD37, wherein binding to a mutant CD37 in which any one or more of the amino acid residues at positions corresponding to positions Y182, D189, T191, I192, D194, K195, V196, I197 and P199 of SEQ ID no 62 (CD37). has/have been substituted with alanines, is reduced as compared to wild type CD37 having the amino acid sequence set forth in SEQ ID NO: 62; reduced binding being determined as zscore (fold change) in binding of said antibody being lowed that −1.5, wherein zscore (fold change) in binding is calculated as set forth in Example 17.

In a further embodiment of the invention the first antigen binding region of the bispecific antibody comprises the CDR sequences:
VH CDR1 sequence set forth in SEQ ID NO: 9,
VH CDR2 sequence set forth in SEQ ID NO: 10,
VH CDR3 sequence set forth in SEQ ID NO: 11,
VL CDR1 sequence set forth in SEQ ID NO: 13,
VL CDR2 sequence: AAS, and
VL CDR3 sequence set forth in SEQ ID NO: 14. [005]

In a further embodiment of the invention the first antigen binding region of the bispecific antibody comprise the VH and VL sequences:
(i) VH sequence set forth in SEQ ID NO: 8 and VL sequence set forth in SEQ ID NO: 12 or
(ii) VH sequence having at least 90% identity, such as at least 95% identity, such as at least 98% identity, such as at least 99% identity and a VL sequence having at least 90% identity, such as at least 95% identity, such as at least 98% identity, such as at least 99% identity with the VH sequence and VL sequences of SEQ ID Nos 8 and 12.

In a further embodiment of the invention the second antigen binding region of the bispecific antibody is obtained from an antibody which competes for binding to human CD37 with a CD37 antibody comprising the CDR sequences selected from the group comprising:
(i) VH CDR1 sequence set forth in SEQ ID NO: 23,
VH CDR2 sequence set forth in SEQ ID NO: 24,
VH CDR3 sequence set forth in SEQ ID NO: 25,
VL CDR1 sequence set forth in SEQ ID NO: 27,
VL CDR2 sequence: YAS, and
VL CDR3 sequence set forth in SEQ ID NO: 28; [016]
(ii) VH CDR1 sequence set forth in SEQ ID NO: 2,
VH CDR2 sequence set forth in SEQ ID NO: 3,
VH CDR3 sequence set forth in SEQ ID NO: 4,
VL CDR1 sequence set forth in SEQ ID NO: 6,
VL CDR2 sequence: EAS, and
VL CDR3 sequence set forth in SEQ ID NO: 7; [004]
(iii) VH CDR1 sequence set forth in SEQ ID NO: 40,
VH CDR2 sequence set forth in SEQ ID NO: 41,
VH CDR3 sequence set forth in SEQ ID NO: 42,
VL CDR1 sequence set forth in SEQ ID NO: 44,
VL CDR2 sequence: FAK, and
VL CDR3 sequence set forth in SEQ ID NO: 45; [G28.1] and
(iv) VH CDR1 sequence set forth in SEQ ID NO: 47,
VH CDR2 sequence set forth in SEQ ID NO: 48,
VH CDR3 sequence set forth in SEQ ID NO: 49,
VL CDR1 sequence set forth in SEQ ID NO: 51,
VL CDR2 sequence: VAT and
VL CDR3 sequence set forth in SEQ ID NO: 52. [37.3]

In a further embodiment of the invention the second antigen binding region of the bispecific antibody is obtained from an antibody which competes for binding to human CD37 with a CD37 antibody comprising the CDR sequences selected from the group consisting of:
(i) VH CDR1 sequence set forth in SEQ ID NO: 23,
VH CDR2 sequence set forth in SEQ ID NO: 24,
VH CDR3 sequence set forth in SEQ ID NO: 25,
VL CDR1 sequence set forth in SEQ ID NO: 27,
VL CDR2 sequence: YAS, and
VL CDR3 sequence set forth in SEQ ID NO: 28; [016]
(ii) VH CDR1 sequence set forth in SEQ ID NO: 2,
VH CDR2 sequence set forth in SEQ ID NO: 3,
VH CDR3 sequence set forth in SEQ ID NO: 4,
VL CDR1 sequence set forth in SEQ ID NO: 6,
VL CDR2 sequence: EAS, and
VL CDR3 sequence set forth in SEQ ID NO: 7; [004]
(iii) VH CDR1 sequence set forth in SEQ ID NO: 40,
VH CDR2 sequence set forth in SEQ ID NO: 41,
VH CDR3 sequence set forth in SEQ ID NO: 42,
VL CDR1 sequence set forth in SEQ ID NO: 44,
VL CDR2 sequence: FAK, and
VL CDR3 sequence set forth in SEQ ID NO: 45; [G28.1] and
(iv) VH CDR1 sequence set forth in SEQ ID NO: 47,
VH CDR2 sequence set forth in SEQ ID NO: 48,
VH CDR3 sequence set forth in SEQ ID NO: 49,
VL CDR1 sequence set forth in SEQ ID NO: 51,
VL CDR2 sequence: VAT and
VL CDR3 sequence set forth in SEQ ID NO: 52. [37.3]

Hereby bispecific antibodies are provided wherein the first and second antigen binding regions bind different epitopes on human CD37. The inventors of the present invention have found that the antibodies having the CDR sequences of antibody 005 (SEQ ID NOs 9, 10, 11 and 13, 13a, 14) and antibody 010 (SEQ ID NOs 16, 17, 18 and 20, 20a, 21) compete for binding to human CD37 and do not compete for binding to CD37 with any of the antibodies having the CDR sequences of antibodies 016 (SEQ ID NOs 23, 24, 25 and 27, 27a, 28), 004 (SEQ ID NOs 2, 3, 4 and 6, 6a, 7), G28.1 (SEQ ID NOs 40, 41, 42 and 44, 44a, 45) and 37.3 (SEQ ID NOs 47, 48, 49 and 51, 51a, 52). The 016, 004, G28.1 and 37.3 antibodies have however been found to compete with each other for binding to human CD37. Thus, a bispecific antibody comprising a first binding arm which is obtained from an antibody which competes for binding with either of or both of the 005 or 010 antibodies and a second binding arm which is obtained from an antibody which competes for binding with any of 016, 004, G28.1 and 37.3 or with all of these is a bispecific antibody which has specificity for two different epitopes on CD37. The inventors have surprisingly found that such bispecific antibodies have favorable CDC potency on CD37 expressing cells compared to treating such cells with a combination of the two monoclonal antibodies which do not compete for binding to CD37. Additionally, the inventors have surprisingly found that such bispecific antibodies have favorable ADCC potency on CD37 expressing cells compared to treating such cells with a combination of the two monoclonal antibodies which do not compete for binding to CD37.

In one embodiment of the invention the bispecific antibody comprises a first antigen binding region which is obtained from an antibody which competes for binding to human CD37 with an antibody having the CDR sequences of antibody 010 and a second binding region which is obtained from an antibody which competes for binding to human CD37 with the antibody having the CDR sequences of 016.

In another embodiment of the invention the bispecific antibody comprises a first antigen binding region which is obtained from an antibody which competes for binding to human CD37 with an antibody having the CDR sequences of antibody 010 and a second binding region which is obtained from an antibody which competes for binding to human CD37 with the antibody having the CDR sequences of 004.

In another embodiment of the invention the bispecific antibody comprises a first antigen binding region which is obtained from an antibody which competes for binding to human CD37 with an antibody having the CDR sequences of antibody 010 and a second binding region which is obtained from an antibody which competes for binding to human CD37 with the antibody having the CDR sequences of G28.1.

In another embodiment of the invention the bispecific antibody comprises a first antigen binding region which is obtained from an antibody which competes for binding to human CD37 with an antibody having the CDR sequences of antibody 010 and a second binding region which is obtained from an antibody which competes for binding to human CD37 with the antibody having the CDR sequences of 37.3.

In one embodiment of the invention the bispecific antibody comprises a first antigen binding region which is obtained from an antibody which competes for binding to human CD37 with an antibody having the CDR sequences of antibody 005 and a second binding region which is obtained from an antibody which competes for binding to human CD37 with the antibody having the CDR sequences of 016.

In another embodiment of the invention the bispecific antibody comprises a first antigen binding region which is obtained from an antibody which competes for binding to human CD37 with an antibody having the CDR sequences of antibody 005 and a second binding region which is obtained from an antibody which competes for binding to human CD37 with the antibody having the CDR sequences of 004.

In another embodiment of the invention the bispecific antibody comprises a first antigen binding region which is obtained from an antibody which competes for binding to human CD37 with an antibody having the CDR sequences of antibody 005 and a second binding region which is obtained from an antibody which competes for binding to human CD37 with the antibody having the CDR sequences of G28.1.

In another embodiment of the invention the bispecific antibody comprises a first antigen binding region which is obtained from an antibody which competes for binding to human CD37 with an antibody having the CDR sequences of antibody 005 and a second binding region which is obtained from an antibody which competes for binding to human CD37 with the antibody having the CDR sequences of 37.3.

Such bispecific antibodies described here may in further embodiments comprise an Fc-Fc interaction enhancing substitution in both Fc regions (i.e. the Fc regions obtained from the first and second parental antibody) of the bispecific antibody where the substitution corresponds to E430G in IgG1 when using EU numbering and which substitution enhances the Fc-Fc interaction of two or more bispecific antibodies of the invention upon binding to membrane-bound target. In another embodiment the Fc-Fc interaction enhancing substitution corresponds to E345K in IgG1 when using EU numbering.

In another embodiment of the invention the bispecific antibody comprises a second antigen binding region which binds to the same epitope on human CD37 as a CD37 antibody comprising the CDR sequences selected from the group comprising:
  (i) VH CDR1 sequence set forth in SEQ ID NO: 23,
      VH CDR2 sequence set forth in SEQ ID NO: 24,
      VH CDR3 sequence set forth in SEQ ID NO: 25,
      VL CDR1 sequence set forth in SEQ ID NO: 27,
      VL CDR2 sequence: YAS, and
      VL CDR3 sequence set forth in SEQ ID NO: 28; [016]
  (ii) VH CDR1 sequence set forth in SEQ ID NO: 2,
      VH CDR2 sequence set forth in SEQ ID NO: 3,
      VH CDR3 sequence set forth in SEQ ID NO: 4,
      VL CDR1 sequence set forth in SEQ ID NO: 6,
      VL CDR2 sequence: EAS, and
      VL CDR3 sequence set forth in SEQ ID NO: 7; [004]
  (iii) VH CDR1 sequence set forth in SEQ ID NO: 40,
      VH CDR2 sequence set forth in SEQ ID NO: 41,
      VH CDR3 sequence set forth in SEQ ID NO: 42,
      VL CDR1 sequence set forth in SEQ ID NO: 44,
      VL CDR2 sequence: FAK, and
      VL CDR3 sequence set forth in SEQ ID NO: 45; [G28.1] and
  (iv) VH CDR1 sequence set forth in SEQ ID NO: 47,
      VH CDR2 sequence set forth in SEQ ID NO: 48,
      VH CDR3 sequence set forth in SEQ ID NO: 49,
      VL CDR1 sequence set forth in SEQ ID NO: 51,
      VL CDR2 sequence: VAT and
      VL CDR3 sequence set forth in SEQ ID NO: 52. [37.3]

In another embodiment of the invention the bispecific antibody comprises a second antigen binding region which binds to the same epitope on human CD37 as a CD37 antibody comprising the CDR sequences selected from the group consisting of:
  a. VH CDR1 sequence set forth in SEQ ID NO: 23,
      VH CDR2 sequence set forth in SEQ ID NO: 24,
      VH CDR3 sequence set forth in SEQ ID NO: 25,
      VL CDR1 sequence set forth in SEQ ID NO: 27,
      VL CDR2 sequence: YAS, and
      VL CDR3 sequence set forth in SEQ ID NO: 28; [016]
  b. VH CDR1 sequence set forth in SEQ ID NO: 2,
      VH CDR2 sequence set forth in SEQ ID NO: 3,
      VH CDR3 sequence set forth in SEQ ID NO: 4,
      VL CDR1 sequence set forth in SEQ ID NO: 6,
      VL CDR2 sequence: EAS, and
      VL CDR3 sequence set forth in SEQ ID NO: 7; [004]
  c. VH CDR1 sequence set forth in SEQ ID NO: 40,
      VH CDR2 sequence set forth in SEQ ID NO: 41,
      VH CDR3 sequence set forth in SEQ ID NO: 42,
      VL CDR1 sequence set forth in SEQ ID NO: 44,
      VL CDR2 sequence: FAK, and VL CDR3 sequence set forth in SEQ ID NO: 45; [G28.1] and
d. VH CDR1 sequence set forth in SEQ ID NO: 47,
VH CDR2 sequence set forth in SEQ ID NO: 48,
VH CDR3 sequence set forth in SEQ ID NO: 49,
VL CDR1 sequence set forth in SEQ ID NO: 51,
VL CDR2 sequence: VAT and
VL CDR3 sequence set forth in SEQ ID NO: 52. [37.3]

In one embodiment of the invention the second antigen binding region of the bispecific antibody has a functional epitope comprising one or more of the amino acids E124, F162, Q163, V164, L165 and H175 of SEQ ID No:62 (CD37).

In one embodiment of the invention said second antigen binding region binds to a functional epitope comprising one or more of the amino acids selected from the group consisting of: E124, F162, Q163, V164, L165 and H175 of SEQ ID No:62 (CD37)

In one embodiment of the invention the second antigen binding region of the bispecific antibody binds to a functional epitope on CD37, wherein binding to a mutant CD37 in which any one or more of the amino acid residues at positions corresponding to positions E124, F162, Q163, V164, L165 and H175 of SEQ ID No:62 (CD37). has/have been substituted with alanines, is reduced as compared to wild type CD37 having the amino acid sequence set forth in SEQ ID NO: 62; reduced binding being determined as zscore (fold change) in binding of said antibody being lowed that −1.5, wherein zscore (fold change) in binding is calculated as set forth in Example 17.

Accordingly, in one embodiment the invention provides a bispecific antibody comprising a first and a second antigen binding region wherein the first antigen binding region of the bispecific antibody binds to the same epitope on human CD37 as an anti-CD37 antibody comprising the CDR sequences of antibody 010 and wherein the second antigen binding region of the bispecific antibody binds to the same epitope on human CD37 as an anti-CD37 antibody comprising the CDR sequences of antibody 016.

In another embodiment the invention provides a bispecific antibody comprising a first and a second antigen binding region wherein the first antigen binding region of the bispecific antibody binds to the same epitope on human CD37 as an anti-CD37 antibody comprising the CDR sequences of antibody 010 and wherein the second antigen binding region of the bispecific antibody binds to the same epitope on human CD37 as an anti-CD37 antibody comprising the CDR sequences of antibody 004.

In another embodiment the invention provides a bispecific antibody comprising a first and a second antigen binding region wherein the first antigen binding region of the bispecific antibody binds to the same epitope on human CD37 as an anti-CD37 antibody comprising the CDR sequences of antibody 010 and wherein the second antigen binding region of the bispecific antibody binds to the same epitope on human CD37 as an anti-CD37 antibody comprising the CDR sequences of antibody G28.1.

In another embodiment the invention provides a bispecific antibody comprising a first and a second antigen binding region wherein the first antigen binding region of the bispecific antibody binds to the same epitope on human CD37 as an anti-CD37 antibody comprising the CDR sequences of antibody 010 and wherein the second antigen binding region of the bispecific antibody binds to the same epitope on human CD37 as an anti-CD37 antibody comprising the CDR sequences of antibody 37.3.

In another embodiment the invention provides a bispecific antibody comprising a first and a second antigen binding region wherein the first antigen binding region of the bispecific antibody binds to the same epitope on human CD37 as an anti-CD37 antibody comprising the CDR sequences of antibody 005 and wherein the second antigen binding region of the bispecific antibody binds to the same epitope on human CD37 as an anti-CD37 antibody comprising the CDR sequences of antibody 016.

In yet another embodiment the invention provides a bispecific antibody comprising a first and a second antigen binding region wherein the first antigen binding region of the bispecific antibody binds to the same epitope on human CD37 as an anti-CD37 antibody comprising the CDR sequences of antibody 005 and wherein the second antigen binding region of the bispecific antibody binds to the same epitope on human CD37 as an anti-CD37 antibody comprising the CDR sequences of antibody 004.

In another embodiment the invention provides a bispecific antibody comprising a first and a second antigen binding region wherein the first antigen binding region of the bispecific antibody binds to the same epitope on human CD37 as an anti-CD37 antibody comprising the CDR sequences of antibody 005 and wherein the second antigen binding region of the bispecific antibody binds to the same epitope on human CD37 as an anti-CD37 antibody comprising the CDR sequences of antibody G28.1.

In another embodiment the invention provides a bispecific antibody comprising a first and a second antigen binding region wherein the first antigen binding region of the bispecific antibody binds to the same epitope on human CD37 as an anti-CD37 antibody comprising the CDR sequences of antibody 005 and wherein the second antigen binding region of the bispecific antibody binds to the same epitope on human CD37 as an anti-CD37 antibody comprising the CDR sequences of antibody 37.3.

In a further embodiment of the invention the second antigen binding region of the bispecific antibody comprises the CDR sequences selected from the group comprising:
(i) VH CDR1 sequence set forth in SEQ ID NO: 23,
VH CDR2 sequence set forth in SEQ ID NO: 24,
VH CDR3 sequence set forth in SEQ ID NO: 25,
VL CDR1 sequence set forth in SEQ ID NO: 27,
VL CDR2 sequence: YAS, and
VL CDR3 sequence set forth in SEQ ID NO: 28; [016]
(ii) VH CDR1 sequence set forth in SEQ ID NO: 2,
VH CDR2 sequence set forth in SEQ ID NO: 3,
VH CDR3 sequence set forth in SEQ ID NO: 4,
VL CDR1 sequence set forth in SEQ ID NO: 6,
VL CDR2 sequence: EAS, and
VL CDR3 sequence set forth in SEQ ID NO: 7; [004]
(iii) VH CDR1 sequence set forth in SEQ ID NO: 40,
VH CDR2 sequence set forth in SEQ ID NO: 41,
VH CDR3 sequence set forth in SEQ ID NO: 42,
VL CDR1 sequence set forth in SEQ ID NO: 44,
VL CDR2 sequence: FAK, and
VL CDR3 sequence set forth in SEQ ID NO: 45; [G28.1] and
(iv) VH CDR1 sequence set forth in SEQ ID NO: 47,
VH CDR2 sequence set forth in SEQ ID NO: 48,
VH CDR3 sequence set forth in SEQ ID NO: 49,
VL CDR1 sequence set forth in SEQ ID NO: 51,
VL CDR2 sequence: VAT and
VL CDR3 sequence set forth in SEQ ID NO: 52. [37.3]

In a further embodiment of the invention the second antigen binding region of the bispecific antibody comprises the CDR sequences selected from the group consisting of:

(i) VH CDR1 sequence set forth in SEQ ID NO: 23,
VH CDR2 sequence set forth in SEQ ID NO: 24,
VH CDR3 sequence set forth in SEQ ID NO: 25,
VL CDR1 sequence set forth in SEQ ID NO: 27,
VL CDR2 sequence: YAS, and
VL CDR3 sequence set forth in SEQ ID NO: 28; [016]
(ii) VH CDR1 sequence set forth in SEQ ID NO: 2,
VH CDR2 sequence set forth in SEQ ID NO: 3,
VH CDR3 sequence set forth in SEQ ID NO: 4,
VL CDR1 sequence set forth in SEQ ID NO: 6,
VL CDR2 sequence: EAS, and
VL CDR3 sequence set forth in SEQ ID NO: 7; [004]
(iii) VH CDR1 sequence set forth in SEQ ID NO: 40,
VH CDR2 sequence set forth in SEQ ID NO: 41,
VH CDR3 sequence set forth in SEQ ID NO: 42,
VL CDR1 sequence set forth in SEQ ID NO: 44,
VL CDR2 sequence: FAK, and
VL CDR3 sequence set forth in SEQ ID NO: 45; [G28.1] and
(iv) VH CDR1 sequence set forth in SEQ ID NO: 47,
VH CDR2 sequence set forth in SEQ ID NO: 48,
VH CDR3 sequence set forth in SEQ ID NO: 49,
VL CDR1 sequence set forth in SEQ ID NO: 51,
VL CDR2 sequence: VAT and
VL CDR3 sequence set forth in SEQ ID NO: 52. [37.3]

Accordingly, the present invention also provides in another embodiment a bispecific antibody comprising a first and a second antigen binding region wherein the first antigen binding region of the bispecific antibody comprises the CDR sequences of antibody 010 (i.e. SEQ ID NOs 16-18 and 20-21) and wherein the second antigen binding region of the bispecific antibody comprises the CDR sequences of antibody 016 (i.e. SEQ ID NOs 23-25 and 27-28). As also described above, such bispecific antibody of the invention further comprises an Fc-Fc interaction enhancing mutation in the Fc region of the antibody. In one embodiment this mutation corresponds to a mutation in position E430 or E345 in IgG1 when using the EU numbering system. In one embodiment the mutation is an E430G substitution. In another embodiment it is an E345K substitution.

The present invention also provides in another embodiment a bispecific antibody comprising a first and a second antigen binding region wherein the first antigen binding region of the bispecific antibody comprises the CDR sequences of antibody 010 (i.e. SEQ ID NOs 16-18 and 20-21) and wherein the second antigen binding region of the bispecific antibody comprises the CDR sequences of antibody 004 (i.e. SEQ ID NOs 2-4 and 6-7).

The present invention also provides in another embodiment a bispecific antibody comprising a first and a second antigen binding region wherein the first antigen binding region of the bispecific antibody comprises the CDR sequences of antibody 010 (i.e. SEQ ID NOs 16-18 and 20-21) and wherein the second antigen binding region of the bispecific antibody comprises the CDR sequences of antibody G28.1 (i.e. SEQ ID NOs 40-42 and 44-45).

The present invention also provides in another embodiment a bispecific antibody comprising a first and a second antigen binding region wherein the first antigen binding region of the bispecific antibody comprises the CDR sequences of antibody 010 (i.e. SEQ ID NOs 16-18 and 20-21) and wherein the second antigen binding region of the bispecific antibody comprises the CDR sequences of antibody 37.3 (i.e. SEQ ID NOs 47-49 and 51-52).

In a further embodiment of the invention the second antigen binding region of the bispecific antibody comprise the VH and VL sequences selected from the group comprising:
(i) VH sequence set forth in SEQ ID NO: 22 and VL sequence set forth in SEQ ID NO: 26 [016] or
(ii) VH sequence set forth in SEQ ID NO: 1 and VL sequence set forth in SEQ ID NO: 5 or
(iii) VH sequence set forth in SEQ ID NO: 39 and VL sequence set forth in SEQ ID NO: 43 [G28.1] or
(iv) VH sequence set forth in SEQ ID NO: 46 and VL sequence set forth in SEQ ID NO: 50 [37.3] or
a VH sequence having at least 90% identity, such as at least 95% identity, such as at least 98% identity, such as at least 99% identity and a VL sequence having at least 90% identity, such as at least 95% identity, such as at least 98% identity, such as at least 99% identity with the VH sequence and VL sequence, respectively, as set forth in any one of (i) to (iv).

In a further embodiment of the invention the second antigen binding region of the bispecific antibody comprise the VH and VL sequences selected from the group consisting of:
(i) VH sequence set forth in SEQ ID NO: 22 and VL sequence set forth in SEQ ID NO: 26 [016],
(ii) VH sequence set forth in SEQ ID NO: 1 and VL sequence set forth in SEQ ID NO: 5 [004],
(iii) VH sequence set forth in SEQ ID NO: 39 and VL sequence set forth in SEQ ID NO: 43 [G28.1],
(iv) VH sequence set forth in SEQ ID NO: 46 and VL sequence set forth in SEQ ID NO: 50 [37.3] and
a VH sequence having at least 90% identity, such as at least 95% identity, such as at least 98% identity, such as at least 99% identity and a VL sequence having at least 90% identity, such as at least 95% identity, such as at least 98% identity, such as at least 99% identity with the VH sequence and VL sequence, respectively, as set forth in any one of (i) to (iv).

Thus, in another embodiment the present invention also provides a bispecific antibody comprising a first and a second antigen binding region wherein the first antigen binding region of the bispecific antibody comprises the VH and VL sequences of antibody 010 (i.e. SEQ ID NOs 15 and 19) and wherein the second antigen binding region of the bispecific antibody comprises the VH and VL sequences of antibody 016 (i.e. SEQ ID NOs 22 and 26).

In another embodiment the present invention also provides a bispecific antibody comprising a first and a second antigen binding region wherein the first antigen binding region of the bispecific antibody comprises the VH and VL sequences of antibody 010 (i.e. SEQ ID Nos 15 and 19) and wherein the second antigen binding region of the bispecific antibody comprises the VH and VL sequences of antibody 004 (i.e. SEQ ID NOs 1 and 5).

In another embodiment the present invention also provides a bispecific antibody comprising a first and a second antigen binding region wherein the first antigen binding region of the bispecific antibody comprises the VH and VL sequences of antibody 010 (i.e. SEQ ID NOs 15 and 19) and wherein the second antigen binding region of the bispecific antibody comprises the VH and VL sequences of antibody G28.1 (i.e. SEQ ID NOs 39 and 43).

In another embodiment the present invention also provides a bispecific antibody comprising a first and a second antigen binding region wherein the first antigen binding region of the bispecific antibody comprises the VH and VL sequences of antibody 010 (i.e. SEQ ID Nos 15 and 19) and wherein the second antigen binding region of the bispecific antibody comprises the VH and VL sequences of antibody 37.3 (i.e. SEQ ID Nos 46 and 50).

In yet another embodiment the present invention provides a bispecific antibody comprising a first and a second antigen binding region wherein the first antigen binding region of the bispecific antibody comprises the VH and VL sequences of antibody 005 (i.e. SEQ ID NOs 8 and 12) and wherein the second antigen binding region of the bispecific antibody comprises the VH and VL sequences of antibody 016 (i.e. SEQ ID NOs 22 and 26).

In another embodiment the present invention also provides a bispecific antibody comprising a first and a second antigen binding region wherein the first antigen binding region of the bispecific antibody comprises the VH and VL sequences of antibody 005 (i.e. SEQ ID NOs 8 and 12) and wherein the second antigen binding region of the bispecific antibody comprises the VH and VL sequences of antibody 004 (i.e. SEQ ID NOs 1 and 5).

In another embodiment the present invention also provides a bispecific antibody comprising a first and a second antigen binding region wherein the first antigen binding region of the bispecific antibody comprises the VH and VL sequences of antibody 005 (i.e. SEQ ID NOs 8 and 12) and wherein the second antigen binding region of the bispecific antibody comprises the VH and VL sequences of antibody G28.1 (i.e. SEQ ID NOs 39 and 43).

In another embodiment the present invention also provides a bispecific antibody comprising a first and a second antigen binding region wherein the first antigen binding region of the bispecific antibody comprises the VH and VL sequences of antibody 005 (i.e. SEQ ID NOs 8 and 12) and wherein the second antigen binding region of the bispecific antibody comprises the VH and VL sequences of antibody 37.3 (i.e. SEQ ID NOs 46 and 50).

In yet other embodiments of the present invention the VH and VL sequences disclosed above may vary within 90% sequence identity.

In yet a different embodiment the present invention provides a CD37 binding molecule comprising one antigen binding region described herein, wherein the CDR sequences are the CDR sequences of one of the antibodies 004, 005, 010, 016, 28.1 or 37.3. in one embodiment such molecule only has one antigen binding region. Hereby the binding molecule has monovalent binding for CD37. Preferably such molecule comprises an intact Fc region of an immunoglobulin. In one embodiment the CD37-binding molecule comprise a second antigen binding region for an irrelevant target which e.g. may be b12.

Fc-Fc Enhancing Mutations

In one embodiment of the invention the one or more Fc-Fc interaction enhancing mutations in said first and second Fc regions of the bispecific antibody are amino acid substitutions. The Fc region of the bispecific antibody can be said to comprise two different Fc regions, one from each parental anti-CD37 antibody. Alternatively, the bispecific antibody may comprise one or more Fc-Fc interaction enhancing mutations in each half-molecule. It is to be understood that the Fc-Fc interaction enhancing mutations are symmetrical, i.e., identical mutations are made in the two Fc regions.

In one embodiment the invention provides a bispecific antibody wherein the one or more Fc-Fc interaction enhancing mutations in said first and second Fc regions are amino acid substitutions at one or more positions corresponding to amino acid positions 430, 440 and 345 in human IgG1 when using the EU numbering system. In one embodiment the invention provides a bispecific antibody wherein the one or more Fc-Fc interaction enhancing mutations in said first and second Fc regions are amino acid substitutions at one or more positions corresponding to amino acid positions 430, 440 and 345 in human IgG1 when using the EU numbering system, with the proviso that the substitution in 440 is 440Y or 440W In another embodiment the invention provides a bispecific antibody comprising at least one substitution in said first and second Fc regions selected from the group comprising: E430G, E345K, E430S, E430F, E430T, E345Q, E345R, E345Y, S440Y and S440W. In a particular preferred embodiment the bispecific antibody comprises at least one substitution in said first and second Fc regions selected from E430G or E345K, preferably E430G. Hereby bispecific antibodies are provided which will have enhanced Fc-Fc interaction between different antibodies having said mutation. It is believed that this mutation cause the antibodies to form oligomers on the target cell and thereby enhancing CDC.

In another embodiment the bispecific antibody contains one further mutation in said Fc regions which mutation is selected from K439E, S440K and S440R. A bispecific antibody having an additional mutation of K439E and a second different antibody or bispecific antibody having an additional S440K or S440R mutation will form oligomers in alternating patterns of the first and the second antibodies. This is thought to be because the additional mutations will cause a preference for interaction between the first and second antibodies rather than interaction between first and first or second and second antibodies due to non-covalent binding between said Fc regions.

It is preferred that the Fc-Fc interaction enhancing mutations in said first and second Fc regions are identical substitutions in said first and second Fc regions. Accordingly, in one preferred embodiment the bispecific antibodies have the same Fc-Fc interaction enhancing mutation in both Fc regions. The Fc region can also be described as Fc chains so that an antibody has two Fc chains which make up a common Fc region of the antibody. Accordingly, in a preferred embodiment the two Fc chains each comprise a substitution of a position selected from the group of positions corresponding to amino acid positions 430, 440 and 345 in human IgG1 when using the EU numbering system. In one embodiment the two Fc chains each comprise an E430G substitution so that a bispecific antibody of the invention comprises two E430G substitutions. In another embodiment the two Fc chains each comprise an E345K substitution so that the bispecific antibody of the invention comprises two E345K substitutions.

In an embodiment of the invention the bispecific antibody is an IgG1 isotype.

In an embodiment of the invention the bispecific antibody is an IgG2 isotype.

In an embodiment of the invention the bispecific antibody is an IgG3 isotype.

In an embodiment of the invention the bispecific antibody is an IgG4 isotype.

In an embodiment of the invention the bispecific antibody is an IgG isotype.

In an embodiment of the invention the bispecific antibody is a combination of the isotypes IgG1, IgG2, IgG3 and IgG4. For example the first half antibody obtained from the first parental antibody may be an IgG1 isotype and the second half antibody obtained from the second parental antibody may be an IgG4 isotype so that the bispecific antibody is a combination of IgG1 and IgG4. In another embodiment it is a combination of IgG1 and IgG2. In another embodiment it is a combination of IgG1 and IgG3. In another embodiment it is a combination of IgG2 and IgG3. In another embodiment it is a combination of IgG2 and IgG4. In another embodiment it is a combination of IgG3 and IgG4. Typically the core hinge will be an IgG1 type core hinge having the sequence CPPC but it could be other hinges which are stable and do not allow Fab arm exchange in vivo which is the case for the IgG4 core hinge having the sequence CPSC.

In a preferred embodiment the bispecific antibody of the invention is a full length antibody.

In yet another embodiment of the invention the bispecific antibody is a human antibody. In yet another embodiment of the invention the bispecific antibody is a humanized antibody. In yet another embodiment of the invention the bispecific antibody is a chimeric antibody. In an embodiment of the invention the bispecific antibody is a combination of human, humanized and chimeric. For example the first half antibody obtained from the first parental antibody may be a human antibody and the second half antibody obtained from the second parental antibody may be a humanized antibody so that the bispecific antibody is a combination of human and humanized. In a preferred embodiment of the invention the bispecific antibody binds both human and cynomolgus monkey CD37, having the sequences set forth in SEQ ID Nos 62 and 63, respectively. This is an advantage as this will allow preclinical toxicology studies to be performed in the cynomolgus monkey with the same bispecific molecule that will later be tested in humans. In cases where the antibodies against a human target do not also bind the target in an animal model it is very difficult to perform the preclinical toxicology studies and the non-clinical safety profile of the molecules, which is a requirement by regulatory authorities.

Bispecific Antibody Formats

The present invention provides bispecific CD37×CD37 antibodies which efficiently promote CDC- and/or ADCC-mediated killing of CD37-expressing tumor cells such as e.g. B-cell derived tumors. Depending on the desired functional properties for a particular use, particular antigen-binding regions can be selected from the set of antibodies or antigen-binding regions provided by the present invention. Many different formats and uses of bispecific antibodies are known in the art, and were reviewed by Kontermann; Drug Discov Today, 2015 July; 20(7):838-47 and; MAbs, 2012 March-April; 4(2):182-97.

A bispecific antibody according to the present invention is not limited to any particular bispecific format or method of producing it, however, a bispecific antibody of the invention should have an intact Fc domain in order to induce enhanced Fc-Fc interactions.

Examples of bispecific antibody molecules which may be used in the present invention comprise (i) a single antibody that has two arms comprising different antigen-binding regions; (ii) a dual-variable-domain antibody (DVD-Ig) where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (iii) a so-called "dock and lock" molecule, based on the "dimerization and docking domain" in Protein Kinase A.

In one embodiment, the bispecific antibody of the present invention is a cross-body or a bispecific antibody obtained via a controlled Fab-arm exchange (such as described in WO2011131746 (Genmab)).

Examples of different classes of bispecific antibodies include but are not limited to (i) IgG-like molecules with complementary CH3 domains to force heterodimerization; (ii) recombinant IgG-like dual targeting molecules, wherein the two sides of the molecule each contain the Fab fragment or part of the Fab fragment of at least two different antibodies; (iii) IgG fusion molecules, wherein full length IgG antibodies are fused to extra Fab fragment or parts of Fab fragment; (iv) Fc fusion molecules, wherein single chain Fv molecules or stabilized diabodies are fused to heavy-chain constant-domains, Fc-regions or parts thereof; (v) Fab fusion molecules, wherein different Fab-fragments are fused together, fused to heavy-chain constant-domains, Fc-regions or parts thereof; and (vi) scFv- and diabody-based and heavy chain antibodies (e.g., domain antibodies, nanobodies) wherein different single chain Fv molecules or different diabodies or different heavy-chain antibodies (e.g. domain antibodies, nanobodies) are fused to an Fc-.

Examples of IgG-like molecules with complementary CH3 domain molecules include but are not limited to the Triomab/Quadroma molecules (Trion Pharma/Fresenius Biotech; Roche, WO2011069104), the so-called Knobs-into-Holes molecules (Genentech, WO9850431), CrossMAbs (Roche, WO2011117329) and the electrostatically-steered molecules (Amgen, EP1870459 and WO2009089004; Chugai, US201000155133; Oncomed, WO2010129304), the LUZ-Y molecules (Genentech, Wranik et al. J. Biol. Chem. 2012, 287(52): 43331-9, doi: 10.1074/jbc.M112.397869. Epub 2012 Nov. 1), DIG-body and PIG-body molecules (Pharmabcine, WO2010134666, WO2014081202), the Strand Exchange Engineered Domain body (SEEDbody) molecules (EMD Serono, WO2007110205), the Biclonics molecules (Merus, WO2013157953), FcAAdp molecules (Regeneron, WO201015792), hinge engineered bispecific IgG1 and IgG2 molecules (Pfizer/Rinat, WO11143545), Azymetric scaffold molecules (Zymeworks/Merck, WO2012058768), mAb-Fv molecules (Xencor, WO2011028952), bivalent bispecific antibodies (WO2009080254) and the DuoBody® molecules (Genmab A/S, WO2011131746).

Examples of recombinant IgG-like dual targeting molecules include but are not limited to Dual Targeting (DT)-Ig molecules (WO2009058383), Two-in-one Antibody (Genentech; Bostrom, et al 2009. Science 323, 1610-1614.), Cross-linked Mabs (Karmanos Cancer Center), mAb2 (F-Star, WO2008003116), Zybody molecules (Zyngenia; LaFleur et al. MAbs. 2013 March-April; 5(2):208-18), approaches with common light chain (Crucell/Merus, U.S. Pat. No. 7,262,028), KABodies (NovImmune, WO2012023053) and CovX-body (CovX/Pfizer; Doppalapudi, V. R., et al 2007. Bioorg. Med. Chem. Lett. 17,501-506.).

Examples of IgG fusion molecules include but are not limited to Dual Variable Domain (DVD)-Ig molecules (Abbott, U.S. Pat. No. 7,612,181), Dual domain double head antibodies (Unilever; Sanofi Aventis, WO20100226923), IgG-like Bispecific molecules (ImClone/Eli Lilly, Lewis et al. Nat Biotechnol. 2014 February; 32(2):191-8), Ts2Ab (MedImmune/AZ; Dimasi et al. J Mol Biol. 2009 Oct. 30; 393(3):672-92) and BsAb molecules (Zymogenetics, WO2010111625), HERCULES molecules (Biogen Idec, US007951918), scFv fusion molecules (Novartis), scFv fusion molecules (Changzhou Adam Biotech Inc, CN 102250246) and TvAb molecules (Roche, WO2012025525, WO2012025530).

Examples of Fc fusion molecules include but are not limited to ScFv/Fc Fusions (Pearce et al., Biochem Mol Biol Int. 1997 September; 42(6):1179-88), SCORPION molecules (Emergent BioSolutions/Trubion, Blankenship μW, et al. AACR 100 th Annual meeting 2009 (Abstract #5465);

Zymogenetics/BMS, WO2010111625), Dual Affinity Retargeting Technology (Fc-DART) molecules (MacroGenics, WO2008157379, WO2010080538) and Dual(ScFv)2-Fab molecules (National Research Center for Antibody Medicine—China).

Examples of Fab fusion bispecific antibodies include but are not limited to F(ab)2 molecules (Medarex/AMGEN; Deo et al J Immunol. 1998 Feb. 15; 160(4):1677-86.), Dual-Action or Bis-Fab molecules (Genentech, Bostrom, et al 2009. Science 323, 1610-1614.), Dock-and-Lock (DNL) molecules (ImmunoMedics, WO2003074569, WO2005004809), Bivalent Bispecific molecules (Biotecnol, Schoonjans, J Immunol. 2000 Dec. 15; 165(12):7050-7.) and Fab-Fv molecules (UCB-Celltech, WO 2009040562 A1).

Examples of scFv-, diabody-based and domain antibodies include but are not limited to Dual Affinity Retargeting Technology (DART) molecules (MacroGenics, WO2008157379, WO2010080538), COMBODY molecules (Epigen Biotech, Zhu et al. Immunol Cell Biol. 2010 August; 88(6):667-75.), and dual targeting nanobodies (Ablynx, Hmila et al., FASEB J. 2010).

In one aspect, the bispecific antibody of the invention comprises a first Fc-region comprising a first CH3 region, and a second Fc-region comprising a second CH3 region, wherein the sequences of the first and second CH3 regions are different and are such that the heterodimeric interaction between said first and second CH3 regions is stronger than each of the homodimeric interactions of said first and second CH3 regions. More details on these interactions and how they can be achieved are provided in WO2011131746 and WO2013060867 (Genmab), which are hereby incorporated by reference.

As described further herein, a stable bispecific CD37× CD37 antibody can be obtained at high yield using a particular method on the basis of one homodimeric starting CD37 antibody and another homodimeric starting CD37 antibody containing only a few, fairly conservative, asymmetrical mutations in the CH3 regions. Asymmetrical mutations mean that the sequences of said first and second CH3 regions contain amino acid substitutions at non-identical positions so that the first and second CH3 regions have different amino acid sequences.

In one aspect, the bispecific antibody as defined in any of the embodiments disclosed herein comprises first and second Fc region, wherein each of said first and second Fc region comprises at least a hinge region, a CH2 and a CH3 region, wherein in said first Fc region at least one of the amino acids in the positions corresponding to a positions selected from the group consisting of T366, L368, K370, D399, F405, Y407, and K409 in a human IgG1 heavy chain has been substituted, and in said second Fc region at least one of the amino acids in the positions corresponding to a position selected from the group consisting of T366, L368, K370, D399, F405, Y407, and K409 in a human IgG1 heavy chain has been substituted, and wherein said first and said second Fc regions are not substituted in the same positions.

Accordingly, in a preferred embodiment of the invention the first Fc region of the bispecific antibody comprises a mutation of the amino acid corresponding to position F405 in human IgG1 and the second Fc region of the bispecific antibody comprises a further mutation of the amino acid corresponding to position K409 in human IgG1. Accordingly, these mutations are asymmetric compared to the above mentioned Fc-Fc interaction enhancing mutations.

In one embodiment of the bispecific antibody as defined in any of the embodiments disclosed herein, the first Fc-region has an amino acid substitution at position 366, and said second Fc-region has an amino acid substitution at a position selected from the group consisting of: 368, 370, 399, 405, 407 and 409. In one embodiment the amino acid at position 366 is selected from Ala, Asp, Glu, His, Asn, Val, or Gln.

In one embodiment of the bispecific antibody as defined in any of the embodiments disclosed herein, the first Fc-region has an amino acid substitution at position 368, and said second Fc-region has an amino acid substitution at a position selected from the group consisting of: 366, 370, 399, 405, 407 and 409.

In one embodiment of the bispecific antibody as defined in any of the embodiments disclosed herein, the first Fc-region has an amino acid substitution at position 370, and said second Fc-region has an amino acid substitution at a position selected from the group consisting of: 366, 368, 399, 405, 407 and 409.

In one embodiment of the bispecific antibody as defined in any of the embodiments disclosed herein, the first Fc-region has an amino acid substitution at position 399, and said second Fc-region has an amino acid substitution at a position selected from the group consisting of: 366, 368, 370, 405, 407 and 409.

In one embodiment of the bispecific antibody as defined in any of the embodiments disclosed herein, the first Fc-region has an amino acid substitution at position 405, and said second Fc-region has an amino acid substitution at a position selected from the group consisting of: 366, 368, 370, 399, 407 and 409.

In one embodiment of the bispecific antibody as defined in any of the embodiments disclosed herein, the first Fc-region has an amino acid substitution at position 407, and said second Fc-region has an amino acid substitution at a position selected from the group consisting of: 366, 368, 370, 399, 405, and 409.

In one embodiment of the bispecific antibody as defined in any of the embodiments disclosed herein, the first Fc-region has an amino acid substitution at position 409, and said second Fc-region has an amino acid substitution at a position selected from the group consisting of: 366, 368, 370, 399, 405, and 407.

Accordingly, in one embodiment of the bispecific antibody as defined in any of the embodiments disclosed herein, the sequences of said first and second Fc-region contain asymmetrical mutations, i.e. mutations at different positions in the two Fc-regions, e.g. a mutation at position 405 in one of the Fc-regions and a mutation at position 409 in the other Fc-region.

In one embodiment of the bispecific antibody as defined in any of the embodiments disclosed herein, the first Fc-region has an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region has an amino-acid substitution at a position selected from the group consisting of: 366, 368, 370, 399, 405 and 407. In one such embodiment, said first Fc-region has an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region has an amino acid other than Phe, e.g. Gly, Ala, Val, Ile, Ser, Thr, Lys, Arg, His, Asp, Asn, Glu, Gln, Pro, Trp, Tyr, Cys, Lys, or Leu, at position 405. In a further embodiment hereof, said first Fc-region has an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region has an amino acid other than Phe, Arg or Gly, e.g.

Leu, Ala, Val, Ile, Ser, Thr, Met, Lys, His, Asp, Asn, Glu, Gln, Pro, Trp, Tyr, or Cys, at position 405.

In another embodiment of the bispecific antibody as defined in any of the embodiments disclosed herein, said first Fc-region comprises a Phe at position 405 and an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region comprises an amino acid other than Phe, e.g. Gly, Ala, Val, Ile, Ser, Thr, Lys, Arg, His, Asp, Asn, Glu, Gln, Pro, Trp, Tyr, Leu, Met, or Cys, at position 405 and a Lys at position 409. In a further embodiment hereof, said first Fc-region comprises a Phe at position 405 and an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region comprises an amino acid other than Phe, Arg or Gly, e.g. Leu, Ala, Val, Ile, Ser, Thr, Met, Lys, His, Asp, Asn, Glu, Gln, Pro, Trp, Tyr, or Cys, at position 405 and a Lys at position 409.

In another embodiment of the bispecific antibody as defined in any of the embodiments disclosed herein, said first Fc-region comprises a Phe at position 405 and an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region comprises a Leu at position 405 and a Lys at position 409. In a further embodiment hereof, said first Fc-region comprises a Phe at position 405 and an Arg at position 409 and said second Fc-region comprises an amino acid other than Phe, Arg or Gly, e.g. Leu, Ala, Val, Ile, Ser, Thr, Lys, Met, His, Asp, Asn, Glu, Gln, Pro, Trp, Tyr, or Cys, at position 405 and a Lys at position 409. In another embodiment, said first Fc-region comprises Phe at position 405 and an Arg at position 409 and said second Fc-region comprises a Leu at position 405 and a Lys at position 409.

In a further embodiment of the bispecific antibody as defined in any of the embodiments disclosed herein, said first Fc-region comprises an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region comprises a Lys at position 409, a Thr at position 370 and a Leu at position 405. In a further embodiment, said first Fc-region comprises an Arg at position 409 and said second Fc-region comprises a Lys at position 409, a Thr at position 370 and a Leu at position 405.

In an even further embodiment of the bispecific antibody as defined in any of the embodiments disclosed herein, said first Fc-region comprises a Lys at position 370, a Phe at position 405 and an Arg at position 409 and said second Fc-region comprises a Lys at position 409, a Thr at position 370 and a Leu at position 405.

In another embodiment of the bispecific antibody as defined in any of the embodiments disclosed herein, said first Fc-region comprises an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region comprises a Lys at position 409 and: a) an Ile at position 350 and a Leu at position 405, or b) a Thr at position 370 and a Leu at position 405.

In another embodiment of the bispecific antibody as defined in any of the embodiments disclosed herein, said first Fc-region comprises an Arg at position 409 and said second Fc region comprises a Lys at position 409 and: a) an Ile at position 350 and a Leu at position 405, or b) a Thr at position 370 and a Leu at position 405.

In another embodiment of the bispecific antibody as defined in any of the embodiments disclosed herein, said first Fc-region comprises a Thr at position 350, a Lys at position 370, a Phe at position 405 and an Arg at position 409 and said second Fc region comprises a Lys at position 409 and: a) an Ile at position 350 and a Leu at position 405, or b) a Thr at position 370 and a Leu at position 405.

In another embodiment of the bispecific antibody as defined in any of the embodiments disclosed herein, said first Fc-region comprises a Thr at position 350, a Lys at position 370, a Phe at position 405 and an Arg at position 409 and said second Fc-region comprises an Ile at position 350, a Thr at position 370, a Leu at position 405 and a Lys at position 409.

In one embodiment of the bispecific antibody as defined in any of the embodiments disclosed herein, said first Fc-region has an amino acid other than Lys, Leu or Met at position 409 and said second Fc-region has an amino acid other than Phe at position 405, such as other than Phe, Arg or Gly at position 405; or said first CH3 region has an amino acid other than Lys, Leu or Met at position 409 and said second CH3 region has an amino acid other than Tyr, Asp, Glu, Phe, Lys, Gln, Arg, Ser or Thr at position 407.

In one embodiment, the bispecific antibody as defined in any of the embodiments disclosed herein comprises a first Fc-region having an amino acid other than Lys, Leu or Met at position 409 and a second Fc-region having an amino acid other than Tyr, Asp, Glu, Phe, Lys, Gln, Arg, Ser or Thr at position 407.

In one embodiment, the bispecific antibody as defined in any of the embodiments disclosed herein comprises a first Fc-region having a Tyr at position 407 and an amino acid other than Lys, Leu or Met at position 409 and a second Fc-region having an amino acid other than Tyr, Asp, Glu, Phe, Lys, Gln, Arg, Ser or Thr at position 407 and a Lys at position 409.

In one embodiment, the bispecific antibody as defined in any of the embodiments disclosed herein comprises a first Fc-region having a Tyr at position 407 and an Arg at position 409 and a second Fc-region having an amino acid other than Tyr, Asp, Glu, Phe, Lys, Gln, Arg, Ser or Thr at position 407 and a Lys at position 409.

In another embodiment, said first Fc-region has an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region has an amino acid other than Tyr, Asp, Glu, Phe, Lys, Gln, Arg, Ser or Thr, e.g. Leu, Met, Gly, Ala, Val, Ile, His, Asn, Pro, Trp, or Cys, at position 407. In another embodiment, said first Fc-region has an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region has an Ala, Gly, His, Ile, Leu, Met, Asn, Val or Trp at position 407.

In another embodiment of the bispecific antibody as defined in any of the embodiments disclosed herein, said first Fc-region has an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region has a Gly, Leu, Met, Asn or Trp at position 407.

In another embodiment of the bispecific antibody as defined in any of the embodiments disclosed herein, said first Fc-region has a Tyr at position 407 and an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region has an amino acid other than Tyr, Asp, Glu, Phe, Lys, Gln, Arg, Ser or Thr, e.g. Leu, Met, Gly, Ala, Val, Ile, His, Asn, Pro, Trp, or Cys, at position 407 and a Lys at position 409.

In another embodiment of the bispecific antibody as defined in any of the embodiments disclosed herein, said first Fc-region has a Tyr at position 407 and an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region has an Ala, Gly, His, Ile, Leu, Met, Asn, Val or Trp at position 407 and a Lys at position 409.

In another embodiment of the bispecific antibody as defined in any of the embodiments disclosed herein, said first Fc-region has a Tyr at position 407 and an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409 and said second Fc-region has a Gly, Leu, Met, Asn or Trp at position 407 and a Lys at position 409.

In another embodiment of the bispecific antibody as defined in any of the embodiments disclosed herein, said first Fc-region has a Tyr at position 407 and an Arg at position 409 and said second Fc-region has an amino acid other than Tyr, Asp, Glu, Phe, Lys, Gln, Arg, Ser or Thr, e.g. Leu, Met, Gly, Ala, Val, Ile, His, Asn, Pro, Trp, or Cys, at position 407 and a Lys at position 409.

In another embodiment of the bispecific antibody as defined in any of the embodiments disclosed herein, said first Fc-region has a Tyr at position 407 and an Arg at position 409 and said second Fc-region has an Ala, Gly, His, Ile, Leu, Met, Asn, Val or Trp at position 407 and a Lys at position 409.

In another embodiment of the bispecific antibody as defined in any of the embodiments disclosed herein, said first Fc-region has a Tyr at position 407 and an Arg at position 409 and said second Fc-region has a Gly, Leu, Met, Asn or Trp at position 407 and a Lys at position 409.

In another embodiment of the bispecific antibody as defined in any of the embodiments disclosed herein, the first Fc-region has an amino acid other than Lys, Leu or Met, e.g. Gly, Ala, Val, Ile, Ser, Thr, Phe, Arg, His, Asp, Asn, Glu, Gln, Pro, Trp, Tyr, or Cys, at position 409, and the second Fc-region has (i) an amino acid other than Phe, Leu and Met, e.g. Gly, Ala, Val, Ile, Ser, Thr, Lys, Arg, His, Asp, Asn, Glu, Gln, Pro, Trp, Tyr, or Cys, at position 368, or (ii) a Trp at position 370, or (iii) an amino acid other than Asp, Cys, Pro, Glu or Gln, e.g. Phe, Leu, Met, Gly, Ala, Val, Ile, Ser, Thr, Lys, Arg, His, Asn, Trp, Tyr, or Cys, at position 399 or (iv) an amino acid other than Lys, Arg, Ser, Thr, or Trp, e.g. Phe, Leu, Met, Ala, Val, Gly, Ile, Asn, His, Asp, Glu, Gln, Pro, Tyr, or Cys, at position 366.

In one embodiment, the first Fc-region has an Arg, Ala, His or Gly at position 409, and the second Fc region has (i) a Lys, Gln, Ala, Asp, Glu, Gly, His, Ile, Asn, Arg, Ser, Thr, Val, or Trp at position 368, or (ii) a Trp at position 370, or (iii) an Ala, Gly, Ile, Leu, Met, Asn, Ser, Thr, Trp, Phe, His, Lys, Arg or Tyr at position 399, or (iv) an Ala, Asp, Glu, His, Asn, Val, Gln, Phe, Gly, Ile, Leu, Met, or Tyr at position 366.

In one embodiment, the first Fc-region has an Arg at position 409, and the second Fc region has (i) an Asp, Glu, Gly, Asn, Arg, Ser, Thr, Val, or Trp at position 368, or (ii) a Trp at position 370, or (iii) a Phe, His, Lys, Arg or Tyr at position 399, or (iv) an Ala, Asp, Glu, His, Asn, Val, Gln at position 366.

In addition to the above-specified amino-acid substitutions, said first and second Fc regions may contain further amino-acid substitutions, deletion or insertions relative to wild-type Fc sequences.

In a preferred embodiment of the invention the second Fc region of the bispecific antibody comprises a mutation corresponding to F405 in human IgG1 and the first Fc region comprises a mutation corresponding to K409 in human IgG1 when using EU numbering.

In one embodiment the mutations at position F405 and K409 are substitutions. In a particular embodiment the substitution at position F405 is an F405L substitution. In another embodiment the substitution at position K409 is a K409R substitution.

In embodiments where the bispecific antibody is an IgG4 isotype the first Fc region may further comprise an F405L substitution and an R409K substitution. In such embodiments the second Fc region is not substituted in any of 405 and 409 amino acid positions.

It is to be understood that except expressly stated otherwise all the mentioned amino acid mutations at the disclosed positions are mutations relative to a human IgG1 and using human IgG1 for numbering using the EU numbering system.

In one embodiment, neither said first nor said second Fc-region comprises a Cys-Pro-Ser-Cys sequence in the core hinge region.

In a further embodiment, both said first and said second Fc-region comprise a Cys-Pro-Pro-Cys sequence in the core hinge region.

Hereby bispecific antibodies are provided which can be produced in high yields and which are stable in vivo.

In another embodiment the bispecific antibody of the invention has increased CDC and/or ADCC effector functions compared to an identical bispecific antibody which does not have the Fc-Fc interaction enhancing mutations. In another embodiment the bispecific antibody of the invention has increased CDC and/or ADCC effector functions compared to a monoclonal parental antibody having a binding region of either the first or the second binding region of the bispecific antibody and having identical Fc-Fc enhancing mutations as the bispecific antibody of the invention.

Method of Preparing Bispecific Antibodies of the Invention

Traditional methods such as the hybrid hybridoma and chemical conjugation methods (Marvin and Zhu (2005) Acta Pharmacol Sin 26:649) can be used in the preparation of the bispecific antibodies of the invention. Co-expression in a host cell of two antibodies, consisting of different heavy and light chains, leads to a mixture of possible antibody products in addition to the desired bispecific antibody, which can then be isolated by, e.g., affinity chromatography or similar methods.

Strategies favoring the formation of a functional bispecific product, upon co-expression of different antibody constructs can also be used, e.g., the method described by Lindhofer et al. (1995 J Immunol 155:219). Fusion of rat and mouse hybridomas producing different antibodies leads to a limited number of heterodimeric proteins because of preferential species-restricted heavy/light chain pairing. Another strategy to promote formation of heterodimers over homodimers is a "knob-into-hole" strategy in which a protuberance is introduced on a first heavy-chain polypeptide and a corresponding cavity in a second heavy-chain polypeptide, such that the protuberance can be positioned in the cavity at the interface of these two heavy chains so as to promote heterodimer formation and hinder homodimer formation. "Protuberances" are constructed by replacing small amino-acid side-chains from the interface of the first polypeptide with larger side chains. Compensatory "cavities" of identical or similar size to the protuberances are created in the interface of the second polypeptide by replacing large amino-acid side-chains with smaller ones (U.S. Pat. No. 5,731,168). EP1870459 (Chugai) and WO2009089004 (Amgen) describe other strategies for favoring heterodimer formation upon co-expression of different antibody domains in a host cell. In these methods, one or more residues that make up the CH3-CH3 interface in both CH3 domains are replaced with a charged amino acid such that homodimer formation is electrostatically unfavorable and heterodimerization is electrostatically favorable. WO2007110205 (Merck) describe yet another strategy, wherein differences between IgA and IgG CH3 domains are exploited to promote heterodimerization.

Another in vitro method for producing bispecific antibodies has been described in WO2008119353 (Genmab), wherein a bispecific antibody is formed by "Fab-arm" or "half-molecule" exchange (swapping of a heavy chain and attached light chain) between two monospecific IgG4- or IgG4-like antibodies upon incubation under reducing conditions. The resulting product is a bispecific antibody having two Fab arms which may comprise different sequences.

A preferred method for preparing the bispecific CD37× CD37 antibodies of the present invention includes the methods described in WO2011131746 and WO2013060867 (Genmab) comprising the following steps:
a) providing a first antibody comprising an Fc region, said Fc region comprising a first CH3 region;
b) providing a second antibody comprising a second Fc region, said Fc region comprising a second CH3 region, wherein the first antibody is a CD37 antibody and the second antibody is a different CD37 antibody;
wherein the sequences of said first and second CH3 regions are different and are such that the heterodimeric interaction between said first and second CH3 regions is stronger than each of the homodimeric interactions of said first and second CH3 regions;
c) incubating said first antibody together with said second antibody under reducing conditions; and
d) obtaining said bispecific antibody.

In one embodiment, said first antibody together with said second antibody are incubated under reducing conditions sufficient to allow the cysteines in the hinge region to undergo disulfide-bond isomerization, wherein the heterodimeric interaction between said first and second antibodies in the resulting heterodimeric antibody is such that no Fab-arm exchange occurs at 0.5 mM GSH after 24 hours at 37° C.

Without being limited to theory, in step c), the heavy-chain disulfide bonds in the hinge regions of the parent antibodies are reduced and the resulting cysteines are then able to form inter heavy-chain disulfide bond with cysteine residues of another parent antibody molecule (originally with a different specificity). In one embodiment of this method, the reducing conditions in step c) comprise the addition of a reducing agent, e.g. a reducing agent selected from the group consisting of: 2-mercaptoethylamine (2-MEA), dithiothreitol (DTT), dithioerythritol (DTE), glutathione, tris(2-carboxyethyl)phosphine (TCEP), L-cysteine and beta-mercapto-ethanol, preferably a reducing agent selected from the group consisting of: 2-mercaptoethylamine, dithiothreitol and tris(2-carboxyethyl)phosphine. In a further embodiment, step c) comprises restoring the conditions to become non-reducing or less reducing, for example by removal of a reducing agent, e.g. by desalting.

For this method any of the CD37 antibodies described herein may be used including first and second CD37 antibodies, comprising a first and/or second Fc region. Examples of such first and second Fc regions, including combination of such first and second Fc regions may include any of those described herein.

In one embodiment of this method, said first and/or second antibodies are full-length antibodies.

The Fc regions of the first and second antibodies may be of any isotype, including, but not limited to, IgG1, IgG2, IgG3 or IgG4. In one embodiment of this method, the Fc regions of both said first and said second antibodies are of the IgG1 isotype. In another embodiment, one of the Fc regions of said antibodies is of the IgG1 isotype and the other of the IgG4 isotype. In the latter embodiment, the resulting bispecific antibody comprises an Fc region of an IgG1 and an Fc region of IgG4 and may thus have interesting intermediate properties with respect to activation of effector functions.

In a further embodiment, one of the antibody starting proteins has been engineered to not bind Protein A, thus allowing to separate the heterodimeric protein from said homodimeric starting protein by passing the product over a protein A column.

As described above, the sequences of the first and second CH3 regions of the homodimeric starting antibodies (the parental antibodies) are different and are such that the heterodimeric interaction between said first and second CH3 regions is stronger than each of the homodimeric interactions of said first and second CH3 regions. More details on these interactions and how they can be achieved are provided in WO2011131746 and WO2013060867 (Genmab), which are hereby incorporated by reference in their entirety.

In particular, a stable bispecific CD37×CD37 antibody can be obtained at high yield using the above method of the invention on the basis of two homodimeric starting antibodies which bind different epitopes of CD37 and contain only a few, fairly conservative, asymmetrical mutations in the CH3 regions. Asymmetrical mutations mean that the sequences of said first and second CH3 regions contain amino acid substitutions at non-identical positions.

The bispecific antibodies of the invention may also be obtained by co-expression of constructs encoding the first and second polypeptides in a single cell. Thus, in a further aspect, the invention relates to a method for producing a bispecific antibody, said method comprising the following steps:
a) providing a first nucleic-acid construct encoding a first polypeptide comprising a first Fc region and a first antigen-binding region of a first antibody heavy chain, said first Fc region comprising a first CH3 region,
b) providing a second nucleic-acid construct encoding a second polypeptide comprising a second Fc region and a second antigen-binding region of a second antibody heavy chain, said second Fc region comprising a second CH3 region,
wherein the sequences of said first and second CH3 regions are different and are such that the heterodimeric interaction between said first and second CH3 regions is stronger than each of the homodimeric interactions of said first and second CH3 regions,
optionally wherein said first and second nucleic acid constructs encode light chain sequences of said first and second antibodies
c) co-expressing said first and second nucleic-acid constructs in a host cell, and
d) obtaining said heterodimeric protein from the cell culture.

Thus, the present invention also relates to a recombinant eukaryotic or prokaryotic host cell which produces a bispecific antibody of the present invention.

In one embodiment of the present invention, the bispecific antibody is obtained by any of the methods according to the present invention.

Suitable expression vectors, including promoters, enhancers, etc., and suitable host cells for the production of antibodies are well-known in the art. Examples of host cells include yeast, bacterial and mammalian cells, such as CHO or HEK cells.

In one embodiment, the bispecific antibody as defined in any of the embodiments disclosed herein comprises a first Fc-region and a second Fc-region, wherein neither said first nor said second Fc-region comprises a Cys-Pro-Ser-Cys sequence in the hinge region.

In one embodiment, the bispecific antibody as defined in any of the embodiments disclosed herein comprises a first Fc-region and a second Fc-region, wherein both of said first and said second Fc-region comprise a Cys-Pro-Pro-Cys sequence in the hinge region.

In one embodiment, the bispecific antibody as defined in any of the embodiments disclosed herein comprises a first Fc-region and a second Fc-region, wherein the first and second Fc-regions are human antibody Fc-regions.

In one embodiment, the bispecific antibody as defined in any of the embodiments disclosed herein comprises a first Fc-region and a second Fc-region, wherein the first and second antigen-binding regions comprise human antibody VH sequences and, optionally, human antibody VL sequences.

In one embodiment, the bispecific antibody as defined in any of the embodiments disclosed herein comprises a first Fc-region and a second Fc-region, wherein the first and second antigen-binding regions are from heavy-chain antibodies.

In one embodiment, the bispecific antibody as defined in any of the embodiments disclosed herein comprises a first Fc-region and a second Fc-region, wherein the first and second antigen-binding regions comprise a first and second light chain.

In further embodiments, the co-expression method according to the invention comprises any of the further features described under the in vitro method above.

Parental Antibodies

In another embodiment the invention relates to the parental antibodies which are used to prepare the bispecific antibodies of the invention.

Thus, in an embodiment the invention relates to an anti-CD37 antibody binding to the same epitope on human CD37 as an anti-CD37 antibody which antibody comprises:
(i) a VH region comprising a CDR1 sequence set forth in SEQ ID NO: 16, a CDR2 sequence set forth in SEQ ID NO: 17 and a CDR3 sequence set forth in SEQ ID NO: 18, and a VL region comprising a CDR1 sequence set forth in SEQ ID NO: 20, and CDR2 sequence: KAS, and CDR3 sequence set forth in SEQ ID NO: 21[010]; or
(ii) a VH region comprising a CDR1 sequence set forth in SEQ ID NO: 9, a CDR2 sequence set forth in SEQ ID NO:10 and a CDR3 sequence set forth in SEQ ID NO: 11, and a VL region comprising a CDR1 sequence set forth in SEQ ID NO: 113, and CDR2 sequence: AAS, and CDR3 sequence set forth in SEQ ID NO: 14[005].

In another embodiment the invention relates to an anti-CD37 antibody which competes for binding with an anti-CD37 antibody comprising:
(i) a VH region comprising a CDR1 sequence set forth in SEQ ID NO: 16, a CDR2 sequence set forth in SEQ ID NO: 17 and a CDR3 sequence set forth in SEQ ID NO: 18, and a VL region comprising a CDR1 sequence set forth in SEQ ID NO: 20, and CDR2 sequence: KAS, and CDR3 sequence set forth in SEQ ID NO: 21 [010]; or
(ii) a VH region comprising a CDR1 sequence set forth in SEQ ID NO: 9, a CDR2 sequence set forth in SEQ ID NO:10 and a CDR3 sequence set forth in SEQ ID NO: 11, and a VL region comprising a CDR1 sequence set forth in SEQ ID NO: 113, and CDR2 sequence: AAS, and CDR3 sequence set forth in SEQ ID NO: 14 [005].

In another embodiment the invention relates to an anti-CD37 antibody comprising:
(i) a VH region comprising a CDR1 sequence set forth in SEQ ID NO: 16, a CDR2 sequence set forth in SEQ ID NO: 17 and a CDR3 sequence set forth in SEQ ID NO: 18, and a VL region comprising a CDR1 sequence set forth in SEQ ID NO: 20, and CDR2 sequence: KAS, and CDR3 sequence set forth in SEQ ID NO: 21 [010]; or
(ii) a VH region comprising a CDR1 sequence set forth in SEQ ID NO: 9, a CDR2 sequence set forth in SEQ ID NO:10 and a CDR3 sequence set forth in SEQ ID NO: 11, and a VL region comprising a CDR1 sequence set forth in SEQ ID NO: 113, and CDR2 sequence: AAS, and CDR3 sequence set forth in SEQ ID NO: 14 [005].

In another embodiment the invention relates to an anti-CD37 antibody which comprises:
(i) a VH region comprising a CDR1 sequence set forth in SEQ ID NO: 23, a CDR2 sequence set forth in SEQ ID NO: 24 and a CDR3 sequence set forth in SEQ ID NO: 25, and a VL region comprising a CDR1 sequence set forth in SEQ ID NO: 27, and CDR2 sequence: YAS, and CDR3 sequence set forth in SEQ ID NO: 28; [016] or
(ii) a VH region comprising a CDR1 sequence set forth in SEQ ID NO: 2, a CDR2 sequence set forth in SEQ ID NO: 3 and a CDR3 sequence set forth in SEQ ID NO: 4, and a VL region comprising a CDR1 sequence set forth in SEQ ID NO: 6, and CDR2 sequence: EAS, and CDR3 sequence set forth in SEQ ID NO: 7. [004]

In another embodiment the invention relates to an antibody as defined above which comprises one or more amino acid mutations in the Fc region of the antibody which mutation(s) enhances the Fc-Fc interaction between the antibodies upon target binding compared to the Fc-Fc interaction between antibodies not having said mutation(s).

It is believed that said enhanced Fc-Fc interaction has the effect that the antibodies form oligomers such as e.g. hexamers on the target cells which oligomers formation causes the effect of enhanced CDC. In a preferred embodiment the one or more amino acid mutations in the Fc region of the antibody is amino acid substitutions at one or more positions corresponding to amino acid positions 430, 440 and 345 in human IgG1 when using the EU numbering system and where the substitution is relative to the amino acid sequence of human IgG1. In one embodiment the one or more amino acid mutations in the Fc region of the antibody is an amino acid substitution at one or more positions corresponding to amino acid positions 430,345 and 440 in human IgG1 when using the EU numbering system, with the proviso that the substitution in 440 is 440Y or 440W. In an embodiment the at least one amino acid substitution in the Fc region is selected from the group comprising: E430G, E345K, E430S, E430F, E430T, E345Q, E345R, E345Y, S440Y and S440W.

In a preferred embodiment the at least one substitution in said Fc region is selected from E430G or E345K, preferably E430G. These Fc-Fc interaction enhancing mutations are symmetrical mutations so that the two Fc chains of the antibody have identical mutations/substitutions.

In a further embodiment the antibody may further comprise a substitution at a position corresponding to 366, 368, 370, 399, 405, 407 and 409 in human IgG1. An antibody having a substitution in one of these amino acid positions is a stable antibody; however, it can, under reducing conditions in a so called "fab arm exchange" reaction, form bispecific antibodies with an antibody having a substitution in another of these amino acid positions and having a different antigen binding region. Under reducing conditions sufficient to allow the cysteines in the hinge region to undergo disulfide-bond isomerization an antibody of the invention will form half molecules each comprising a single antigen binding site and an Fc region. The substitutions at non-identical positions in any of positions corresponding to 366, 368, 370, 399, 405, 407 and 409 in human IgG1 will cause the half molecules of the first antibody to favor dimerization with half molecules of the second antibody so that bispecific (heterodimeric) antibodies will form when the reducing conditions are removed and the disulfide bonds in the hinge region re-forms.

Thus, two antibodies of the present invention having different antigen binding regions and binding different epitopes on CD37 and containing a substitution in both Fc chains (Fc regions) in any of the amino acid positions corresponding to 366, 368, 370, 399, 405, 407 and 409 in human IgG1 but in non-identical positions may be suitable for preparing a bispecific antibody of the invention.

In one embodiment, the first antibody has an amino acid substitution at position 366, and said second homodimeric protein has an amino acid substitution at a position selected from the group consisting of: 368, 370, 399, 405, 407 and 409. In one embodiment the amino acid at position 366 is selected from Arg, Lys, Asn, Gln, Tyr, Glu and Gly.

In one embodiment, the first antibody has an amino acid substitution at position 368, and said second antibody has an amino acid substitution at a position selected from the group consisting of: 366, 370, 399, 405, 407 and 409.

In one embodiment, the first antibody has an amino acid substitution at position 370, and said second antibody has an amino acid substitution at a position selected from the group consisting of: 366, 368, 399, 405, 407 and 409.

In one embodiment, the first antibody has an amino acid substitution at position 399, and said second antibody has an amino acid substitution at a position selected from the group consisting of: 366, 368, 370, 405, 407 and 409.

In one embodiment, the first antibody has an amino acid substitution at position 405, and said second antibody has an amino acid substitution at a position selected from the group consisting of: 366, 368, 370, 399, 407 and 409.

In one embodiment, the first antibody has an amino acid substitution at position 407, and said second antibody has an amino acid substitution at a position selected from the group consisting of: 366, 368, 370, 399, 405, and 409.

In one embodiment, the first antibody has an amino acid substitution at position 409, and said second antibody has an amino acid substitution at a position selected from the group consisting of: 366, 368, 370, 399, 405, and 407.

In one embodiment, the first antibody has an amino acid other than Lys, Leu or Met at position 409 such as an amino acid selected from the group comprising: Gly, Ala, Val, Ile, Ser, Thr, Arg, His, Asp, Asn, Glu, Gln, Trp, Phe, or Tyr at position 409 and said second antibody has an amino-acid substitution at a position selected from the group consisting of: 366, 368, 370, 399, 405 and 407.

In one such embodiment, said first antibody has an amino acid other than Lys, Leu or Met at position 409 such as an amino acid selected from the group comprising: Gly, Ala, Val, Ile, Ser, Thr, Arg, His, Asp, Asn, Glu, Gln, Trp, Phe, or Tyr at position 409 and said second antibody has an amino acid other than Phe at position 405 such as an amino acid selected from the group comprising: Gly, Ala, Val, Leu, Ile, Ser, Thr, Lys, Arg, His, Asp, Asn, Glu, Gln, Trp, Met or Tyr at the position corresponding to 405 in IgG1. In a further embodiment hereof, said first antibody has an amino acid other than Lys, Leu or Met at position 409 and said second antibody has an amino acid other than Phe, Arg or Gly at position 405.

In another embodiment, said first antibody comprises a Phe at position 405 and an amino acid other than Lys, Leu or Met at position 409 and said second antibody comprises an amino acid other than Phe at position 405 and a Lys at position 409.

In another embodiment, said first antibody comprises Phe at position 405 and an Arg at position 409 and said second antibody comprises a Leu at position 405 and a Lys at position 409. In embodiments where the antibodies are of IgG1, IgG2 or IgG3 isotypes the first antibody may comprise an F405L substitution and the second antibody may comprise a K409R substitution or vice versa. However, in embodiments where the antibodies are both of the IgG4 isotypes the amino acid in position 409 is naturally an Arg (R). Thus, in such embodiments the first antibody is not substituted in position 409 but naturally has an R409 and the second antibody comprises F405L and R405K substitutions, or vice versa; the second antibody is not substituted in position 409 but naturally has an R409 and the first antibody comprises F405L and R405K substitutions. In embodiments where one or both of the first and the second antibodies are of the IgG4 isotype Accordingly, in one embodiment the antibody of the invention may comprise a substitution corresponding to F405L in human IgG1. In another embodiment an antibody of the invention may comprise a substitution corresponding to K409R in human IgG1. Such two different antibodies are suitable for preparing a bispecific antibody of the invention. In a particularly preferred embodiment a first antibody of the invention comprises an F405L and an E430G substitution and a second antibody of the invention comprises a K409R and an E430G substitution. Hereby antibodies are provided which may form bispecific antibodies of the invention which bispecific antibodies comprise a first half molecule comprising F405L+E430G substitutions and a second half molecule comprising K409R+E430G when using IgG1 for numbering. In embodiments where the isotype is IgG4 the first half molecule comprises F405L+R409K+E430G substitutions and the second half molecule comprises an E430G when using IgG4 for numbering. Preferably, in such IgG4 embodiments the core hinge region is substituted from a 'CPSC' amino acid sequence to a 'CPPC' sequence to make the bispecific antibody more stable in vivo and/or in vitro compared to an IgG4 antibody having the CPSC core hinge.

In one embodiment of the invention the first antibody comprises a VH region comprising a CDR1 sequence set forth in SEQ ID NO: 16, a CDR2 sequence set forth in SEQ ID NO: 17 and a CDR3 sequence set forth in SEQ ID NO: 18, and a VL region comprising a CDR1 sequence set forth in SEQ ID NO: 20, and CDR2 sequence: KAS, and CDR3 sequence set forth in SEQ ID NO: 21 [010]; and an Fc region comprising an F405L substitution and on or more Fc-Fc interaction enhancing mutations. In a preferred embodiment the Fc-Fc interaction enhancing mutations are substitutions at one or more amino acid positions selected from the group comprising: 430, 345 and 440, such as E430G, E345K, E430S, E430F, E430T, E345Q, E345R, E345Y, S440Y and S440W. In a preferred embodiment it is E430G.

In another embodiment of the invention the first antibody comprises a VH region comprising a CDR1 sequence set forth in SEQ ID NO: 16, a CDR2 sequence set forth in SEQ ID NO: 17 and a CDR3 sequence set forth in SEQ ID NO: 18, and a VL region comprising a CDR1 sequence set forth in SEQ ID NO: 20, and CDR2 sequence: KAS, and CDR3 sequence set forth in SEQ ID NO: 21 [010]; and an Fc region comprising an K409R substitution and on or more Fc-Fc interaction enhancing mutations. In a preferred embodiment the Fc-Fc interaction enhancing mutations are substitutions at one or more amino acid positions selected from the group comprising: 430, 345 and 440, such as E430G, E345K, E430S, E430F, E430T, E345Q, E345R, E345Y, S440Y and S440W. In a preferred embodiment it is E430G.

In another embodiment of the invention the first antibody comprises a VH region comprising a CDR1 sequence set forth in SEQ ID NO: 9, a CDR2 sequence set forth in SEQ ID NO:10 and a CDR3 sequence set forth in SEQ ID NO: 11, and a VL region comprising a CDR1 sequence set forth in SEQ ID NO: 113, and CDR2 sequence: AAS, and CDR3 sequence set forth in SEQ ID NO: 14 [005]; and an Fc region comprising an F405L substitution and on or more Fc-Fc interaction enhancing mutations. In a preferred embodiment the Fc-Fc interaction enhancing mutations are substitutions at one or more amino acid positions selected from the group comprising: 430, 345 and 440, such as E430G, E345K, E430S, E430F, E430T, E345Q, E345R, E345Y, S440Y and S440W. In a preferred embodiment it is E430G.

In yet another embodiment of the invention the first antibody comprises a VH region comprising a CDR1 sequence set forth in SEQ ID NO: 9, a CDR2 sequence set forth in SEQ ID NO:10 and a CDR3 sequence set forth in SEQ ID NO: 11, and a VL region comprising a CDR1 sequence set forth in SEQ ID NO: 113, and CDR2 sequence: AAS, and CDR3 sequence set forth in SEQ ID NO: 14 [005]; and an Fc region comprising an K409R substitution and on or more Fc-Fc interaction enhancing mutations. In a preferred embodiment the Fc-Fc interaction enhancing mutations are substitutions at one or more amino acid positions selected from the group comprising: 430, 345 and 440, such as E430G, E345K, E430S, E430F, E430T, E345Q, E345R, E345Y, S440Y and S440W. In a preferred embodiment it is E430G.

In one embodiment of the invention the second antibody comprises a VH region comprising a CDR1 sequence set forth in SEQ ID NO: 23, a CDR2 sequence set forth in SEQ ID NO: 24 and a CDR3 sequence set forth in SEQ ID NO: 25, and a VL region comprising a CDR1 sequence set forth in SEQ ID NO: 27, and CDR2 sequence: YAS, and CDR3 sequence set forth in SEQ ID NO: 28 [016]; and an Fc region comprising an F405L substitution and on or more Fc-Fc interaction enhancing mutations. In a preferred embodiment the Fc-Fc interaction enhancing mutations are substitutions at one or more amino acid positions selected from the group comprising: 430, 345 and 440, such as E430G, E345K, E430S, E430F, E430T, E345Q, E345R, E345Y, S440Y and S440W. In a preferred embodiment it is E430G.

In another embodiment of the invention the second antibody comprises a VH region comprising a CDR1 sequence set forth in SEQ ID NO: 23, a CDR2 sequence set forth in SEQ ID NO: 24 and a CDR3 sequence set forth in SEQ ID NO: 25, and a VL region comprising a CDR1 sequence set forth in SEQ ID NO: 27, and CDR2 sequence: YAS, and CDR3 sequence set forth in SEQ ID NO: 28 [016]; and an Fc region comprising an K409R substitution and on or more Fc-Fc interaction enhancing mutations. In a preferred embodiment the Fc-Fc interaction enhancing mutations are substitutions at one or more amino acid positions selected from the group comprising: 430, 345 and 440, such as E430G, E345K, E430S, E430F, E430T, E345Q, E345R, E345Y, S440Y and S440W. In a preferred embodiment it is E430G.

In another embodiment of the invention the second antibody comprises a VH region comprising a CDR1 sequence set forth in SEQ ID NO: 2, a CDR2 sequence set forth in SEQ ID NO: 3 and a CDR3 sequence set forth in SEQ ID NO: 4, and a VL region comprising a CDR1 sequence set forth in SEQ ID NO: 6, and CDR2 sequence: EAS, and CDR3 sequence set forth in SEQ ID NO: 7 [004]; and an Fc region comprising an F405L substitution and on or more Fc-Fc interaction enhancing mutations. In a preferred embodiment the Fc-Fc interaction enhancing mutations are substitutions at one or more amino acid positions selected from the group comprising: 430, 345 and 440, such as E430G, E345K, E430S, E430F, E430T, E345Q, E345R, E345Y, S440Y and S440W. In a preferred embodiment it is E430G.

In yet another embodiment of the invention the second antibody comprises a VH region comprising a CDR1 sequence set forth in SEQ ID NO: 2, a CDR2 sequence set forth in SEQ ID NO: 3 and a CDR3 sequence set forth in SEQ ID NO: 4, and a VL region comprising a CDR1 sequence set forth in SEQ ID NO: 6, and CDR2 sequence: EAS, and CDR3 sequence set forth in SEQ ID NO: 7 [004]; and an Fc region comprising an K409R substitution and on or more Fc-Fc interaction enhancing mutations. In a preferred embodiment the Fc-Fc interaction enhancing mutations are substitutions at one or more amino acid positions selected from the group comprising: 430, 345 and 440, such as E430G, E345K, E430S, E430F, E430T, E345Q, E345R, E345Y, S440Y and S440W. In a preferred embodiment it is E430G.

In another embodiment of the invention the second antibody comprises a VH region comprising a CDR1 sequence set forth in SEQ ID NO: 40, a CDR2 sequence set forth in SEQ ID NO: 41 and a CDR3 sequence set forth in SEQ ID NO: 42, and a VL region comprising a CDR1 sequence set forth in SEQ ID NO: 44, and CDR2 sequence: FAK, and CDR3 sequence set forth in SEQ ID NO: 45 [G28.1]; and an Fc region comprising an F405L substitution and on or more Fc-Fc interaction enhancing mutations. In a preferred embodiment the Fc-Fc interaction enhancing mutations are substitutions at one or more amino acid positions selected from the group comprising: 430, 345 and 440, such as E430G, E345K, E430S, E430F, E430T, E345Q, E345R, E345Y, S440Y and S440W. In a preferred embodiment it is E430G.

In yet another embodiment of the invention the second antibody comprises a VH region comprising a CDR1 sequence set forth in SEQ ID NO: 40, a CDR2 sequence set forth in SEQ ID NO: 41 and a CDR3 sequence set forth in SEQ ID NO: 42, and a VL region comprising a CDR1 sequence set forth in SEQ ID NO: 44, and CDR2 sequence: FAK, and CDR3 sequence set forth in SEQ ID NO: 45 [G28.1]; and an Fc region comprising an K409R substitution and on or more Fc-Fc interaction enhancing mutations. In a preferred embodiment the Fc-Fc interaction enhancing mutations are substitutions at one or more amino acid positions selected from the group comprising: 430, 345 and 440, such as E430G, E345K, E430S, E430F, E430T, E345Q, E345R, E345Y, S440Y and S440W. In a preferred embodiment it is E430G.

In another embodiment of the invention the second antibody comprises a VH region comprising a CDR1 sequence set forth in SEQ ID NO: 47, a CDR2 sequence set forth in SEQ ID NO: 48 and a CDR3 sequence set forth in SEQ ID NO: 49, and a VL region comprising a CDR1 sequence set forth in SEQ ID NO: 51, and CDR2 sequence: VAT, and CDR3 sequence set forth in SEQ ID NO: 52 [37.3]; and an Fc region comprising an F405L substitution and on or more Fc-Fc interaction enhancing mutations. In a preferred embodiment the Fc-Fc interaction enhancing mutations are substitutions at one or more amino acid positions selected from the group comprising: 430, 345 and 440, such as E430G, E345K, E430S, E430F, E430T, E345Q, E345R, E345Y, S440Y and S440W. In a preferred embodiment it is E430G.

In yet another embodiment of the invention the second antibody comprises a VH region comprising a CDR1 sequence set forth in SEQ ID NO: 47, a CDR2 sequence set forth in SEQ ID NO: 48 and a CDR3 sequence set forth in SEQ ID NO: 49, and a VL region comprising a CDR1 sequence set forth in SEQ ID NO: 51, and CDR2 sequence: VAT, and CDR3 sequence set forth in SEQ ID NO: 52 [37.3]; and an Fc region comprising an K409R substitution and on or more Fc-Fc interaction enhancing mutations. In a preferred embodiment the Fc-Fc interaction enhancing mutations are substitutions at one or more amino acid positions selected from the group comprising: 430, 345 and 440, such as E430G, E345K, E430S, E430F, E430T, E345Q, E345R, E345Y, S440Y and S440W. In a preferred embodiment it is E430G.

Accordingly, the invention also relates to an anti-CD37 antibody which binds to human CD37 which antibody comprises:
(i) a VH region comprising a CDR1 sequence set forth in SEQ ID NO: 40, a CDR2 sequence set forth in SEQ ID NO: 41 and a CDR3 sequence set forth in SEQ ID NO: 42, and a VL region comprising a CDR1 sequence set forth in SEQ ID NO: 44, and CDR2 sequence: FAK, and CDR3 sequence set forth in SEQ ID NO: 45 [G28.1] or
(ii) a VH region comprising a CDR1 sequence set forth in SEQ ID NO: 47, a CDR2 sequence set forth in SEQ ID NO: 48 and a CDR3 sequence set forth in SEQ ID NO: 49, and a VL region comprising a CDR1 sequence set forth in SEQ ID NO: 51, and CDR2 sequence: VAT, and CDR3 sequence set forth in SEQ ID NO: 52 [37.3];
(iii) and wherein the antibody of (i) or (ii) comprises an Fc region comprising at least one amino acid substitution selected from the group comprising: E430G, E345K, E430S, E430F, E430T, E345Q, E345R, E345Y, S440Y and S440W; and
(iv) wherein optionally the Fc region further comprises a mutation of either K409R or F405L.

As mentioned above the anti-CD37 antibodies of the invention may be an IgG1, IgG2, IgG3 or IgG4 isotype. In one embodiment the anti-CD37 antibody of the invention is of an IgG isotype.

In one embodiment, the antibody of the invention is human, humanized or chimeric.

In one embodiment, the antibody of the invention binds to both the human and the cynomolgos CD37 antigens.

Further Embodiments of the Invention

In another embodiment the invention relates to a composition comprising a bispecific antibody of the invention and further comprising a monospecific anti-CD37 antibody, preferably an anti-CD37 antibody having the antigen binding region of either the first or second antigen binding region of the bispecific antibody.

In one embodiment the invention relates to a pharmaceutical composition comprising a bispecific antibody of the invention or an anti-CD37 antibody of the invention and a pharmaceutically acceptable carrier.

In another embodiment the invention relates to a bispecific antibody of the invention or an antibody of the invention or a composition of the invention for use as a medicament.

In one embodiment of the invention the bispecific antibody of the invention is for use in the treatment of cancer, autoimmune disease or inflammatory disorders.

In one embodiment of the invention the anti-CD37 antibody of the invention is for use in the treatment of cancer, autoimmune disease or inflammatory disorders.

In one embodiment of the invention the composition of the invention is for use in the treatment of cancer, autoimmune disease or inflammatory disorders.

In another embodiment the invention relates to a bispecific antibody of the invention for use in the treatment of allergy, transplantation rejection or a B-cell malignancy, such as non-Hodgkin lymphoma (NHL), chronic lymphocytic leukemia (CLL), follicular lymphoma (FL), mantle cell lymphoma (MCL), plasma cell leukemia (PCL), diffuse large B-cell lymphoma (DLBCL), or acute lymphoblastic leukemia (ALL).

In another embodiment the invention relates to a bispecific antibody of the invention for use in the treatment of rheumatoid arthritis such as acute arthritis, chronic rheumatoid arthritis, gout or gouty arthritis, acute gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, and juvenile-onset rheumatoid arthritis, osteoarthritis, arthritis chronica progrediente, arthritis deformans, polyarthritis chronica primaria, reactive arthritis, and ankylosing spondylids) systemic lupus erythematosus (SLE) such as cutaneous SLE or subacute cutaneous SLE, neonatal lupus syndrome (NLE), and lupus erythematosis disseminates, multiple sclerosis, inflammatory bowel disease (IBD) which includes ulcerative colitis and Crohn's disease, Chronic obstructive pulmonary disease (COPD), psoriasis, IgA nephropathy, IgM polyneuropathies, myasthenia gravis, diabetes mellitus, Reynaud's syndrome, and glomerulonephritis, pustulosis palmoplantaris (PPP), erosive lichen planus, pemphigus bullosa, epidermolysis bullosa, contact dermatitis and atopic dermatitis, polyradiculitis including Guillain-Barre syndrome.

In another embodiment the invention relates to an anti-CD37 antibody of the invention for use in the treatment of allergy, transplantation rejection or a B-cell malignancy.

In another embodiment the invention relates to an anti-CD37 antibody of the invention for use in the treatment of allergy, transplantation rejection or a B-cell malignancy, such as non-Hodgkin lymphoma (NHL), chronic lymphocytic leukemia (CLL), follicular lymphoma (FL), mantle cell lymphoma (MCL), plasma cell leukemia (PCL), diffuse large B-cell lymphoma (DLBCL), or acute lymphoblastic leukemia (ALL).

In another embodiment the invention relates to an anti-CD37 antibody of the invention for use in the treatment of rheumatoid arthritis such as acute arthritis, chronic rheumatoid arthritis, gout or gouty arthritis, acute gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, and juvenile-onset rheumatoid arthritis, osteoarthritis, arthritis chronica progrediente, arthritis deformans, polyarthritis chronica primaria, reactive arthritis, and ankylosing spondylids) systemic lupus erythematosus (SLE) such as cutaneous SLE or subacute cutaneous SLE, neonatal lupus syndrome (NLE), and lupus erythematosis disseminates, multiple sclerosis, inflammatory bowel disease (IBD) which includes ulcerative colitis and Crohn's disease, Chronic obstructive pulmonary disease (COPD), psoriasis, IgA nephropathy, IgM polyneuropathies, myasthenia gravis, diabetes mellitus, Reynaud's syndrome, and glomerulonephritis, pustulosis palmoplantaris (PPP), erosive lichen planus, pemphigus bullosa, epidermolysis bullosa, contact dermatitis and atopic dermatitis, polyradiculitis including Guillain-Barre syndrome.

In another embodiment the invention relates to the bispecific antibody of the invention for use in combination with one or more further therapeutic agents. In another embodiment of the invention the anti-CD37 antibodies of the invention is for use in combination with one or more further therapeutic agents. The one or more further therapeutic agent may e.g. be selected from the group comprising: doxorubicin, cisplatin, bleomycin, carmustine, cyclophosphamide, chlorambucil, bendamustine, vincristine, fludarabine, ibrutinib and an anti-CD 20 antibody such as rituximab, ofatumumab, Obinutuzumab, Veltuzumab, Ocaratuzumab, Ocrelizumab or TRU-015.

In a preferred embodiment of the invention the further therapeutic agent is an anti-CD20 antibody.

In one embodiment of the invention the anti-CD20 antibody is capable of binding to human CD20 having the sequences set forth in SEQ ID No: 72.

In one embodiment of the invention the anti-CD20 antibody is capable of binding to cynomolgus monkey CD20 having the sequences set forth in SEQ ID No: 73.

In one embodiment of the invention the anti-CD20 antibody is capable of binding to human and cynomolgus monkey CD20 having the sequences set forth in SEQ ID Nos 72 and 73, respectively.

In one embodiment of the invention the anti-CD20 antibody is capable of binding to an epitope on human CD20, which does not comprise or require the amino acid residues alanine at position 170 or proline at position 172, but which comprises or requires the amino acid residues asparagine at position 163 and asparagine at position 166 of SEQ ID No. 72. Examples of such antibodies are the antibodies denoted 2F2 and 7D8 as disclosed in WO2004035607 (Genmab) and the antibody denoted 2C6 as disclosed in WO2005103081 (Genmab). The CDR sequences of 7D8 are disclosed in Table 1.

In one embodiment of the invention the anti-CD20 antibody is capable of binding to an epitope on human CD20, which does not comprise or require the amino acid residues alanine at position 170 or proline at position 172 of SEQ ID No. 72. An example of such an antibody is 11B8 as disclosed in WO2004035607 (Genmab). The CDR sequences of 11B8 are disclosed in Table 1.

In one embodiment of the invention the anti-CD20 antibody is capable of binding to a discontinuous epitope on human CD20, wherein the epitope comprises part of the first small extracellular loop and part of the second extracellular loop.

In one embodiment of the invention the anti-CD20 antibody is capable of binding to a discontinuous epitope on human CD20, wherein the epitope has residues AGIYAP of the small first extracellular loop and residues MESLNFIRAHTPY of the second extracellular loop.

Anti-CD20 antibodies may characterize as type-I and type II anti-CD20 antibodies. Type I anti-CD20 antibodies, have high CDC and ADCC activity, but low apoptosis activity, such as ofatumumab (2F2) and rituximab, whereas type II anti-CD20 antibodies, having low or no CDC activity, but high ADCC and apoptosis activity, such as obinutuzumab and 11B8. Also, type I antibodies induce CD20 to redistribute into large detergent resistant microdomains (rafts), whereas type II antibodies do not.

In one embodiment of the invention the anti-CD20 antibody comprises an antigen-binding region capable of binding to human CD20, wherein the antigen-binding region competes for binding to human CD20 with an anti-CD20 antibody comprising the variable heavy chain (VH) sequence and variable light chain (VL) as set forth in SEQ ID No 74 and SEQ ID No 78 respectively.

In one embodiment of the invention the anti-CD20 antibody comprises an antigen-binding region capable of binding to human CD20, wherein the antigen-binding region competes for binding to human CD20 with an anti-CD20 antibody comprising the variable heavy chain (VH) sequence and variable light chain (VL) as set forth in SEQ ID No 81 and SEQ ID No 109 respectively.

In one embodiment of the invention the anti-CD20 antibody comprises an antigen-binding region capable of binding to human CD20, wherein the antigen-binding region competes for binding to human CD20 with an anti-CD20 antibody comprising the variable heavy chain (VH) sequence and variable light chain (VL) as set forth in SEQ ID No 94 and SEQ ID No 98 respectively.

In one embodiment of the invention the anti-CD20 antibody comprises an antigen-binding region capable of binding to human CD20, wherein the antigen-binding region competes for binding to human CD20 with an anti-CD20 antibody comprising the variable heavy chain (VH) sequence and variable light chain (VL) as set forth in SEQ ID No 87 and SEQ ID No 91 respectively.

In one embodiment of the invention the anti-CD20 antibody comprises an antigen-binding region capable of binding to human CD20, wherein the antigen-binding region competes for binding to human CD20 with an anti-CD20 antibody comprising the variable heavy chain (VH) sequence and variable light chain (VL) as set forth in SEQ ID No 101 and SEQ ID No 105 respectively.

In one embodiment of the invention the anti-CD20 antibody comprises an antigen-binding region capable of binding to human CD20 comprising the CDR sequences:
VH CDR1 sequence set forth in SEQ ID NO:75,
VH CDR2 sequence set forth in SEQ ID NO:76,
VH CDR3 sequence set forth in SEQ ID NO:77,
VL CDR1 sequence set forth in SEQ ID NO:79
VL CDR2 sequence DAS, and
VL CDR3 sequence set forth in SEQ ID NO: 80. [7D8]

In one embodiment of the invention the anti-CD20 antibody comprises an antigen-binding region capable of binding to human CD20 comprising the CDR sequences:
VH CDR1 sequence set forth in SEQ ID NO:82,
VH CDR2 sequence set forth in SEQ ID NO:83,
VH CDR3 sequence set forth in SEQ ID NO:84, VL CDR1 sequence set forth in SEQ ID NO:85
VL CDR2 sequence DAS, and
VL CDR3 sequence set forth in SEQ ID NO: 86. [1188]

In one embodiment of the invention the anti-CD20 antibody comprises an antigen-binding region capable of binding to human CD20 comprising the CDR sequences:
VH CDR1 sequence set forth in SEQ ID NO:95,
VH CDR2 sequence set forth in SEQ ID NO:96,
VH CDR3 sequence set forth in SEQ ID NO:97,
VL CDR1 sequence set forth in SEQ ID NO:99,
VL CDR2 sequence ATS, and
VL CDR3 sequence set forth in SEQ ID NO: 100. [Rituximab]

In one embodiment of the invention the anti-CD20 antibody comprises an antigen-binding region capable of binding to human CD20 comprising the CDR sequences:
VH CDR1 sequence set forth in SEQ ID NO:88,
VH CDR2 sequence set forth in SEQ ID NO:89,
VH CDR3 sequence set forth in SEQ ID NO:90,
VL CDR1 sequence set forth in SEQ ID NO:92
VL CDR2 sequence DAS, and
VL CDR3 sequence set forth in SEQ ID NO: 93. [ofatumumab]

In one embodiment of the invention the anti-CD20 antibody comprises an antigen-binding region capable of binding to human CD20 comprising the CDR sequences:
VH CDR1 sequence set forth in SEQ ID NO:102,
VH CDR2 sequence set forth in SEQ ID NO:103,
VH CDR3 sequence set forth in SEQ ID NO:104,
VL CDR1 sequence set forth in SEQ ID NO:106
VL CDR2 sequence QMS, and
VL CDR3 sequence set forth in SEQ ID NO: 107. [obinutuzumab]

In one embodiment of the invention the anti-CD20 antibody comprises an antigen-binding region capable of binding to human CD20 comprising the CDR sequences selected form the group consisting of:
i) VH CDR1 sequence set forth in SEQ ID NO:75,
  VH CDR2 sequence set forth in SEQ ID NO:76,
  VH CDR3 sequence set forth in SEQ ID NO:77,
  VL CDR1 sequence set forth in SEQ ID NO:79
  VL CDR2 sequence DAS, and
  VL CDR3 sequence set forth in SEQ ID NO: 80. [7D8];
ii) VH CDR1 sequence set forth in SEQ ID NO:82,
  VH CDR2 sequence set forth in SEQ ID NO:83,
  VH CDR3 sequence set forth in SEQ ID NO:84,
  VL CDR1 sequence set forth in SEQ ID NO:85
  VL CDR2 sequence DAS, and
  VL CDR3 sequence set forth in SEQ ID NO: 86. [1188];
iii) VH CDR1 sequence set forth in SEQ ID NO:95,
  VH CDR2 sequence set forth in SEQ ID NO:96,
  VH CDR3 sequence set forth in SEQ ID NO:97,
  VL CDR1 sequence set forth in SEQ ID NO:99,
  VL CDR2 sequence ATS, and
  VL CDR3 sequence set forth in SEQ ID NO: 100. [Rituximab];
iv) VH CDR1 sequence set forth in SEQ ID NO:88,
  VH CDR2 sequence set forth in SEQ ID NO:89,
  VH CDR3 sequence set forth in SEQ ID NO:90,
  VL CDR1 sequence set forth in SEQ ID NO:92
  VL CDR2 sequence DAS, and
  VL CDR3 sequence set forth in SEQ ID NO: 93. [ofatumumab]; and
v) VH CDR1 sequence set forth in SEQ ID NO:102,
  VH CDR2 sequence set forth in SEQ ID NO:103,
  VH CDR3 sequence set forth in SEQ ID NO:104,
  VL CDR1 sequence set forth in SEQ ID NO:106
  VL CDR2 sequence QMS, and
  VL CDR3 sequence set forth in SEQ ID NO: 107. [obinutuzumab].

In another embodiment the invention relates to use of the bispecific antibody of the invention or the anti-CD37 antibody of the invention for the manufacture of a medicament. In another embodiment hereof the use is for the manufacture of a medicament for the treatment of cancer, autoimmune diseases or an inflammatory diseases such as allergy, transplantation rejection or a B-cell malignancy, such as non-Hodgkin lymphoma (NHL), chronic lymphocytic leukemia (CLL), follicular lymphoma (FL), mantle cell lymphoma (MCL), plasma cell leukemia (PCL), diffuse large B-cell lymphoma (DLBCL), or acute lymphoblastic leukemia (ALL), rheumatoid arthritis such as acute arthritis, chronic rheumatoid arthritis, gout or gouty arthritis, acute gouty arthritis, acute immunological arthritis, chronic inflammatory arthritis, degenerative arthritis, type II collagen-induced arthritis, infectious arthritis, Lyme arthritis, proliferative arthritis, psoriatic arthritis, Still's disease, vertebral arthritis, and juvenile-onset rheumatoid arthritis, osteoarthritis, arthritis chronica progrediente, arthritis deformans, polyarthritis chronica primaria, reactive arthritis, and ankylosing spondylids) systemic lupus erythematosus (SLE) such as cutaneous SLE or subacute cutaneous SLE, neonatal lupus syndrome (NLE), and lupus erythematosis disseminates, multiple sclerosis, inflammatory bowel disease (IBD) which includes ulcerative colitis and Crohn's disease, Chronic obstructive pulmonary disease (COPD), psoriasis, IgA nephropathy, IgM polyneuropathies, myasthenia gravis, diabetes mellitus, Reynaud's syndrome, and glomerulonephritis, pustulosis palmoplantaris (PPP), erosive lichen planus, pemphigus bullosa, epidermolysis bullosa, contact dermatitis and atopic dermatitis, polyradiculitis including Guillain-Barre syndrome.

In another embodiment the invention relates to a method of inducing cell death, or inhibiting growth and/or proliferation of a tumor cell expressing CD37 comprising administering to an individual in need thereof an effective amount of a bispecific antibody of the invention or an anti-CD37 antibody of the invention. In certain embodiments the method is for treating an individual having allergy, transplantation rejection or a B-cell malignancy, such as non-Hodgkin lymphoma (NHL), chronic lymphocytic leukemia (CLL), follicular lymphoma (FL), mantle cell lymphoma (MCL), plasma cell leukemia (PCL), diffuse large B-cell lymphoma (DLBCL), or acute lymphoblastic leukemia (ALL), comprising administering to said individual an effective amount of the bispecific antibody of the invention or the anti-CD37 antibody of the invention. In certain embodiments the method comprises administering one or more further therapeutic agents in combination with said antibody or said bispecific antibody such as e.g. doxorubicin, cisplatin, bleomycin, carmustine, cyclophosphamide, chlorambucil, bendamustine, vincristine, fludarabine, ibrutinib or an anti-CD20 antibody such as rituximab, ofatumumab, obinutuzumab, veltuzumab, ocaratuzumab, ocrelizumab or TRU-015.

In one embodiment of the invention the further therapeutic agent is selected from the group comprising: cyclophosphamide, chlorambucil, bendamustine, ifosfamide, cisplatin, carboplatin, oxaliplatin, carmustine, prednisone, dexamethasone, fludarabine, pentostatin, cladribine, fluorouracil, gemcitabine, cytarabine, methotrexate, pralatrexate, gemcitabine, vincristine, paclitaxel, docetaxel, doxorubicin, mitoxantrone, etoposide, topotecan, irinotecan, bleomycin, CD20- specific rituximab, obinutuzumab and ofatumumab, CD52-specific alemtuzumab, CD30-specific brentuximab, JNJ-63709178, JNJ-64007957, HuMax-IL8, anti-DR5, anti-VEGF, anti-CD38, anti-PD-1, anti-PD-L1, anti-CTLA4, anti-CD40, anti-CD137, anti-GITR, anti-VISTA, antibodies specific for other immunomodulatory targets, brentuximab vedotin, HuMax-TAC-ADC, Interferon, thalidomide, lenalidomide, Axicabtagene ciloleucel, bortezomib, romidepsin, belinostat, vorinostat, ibrutinib, acalabrutinib, idelalisib, copanlisib, sorafenib, sunitinib, everolimus, recombinant human TRAIL, birinapant, and venetoclax.

In one embodiment of the invention the further therapeutic agent is selected from the group comprising: ibrutinib, rituximab, venetoclax, CHOP (cyclophosphamide, doxorubicin, vincristine, and prednisone), bendamustine, fludarabine, cyclophosphamide, and chlorambucil.

In one embodiment of the invention the further therapeutic agent is selected from the group comprising: ibrutinib, rituximab and venetoclax.

In a further aspect, the invention relates to a nucleic acid construct encoding one or more sequences set out in Table 1. In a further aspect the invention relates to a nucleic acid construct encoding one or more sequences selected from the group comprising SEQ ID NOs: 1, 2, 3, 4, 5, 6, 6a, 7, 8, 9, 10, 11, 12, 13, 13a, 14, 15, 16, 17, 18, 19, 20, 20a, 21, 22, 23, 24, 25, 26, 27, 27a, 28, 29, 30, 30a and 31.

The invention further relates to a nucleic acid construct encoding the VH and/or VL region of the bispecific antibody or the anti-CD37 antibody of any of the embodiments herein.

The invention further relates to a nucleic acid construct encoding the bispecific antibody or the anti-CD37 antibody of any of the embodiments herein.

In a further embodiment the invention relates to an expression vector comprising one or more nucleic acid constructs specified above. In another embodiment the invention relates to a host cell comprising an expression vector as defined above.

An expression vector in the context of the present invention may be any suitable vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, a CD37 antibody-encoding nucleic acid is comprised in a naked DNA or RNA vector, including, for example, a linear expression element (as described in for instance Sykes and Johnston, Nat Biotech 17, 355 59 (1997)), a compacted nucleic acid vector (as described in for instance U.S. Pat. No. 6,077,835 and/or WO 00/70087), a plasmid vector such as pBR322, pUC 19/18, or pUC 118/119, a "midge" minimally-sized nucleic acid vector (as described in for instance Schakowski et al., Mol Ther 3, 793 800 (2001)), or as a precipitated nucleic acid vector construct, such as a CaPO4-precipitated construct (as described in for instance WO200046147, Benvenisty and Reshef, PNAS USA 83, 9551 55 (1986), Wigler et al., Cell 14, 725 (1978), and Coraro and Pearson, Somatic Cell Genetics 7, 603 (1981)). Such nucleic acid vectors and the usage thereof are well known in the art (see for instance U.S. Pat. Nos. 5,589,466 and 5,973,972).

In one embodiment, the vector is suitable for expression of the CD37 antibodies in a bacterial cell. Examples of such vectors include expression vectors such as BlueScript (Stratagene), pIN vectors (Van Heeke & Schuster, J Biol Chem 264, 5503 5509 (1989), pET vectors (Novagen, Madison Wis.) and the like).

An expression vector may also or alternatively be a vector suitable for expression in a yeast system. Any vector suitable for expression in a yeast system may be employed. Suitable vectors include, for example, vectors comprising constitutive or inducible promoters such as alpha factor, alcohol oxidase and PGH (reviewed in: F. Ausubel et al., ed. Current Protocols in Molecular Biology, Greene Publishing and Wiley InterScience New York (1987), and Grant et al., Methods in Enzymol 153, 516 544 (1987)).

An expression vector may also or alternatively be a vector suitable for expression in mammalian cells, e.g. a vector comprising glutamine synthetase as a selectable marker, such as the vectors described in Bebbington (1992) Biotechnology (NY) 10:169-175.

A nucleic acid and/or vector may also comprises a nucleic acid sequence encoding a secretion/localization sequence, which can target a polypeptide, such as a nascent polypeptide chain, to the periplasmic space or into cell culture media. Such sequences are known in the art, and include secretion leader or signal peptides.

The expression vector may comprise or be associated with any suitable promoter, enhancer, and other expression-facilitating elements. Examples of such elements include strong expression promoters (e. g., human CMV IE promoter/enhancer as well as RSV, SV40, SL3 3, MMTV, and HIV LTR promoters), effective poly (A) termination sequences, an origin of replication for plasmid product in *E. coli*, an antibiotic resistance gene as selectable marker, and/or a convenient cloning site (e.g., a polylinker). Nucleic acids may also comprise an inducible promoter as opposed to a constitutive promoter such as CMV IE.

In one embodiment, the CD37 antibody-encoding expression vector may be positioned in and/or delivered to the host cell or host animal via a viral vector.

Thus the present invention also relates to a recombinant eukaryotic or prokaryotic host cell which produces a bispecific antibody of the present invention, such as a transfectoma.

The invention further relates to an anti-idiotypic antibody, which binds to the antigen binding region of the antibody or the bispecific antibody of the invention.

An in vitro method for detecting the presence of a human CD37 antigen or a cell expressing human CD37 in a sample, said method comprising:

(i) contacting the sample with the bispecific antibody of any of the above embodiments or the antibody of any of the embodiments herein under conditions that allow for formation of a complex between the antibody or the bispecific antibody and CD37; and (ii) detecting the formation of a complex.

An in vivo method for detecting the presence of a human CD37 antigen, or a cell expressing human CD37 in a subject, said method comprising:

(i) administering the bispecific antibody of any of the above embodiments or the antibody of any of the embodiments herein under conditions that allow for formation of a complex between the antibody or the bispecific antibody and CD37; and (ii) detecting the formed complex.

Sequences

TABLE 1

| SEQ ID NO: | LABEL | SEQUENCE |
|---|---|---|
| 1 | VH-004-H5L2 | EVQLVESGGGLVQPGGSLRLSCAASGFSLSTYDMSWVRQAPGKGLE WVSIIYSSVGAYYASWAKGRFTISRDNSKNTLYLQMNSLRAEDTAVY YCAREYGASSSDYIFSLWGQGTLVTVSS |
| 2 | VH-004-H5L2-CDR1 | GFSLSTYD |
| 3 | VH-004-H5L2-CDR2 | IYSSVGA |
| 4 | VH-004-H5L2-CDR3 | AREYGASSSDYIFSL |
| 5 | VL-004-H5L2 | AQVLTQSPSPLSASVGDRVTITCQASQSVYNSQNLAWYQQKPGKAP KLLIYEASKLASGVPSRFKGSGSGTEFTLTISSLQPDDFATYYCQGEFS CISADCTAFGGGTKVEIK |
| 6 | VH-004-H5L2-CDR1 | QSVYNSQN |
|  | VH-004-H5L2-CDR2 | EAS |
| 7 | VH-004-H5L2-CDR3 | QGEFSCISADCTA |
| 8 | VH-005-H1L2 | EQSVVESGGGLVQPGGSLRLSCTVSGFSLSSNAMNWVRQAPGKGLE WIGLIYASGNTDYASWAKGRFTISKTSTTVYLKITSPTAEDTATYFCA REGSVWGAAFDPWGQGTLVTVSS |
| 9 | VH-005-H1L2-CDR1 | GFSLSSNA |
| 10 | VH-005-H1L2-CDR2 | IYASGNT |
| 11 | VH-005-H1L2-CDR3 | AREGSVWGAAFDP |
| 12 | VL-005-H1L2 | AYDMTQSPSSVSASVGDRVTITCQASQSISNWLAWYQQKPGKAPK QLIYAASTLASGVPSRFKGSGSGTDFTLTISSLQPEDFATYYCQQGYS NSNIDNTFGGGTKVEIK |
| 13 | VL-005-H1L2-CDR1 | QSISNW |
|  | VL-005-H1L2-CDR2 | AAS |
| 14 | VL-005-H1L2-CDR3 | QQGYSNSNIDNT |
| 15 | VH-010-H5L2 | EVQLVESGGGLVQPGGSLRLSCAASGFSLSYNAMNWVRQAPGKGLE WVSIIFASGRTDYASWAKGRFTISRDNSKNTLYLQMNSLRAEDTAVY YCAREGSTWGDALDPWGQGTLVTVSS |
| 16 | VH-010-H5L2-CDR1 | GFSLSYNA |
| 17 | VH-010-H5L2-CDR2 | IFASGRT |
| 18 | VH-010-H5L2-CDR3 | AREGSTWGDALDP |
| 19 | VL-010-H5L2 | AYDMTQSPSTLSASVGDRVTITCQASQNIIDYLAWYQQKPGKAPKLL IHKASTLASGVPSRFKGSGSGTEFTLTISSLQPDDFATYYCQQGYSNS NIDNTFGGGTKVEIK |
| 20 | VL-010-H5L2-CDR1 | QNIIDY |
|  | VL-010-H5L2-CDR2 | KAS |

TABLE 1-continued

| SEQ ID NO: | LABEL | SEQUENCE |
|---|---|---|
| 21 | VL-010-H5L2-CDR3 | QQGYSNSNIDNT |
| 22 | VH-016-H5L2 | EVQLVESGGGLVQPGGSLRLSCAASGFSLSNYNMGWVRQAPGKGLEWVSVIDASGTTYYATWAKGRFTISRDNSKNTLYLQMNSLRAEDTATYYCARELLYFGSSYYDLWGQGTLVTVSS |
| 23 | VH-016-H5L2-CDR1 | GFSLSNYN |
| 24 | VH-016-H5L2-CDR2 | IDASGTT |
| 25 | VH-016-H5L2-CDR3 | ARELLYFGSSYYDL |
| 26 | VL-016-H5L2 | DVVMTQSPSTLSASVGDRVTITCQASQNIDSNLAWYQQKPGKAPKFLIYYASNLPFGVPSRFKGSGSGTEFTLTISSLQPDDFATYYCQCADVGSTYVAAFGGGTKVEIK |
| 27 | VL-016-H5L2-CDR1 | QNIDSN |
|  | VL-016-H5L2-CDR2 | YAS |
| 28 | VL-016-H5L2-CDR3 | QCADVGSTYVAA |
| 29 | VL-016-H5L2-C905 | DVVMTQSPSTLSASVGDRVTITCQASQNIDSNLAWYQQKPGKAPKFLIYYASNLPFGVPSRFKGSGSGTEFTLTISSLQPDDFATYYCQSADVGSTYVAAFGGGTKVEIK |
| 30 | VL-016-H5L2-C905-CDR1 | QNIDSN |
|  | VL-016-H5L2-C905-CDR2 | YAS |
| 31 | VL-016-H5L2-C905-CDR3 | QSADVGSTYVAA |
| 32 | VH-b12 | QVQLVQSGAEVKKPGASVKVSCQASGYRFSNFVIHWVRQAPGQRFEWMGWINPYNGNKEFSAKFQDRVTFTADTSANTAYMELRSLRSADTAVYYCARVGPYSWDDSPQDNYYMDVWGKGTTVIVSS |
| 33 | VH-b12-CDR1 | GYRFSNFV |
| 34 | VH-b12-CDR2 | INPYNGNK |
| 35 | VH-b12-CDR3 | ARVGPYSWDDSPQDNYYMDV |
| 36 | VL-b12 | EIVLTQSPGTLSLSPGERATFSCRSSHSIRSRRVAWYQHKPGQAPRLVIHGVSNRASGISDRFSGSGSGTDFTLTITRVEPEDFALYYCQVYGASSYTFGQGTKLERK |
| 37 | VL-b12-CDR1 | HSIRSRR |
|  | VL-b12-CDR2 | GVS |
| 38 | VL-b12-CDR3 | QVYGASSYT |
| 39 | VH-G28.1 | AVQLQQSGPELEKPGASVKISCKASGYSFTGYNMNWVKQNNGKSLEWIGNIDPYYGGTTYNRKFKGKATLTVDKSSSTAYMQLKSLTSEDSAVYYCARSVGPMDYWGQGTSVTVSS |
| 40 | VH-G28.1-CDR1 | GYSFTGYN |
| 41 | VH-G28.1-CDR2 | IDPYYGGT |
| 42 | VH-G28.1-CDR3 | ARSVGPMDY |
| 43 | VL-G28.1 | DIQMTQSPASLSASVGETVTITCRTSENVYSYLAWYQQKQGKSPQLLVSFAKTLAEGVPSRFSGSGSGTQFSLKISSLQPEDSGSYFCQHHSDNPWTFGGGTELEIK |

TABLE 1-continued

| SEQ ID NO: | LABEL | SEQUENCE |
|---|---|---|
| 44 | VL-G28.1-CDR1 | ENVYSY |
|  | VL-G28.1-CDR2 | FAK |
| 45 | VL-G28.1-CDR3 | QHHSDNPWT |
| 46 | VH-37.3 | QVQVKESGPGLVAPSQSLSITCTVSGFSLTTSGVSWVRQPPGKGLE WLGVIWGDGSTNYHSALKSRLSIKKDHSKSQVFLKLNSLQTDDTAT YYCAKGGYSLAHWGQGTLVTVSA |
| 47 | VH-37.3-CDR1 | GFSLTTSG |
| 48 | VH-37.3-CDR2 | IWGDGST |
| 49 | VH-37.3-CDR3 | AKGGYSLAH |
| 50 | VL-37.3 | DIQMTQSPASLSVSVGETVTITCRASENIRSNLAWYQQKGKSPQLL VNVATNLADGVPSRFSGSGSGTQYSLKINSLQSEDFGTYYCQHYWG TTWTFGGGTKLEIK |
| 51 | VL-37.3-CDR1 | ENIRSN |
|  | VL-37.3-CDR2 | VAT |
| 52 | VL-37.3-CDR3 | QHYWGTTWT |
| 53 | IgG1-Fc | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKRVEPKSCDKTHTCPPCPAPELLGGPSVFLFPPKPKDTLMISRTPEVT CVVVDVSHEDPEVKFNWYVDGVEVHNAKTKPREEQYNSTYRVVSVL TVLHQDWLNGKEYKCKVSNKALPAPIEKTISKAKGQPREPQVYTLPPS REEMTKNQVSLTCLVKGFYPSDIAVEWESNGQPENNYKTTPPVLDSD GSFFLYSKLTVDKSRWQQGNVFSCSVMHEALHNHYTQKSLSLSPGK |
| 54 | IgG1-Fc-delK | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKRVEPKSCDKTHTCPPCPAPELLGGPSVFLFPPKPKDTLMISRTPEVT CVVVDVSHEDPEVKFNWYVDGVEVHNAKTKPREEQYNSTYRVVSVL TVLHQDWLNGKEYKCKVSNKALPAPIEKTISKAKGQPREPQVYTLPPS REEMTKNQVSLTCLVKGFYPSDIAVEWESNGQPENNYKTTPPVLDSD GSFFLYSKLTVDKSRWQQGNVFSCSVMHEALHNHYTQKSLSLSPG. |
| 55 | IgG1-E430G-Fc | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKRVEPKSCDKTHTCPPCPAPELLGGPSVFLFPPKPKDTLMISRTPEVT CVVVDVSHEDPEVKFNWYVDGVEVHNAKTKPREEQYNSTYRVVSVL TVLHQDWLNGKEYKCKVSNKALPAPIEKTISKAKGQPREPQVYTLPPS REEMTKNQVSLTCLVKGFYPSDIAVEWESNGQPENNYKTTPPVLDSD GSFFLYSKLTVDKSRWQQGNVFSCSVMHGALHNHYTQKSLSLSPGK |
| 56 | IgG1-E345R-Fc | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKRVEPKSCDKTHTCPPCPAPELLGGPSVFLFPPKPKDTLMISRTPEVT CVVVDVSHEDPEVKFNWYVDGVEVHNAKTKPREEQYNSTYRVVSVL TVLHQDWLNGKEYKCKVSNKALPAPIEKTISKAKGQPRRPQVYTLPP SREEMTKNQVSLTCLVKGFYPSDIAVEWESNGQPENNYKTTPPVLDS DGSFFLYSKLTVDKSRWQQGNVFSCSVMHEALHNHYTQKSLSLSPG K |
| 57 | IgG1-F405L-Fc | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKRVEPKSCDKTHTCPPCPAPELLGGPSVFLFPPKPKDTLMISRTPEVT CVVVDVSHEDPEVKFNWYVDGVEVHNAKTKPREEQYNSTYRVVSVL TVLHQDWLNGKEYKCKVSNKALPAPIEKTISKAKGQPREPQVYTLPPS REEMTKNQVSLTCLVKGFYPSDIAVEWESNGQPENNYKTTPPVLDSD GSFLLYSKLTVDKSRWQQGNVFSCSVMHEALHNHYTQKSLSLSPGK |
| 58 | IgG1-K409R-Fc | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKRVEPKSCDKTHTCPPCPAPELLGGPSVFLFPPKPKDTLMISRTPEVT CVVVDVSHEDPEVKFNWYVDGVEVHNAKTKPREEQYNSTYRVVSVL TVLHQDWLNGKEYKCKVSNKALPAPIEKTISKAKGQPREPQVYTLPPS REEMTKNQVSLTCLVKGFYPSDIAVEWESNGQPENNYKTTPPVLDSD GSFFLYSRLTVDKSRWQQGNVFSCSVMHEALHNHYTQKSLSLSPGK |
| 59 | IgG1-F405L-E430G-Fc | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKRVEPKSCDKTHTCPPCPAPELLGGPSVFLFPPKPKDTLMISRTPEVT CVVVDVSHEDPEVKFNWYVDGVEVHNAKTKPREEQYNSTYRVVSVL |

TABLE 1-continued

| SEQ ID NO: | LABEL | SEQUENCE |
|---|---|---|
| | | TVLHQDWLNGKEYKCKVSNKALPAPIEKTISKAKGQPREPQVYTLPPS<br>REEMTKNQVSLTCLVKGFYPSDIAVEWESNGQPENNYKTTPPVLDSD<br>GSFLLYSKLTVDKSRWQQGNVFSCSVMHGALHNHYTQKSLSLSPGK |
| 60 | IgG1-K409R-<br>E430G-Fc | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKRVEPKSCDKTHTCPPCPAPELLGGPSVFLFPPKPKDTLMISRTPEVT<br>CVVVDVSHEDPEVKFNWYVDGVEVHNAKTKPREEQYNSTYRVVSVL<br>TVLHQDWLNGKEYKCKVSNKALPAPIEKTISKAKGQPREPQVYTLPPS<br>REEMTKNQVSLTCLVKGFYPSDIAVEWESNGQPENNYKTTPPVLDSD<br>GSFFLYSRLTVDKSRWQQGNVFSCSVMHGALHNHYTQKSLSLSPGK |
| 61 | Kappa-C | RTVAAPSVFIFPPSDEQLKSGTASVVCLLNNFYPREAKVQWKVDNAL<br>QSGNSQESVTEQDSKDSTYSLSSTLTLSKADYEKHKVYACEVTHQGL<br>SSPVTKSFNRGEC |
| 62 | Human CD37 | MSAQESCLSLIKYFLFVFNLFFFVLGSLIFCFGIWILIDKTSFVSFVGLA<br>FVPLQIWSKVLAISGIFTMGIALLGCVGALKELRCLLGLYFGMLLLLFA<br>TQITLGILISTQRAQLERSLRDVVEKTIQKYGTNPEETAAEESWDYVQ<br>FQLRCCGWHYPQDWFQVLILRGNGSEAHRVPCSCYNLSATNDSTIL<br>DKVILPQLSRLGHLARSRHSADICAVPAESHIYREGCAQGLQKWLHN<br>NLISIVGICLGVGLLELGFMTLSIFLCRNLDHVYNRLARYR |
| 63 | Cynomolgus<br>CD37 (mfCD37) | MSAQESCLSLIKYFLFVFNLFFFVLGSLIFCFGIWILIDKTSFVSFVGLA<br>FVPLQIWSKVLAISGVFTMGLALLGCVGALKELRCLLGLYFGMLLLLFA<br>TQITLGILISTQRAQLERSLQDIVEKTIQKYHTNPEETAAEESWDYVQF<br>QLRCCGWHSPQDWFQVLTLRGNGSEAHRVPCSCYNLSATNDSTILD<br>KVILPQLSRLGQLARSRHSTDICAVPANSHIYREGCARSLQKWLHNN<br>LISIVGICLGVGLLELGFMTLSIFLCRNLDHVYNRLARYR |
| 64 | CD37EC2-FcHis | MWWRLWWLLLLLLLLWPMVWARAQLERSLRDVVEKTIQKYGTNPEE<br>TAAEESWDYVQFQLRCCGWHYPQDWFQVLILRGNGSEAHRVPCSC<br>YNLSATNDSTILDKVILPQLSRLGHLARSRHSADICAVPAESHIYREG<br>CAQGLQKWLHNNPKSCDKTHTCPPCPAPEAEGAPSVFLFPPKPKDTL<br>MISRTPEVTCVVVDVSHEDPEVKFNWYVDGVEVHNAKTKPREEQYN<br>STYRVVSVLTVLHQDWLNGKEYKCKVSNKALPAPIEKTISKAKGQPR<br>EPQVYTLPPSREEMTKNQVSLTCLVKGFYPSDIAVEWESNGQPENNY<br>KTAPPVLDSDGSFFLYSKLTVDKSRWQQGNVFSCSVMHEALHNHYT<br>QKSLSLSPGKHHHHHHHH |
| 65 | CD37MfEC2-FcHis | MWWRLWLLLLLLLLWPMVWARAQLERSLQDIVEKTIQKYHTNPEE<br>TAAEESWDYVQFQLRCCGWHSPQDWFQVLTLRGNGSEAHRVPCSC<br>YNLSATNDSTILDKVILPQLSRLGQLARSRHSTDICAVPANSHIYREG<br>CARSLQKWLHNNPKSCDKTHTCPPCPAPEAEGAPSVFLFPPKPKDTL<br>MISRTPEVTCVVVDVSHEDPEVKFNWYVDGVEVHNAKTKPREEQYN<br>STYRVVSVLTVLHQDWLNGKEYKCKVSNKALPAPIEKTISKAKGQPR<br>EPQVYTLPPSREEMTKNQVSLTCLVKGFYPSDIAVEWESNGQPENNY<br>KTAPPVLDSDGSFFLYSKLTVDKSRWQQGNVFSCSVMHEALHNHYT<br>QKSLSLSPGKHHHHHHHH |
| 66 | IgG1-F405L-<br>E345R | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKRVEPKSCDKTHTCPPCPAPELLGGPSVFLFPPKPKDTLMISRTPEVT<br>CVVVDVSHEDPEVKFNWYVDGVEVHNAKTKPREEQYNSTYRVVSVL<br>TVLHQDWLNGKEYKCKVSNKALPAPIEKTISKAKGQPRRPQVYTLPP<br>SREEMTKNQVSLTCLVKGFYPSDIAVEWESNGQPENNYKTTPPVLDS<br>DGSFLLYSKLTVDKSRWQQGNVFSCSVMHEALHNHYTQKSLSLSPG<br>K |
| 67 | IgG1-F405L-<br>E345K | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKRVEPKSCDKTHTCPPCPAPELLGGPSVFLFPPKPKDTLMISRTPEVT<br>CVVVDVSHEDPEVKFNWYVDGVEVHNAKTKPREEQYNSTYRVVSVL<br>TVLHQDWLNGKEYKCKVSNKALPAPIEKTISKAKGQPRKPQVYTLPPS<br>REEMTKNQVSLTCLVKGFYPSDIAVEWESNGQPENNYKTTPPVLDSD<br>GSFLLYSKLTVDKSRWQQGNVFSCSVMHEALHNHYTQKSLSLSPGK |
| 68 | IgG1-F405L-<br>E430S | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKRVEPKSCDKTHTCPPCPAPELLGGPSVFLFPPKPKDTLMISRTPEVT<br>CVVVDVSHEDPEVKFNWYVDGVEVHNAKTKPREEQYNSTYRVVSVL<br>TVLHQDWLNGKEYKCKVSNKALPAPIEKTISKAKGQPREPQVYTLPPS<br>REEMTKNQVSLTCLVKGFYPSDIAVEWESNGQPENNYKTTPPVLDSD<br>GSFLLYSKLTVDKSRWQQGNVFSCSVMHSALHNHYTQKSLSLSPGK |
| 69 | IgG1-K409R-<br>E345R | ASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKV<br>DKRVEPKSCDKTHTCPPCPAPELLGGPSVFLFPPKPKDTLMISRTPEVT |

TABLE 1-continued

| SEQ ID NO: | LABEL | SEQUENCE |
|---|---|---|
| | | CVVVDVSHEDPEVKFNWYVDGVEVHNAKTKPREEQYNSTYRVVSVL TVLHQDWLNGKEYKCKVSNKALPAPIEKTISKAKGQPRRPQVYTLPP SREEMTKNQVSLTCLVKGFYPSDIAVEWESNGQPENNYKTTPPVLDS DGSFFLYSRLTVDKSRWQQGNVFSCSVMHEALHNHYTQKSLSLSPG K |
| 70 | IgG1-K409R-E345K | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKRVEPKSCDKTHTCPPCPAPELLGGPSVFLFPPKPKDTLMISRTPEVT CVVVDVSHEDPEVKFNWYVDGVEVHNAKTKPREEQYNSTYRVVSVL TVLHQDWLNGKEYKCKVSNKALPAPIEKTISKAKGQPRKPQVYTLPPS REEMTKNQVSLTCLVKGFYPSDIAVEWESNGQPENNYKTTPPVLDSD GSFFLYSRLTVDKSRWQQGNVFSCSVMHEALHNHYTQKSLSLSPGK |
| 71 | IgG1-K409R-E430S | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKRVEPKSCDKTHTCPPCPAPELLGGPSVFLFPPKPKDTLMISRTPEVT CVVVDVSHEDPEVKFNWYVDGVEVHNAKTKPREEQYNSTYRVVSVL TVLHQDWLNGKEYKCKVSNKALPAPIEKTISKAKGQPREPQVYTLPPS REEMTKNQVSLTCLVKGFYPSDIAVEWESNGQPENNYKTTPPVLDSD GSFFLYSRLTVDKSRWQQGNVFSCSVMHSALHNHYTQKSLSLSPGK |
| 72 | Human CD20 | MTTPRNSVNGTFPAEPMKGPIAMQSGPKPLFRRMSSLVGPTQSFFMR ESKTLGAVQIMNGLFHIALGGLLMIPAGIYAPICVTVWYPLWGGIMYII SGSLLAATEKNSRKCLVGKMIMNSLSLFAAISGMILSIMDILNIKISH FLKMESLNFIRAHTPYINIYNCEPANPSEKNSPSTQYCYSIQSLFLGILS VMLIFAFFQELVIAGIVENEWKRTCSRPKSNIVLLSAEEKKEQTIEIKE EVVGLTETSSQPKNEEDIEIIPIQEEEEEETETNFPEPPQDQESSPIEN DSSP |
| 73 | Cynomolgus monkey CD20 | MTTPRNSVNGTFPAEPMKGPIAMQPGPKPLLRRMSSLVGPTQSFFMR ESKALGAVQIMNGLFHIALGGLLMIPAGIYAPICVTVWYPLWGGIMYII SGSLLAATEKNSRKCLVGKMIMNSLSLFAAISGMILSIMDILNIKISH FLKMESLNFIRVHTPYINIYNCEPANPSEKNSPSTQYCYSIQSLFLGILS VMLIFAFFQELVIAGIVENEWRRTCSRPKSSVVLLSAEEKKEQVIEIKE EVVGLTETSSQPKNEEDIEIIPIQEEEEEETETNFPEPPQDQESSPIEN DSSP |
| 74 | VH CD20-7D8 | EVQLVESGGGLVQPDRSLRLSCAASGFTFHDYAMHWVRQAPGKGL EWVSTISWNSGTIGYADSVKGRFTISRDNAKNSLYLQMNSLRAEDT ALYYCAKDIQYGNYYYGMDVWGGTTVTVSS |
| 75 | VH CD20-7D8 CDR1 | GFTFHDYA |
| 76 | VH CD20-7D8 CDR2 | ISWNSGTI |
| 77 | VH CD20-7D8 CDR3 | AKDIQYGNYYYGMDV |
| 78 | VL CD20-7D8 | EIVLTQSPATLSLSPGERATLSCRASQSVSSYLAWYQQKPGQAPRLL IYDASNRATGIPARFSGSGSGTDFTLTISSLEPEDFAVYYCQQRSNW PITFGQGTRLEIK |
| 79 | VL CD20-7D8 CDR1 | QSVSSY |
| | VL CD20-7D8 CDR2 | DAS |
| 80 | VL CD20-7D8 CDR3 | QQRSNWPIT |
| 81 | VH CD20-11B8 | EVQLVQSGGGLVHPGGSLRLSCTGSGFTFSYHAMHWVRQAPGKGL EWVSIIGTGGVTYYADSVKGRFTISRDNVKNSLYLQMNSLRAEDMA VYYCARDYYGAGSFYDGLYGMDVWGGTTVTVSS |
| 82 | VH CD20-11B8 CDR1 | GFTFSYHA |
| 83 | VH CD20-11B8 CDR2 | IGTGGVT |
| 84 | VH CD20-11B8 CDR3 | ARDYYGAGSFYDGLYGMDV |

TABLE 1-continued

| SEQ ID NO: | LABEL | SEQUENCE |
|---|---|---|
| 85 | VL CD20-11B8 CDR1 | QSVSSY |
|  | VL CD20-11B8 CDR2 | DAS |
| 86 | VL CD20-11B8 CDR3 | QQRSDWPLT |
| 87 | VH CD20-ofatumumab | EVQLVESGGGLVQPGRSLRLSCAASGFTFNDYAMHWVRQAPGKGL EWVSTISWNSGSIGYADSVKGRFTISRDNAKKSLYLQMNSLRAEDT ALYYCAKDIQYGNYYYGMDVWGGTTVTVSS |
| 88 | VL CD20-ofatumumab CDR1 | GFTFNDYA |
| 89 | VH CD20-ofatumumab CDR2 | ISWNSGSI |
| 90 | VH CD20-ofatumumab CDR3 | AKDIQYGNYYYGMDV |
| 91 | VL CD20-ofatumumab | EIVLTQSPATLSLSPGERATLSCRASQSVSSYLAWYQQKPGQAPRLL IYDASNRATGIPARFSGSGSGTDFTLTISSLEPEDFAVYYCQQRSNW PITFGQGTRLEIK |
| 92 | VL CD20-ofatumumab CDR1 | QSVSSY |
|  | VL CD20-ofatumumab | DAS |
| 93 | VL CD20-ofatumumab CDR3 | QQRSNWPIT |
| 94 | VH CD20-rituximab | QVQLQQPGAELVKPGASVKMSCKASGYTFTSYNMHWVKQTPGRG LEWIGAIYPGNGDTSYNQKFKGKATLTADKSSSTAYMQLSSLTSED SAVYYCARST YYGGDWYFNVWGAGTTVTVSA |
| 95 | VH CD20-rituximab CDR1 | GYTFTSYN |
| 96 | VH CD20-rituximab CDR2 | IYPGNGDT |
| 97 | VH CD20-rituximab CDR3 | ARSTYYGGDWYFNV |
| 98 | VL CD20-rituximab | QIVLSQSPAILSASPGEKVTMTCRASSSVSYIHWFQQKPGSSPKPWI YATSNLASGVPVRFSGSGSGTSYSLTISRVEAEDAATYYCQQWTSN PPT**FGGGTKLEIK |
| 99 | VL CD20-rituximab CDR1 | SSVSY |
|  | VL CD20-rituximab CDR2 | ATS |
| 100 | VL CD20-rituximab CDR3 | QQWTSNPPT |
| 101 | VH CD20-obinutuzumab | QVQLVQSGAEVKKPGSSVKVSCKASGYAFSYSWINWVRQAPGQG LEWMGRIFPGDGDTDYNGKFKGRVTITADKSTSTAYMELSSLRSED TAVYYCARNVFDGYWLVYWGQGTLVTVSS |
| 102 | VH CD20-obinutuzumab CDR1 | GYAFSYSW |

TABLE 1-continued

| SEQ ID NO: | LABEL | SEQUENCE |
|---|---|---|
| 103 | VH CD20-obinutuzumab CDR2 | IFPGDGDT |
| 104 | VH CD20-obinutuzumab CDR3 | ARNVFDGYWLVY |
| 105 | VL CD20-obinutuzumab | DIVMTQTPLSLPVTPGEPASISCRSSKSLLHSNGITYLYWYLQKPGQSPQLLIYQMSNLVSGVPDRFSGSGSGTDFTLKISRVEAEDVGVYYCAQNLELPYTFGGGTKVEIK |
| 106 | VL CD20-obinutuzumab CDR1 | KSLLHSNGITY |
|  | VL CD20-obinutuzumab CDR2 | QMS |
| 107 | VL CD20-obinutuzumab CDR3 | AQNLELPYT |
| 108 | IgG1-S239D-I332E | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPDVFLFPPKPKDTLMISRTPEVTCVVVDVSHEDPEVKFNWYVDGVEVHNAKTKPREEQYNSTYRVVSVLTVLHQDWLNGKEYKCKVSNKALPAPEEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 109 | VL CD20 1188 | EIVLTQSPATLSLSPGERATLSCRASQSVSSYLAWYQQKPGQAPRLLIYDASNRATGIPARFSGSGSGTDFTLTISSLEPEDFAVYYCQQRSDWPLTFGGGTKVEIK |
| 110 | VH CD37-004 | QSVEESGGRLVTPGTPLTLTCTVSGFSLSTYDMSWVRQAPGKGLEWIGIIYSSVGAYYASWAKGRFTFSKTSTTVDLKITSPTTEDTATYFCAREYGASSSDYIFSLWGQGTLVTVSS |
| 2 | VH CD37-004 CDR1 | GFSLSTYD |
| 3 | VH CD37-004 CDR2 | IYSSVGA |
| 4 | VH CD37-004 CDR3 | AREYGASSSDYIFSL |
| 111 | VL CD37-004 | AQVLTQTPSPVSAAVGGTVTINCQASQSVYNSQNLAWYQQKPGQPPKLLIYEASKLASGVPSRFKGSGSGTQFTLTISGVQSDDAATYYCQGEFSCISADCTAFGGGTEVVVK |
| 6 | VL CD37-004 CDR1 | QSVYNSQN |
|  | VL CD37-004 CDR2 | EAS |
| 7 | VL CD37-004 CDR3 | QGEFSCISADCTA |
| 112 | VH CD37-005 | QSVEESGGRLVTPGTPLTLTCTVSGFSLSSNAMNWVRQAPGKGLEWIGLIYASGNTDYASWAKGRFTISKTSTTVDLKITSPTTEDTATYFCAREGSVWGAAFDPWGPGTLVTVSS |
| 9 | VH CD37-005 CDR1 | GFSLSSNA |
| 10 | VH CD37-005 CDR2 | IYASGNT |
| 11 | VH CD37-005 CDR3 | AREGSVWGAAFDP |
| 113 | VL CD37-005 | AYDMTQTPASVEVAVGGTVTIKCQASQSISNWLAWYQQKPGQPPKQLIYAASTLASGVPSRFKGSGSGTQFTLTISGVESADAATYYCQQGYSNSNIDNTFGGGTEVVVK |

TABLE 1-continued

| SEQ ID NO: | LABEL | SEQUENCE |
|---|---|---|
| 13 | VL CD37-005 CDR1 | QSISNW |
|  | VL CD37-005 CDR2 | AAS |
| 14 | VL CD37-005 CDR3 | QQGYSNSNIDNT |
| 114 | VH CD37-010 | QSVEESGGRLVTPGTPLTLTCTVSGFSLSYNAMNWVRQAPGKGLEWI GIIFASGRTDYASWAKGRFTISKTSTTVELKITSPTTEDTATYFCAREG STWGDALDPWGPGTLVTVSS |
| 16 | VH CD37-010 CDR1 | GFSLSYNA |
| 17 | VH CD37-010 CDR2 | IFASGRT |
| 18 | VH CD37-010 CDR3 | AREGSTWGDALDP |
| 115 | VL CD37-010 | AYDMTQTPSSVEAAVGGTVTIKCQASQNIIDYLAWYQQKPGQPPQLL IHKASTLASGVPSRFKGSGSGTQFTLTISGVQSDDAATYYCQQGYSN SNIDNTFGGGTEVVVK |
| 20 | VL CD37-010 CDR1 | QNIIDY |
|  | VL CD37-010 CDR2 | KAS |
| 21 | VL CD37-010 CDR3 | QQGYSNSNIDNT |
| 116 | VH CD37-016 | QSVEESGGRLVTPGTPLTLTCTVSGFSLSNYNMGWVRQAPGKGLEW IGVIDASGTTYYATWAKGRFTCSKTSSTVELKMTSLTTEDTATYFCAR ELLYFGSSYYDLWGQGTLVTVSS |
| 23 | VH CD37-016 CDR1 | GFSLSNYN |
| 24 | VH CD37-016 CDR2 | IDASGTT |
| 25 | VH CD37-016 CDR3 | ARELLYFGSSYYDL |
| 117 | VL CD37-016 | DVVMTQTPASVSEPVGGTVTIKCQASQNIDSNLAWYQQKPGQPPKF LIYYASNLPFGVSSRFKGSGSGTQFTLTISDLESADAATYYCQCADVG STYVAAFGGGTEVVVK |
| 27 | VL CD37-016 CDR1 | QNIDSN |
|  | VL CD37-016 CDR2 | YAS |
| 28 | VL CD37-016 CDR3 | QCADVGSTYVAA |

EXAMPLES

Example 1: Generation of CD37 Specific Antibodies in Rabbits

Expression Constructs for CD37

The following codon-optimized constructs for expression of full-length CD37 variants were generated: human (*Homo sapiens*) CD37 (Genbank accession no. NP_001765) (SEQ ID NO: 62), cynomolgus monkey (*Macaca fascicularis*) CD37 ((mfCD37) (SEQ ID NO: 63). In addition, the following codon-optimized constructs for expression of various CD37 ECD variants were generated: a signal peptide encoding sequence followed by the second extracellular domain (EC2) of human CD37 (aa 112-241), fused to the Fc (CH2-CH3) domain of human IgG with a C-terminal His tag (CD37EC2-FcHis, SEQ ID NO: 64), and a similar construct for mfCD37 (CD37mfEC2-FcHis, SEQ ID NO: 65). The constructs contained suitable restriction sites for cloning and an optimal Kozak (GCCGCCACC) sequence [Kozak et al. (1999) Gene 234: 187-208]. The constructs were cloned in the mammalian expression vector pcDNA3.3 (Invitrogen) or an equivalent vector.

Transient Expression in CHO and HEK Cells

Membrane proteins were transiently transfected in Freestyle 293-F (HEK293F) cells (Life technologies, USA)

using 293fectin (Life technologies) essentially as described by the manufacturer, or in Freesyle CHO-S cells (CHO) (Life technologies) by using the Freestyle Max reagent (Life technologies) essentially as described by the manufacturer. Soluble proteins were transiently expressed in Expi293 cells (Life technologies) by using the ExpiFectamine 293 reagent (Life technologies), essentially as described by the manufacturer.

The Fc fusion proteins (CD37mfEC2-FcHis and CD37EC2-FcHis) were purified from cell culture supernatant using protein A affinity chromatography.

Immunization of Rabbits

Immunization of rabbits was performed at MAB Discovery GMBH (Neuried, Germany). Rabbits were repeatedly immunized with a mixture of CD37EC2-FcHis and CD37mfEC2-FcHis or HEK293F cells transiently expressing human or mfCD37. The blood of these animals was collected and B lymphocytes were isolated. Using a MAB Discovery proprietary process, single B-cells were sorted into wells of microtiter plates and further propagated. The supernatants of these single B-cells were analyzed for specific binding to CHO-S cells transiently expressing CD37 (CHO-CD37) and mfCD37 (CHO-mfCD37).

Recombinant Antibody Production

Upon analyzing the primary screening results, primary hits were selected for sequencing, recombinant mAb production and purification. Unique variable heavy chain (VH) and light chain (VL) encoding regions were gene synthesized and cloned into mammalian expression vectors containing the human IgG1 constant region encoding sequences (Ig Kappa chain and IgG1 allotype G1m (f) containing an E430G mutation (EU numbering) heavy chain). During this process an unfavorable, unpaired cysteine in some antibody light chains was replaced by a serine.

Recombinant chimeric antibodies were produced in HEK 293 cells by transiently cotransfecting the heavy chain (HC) and light chain (LC) encoding expression vectors using an automated procedure on a Tecan Freedom Evo platform. Immunoglobulins were purified from the cell supernatant using affinity purification (Protein A) on a Dionex Ultimate 3000 HPLC system.

The reactivity of the produced chimeric (VH rabbit, Fc human) monoclonal antibodies (mAbs) containing a mutation E430G was re-analyzed for binding to CHO-CD37 or CHO-mfCD37 cells. In addition, binding to the human lymphoma cell line Daudi and functionality in the CDC assay on Daudi cells was analyzed.

Example 2: Humanization of Rabbit Chimeric Antibodies

Generation of Humanized Antibody Sequences

Humanized antibody sequences from rabbit antibodies rabbit-anti-CD37-004, -005, -010 and -016 were generated at Antitope (Cambridge, UK). Humanized antibody sequences were generated using germline humanization (CDR-grafting) technology. Humanized V region genes were designed based upon human germline sequences with closest homology to the VH and Vκ amino acid sequences of the rabbit and murine antibodies. A series of four to six VH and four or five VK (VL) germline humanized V-region genes were designed for each of the rabbit antibodies.

Structural models of the rabbit antibody V regions were produced using Swiss PDB and analyzed in order to identify amino acids in the V region frameworks that may be important for the binding properties of the antibody. These amino acids were noted for incorporation into one or more variant CDR-grafted antibodies.

The heavy and light chain V region amino acid sequence were compared against a database of human germline V and J segment sequences in order to identify the heavy and light chain human sequences with the greatest degree of homology for use as human variable domain frameworks. The germline sequences used as the basis for the humanized designs are shown in Table 2.

TABLE 2

Closest matching human germline V segment and J segment sequences.

| | Heavy chain | | Light chain (κ) | |
|---|---|---|---|---|
| Rabbit anti-CD37- | Human V region germline segment | Human J region germline segment | Human V region germline segment | Human J region germline segment |
| 004 | IGHV3-53*04 | IGHJ4 | IGKV1-5*01 | IGKJ4 |
| 005 | IGHV3-53*04 | IGHJ4 | IGKV1-12*01 | IGKJ4 |
| 010 | IGHV3-53*04 | IGHJ4 | IGKV1-5*03 | IGKJ4 |
| 016 | IGHV3-53*04 | IGHJ4 | IGKV1-12*01 | IGKJ4 |

A series of humanized heavy and light chain V regions were then designed by grafting the CDRs onto the frameworks and, if necessary, by back-mutating residues which may be critical for the antibody binding properties, as identified in the structural modelling, to rabbit residues. Variant sequences with the lowest incidence of potential T cell epitopes were then selected using Antitope's proprietary in silico technologies, iTope™ and TCED™ (T Cell Epitope Database) (Perry, L. C. A, Jones, T. D. and Baker, M. P. New Approaches to Prediction of Immune Responses to Therapeutic Proteins during Preclinical Development (2008). Drugs in R&D 9 (6): 385-396; Bryson, C. J., Jones, T. D. and Baker, M. P. Prediction of Immunogenicity of Therapeutic Proteins (2010). Biodrugs 24 (1):1-8). Finally, the nucleotide sequences of the designed variants have been codon-optimized.

For antibody IgG1-016-H5L2 a variant with a point mutation in the variable domain was generated to replace a free cysteine: IgG1-016-H5L2-LC90S (also generated with additional F405L and E430G mutations). This mutant was generated by gene synthesis (Geneart).

The variable region sequences of the humanized CD37 antibodies are shown in the Sequence Listing herein and in Table 1 above.

Example 3: Generation of Bispecific Antibodies

Bispecific IgG1 antibodies were generated by Fab-arm-exchange under controlled reducing conditions. The basis for this method is the use of complementary CH3 domains, which promote the formation of heterodimers under specific assay conditions as described in WO2011/131746. The F405L and K409R (EU numbering) mutations were introduced in CD37 antibodies to create antibody pairs with complementary CH3 domains. The F405L and K409R mutations were in certain cases combined with E430G mutation.

To generate bispecific antibodies, the two parental complementary antibodies, each antibody at a final concentration of 0.5 mg/mL, were incubated with 75 mM 2-mercaptoethylamine-HCl (2-MEA) in a total volume of 100 μL TE at 31° C. for 5 hours. The reduction reaction was stopped by removing the reducing agent 2-MEA using spin columns (Microcon centrifugal filters, 30 k, Millipore) according to the manufacturer's protocol.

Example 4: Expression Constructs for Antibodies, Transient Expression and Purification For antibody expression the VH and VL sequences were cloned in expression vectors (pcDNA3.3) containing, in case of the VH, the relevant constant heavy chain (HC), in certain cases containing a F405L or K409R mutation and/or an E345R or E430G mutation, and, in case of the VL, light chain (LC) regions.

Antibodies were expressed as IgG1,κ. Plasmid DNA mixtures encoding both heavy and light chains of antibodies were transiently transfected in Expi293F cells (Life technologies, USA) using 293fectin (Life technologies) essentially as described by Vink et al. (Vink et al., Methods, 65 (1), 5-10 2014). Next, antibodies were purified by immobilized protein G chromatography.

The following antibodies were used in the examples:
Wild-Type IgG1 Antibodies:
IgG1-004-H5L2 (having the VH and VL sequences set forth in SEQ ID NO:1 and SEQ ID NO:5)
IgG1-005-H1L2 (having the VH and VL sequences set forth in SEQ ID NO:8 and SEQ ID NO:12)
IgG1-010-H5L2 (having the VH and VL sequences set forth in SEQ ID NO:15 and SEQ ID NO:19)
IgG1-016-H5L2 (having the VH and VL sequences set forth in SEQ ID NO:22 and SEQ ID NO:26)
IgG1-G28.1 (having the VH and VL sequences set forth in SEQ ID NO:39 and SEQ ID NO:43—based on SEQ ID No 1 and 3 in EP2241577)
IgG1-G28.1-K409R-delK (also containing a C-terminal heavy chain mutation 445-PG-446)
IgG1-37.3 (having the VH and VL sequences set forth in SEQ ID NO:46 and SEQ ID NO:50—based on SEQ ID No 55 and 72 in WO2011/112978)
IgG1-b12 ((having the VH and VL sequences set forth in SEQ ID NO:32 and SEQ ID NO:36—based on the gp120 specific antibody b12 [Barbas, CF. J Mol Biol. 1993 Apr. 5; 230(3):812-23])
IgG1 Antibodies with Fc-Fc Interaction-Enhancing Mutation E430G:
IgG1-004-H5L2-E430G
IgG1-005-H1L2-E430G
IgG1-010-H5L2-E430G
IgG1-016-H5L2-E430G
IgG1-G28.1-E430G
IgG1-37.3-E430G
IgG1-b12-E430G
IgG1-005-H1L2-K409R-E430G
IgG1-010-H5L2-K409R-E430G
IgG1-016-H5L2-F405L-E430G
IgG1-016-H5L2-LC90S-F405L-E430G
IgG1-004-E430G
IgG1-005-E430G
IgG1-010-E430G
IgG1-016-E430G
IgG1 Antibodies with Fc-Fc Interaction-Enhancing Mutation E430S:
IgG1-010-H5L2-K409R-E430S
IgG1-016-H5L2-F405L-E430S
IgG1 Antibodies with Fc-Fc Interaction Enhancing Mutation E345K:
IgG1-010-H5L2-K409R-E345K
IgG1-016-H5L2-F405L-E345K
IgG1 Antibodies with Fc-Fc Interaction Enhancing Mutation E345R:
IgG1-G28.1-E345R
IgG1-b12-E345R
IgG1-010-H5L2-K409R-E345R
IgG1-016-H5L2-F405L-E345R
Bispecific Antibodies
bsIgG1-016-H5L2-F405LxIgG1-IgG1-005-H1L2-K409R
bsIgG1-016-H5L2-F405LxIgG1-010-H5L2-K409R
Bispecific Antibodies with Fc-Fc Interaction Enhancing Mutation E430G:
bsIgG1-016-H5L2-LC90S-F405L-E430Gx005-H1L2-K409R-E430G
bsIgG1-016-H5L2-LC90S-F405L-E430Gx010-H5L2-K409R-E430G
bsIgG1-016-H5L2-LC90S-F405L-E430Gxb12-K409R-E430G
bsIgG1-b12-F405L-E430Gx010-H5L2-K409R-E430G
bsIgG1-b12-F405L-E430Gx005-H1L2-K409R-E430G
IgG1 antibody with FcγR-interaction enhancing mutation S239D-I332E:
IgG1-G28.1-S239D-I332E Example 5: Introduction of an Fc-Fc Interaction Enhancing Mutation into CD37 Antibodies Results in Enhanced, De Novo Capacity to Induce Complement Dependent Cytotoxicity (CDC)

Determination of Complement Dependent Cytotoxicity (CDC)

In a first experiment, tumor cells derived from an untreated CLL patient (AllCells, California, USA), were resuspended in RPMI containing 0.2% BSA (bovine serum albumin) and plated into polystyrene 96-well round-bottom plates (Greiner bio-one Cat #650101) at a density of $0.2 \times 10^5$ cells/well (40 μL/well) and 40 μL of a concentration series of IgG1-G28.1-K409R-delK, IgG1-G28.1-6345R or IgG1-b12-6345R (0.003-10 μg/mL final antibody concentration). IgG1-b12-E345R (based on the gp120 specific antibody b12 [Barbas, CF. J Mol Biol. 1993 Apr. 5; 230(3):812-23]) was used as negative control. For IgG1-G28.1-K409R-delK, it should be noted that the K409R mutation has no effect on binding capacity or capacity to induce CDC. Similarly, the delK (445-PG-446) mutation, which had been introduced into the antibody to facilitate biochemical analysis, did not affect target binding or capacity to induce CDC (see below).

After incubation (RT, 10 min while shaking), 20 μL of pooled normal human serum (NHS Cat #M0008 Sanquin, Amsterdam, The Netherlands) was added to each well as a source of complement and plates were incubated at 37° C. for 45 minutes. The reaction was stopped by cooling the plates on ice. Next, propidium iodide (PI; 10 μL of a 10 μg/mL solution; Sigma-Aldrich Chemie B.V., Zwijndrecht, The Netherlands) was added and lysis was detected by measurement of the percentage of dead cells (corresponding to PI-positive cells) by flow cytometry (FACS Canto II; BD Biosciences). Graphs were generated using best-fit values of a non-linear dose-response fit with log-transformed concentrations in GraphPad Prism V6.04 software (GraphPad Software, San Diego, Calif., USA).

In a second experiment, tumor cells from another untreated CLL patient (AllCells, California, USA) were resuspended in RPMI containing 0.2% BSA, were plated into polystyrene 96-well round-bottom plates (Greiner bio-one Cat #650101) at a density of $0.5 \times 10^5$ cells/well (30 μL/well) and 50 μL of a concentration series of IgG1-G28.1, IgG1-G28.1-6430G or IgG1-b12 was added (0.003-10

µg/mL final antibody concentration in 3.33× serial dilutions). After incubation (RT, 15 min), 20 µL of pooled normal human serum (NHS Cat #M0008 Sanquin, Amsterdam, The Netherlands) was added to each well as a source of complement and plates were incubated at 37° C. for 45 minutes. The reaction was stopped by cooling the plates on ice. Next, propidium iodide (PI; 20 µL of a 10 µg/mL solution; Sigma-Aldrich Chemie B.V., Zwijndrecht, The Netherlands) was added and lysis was detected by measurement of the percentage of dead cells (corresponding to PI-positive cells) by flow cytometry (FACS Canto II; BD Biosciences). Graphs were generated using best-fit values of a non-linear dose-response fit with log-transformed concentrations in GraphPad Prism V6.04 software (GraphPad Software, San Diego, Calif., USA).

Figure 1A:
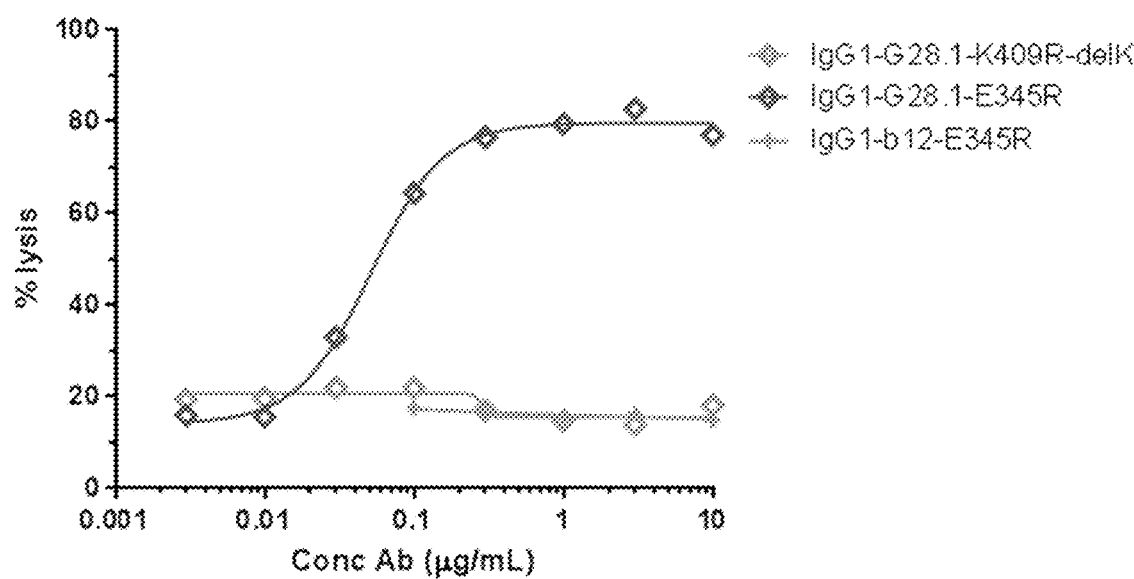
FIGS. 1A and 1B: CDC mediated by G28.1 variants on primary CLL tumor cells. The capacity to induce CDC on primary CLL tumor cells of (FIG. 1A) IgG1-G28.1-K409R-delK, IgG1-G28.1-E345R or IgG1-b12-E345R (cells: Patient derived, Newly Diagnosed/Untreated (PB=peripheral blood derived)) and (FIG. 1B) IgG1-G28.1, IgG1-G28.1-E430G or IgG1-b12 (cells: Patient derived, Newly Diagnosed/Untreated (BM=bone marrow derived)) was determined in vitro. Data shown are % lysis determined by measurement of the percentage of dead cells (corresponding to PI-positive cells) by flow cytometry.
Figure 1B:
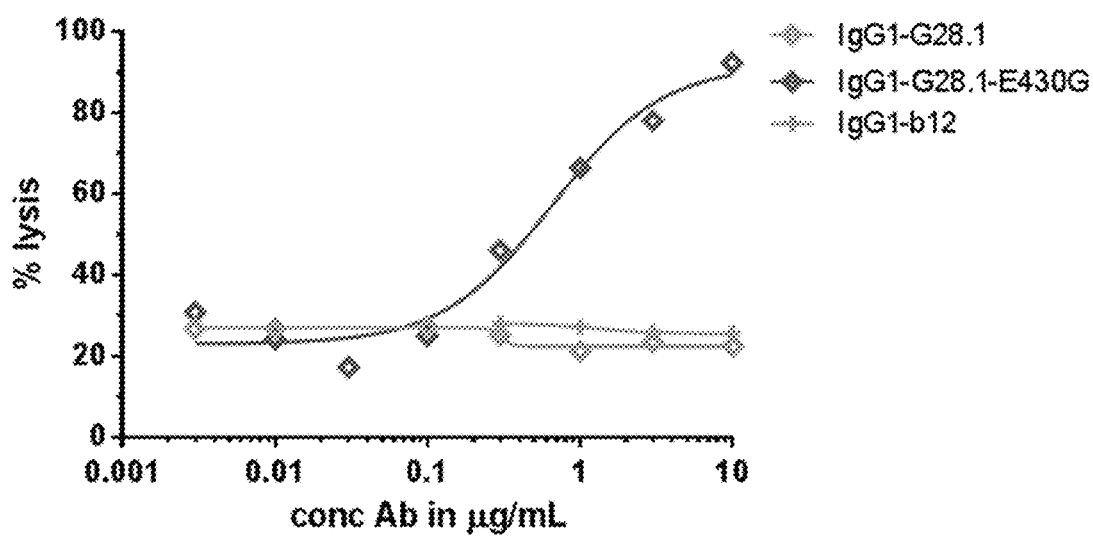

FIGS. 1A and B show that CD37 antibody G28.1 without the Fc-Fc interaction enhancing E345R or E430G mutation (IgG1-G28.1 or IgG1-G28.1-K409R-delK) did not induce CDC on primary tumor cells from CLL patients, whereas G28.1 with the Fc-Fc interaction enhancing mutations E345R or E430G (IgG1-G28.1-E345R or IgG1-G28.1-E430G) induced profound, dose-dependent CDC of primary CLL cells.

Quantitative Determination of Cell Surface Antigens by Flow Cytometry (Qifi)

The CD37 and membrane complement regulatory proteins (mCRP; CD46, CD55 and CD59) expression levels on CLL tumor cells were determined using the Human IgG Calibrator Kit (Biocytix Cat #CP010). Briefly, tumor cells derived from a CLL patient (as in first experiment described above), resuspended in RPMI containing 0.2% BSA, were plated into polystyrene 96-well round-bottom plates (Greiner bio-one Cat #650101) at a density of 0.5×10⁵ cells/well (30 µL/well), centrifuged and 50 µL of CD37 (Abcam, cat. no. 76522) or control mouse antibody (Purified Mouse IgG1,κ Isotype Control, Clone MOPC-21; BD cat. no. 555746) was added. After incubation (4° C., 30 min), 50 µL of calibration beads were added into separate wells. After washing the beads and cells twice (150 µL FACS buffer, centrifuging for 3 minutes at 300×g at 4° C. in between wash steps), 50 µL/well secondary antibody (FITC-conjugated) dilution, as provided in the Human IgG Calibrator Kit, was added. After incubation in the dark (4° C., 45 min) cells were washed twice with FACS buffer and cells were resuspended in 35 µL FACS buffer and analyzed by flow cytometry (Intellicyt iQue™ screener). The antigen quantity was determined by calculating the antibody-binding capacity based on the calibration curve, according to the manufacturer's guidelines.

Figure 2:
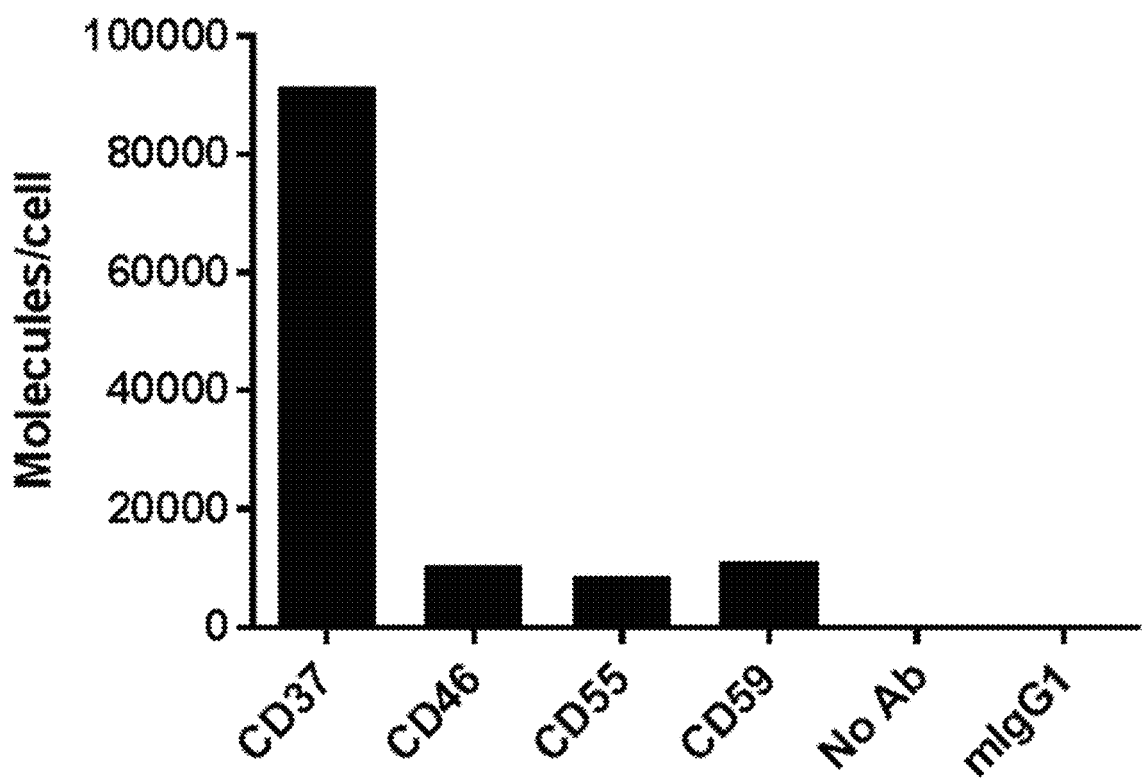
FIG. 2: Quantitative determination of CD37, CD46, CD55 and CD59 expression levels on CLL tumor cells. Expression levels of CD37, CD46, CD55 and CD59 on CLL cells from one patient (Patient VM-PB0005 Newly Diagnosed/Untreated) were determined by flow cytometry. Antigen quantity is shown as molecules/cell. mIgG1 is Mouse IgG1,κ Isotype Control.

FIG. 2 shows that CD37 was highly expressed on primary tumor cells from this CLL patient. The patient showed normal expression levels of mCRP's.

Example 6: Binding of CD37 Antibodies and Variants Thereof to Cell Surface Expressed CD37

Binding to cell surface expressed CD37 (Daudi cells, CHO cells expressing cynomolgus CD37) was determined by flow cytometry. Cells, resuspended in RPMI containing 0.2% BSA, were seeded at 100,000 cells/well in polystyrene 96 well round-bottom plates (Greiner bio-one Cat #650101) and centrifuged for 3 minutes at 300×g, 4° C. Serial dilutions (0.003-10 µg/mL final antibody concentration in 3.33× serial dilutions) of CD37 or control antibodies were added and cells were incubated for 30 minutes at 4° C. Plates were washed/centrifuged twice using FACS buffer (PBS/0.1% BSA/0.01% Na-Azide). Next, cells were incubated for 30 minutes at 4° C. with R-Phycoerythrin (PE)-conjugated goat-anti-human IgG F(ab')2 (Jackson ImmunoResearch Laboratories, Inc., West Grove, Pa.; cat #: 109-116-098) diluted 1/100 in PBS/0.1% BSA/0.01% Na-Azide. Cells were washed/centrifuged twice using FACS buffer, resuspended in 30 µL FACS buffer and analyzed by determining mean fluorescent intensities using an Intellicyt iQue™ screener (Westburg). Binding curves were generated using non-linear regression (sigmoidal dose-response with variable slope) analyses within GraphPad Prism V6.04 software (GraphPad Software, Sand Diego, Calif., USA).

Binding to Daudi Cells

Figure 3:
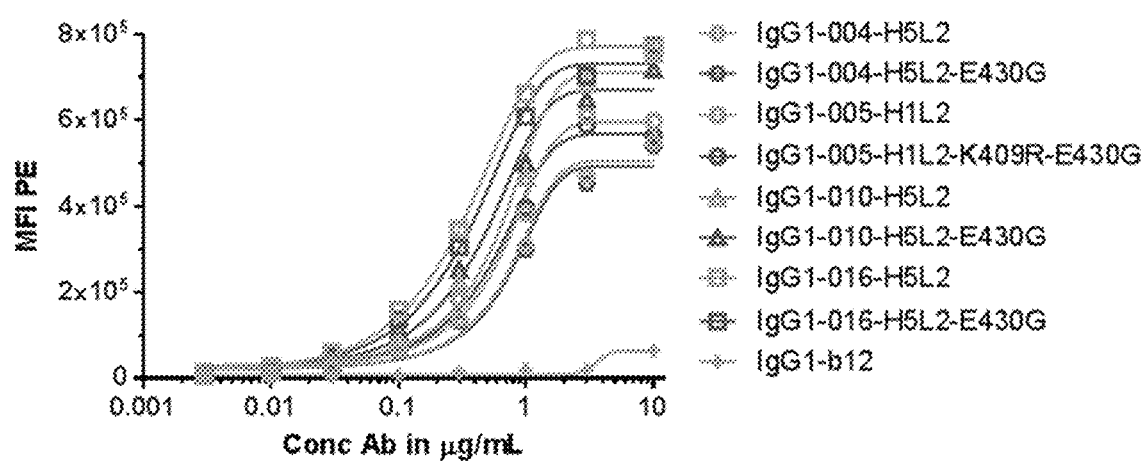
FIG. 3: Binding of humanized CD37 antibodies and variants thereof to Daudi cells. Binding of IgG1-004-H5L2, IgG1-004-H5L2-E430G, IgG1-005-H1L2, IgG1-005-H1L2-E430G, IgG1-010-H5L2, IgG1-010-H5L2-E430G, IgG1-016-H5L2 and IgG1-016-H5L2-E430G to Daudi cells was determined by flow cytometry. Data shown are mean fluorescence intensity (MFI) values, for one representative experiment.

FIG. 3 shows that humanized CD37 antibodies IgG1-004-H5L2, IgG1-005-H1L2, IgG1-010-H5L2 and IgG1-016-H5L2 showed dose-dependent binding to Daudi cells. Introduction of the Fc-Fc interaction enhancing E430G mutation, and for IgG1-005-H1L2 also the K409R mutation, into these antibodies did not affect the binding.

Figure 4:
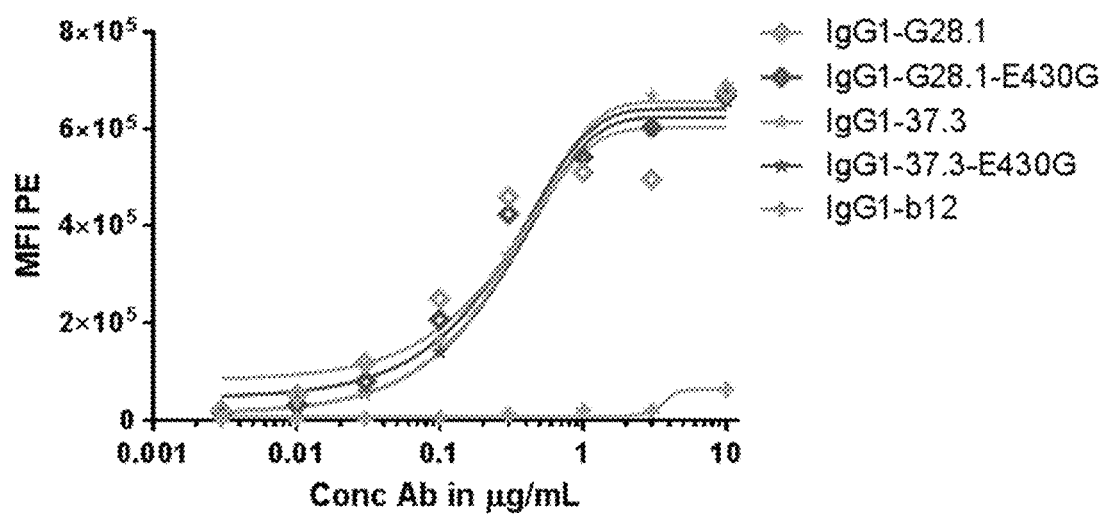
FIG. 4: Binding of G28.1 and 37.3 and variants thereof to Daudi cells. Binding of IgG1-G28.1, IgG1-G28.1-E430G, IgG1-37.3 and IgG1-37.3-E430G to Daudi cells was determined by flow cytometry. Data shown are mean fluorescence intensity (MFI) values, for one representative experiment.

FIG. 4 shows that introduction of the E430G mutation into IgG1-G28.1 or IgG1-37.3 did not affect the binding to Daudi cells.

Figure 5:
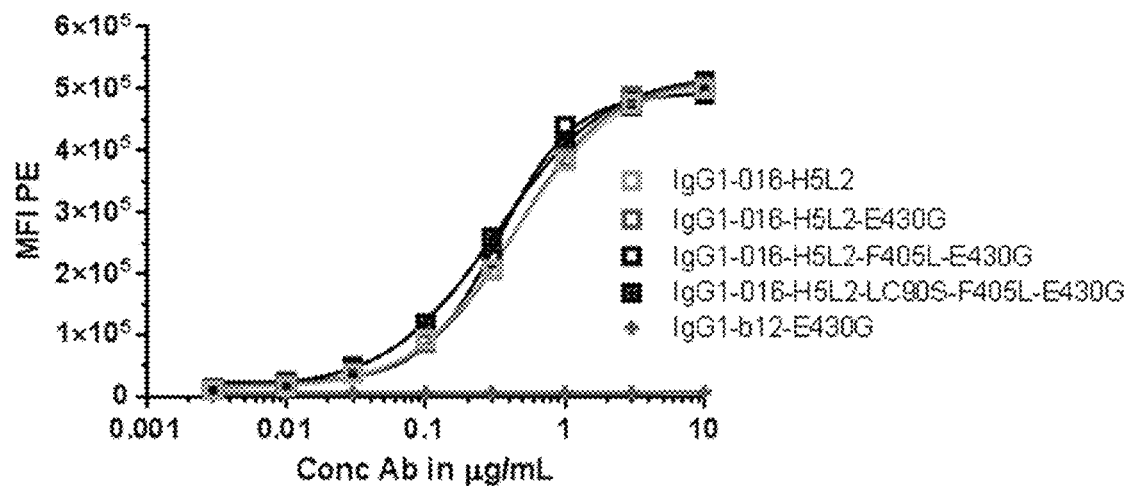
FIG. 5: Binding of variants of humanized CD37 antibody IgG1-016-H5L2 to Daudi cells. Binding of IgG1-016-H5L2, IgG1-016-H5L2-E430G, IgG1-016-H5L2-F405L-E430G and IgG1-016-H5L2-LC90S-F405L-E430G to Daudi cells was determined by flow cytometry. Data shown are mean fluorescence intensity (MFI) values, for one representative experiment.

For antibody IgG1-016-H5L2 a variant with a point mutation in the variable domain was generated to replace a free cysteine in the light chain: IgG1-016-H5L2-LC90S. This variant was also generated with additional F405L and E430G mutations that were previously shown to not affect target binding characteristics. FIG. 5 shows that the IgG1-016-H5L2, IgG1-016-H5L2-E430G, IgG1-016-H5L2-F405L-E430G and IgG1-016-H5L2-LC90S-F405L-E430G all showed comparable binding to Daudi cells, thus that the LC90S mutation did not affect binding.

Binding to CHO Cells Expressing Cynomolgus Monkey CD37

Figure 6:
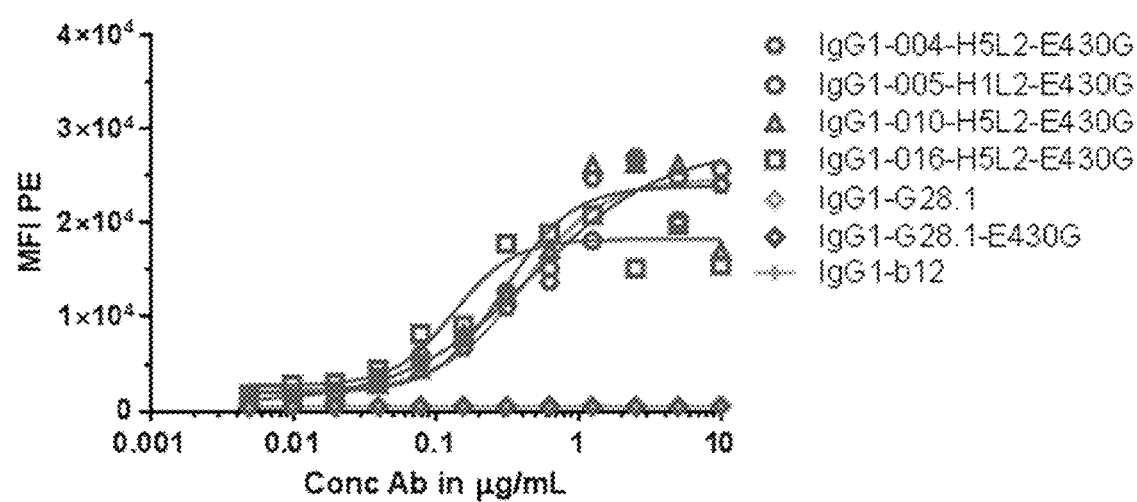
FIG. 6: Binding of CD37 antibody variants to CHO cells expressing cynomolgus CD37. Binding of IgG1-004-H5L2-E430G, IgG1-005-H1L2-E430G, IgG1-010-H5L2-E430G, IgG1-016-H5L2-E430G, IgG1-G28.1 and IgG1-G28.1-E430G was determined by flow cytometry. Data shown are mean fluorescence intensity (MFI) values, for one representative experiment.

Binding to CHO cells expressing cynomolgus monkey CD37 was determined by flow cytometry using a method as described above. FIG. 6 shows that IgG1-004-H5L2-E430G, IgG1-005-H1L2-E430G, IgG1-010-H5L2-E430G and IgG1-016-H5L2-E430G showed dose-dependent binding to CHO cells expressing cynomolgus monkey CD37. IgG1-G28.1 and IgG1-28.1-E430G did not bind to CHO cells expressing cynomolgus CD37.

Example 7: Identification of CD37 Antibodies that do not Compete for Binding to CD37

(Lack of) Binding Competition—Determined by Flow Cytometry

CD37 antibodies were labeled with Alexa Fluor 488 NHS Ester (Succinimidyl Ester). 1 mg of CD37 antibody (dissolved in PBS) was transferred to a 1 ml micro-centrifuge vial (reaction vial). The pH was raised by addition of a 10% volume of 1 M sodium bicarbonate buffer (pH 9). Immediately before use, 1 mg Alexa Fluor 488 NHS Ester (adjusted to room temperature) was dissolved in 100 µL DMSO. The labeling reaction was initiated by addition of 10 µL of the fresh Alexa dye solution per mg antibody. Reaction vials were capped and mixed gently by inversion. After 1 hour incubation at room temperature, the reaction was quenched by addition of 50 µL 1M Tris to each reaction vial. Unreacted dye was removed from the Alexa-labeled antibody by gel filtration using BioRad PDP10 columns equilibrated with borate saline buffer, according to the manufacturer's directions. Alexa-labeled antibodies were stored at 4° C. and protected from light.

Binding competition between different CD37 antibodies was determined by flow cytometry. Raji cells (ATCC, CCL-86) were resuspended in Raji medium (RPMI 1640, 10%

FBS, 100 U/mL penicillin, 100 µg/mL streptomycin, 10 mM HEPES and 1 mM pyruvate) at a concentration of 1×10$^7$ cells/mL. Next, 30 µL aliquots of the cell suspension were transferred into FACS tubes together with 30 µL aliquots (40 µg/mL final concentration) of unlabeled antibody solutions. The mixture was incubated at 37° C. for 15 min while shaking gently. Next, A488-labeled antibody dilutions were prepared and after incubation, 10 µL of the labeled antibodies (4 µg/mL final antibody concentration) was transferred to the FACS tubes containing the unlabeled antibodies and cells. The mixture was incubated at 37° C. for 15 min while shaking gently. After incubation, samples were quenched by adding 4 mL of ice cold PBS, centrifuged for 3 min at 4° C. at 2000 rpm, aspirated twice and subsequently resuspended in 125 µL of PBS. Binding competition was analyzed by determining mean fluorescent intensities using a BD FACSCalibur (BD Biosciences). Fluorescence intensities were converted to Molecules of Equivalent Soluble Fluorochome (MESF) for quantitation.

Figure 7A:
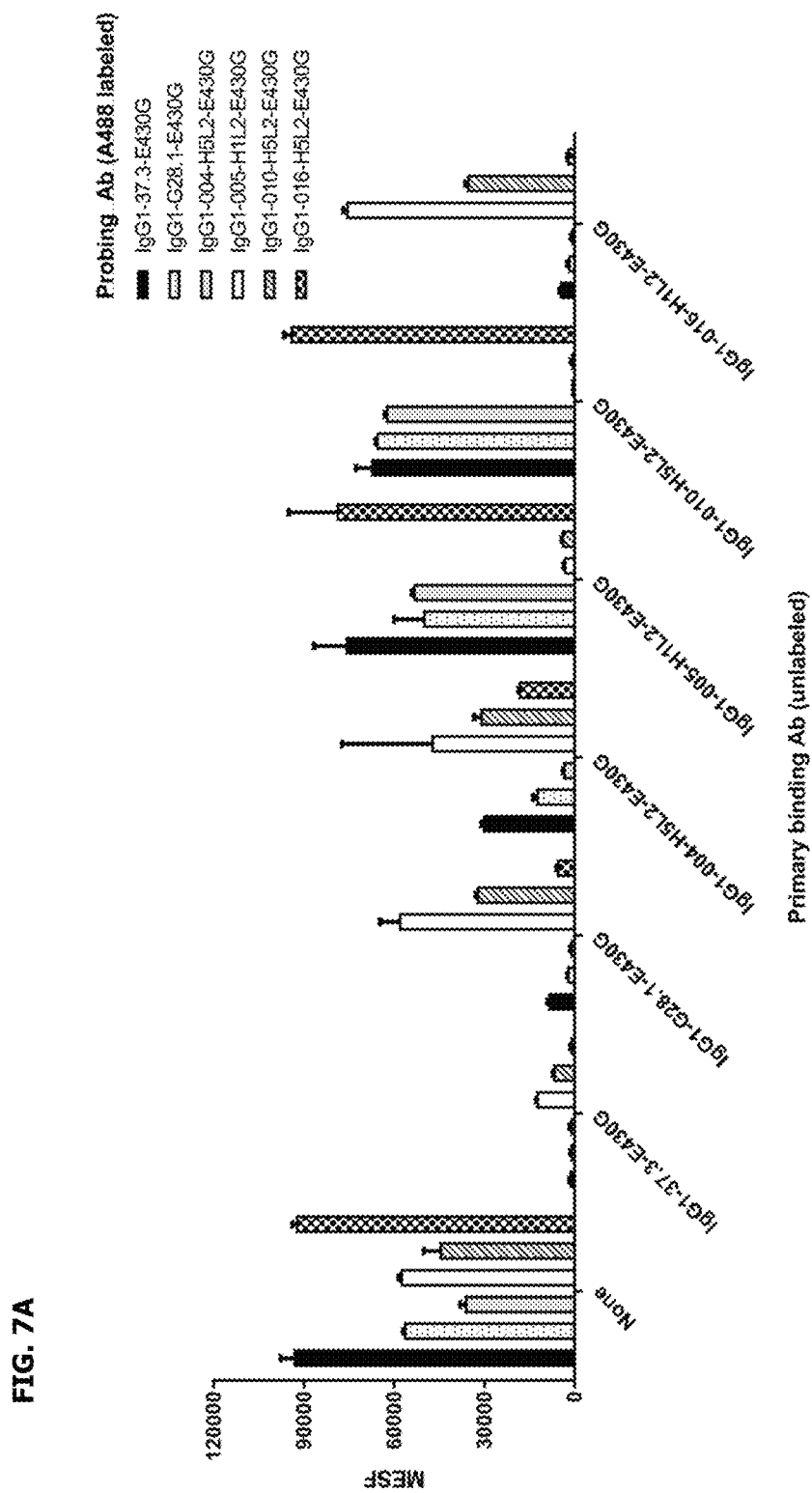
FIGS. 7A-7G: Determination of binding competition between CD37 antibodies, and CDC mediated by humanized CD37 antibodies, variants thereof and combinations of CD37 antibodies on Raji cells.

FIG. 7A and FIG. 8 show that pre-incubation of Raji cells with IgG1-005-H1L2-E430G and IgG1-010-H5L2-E430G blocked subsequent binding of IgG1-005-H1L2-E430G and IgG1-010-H5L2E430G, but not of IgG1-37.3-E430G, IgG1-G28.1-E430G, IgG1-004-H5L2-E430G and IgG1-016-H5L2-E430G.

Pre-incubation of Raji cells with IgG1-004-H5L2-E430G substantially reduced subsequent binding of IgG1-37.3-E430G, IgG1-G28.1-E430G, IgG1-004-H5L2-E430G and IgG1-016-H5L2-E430G, but not of IgG1-005-H1L2-E430G and IgG1-010-H5L2-E430G.

Pre-incubation of Raji cells with IgG1-016-H5L2-E430G blocked subsequent binding of IgG1-37.3-E430G, IgG1-G28.1-E430G, IgG1-004-H5L2-E430G and IgG1-016-H5L2-E430G, but not of IgG1-005-H1L2-E430G and IgG1-010-H5L2-E430G.

Pre-incubation of cells with IgG1-37.3-E430G blocked the subsequent binding of all tested antibodies. However, as discussed above pre-incubating with either of IgG1-005-H1L2-E430G or IgG1-010-H5L2-E430G did not block the binding of IgG1-37.3-E430G.

Pre-incubation of cells with IgG1-G28.1-E430G blocked the subsequent binding of IgG1-37.3-E430G, IgG1-G28.1-E430G, IgG1-004-H5L2-E430G and IgG1-016-H5L2-E430G, but not of IgG1-005-H1L2-E430G and IgG1-010-H5L2-E430G.

(Lack of) Binding Competition—Determined by Functional Screening Using a CDC Assay To determine whether non-cross-blocking CD37 antibodies show enhanced CDC when combined, and to confirm the potential to functionally combine non-cross-blocking CD37 antibodies, a CDC assay using individual CD37 antibodies and combinations thereof was performed.

Raji cells, resuspended in RPMI containing 0.2% BSA, were plated into polystyrene 96-well round-bottom plates (Greiner bio-one Cat #650101) at a density of 1×10$^5$ cells/well (30 µL/well) and 50 µL of humanized CD37 antibodies, variants thereof, combinations thereof or control antibody IgG1-b12 was added (10 µg/mL final antibody concentration, combinations 5+5 µg/mL). After incubation (RT, 15 min, while shaking), 20 µL of pooled normal human serum (NHS Cat #M0008 Sanquin, Amsterdam, The Netherlands) was added to each well and plates were incubated at 37° C. for 45 minutes. Plates were centrifuged (3 minutes, 1200 rpm) and supernatant was discarded. Propidium iodide (PI; 30 µL of a 1.67 µg/mL solution; Sigma-Aldrich Chemie B.V., Zwijndrecht, The Netherlands) was added and lysis was detected by measurement of the percentage of dead cells (corresponding to PI-positive cells) by flow cytometry (Intellicyt iQue™ screener, Westburg). Data was analyzed using GraphPad Prism software (Graphpad software, San Diego, Calif., USA).

Figure 7B:
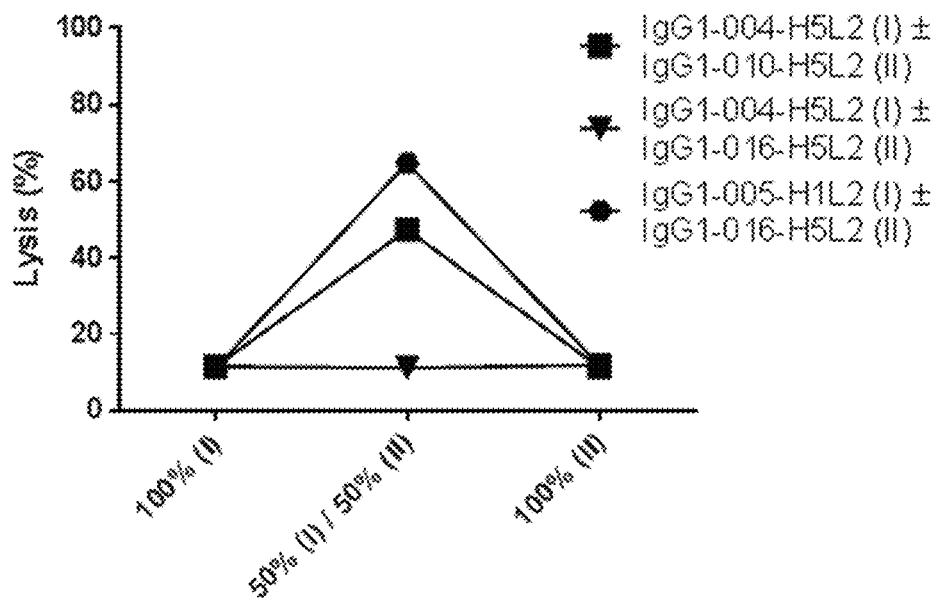
Figure 7C:
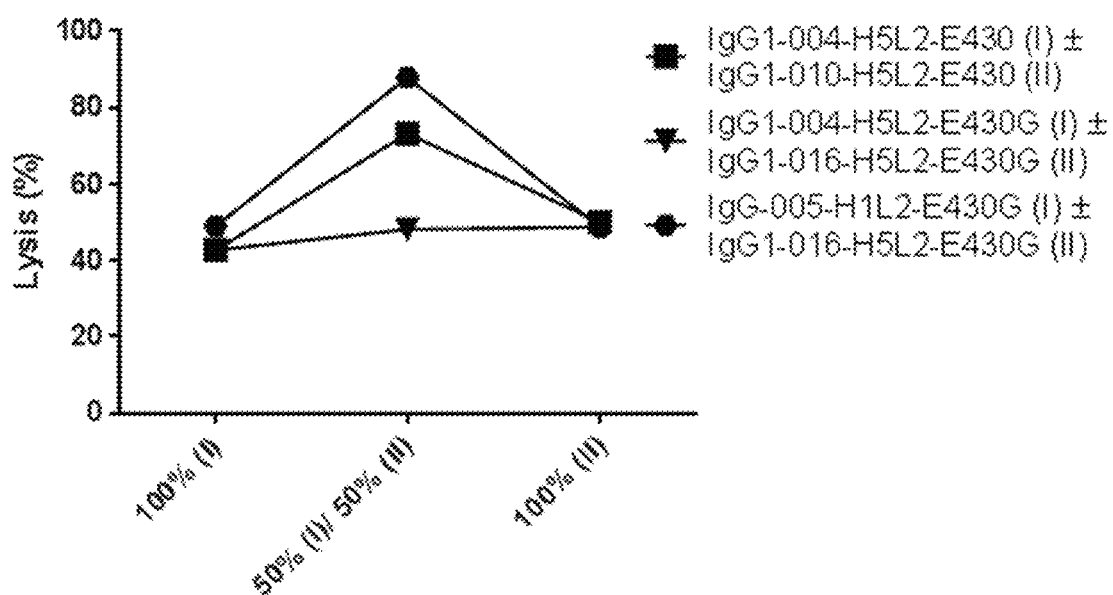

FIGS. 7B and C show that the combination of IgG1-004-H5L2 plus IgG1-010-H5L2 (with or without E430G mutation) and the combination of IgG1-005-H1L2 plus IgG1-016-H5L2 (with or without E430G mutation induced enhanced CDC compared to their individual counterparts. The combination of IgG1-004-H5L2 plus IgG1-016-H5L2 (with or without E430G mutation) did not induce enhanced CDC compared to their individual counterparts.

Figure 7D:
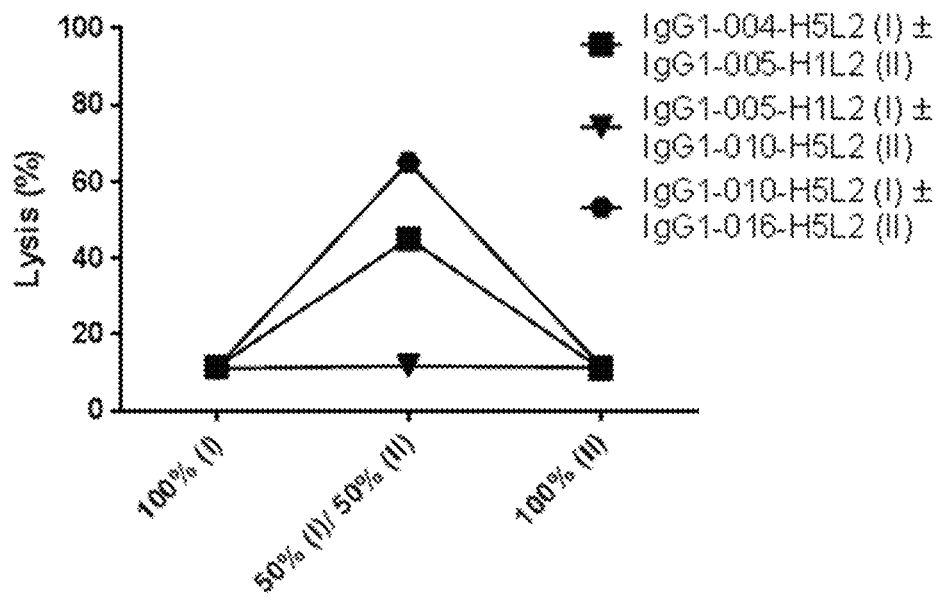
Figure 7E:
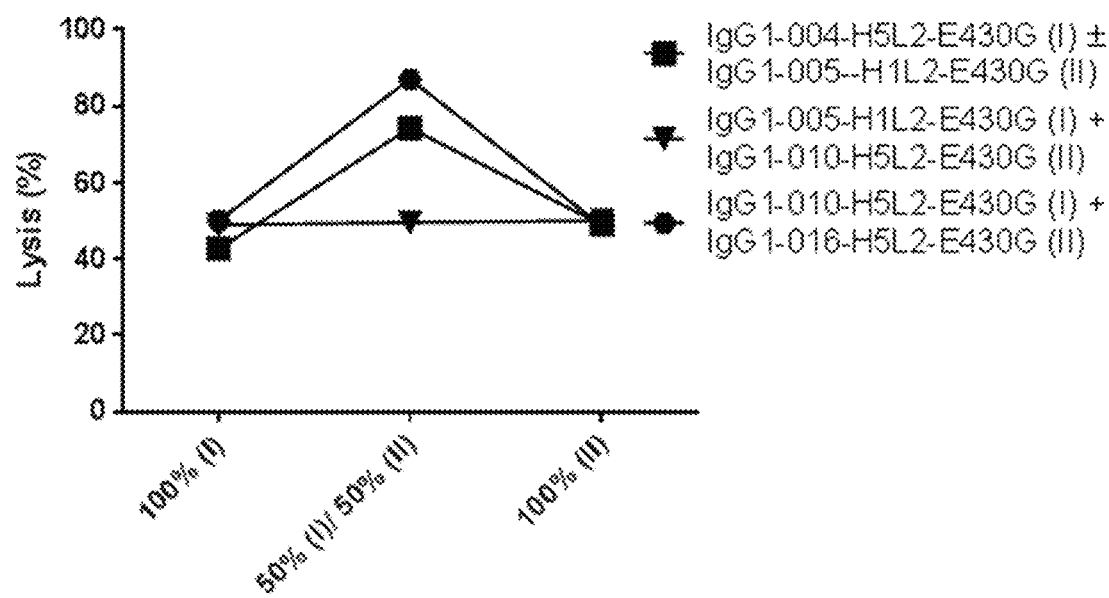

FIGS. 7D and E show that the combination of IgG1-004-H5L2 plus IgG1-005-H1L2 (with or without E430G mutation) and the combination of IgG1-010-H5L2 plus IgG1-016-H5L2 (with or without E430G mutation induced enhanced CDC compared to their individual counterparts. The combination of IgG1-005-H1L2 plus IgG1-010-H5L2 (with or without E430G mutation) did not induce enhanced CDC compared to their individual counterparts.

Figure 7F:
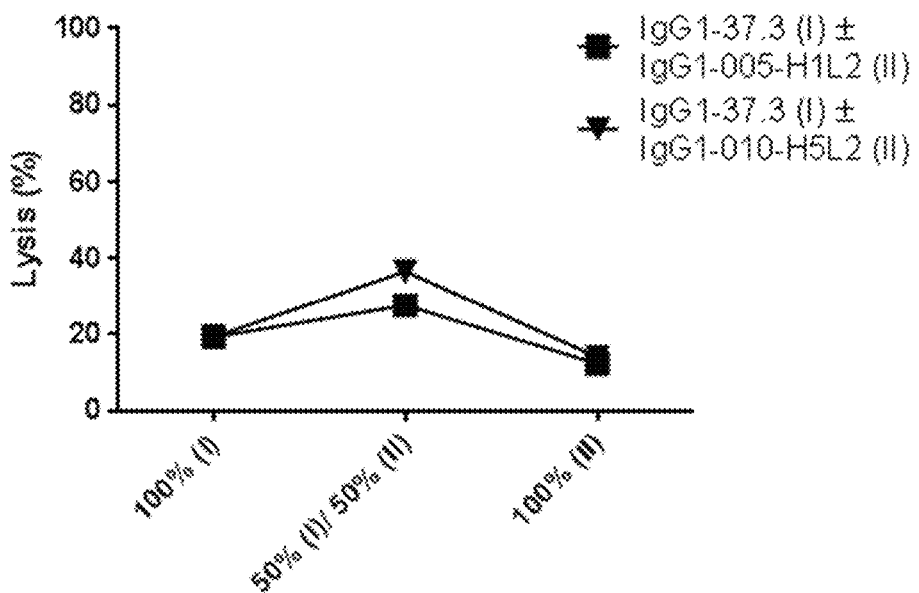
Figure 7G:
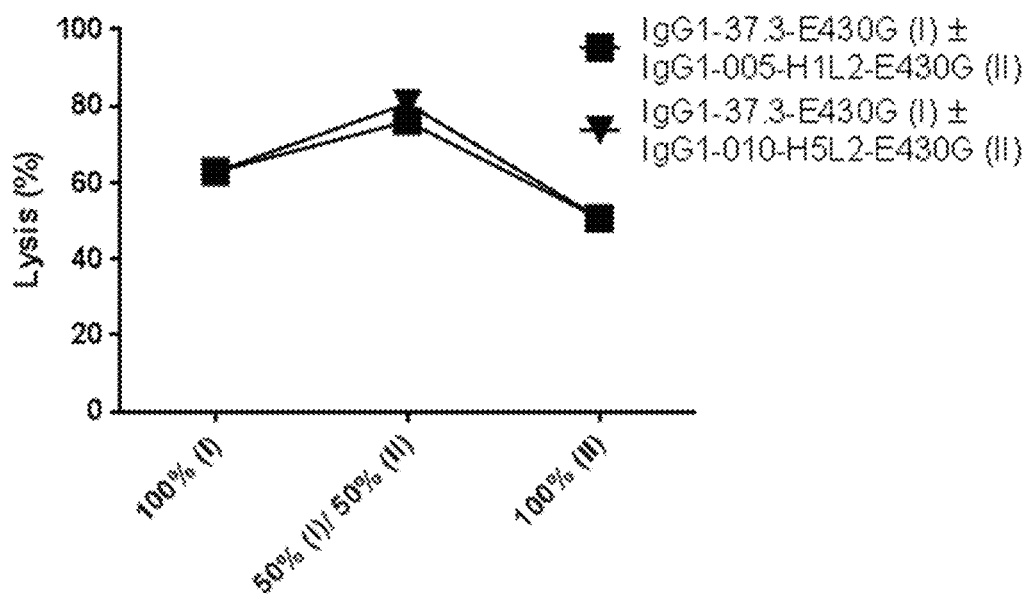

FIGS. 7F and G show that the combination of IgG1-37.3 plus IgG1-005-H1L2 (with or without E430G mutation) and the combination of IgG1-37.3 plus IgG1-010-H5L2 (with or without E430G mutation induced enhanced CDC compared to their individual counterparts.

Hence, functional combination studies confirmed the results of the binding competition studies for described CD37 antibodies and showed that non-cross-blocking CD37 antibodies can functionally be combined.

Example 8: Introducing an Fc-Fc Interaction Enhancing Mutation into Humanized CD37 Antibodies Results in Enhanced, De Novo Capacity to Induce Complement Dependent Cytotoxicity (CDC)

Daudi cells, resuspended in RPMI containing 0.2% BSA, were plated into polystyrene 96-well round-bottom plates (Greiner bio-one Cat #650101) at a density of 1×10$^5$ cells/well (30 µL/well) and 50 µL of a concentration series of humanized CD37 antibodies and variants thereof, or control antibody IgG1-b12, was added (0.003-10 µg/mL final antibody concentration in 3.33× serial dilutions). After incubation (RT, 15 min), 20 µL of pooled normal human serum (NHS, Cat #M0008 Sanquin, Amsterdam, The Netherlands) was added to each well and plates were incubated at 37° C. for 45 minutes. Plates were centrifuged (3 minutes, 1200 rpm) and supernatant was discarded. Propidium iodide (PI; 30 µL of a 1.67 µg/mL solution; Sigma-Aldrich Chemie B.V., Zwijndrecht, The Netherlands) was added and lysis was detected by measurement of the percentage of dead cells (corresponding to PI-positive cells) by flow cytometry (Intellicyt iQue™ screener, Westburg). Graphs were generated using best-fit values of a non-linear dose-response fit with log-transformed concentrations in GraphPad Prism V6.04 software (GraphPad Software, San Diego, Calif., USA).

Figure 9:
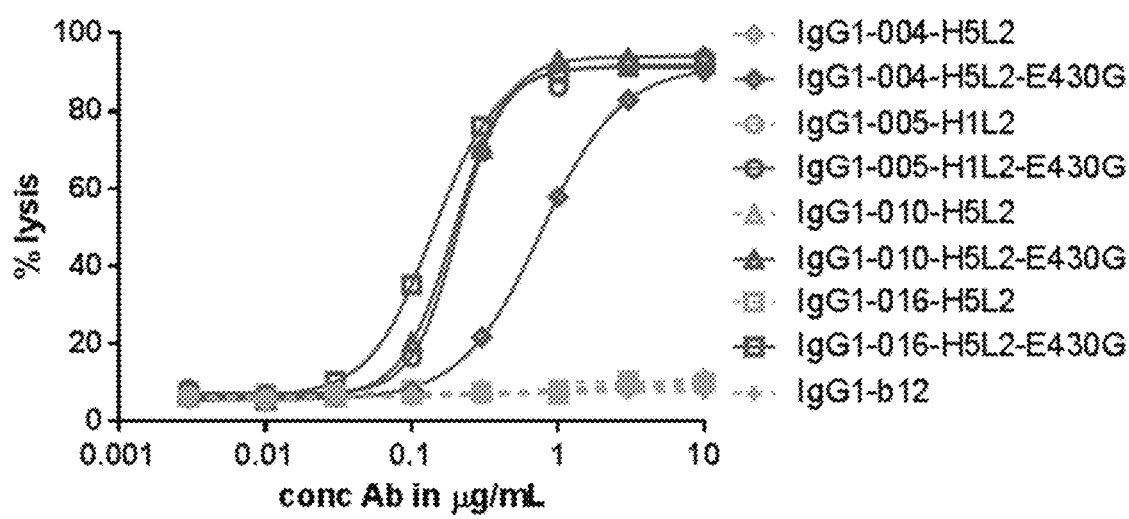
FIG. 9: CDC mediated by humanized CD37 antibodies and variants thereof on Daudi cells. The capacity to induce CDC on Daudi cells of IgG1-004-H5L2, IgG1-004-H5L2-E430G, IgG1-005-H1L2, IgG1-005-H1L2-E430G, IgG1-010-H5L2, IgG1-010-H5L2-E430G, IgG1-016-H5L2 and IgG1-016-H5L2-E430G was determined in vitro. Data shown are % lysis determined by measurement of the percentage of dead cells (corresponding to PI-positive cells) by flow cytometry.

FIG. 9 shows that IgG1-004-H5L2, IgG1-005-H1L2, IgG1-010-H5L2 and IgG1-016-H5L2 did not induce CDC in Daudi cells. Upon introduction of the Fc-Fc interaction enhancing E430G mutation, these antibodies (IgG1-004-H5L2-E430G, IgG1-005-H1L2-E430G, IgG1-010-H5L2-E430G and IgG1-016-H5L2-E430G) induced profound, dose-dependent CDC of Daudi cells.

Figure 10A:
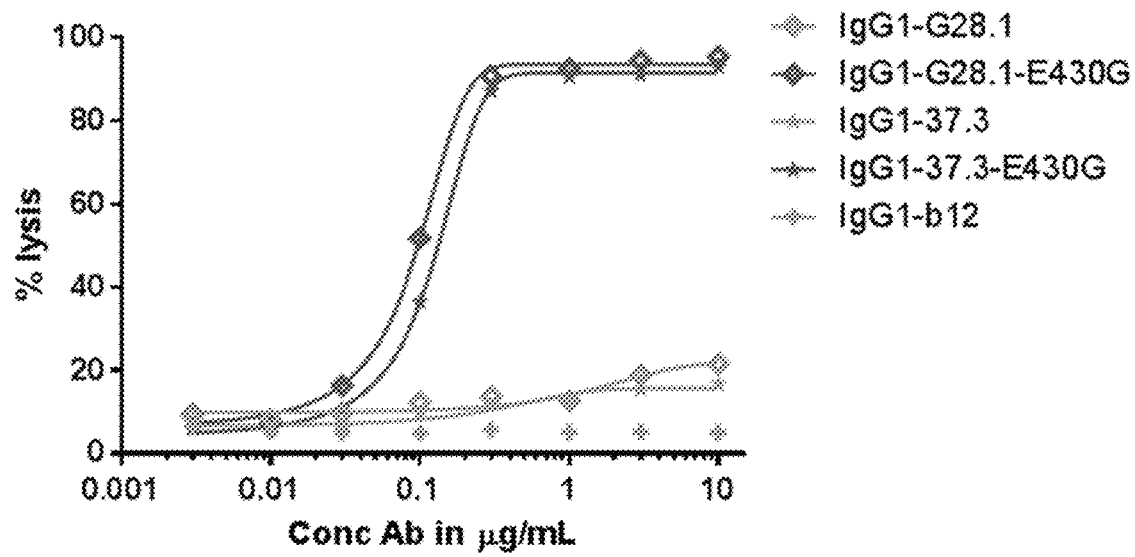
FIGS. 10A-10C: CDC mediated by G28.1 and 37.3 and variants thereof, and CDC in Daudi cells mediated by humanized CD37 antibodies with different Fc-Fc interaction enhancing mutations on Daudi cells.

FIG. 10A shows that IgG1-G28.1 and IgG1-37.3 did not induce CDC on Daudi cells. Upon introduction of the Fc-Fc interaction enhancing E430G mutation, these antibodies (IgG1-G28.1-E430G and IgG1-37.3-E430G) induced profound, dose-dependent CDC of Daudi cells.

Figure 11:
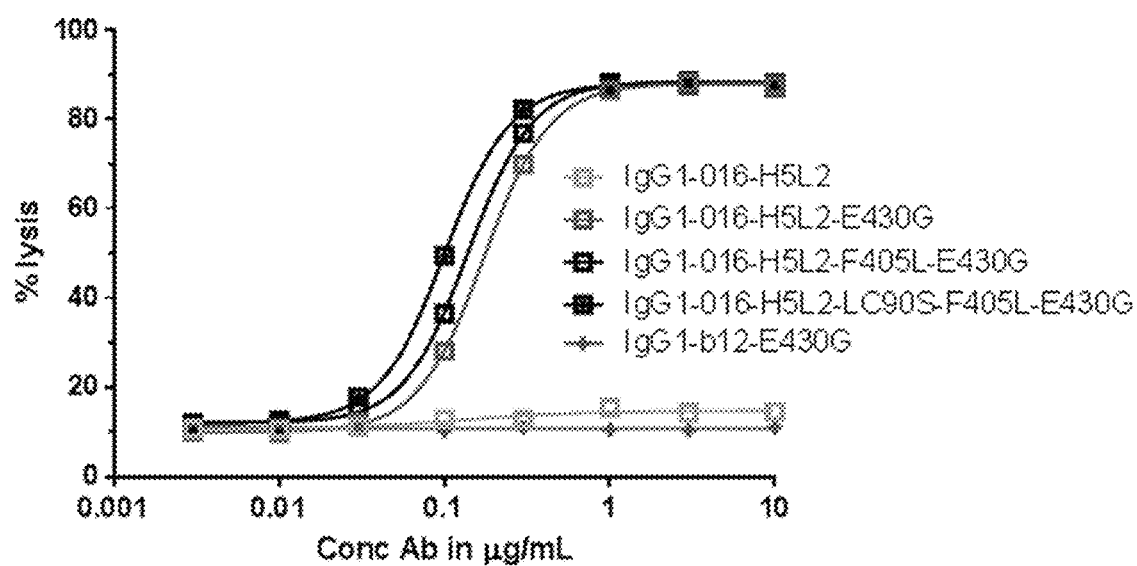
FIG. 11: CDC mediated by variants of humanized antibody IgG1-016-H5L2 on Daudi cells. The capacity to induce CDC on Daudi cells of IgG1-016-H5L2, IgG1-016-H5L2-E430G, IgG1-016-H5L2-F405L-E430G and IgG1-016-H5L2-LC90S-F405L-E430G was determined in vitro. Data shown are % lysis determined by measurement of the percentage of dead cells (corresponding to PI-positive cells) by flow cytometry.

For antibody IgG1-016-H5L2 a variant with a point mutation in the variable domain was generated to replace a free cysteine in the light chain: IgG1-016-H5L2-LC90S. In addition, this variant was also generated with an F405L mutation (previously shown not to affect target binding or CDC) and an Fc-Fc interaction enhancing E430G mutation. FIG. 11 shows that the IgG1-016-H5L2-E430G, IgG1-016-H5L2-F405L-E430G and IgG1-016-H5L2-LC90S-F405L-E430G all showed comparable activity in an in vitro CDC assay, thus that the LC90S mutation did not affect the capacity to induce CDC. IgG1-016-H5L2 did not induce CDC on Daudi cells.

Figure 10B:
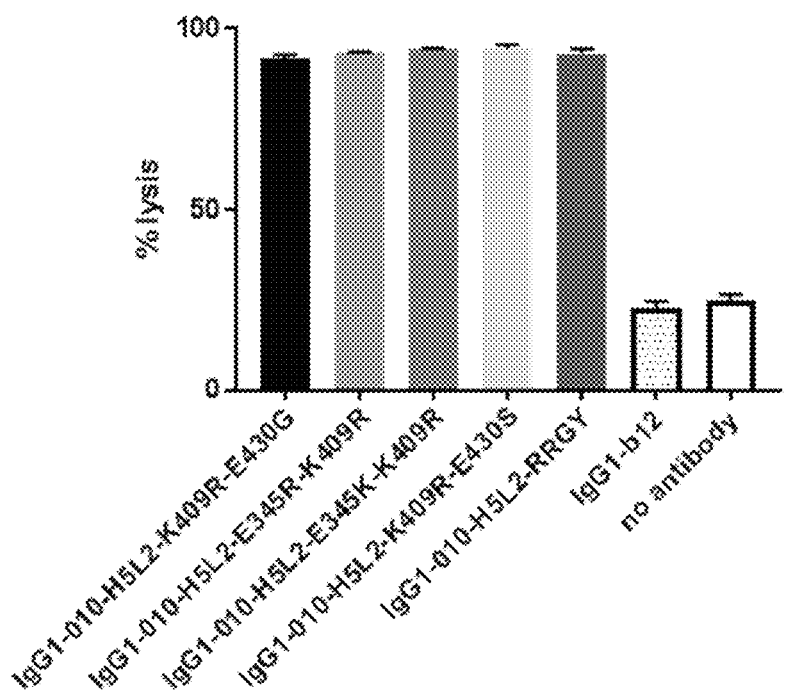
Figure 10C:
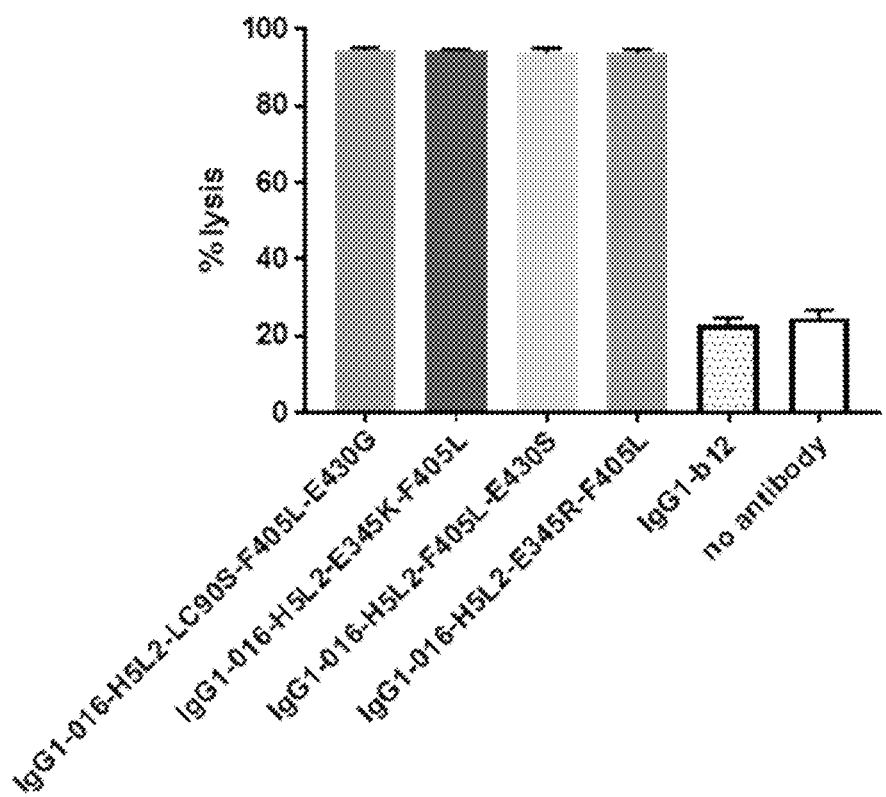

Also, introduction of other Fc-Fc interaction enhancing mutations, E345K, E345R, E430S and RRGY, in IgG1-010-H5L2 and IgG1-016-H5L2 resulted in profound CDC of Daudi cells. FIGS. 10B and C show that maximum lysis of Daudi cell was comparable for all tested Fc-Fc interaction enhancing mutations.

Figure 12A:
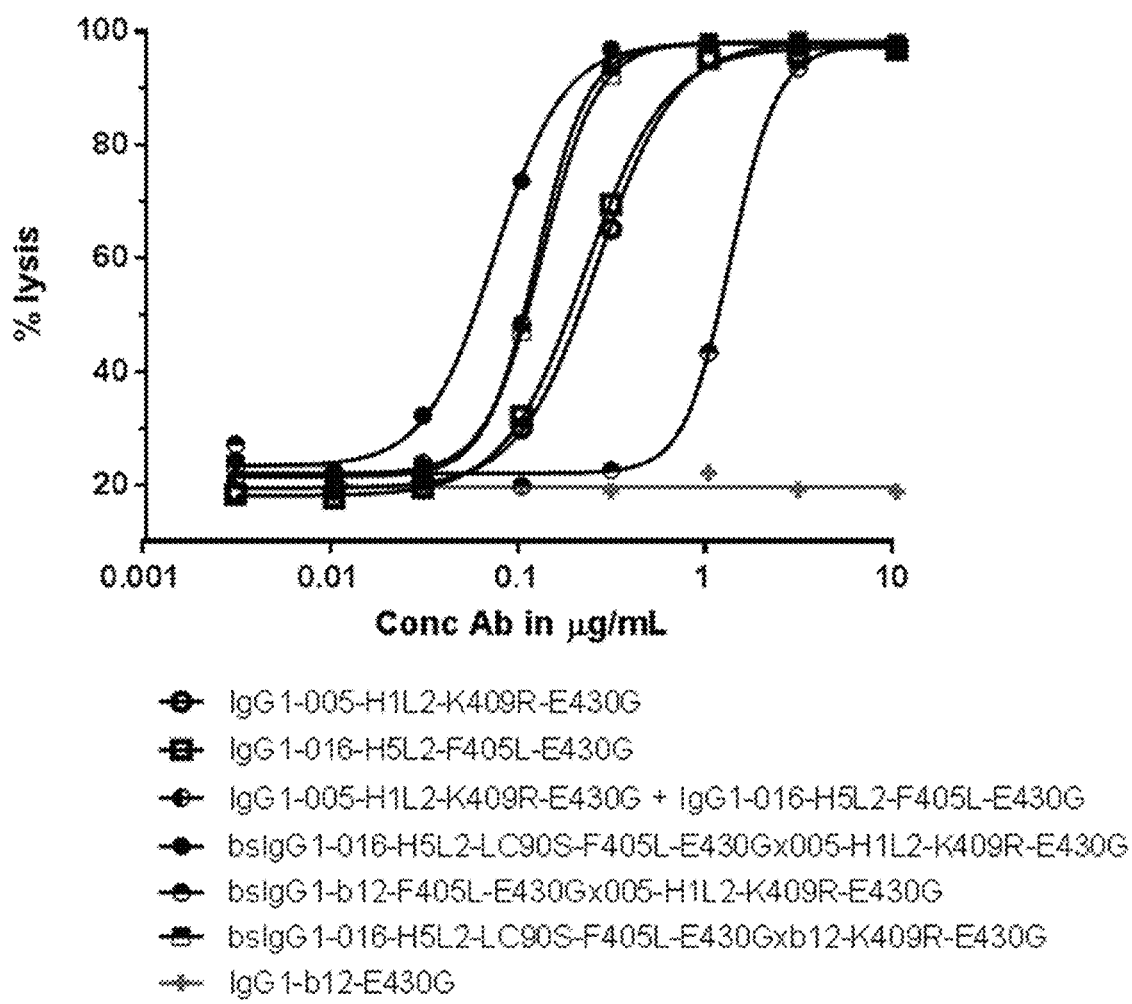
FIGS. 12A-12E: CDC mediated by bispecific CD37 antibodies with an Fc-Fc interaction enhancing mutation, (combinations of) CD37 antibodies with an Fc-Fc interaction enhancing mutation, and monovalent CD37-binding antibodies with an Fc-Fc interaction enhancing mutation on Daudi cells; and CDC activity of CD37 antibody variants with an Fc-Fc interaction enhancing mutation, and combinations thereof, on OCI-Ly-7 cells.

Example 9: Bispecific CD37 Antibodies with an Fc-Fc Interaction Enhancing Mutation are More Potent in Inducing CDC than Monospecific Bivalent CD37 Antibodies with an Fc-Fc Interaction Enhancing Mutation Due to Monovalent Binding and Dual Epitope Targeting F405L or K409R mutations were introduced into humanized CD37 antibodies containing the E430G mutation, to allow for the generation of bispecific antibodies (bsIgG1) with two CD37-specific Fab-arms that do not compete for binding to CD37. The capacity of bispecific CD37 antibodies containing the E430G mutation to induce CDC was determined as described above, and compared to that of CD37 monospecific bivalent antibodies containing the E430G mutation, a combination of two CD37 monospecific bivalent antibodies containing the E430G mutation that do not compete for binding to CD37 (with the end concentration of the combined antibodies together identical to the concentration of the individual bispecific antibodies), monovalent CD37 antibodies containing the E430G mutation (i.e. bispecific antibodies containing one CD37-specific Fab arm and one non-binding Fab-arm derived from IgG1-b12, and containing the E430G mutation) or a combination of two monovalent CD37 antibodies containing the E430G mutation that do not compete for binding to CD37.
CDC on Daudi Cells FIG. 12A shows that bsIgG1-016-H5L2-LC90S-F405L-E430Gx005-H1L2-K409R-E430G was more potent than either IgG1-005-H1L2-E430G or IgG1-016-H5L2-E430G in inducing CDC on Daudi cells. The bispecific bsIgG1-016-H5L2-LC90S-F405L-E430Gx005-H1L2-K409R-E430G was also more potent than a combination of IgG1-005-H1L2-K409R-E430G plus IgG1-016-H5L2-F405L-E430G. Monovalent CD37-binding antibodies bsIgG1-b12-F405L-E430Gx005-H1L2-K409R-E430G and bsIgG1-016-H5L2-LC90S-F405L-E430Gxb12-K409R-E430G also induced CDC on Daudi cells, but were less efficient in doing so than bsIgG1-016-H5L2-LC90S-F405L-E430Gx005-H1L2-K409R-E430G.

Figure 12B:
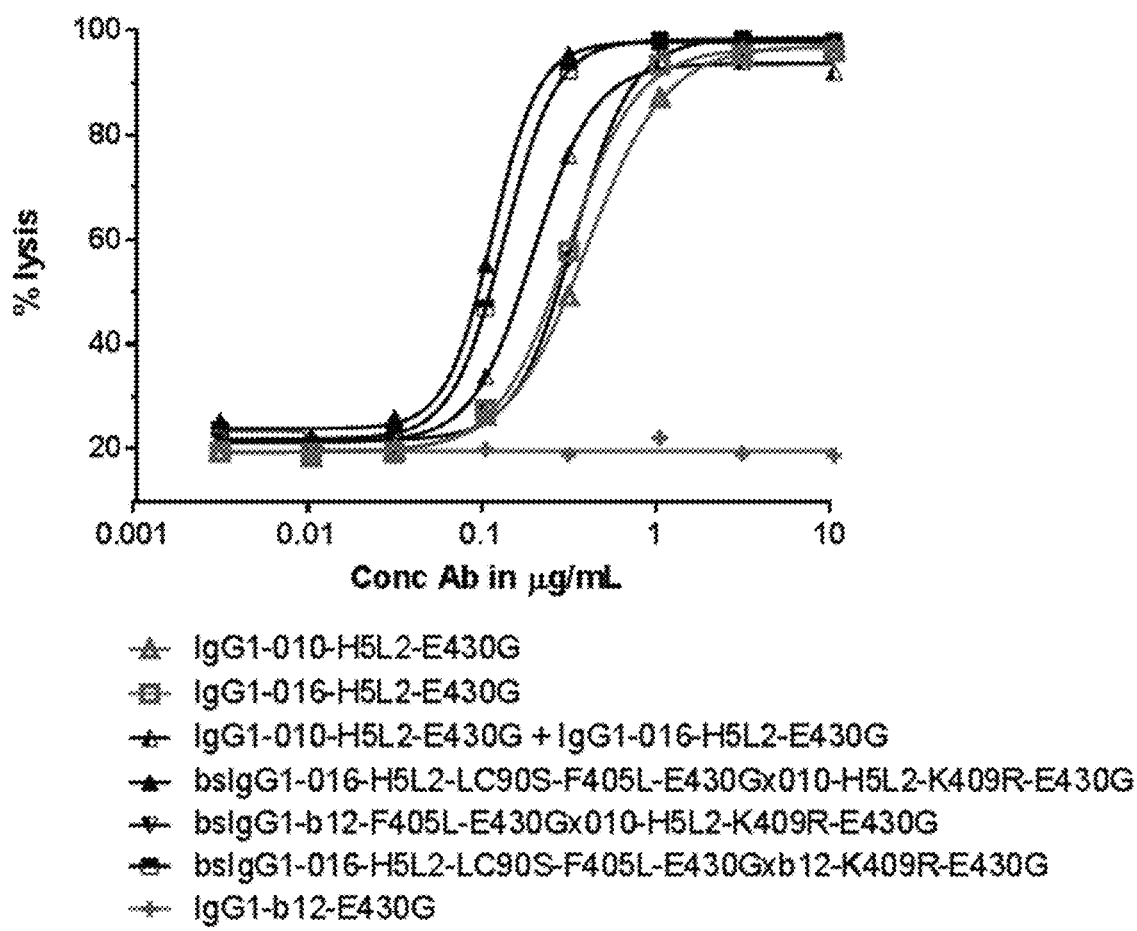

FIG. 12B shows that bsIgG1-016-H5L2-LC90S-F405L-E430Gx010-H5L2-K409R-E430G was more potent than either IgG1-010-H5L2-E430G or IgG1-016-H5L2-E430G in inducing CDC on Daudi cells. The bispecific bsIgG1-016-H5L2-LC90S-F405L-E430Gx010-H5L2-K409R-E430G was also more potent than a combination of IgG1-010-H5L2-E430G plus IgG1-016-H5L2-E430G. Monovalent binding antibodies bsIgG1-016-H5L2-LC90S-F405L-E430Gxb12-K409R-E430G and bsIgG1-b12-F405L-E430Gx010-H5L2-K409R-E430G also induced CDC on Daudi cells, with bsIgG1-b12-F405L-E430Gx010-H5L2-K409R-E430G being less potent and bsIgG1-016-H5L2-LC90S-F405L-E430Gxb12-K409R-E430G being equally potent compared to bsIgG1-016-H5L2-LC90S-F405L-E430Gx010-H5L2-K409R-E430G.

Figure 12C:
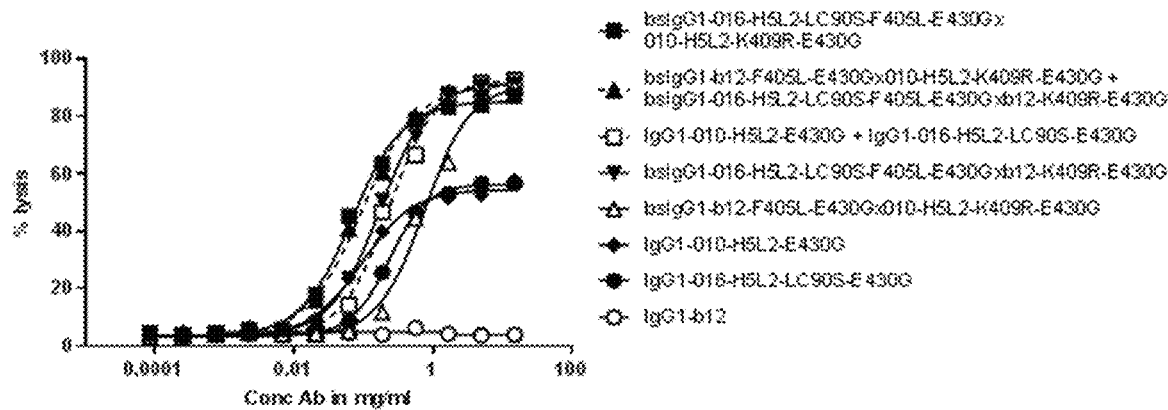
Figure 12D:
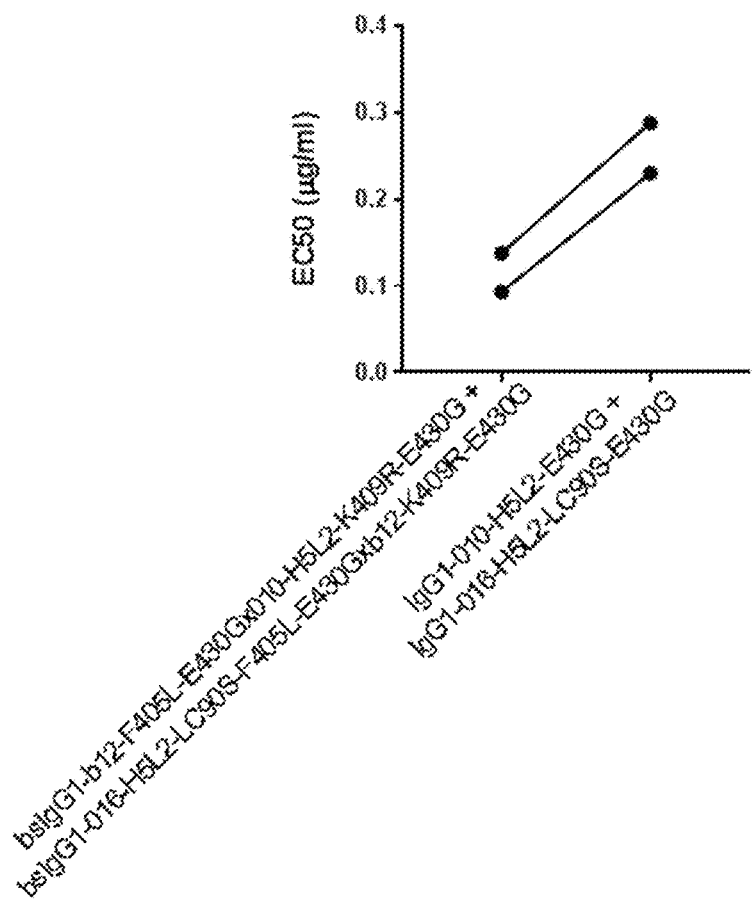
Figure 12E:
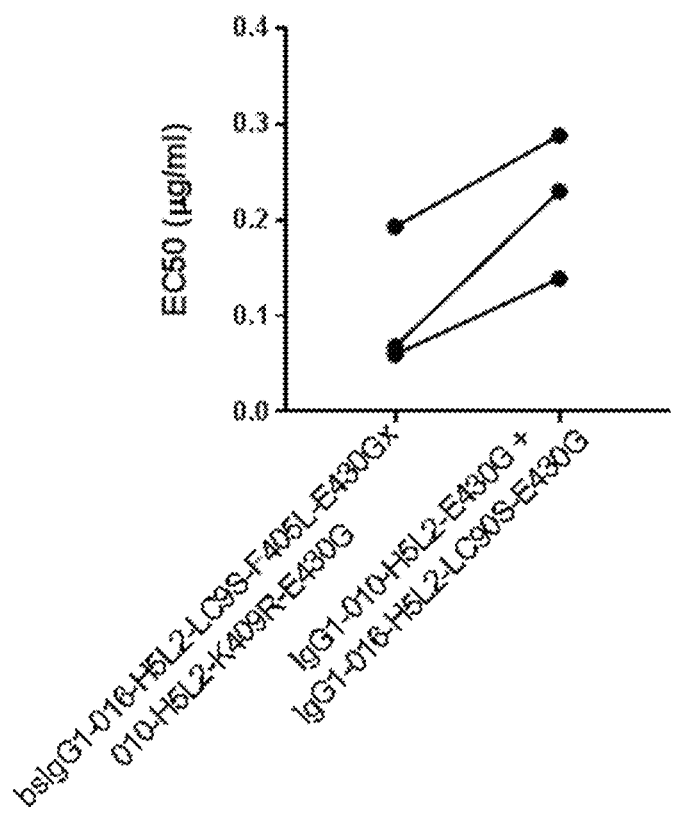
Figure 13A:
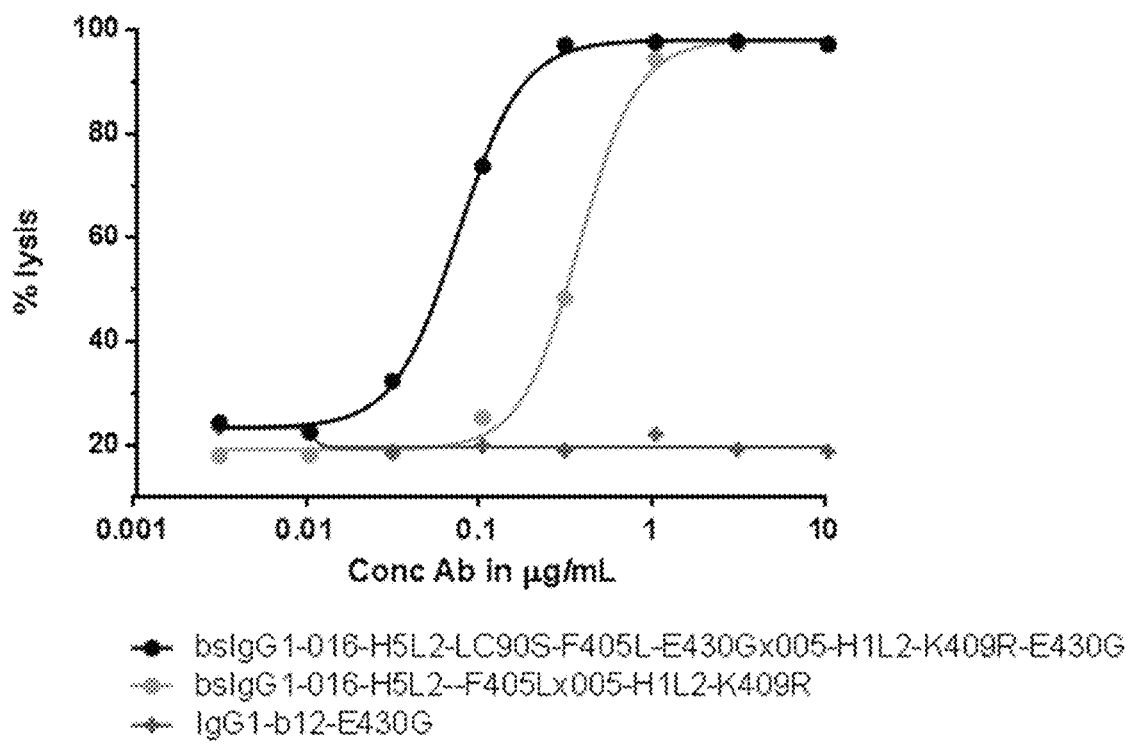
FIGS. 13A and 13B: CDC mediated by bispecific CD37 antibodies and by bispecific CD37 antibodies with an Fc-Fc interaction enhancing mutation on Daudi cells. The capacity to induce CDC on Daudi cells of (FIG. 13A) bsIgG1-016-H5L2-F405Lx005-H1L2-K409R and bsIgG1-016-H5L2-LC90S-F405L-E430Gx005-H1L2-K409R-E430G, and (FIG. 13B) bsIgG1-016-H5L2-F405Lx010-H5L2-K409R and bsIgG1-016-H5L2-LC90S-F405L-E430Gx010-H5L2-K409R-E430G was determined in vitro. Data shown are % lysis determined by measurement of the percentage of dead cells (corresponding to PI-positive cells) by flow cytometry.
Figure 13B:
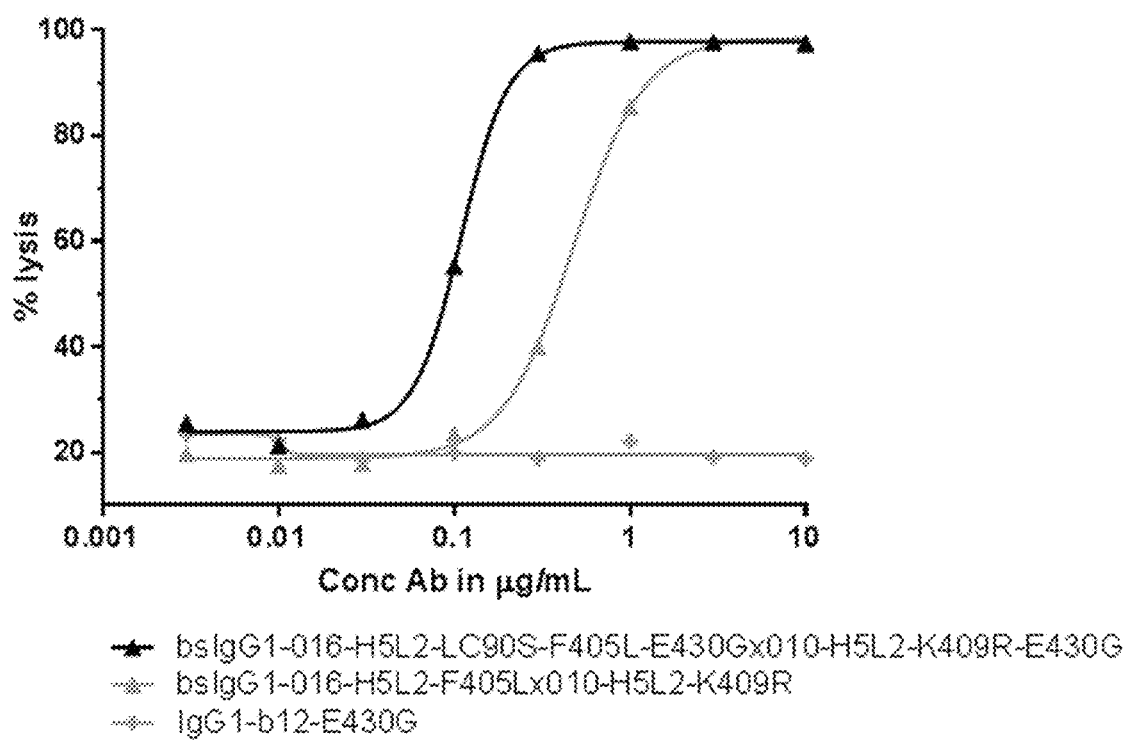

The capacity to induce CDC by bispecific CD37 antibodies containing the E430G mutation was also compared to that of bispecific CD37 antibodies without the E430G mutation. FIG. 13 shows that bsIgG1-016-H5L2-F405Lx005-H1L2-K409R as well as bsIgG1-016-H5L2-F405Lx010-H5L2-K409R were capable of inducing CDC on Daudi cells, but were less potent in doing so compared to their E430G containing counterparts bsIgG1-016-H5L2-LC90S-F405L-E430Gx005-H1L2-K409R-E430G and bsIgG1-016-H5L2-LC90S-F405L-E430Gx010-H5L2-K409R-E430G.
CDC on OCI-Ly-7 Cells FIG. 12C shows that monovalent binding antibodies bsIgG1-016-H5L2-LC90S-F405L-E430Gxb12-K409R-E430G and bsIgG1-b12-F405L-E430Gx010-H5L2-K409R-E430G were more potent in inducing CDC on OCI-Ly-7 cells compared to their monospecific bivalent binding counterparts, IgG1-016-H5L2-E430G and IgG1-010-H5L2-E430G. The combination of monovalent binding antibodies (bsIgG1-016-H5L2-LC90S-F405L-E430Gxb12-K409R-E430G plus bsIgG1-b12-F405L-E430Gx010-H5L2-K409R-E430G) was more potent than the combination of bivalent antibodies (IgG1-010-H5L2-E430G plus IgG1-016-H5L2-E430G), as demonstrated by a consistent lower EC50 in two independent experiments (FIG. 12D). Also, bsIgG1-016-H5L2-LC90S-F405L-E430Gx010-H5L2-K409R-E430G was more potent in inducing CDC on OCI-Ly-7 cells than the combination of bivalent antibodies (IgG1-010-H5L2-E430G plus IgG1-016-H5L2-E430G), as demonstrated by a consistent lower EC50 in three independent experiments (FIG. 12E).

The potency of the combination of monovalent binding antibodies (bsIgG1-016-H5L2-LC90S-F405L-E430Gxb12-K409R-E430G plus bsIgG1-b12-F405L-E430Gx010-H5L2-K409R-E430G) and of bsIgG1-016-H5L2-LC90S-F405L-E430Gx010-H5L2-K409R-E430G in inducing CDC in OCI-Ly-7 cells was comparable.
CDC on Primary CLL Tumor Cells The capacity of bispecific CD37 antibodies containing the E430G mutation to induce CDC on tumor cells derived from a CLL patient was determined as described above, and compared to that of CD37 antibodies containing the E430G mutation or a combination of CD37 antibodies containing the E430G mutation or monovalent CD37 antibodies containing the E430G mutation.

FIG. 14A shows that bsIgG1-016-H5L2-LC90S-F405L-E430Gx005-H1L2-K409R-E430G was more potent than either IgG1-005-H1L2-K409R-E430G or IgG1-016-H5L2-F405L-E430G in inducing CDC on primary CLL tumor cells. The bispecific bsIgG1-016-H5L2-LC90S-F405L-E430Gx005-H1L2-K409R-E430G was also more potent than a combination of IgG1-005-H1L2-K409R-E430G plus IgG1-016-H5L2-F405L-E430G. Monovalent binding antibodies bsIgG1-b12-F405L-E430Gx005-H1L2-K409R-E430G and bsIgG1-016-H5L2-LC90S-F405L-E430Gxb12-K409R-E430G also induced CDC on primary CLL tumor cells, but were less efficient in doing so than bsIgG1-016-H5L2-LC90S-F405L-E430Gx005-H1L2-K409R-E430G.

FIG. 14B shows that bsIgG1-016-H5L2-LC90S-F405L-E430Gx010-H5L2-K409R-E430G was more potent than either IgG1-010-H5L2-E430G or IgG1-016-H5L2-E430G in inducing CDC on primary CLL tumor cells. The bispecific bsIgG1-016-H5L2-LC90S-F405L-E430Gx010-H5L2-K409R-E430G was also more potent than a combination of IgG1-010-H5L2-E430G plus IgG1-016-H5L2-E430G. Monovalent binding antibodies bsIgG1-016-H5L2-LC90S-F405L-E430Gxb12-K409R-E430G and bsIgG1-b12-F405L-E430Gx010-H5L2-K409R-E430G also induced CDC on primary CLL tumor cells, with bsIgG1-b12-F405L-E430Gx010-H5L2-K409R-E430G being less potent and bsIgG1-016-H5L2-LC90S-F405L-E430Gxb12-K409R-E430G being equally potent compared to bsIgG1-016-H5L2-LC90S-F405L-E430Gx010-H5L2-K409R-E430G.

Example 10: Bispecific CD37 Antibodies with an Fc-Fc Interaction Enhancing Mutation Induce CDC on a Variety of B Cell Lymphoma Cell Lines with a Wide Range of CD37 Expression The capacity of bsIgG1-016-H5L2-LC90S-F405L-E430Gx010-H5L2-K409R-E430G, at a concentration of 10 µg/mL, to induce CDC was determined (as described above) on a range of B cell lymphoma cell lines, derived from a variety of B cell lymphoma subtypes. The expression levels of CD37 molecules on the cell surface of these cell lines were determined by quantitative flow cytometry as described above.

Table 3 gives an overview of the cell lines tested.

TABLE 3

B cell lymphoma cell lines.

| Cell line | Lymphoma type | Source |
| --- | --- | --- |
| JVM-2 | MCL | DSMZ; ACC 12 |
| JVM-13 | MCL | ATCC; CRL-3003 |
| Jeko-1 | MCL | DSMZ; ACC 553 |
| Z-138 | MCL | ATCC; CRL-3001 |
| Daudi | Burkitt's | ATCC; CCL-213 |
| Raji | Burkitt's | ATCC; CCL-86 |
| Wien-133 | Burkitt's | BioAnaLab, Oxford, U.K |
| SU-DHL-8 | DLBCL | DSMZ; ACC 573 |
| OCI-Ly19 | DLBCL | DSMZ; ACC 528 |
| OCI-Ly7 | DLBCL | DSMZ; ACC 688 |
| SU-DHL-4 | DLBCL | DSMZ; ACC 495 |
| RC-K8 | DLBCL | DSMZ; ACC 561 |
| U-2932 | DLBCL | DSMZ; ACC 633 |
| WIL-2S | Plasmablastic | ATCC; CRL-8885 |
| RI-1 | DLBCL | DSMZ; ACC 585 |
| WSU-DLCL2 | DLBCL | DSMZ; ACC 575 |

FIG. 15 shows that bsIgG1-016-H5L2-LC90S-F405L-E430Gx010-H5L2-K409R-E430G induced CDC on a wide range of B cell lymphoma cell lines, derived from various B cell lymphoma types.

Example 11: Bispecific CD37 Antibodies with an Fc-Fc Interaction Enhancing Mutation are More Potent in Inducing Antibody-Dependent Cell-Mediated Cytotoxicity (ADCC)

Labeling of Target Cells

The capacity of CD37 antibodies to induce ADCC was determined by a chromium release assay. Daudi or Raji cells were collected ($5 \times 10^6$ cells/mL) in 1 mL culture medium (RPMI 1640 supplemented with 10% Donor Bovine Serum with Iron (DBSI; ThermoFischer, Cat #10371029) and Penicillin Streptomycin mixture (pen/strep), to which 100 µCi $^{51}$Cr (Chromium-51; PerkinElmer, Cat #NEZ030005MC) had been added. Cells were incubated in a water bath at 37° C. for 1 hour while shaking. After washing of the cells (twice in PBS, 1500 rpm, 5 min), the cells were resuspended in RPMI 1640/10% DBSI/pen/strep and counted by trypan blue exclusion. Cells were diluted to a density of $1 \times 10^5$ cells/mL.

Preparation of Effector Cells

Peripheral blood mononuclear cells from healthy volunteers (Sanquin, Amsterdam, The Netherlands) were isolated from 45 mL of freshly drawn heparin blood (buffy coats) by Ficoll density centrifugation (Bio Whittaker; lymphocyte separation medium, cat 17-829E) according to the manufacturer's instructions. After resuspension of cells in RPMI 1640/10% DBSI/pen/strep, cells were counted by trypan blue exclusion and diluted to a density of 1×107 cells/mL.

ADCC Assay Procedure

50 µL of $^{51}$Cr-labeled targets cells were pipetted into 96-well round-bottom microtiter plates (Greiner Bio-One; Cat #650101), and 50 µL of a concentration series of (1.5-5,000 ng/mL final concentrations in 3-fold dilutions) CD37 or control antibodies, diluted in RPMI 1640/10% DBSI/pen/strep was added. Cells were incubated at room temperature (RT) for 15 min and 50 µL effector cells were added, resulting in an effector to target ratio of 100:1. Cells were incubated for 4 hours at 37° C. and 5% CO2. For determination of maximal lysis, 50 µL 51Cr-labeled Daudi cells (5.000 cells) were incubated with 100 µL 5% Triton-X100; for determination of spontaneous lysis (background lysis), 5,000 51Cr-labeled Daudi cells were incubated in 150 µL medium without any antibody or effector cells. The level of antibody-independent cell lysis was determined by incubating 5,000 Daudi cells with 500,000 PBMCs without antibody. Plates were centrifuged (1200 rpm, 10 min) and 25 µL of supernatant was transferred to 100 µL Microscint-40 solution (Packard, Cat #6013641) in 96-Wells plates. Plates were sealed and shaken for 15 minutes at 800 rpm and released 51Cr was counted using a scintillation counter (TopCount®, PerkinElmer). The percentage specific lysis was calculated as follows:

% specific lysis=(cpm sample−cpm spontaneous lysis)/(cpm maximal lysis−cpm spontaneous lysis) wherein cpm is counts per minute.

FIG. 16A shows that bsIgG1-016-H5L2-LC90S-F405L-E430Gx005-H1L2-K409R-E430G was more potent than either IgG1-005-H1L2-K409R-E430G or IgG1-016-H5L2-F409L-E430G or than a combination of IgG1-005-H1L2-K409R-E430G plus IgG1-016-H5L2-F405L-E430G in inducing ADCC on Daudi cells.

FIG. 16B shows that bsIgG1-016-H5L2-LC90S-F405L-E430Gx010-H5L2-K409R-E430G was more potent than either IgG1-010-H5L2-E430G or IgG1-016-H5L2-E430G or a combination of IgG1-010-H5L2-E430G plus IgG1-016-H5L2-E430G in inducing ADCC on Daudi cells.

FIG. 16C shows similar results as FIG. 16B for PBMCs from a different donor, and in addition shows that bsIgG1-016-H5L2-LC90S-F405L-E430Gx010-H5L2-K409R-E430G was more potent than monovalent binding antibodies bsIgG1-016-H5L2-LC90S-F405L-E430Gxb12-K409R-E430G and bsIgG1-b12-F405L-E430Gx010-H5L2-K409R-E430G in inducing ADCC on Raji cells.

Example 12: Bispecific CD37 Antibodies with an Fc-Fc Interaction Enhancing Mutation Induce Potent Ex Vivo CDC in Primary Tumor Cells from Patients with Various B Cell Malignancies The CDC efficacy of bsIgG1-016-H5L2-LC90S-F405Lx010-H5L2-K409R-E430G was analyzed using primary patient-derived tumor cells from five different B cell malignancies: chronic lymphocytic leukemia (CLL), follicular lymphoma (FL), diffuse large B cell lymphoma (DLBCL), mantle cell lymphoma (MCL) and Non-Hodgkin's lymphoma (not further specified). All patient samples were obtained after written informed consent and stored using protocols approved by the VUmc Medical Ethical Committee in accordance with the declaration of Helsinki. Patient bone marrow mononuclear cells (BMNCs) or peripheral blood mononuclear cells (PBMCs) were isolated by density-gradient centrifugation (Ficoll-Paque PLUS, GE Healthcare) from bone marrow aspirates or peripheral blood samples of patients. Cells were either used directly or stored in liquid nitrogen until further use.

Patient lymph node tissue was dissected into small fragments and collected in α-MEM medium (ThermoFischer Scientific, Waltham, Mass.) containing 1% Penicillin-Streptomycin, 0.2% heparin and 5% platelet lysate and left overnight at 37° C. After incubation, the supernatant (non-stromal cell compartment including tumor cells) was collected and cells were filtered using a 70 μM Easy Strainer (Greiner Bio-one). Cells were counted, resuspended in RPMI 1640 medium containing 25% heat-inactivated FBS and 10% DMSO, and frozen in liquid nitrogen until further use.

The CD37 and membrane complement regulatory proteins (mCRP; CD46, CD55 and CD59) expression levels on isolated patient cells were determined using a QifiKit (DAKO, cat. no. K007811). Cells were incubated with the purified antibodies CD37 (BD, cat. no. 555456), CD46 (BioLegend, cat. no. 352404), CD55 (BioLegend, cat. no. 311302), CD59 (BioLegend, cat. no. 304702), and b12 (Genmab) at 4° C. for 30 min. After this the method as provided by the QifiKit manufacturer was used. After the final step of Qifi kit procedure, cells were incubated with lymphoma cell specific markers to enable tumor cell identification. FIG. 17 shows the expression levels per indication.

The patient-derived tumor cells were opsonized with 10 μg/mL or 100 μg/mL bsIgG1-016-H5L2-LC90S-F405Lx010-H5L2-K409R-E430G and CDC induction was assessed in the presence of 20% pooled NHS. The following cell markers were used to identify different cell populations: CD45-KO (Beckman Coulter B36294), CD19-PC7 (Beckman Coulter, cat. no. IM3628), CD3-V450 (BD, cat. no. 560365), CD5-APC (BD, cat. no. 345783), CD5-PE (DAKO, cat. no. R084201), CD10-APC-H7 (BD, cat. no. 655404), CD10-PE (DAKO, cat. no. R084201), CD23-FITC (Biolegend, cat. no. 338505), lambda-APC-H7 (BD, cat. no. 656648), kappa-PE (DAKO, cat. no. R043601) and lambda-FITC (Emelca Bioscience CYT-LAMBF). Within the CD45+ cell population, malignant B cells were defined by different markers depending on the indication: CD3−/CD19+/CD5+ (CLL), CD3−/CD19+/CD10+ (FL, DLBCL), CD3−/CD19+/CD5+/CD23− (MCL). In case malignant B cells could not be identified based on these markers, malignant cells were identified based on clonality using kappa/lambda staining. In a few samples, malignant B cells could also not be identified based on clonality; in these cases the total B cell population was assessed, without distinction between normal and malignant B cells. Killing was calculated as the fraction of 7-amino actinomycin D (7-AAD; BD, cat. no. 555816) positive malignant B cells (%) determined by an LSRFortessa flow cytometer (BD Biosciences, San Jose, Calif.).

FIG. 18 shows that bsIgG1-016-H5L2-LC90S-F405Lx010-H5L2-K409R-E430G was highly potent (lysis of more than 50%) in inducing CDC in tumor cells derived patients with CLL, FL, MCL, DLBCL or B-NHL (not further specified). In cells from one patient with relapsed/refractory FL, bsIgG1-016-H5L2-LC90S-F405Lx010-H5L2-K409R-E430G was less capable of inducing CDC.

Example 13: Binding of a Bispecific CD37 Antibody with an Fc-Fc Interaction Enhancing Mutation to Human or Cynomolgus Monkey B Cells in Whole Blood, and Induction of Cytotoxicity in B Cells in Whole Blood Binding to Human or Cynomolgus Monkey B Cells Binding to human or cynomolgus monkey B cells was determined in a whole blood binding assay. Heparin-treated human blood from healthy volunteers was derived from UMC Utrecht (Utrecht, The Netherlands), hirudin-treated blood from cynomolgus monkeys was derived from Covance (Munster, Germany). Blood was aliquoted to wells of a 96-well round-bottom plate (Greiner Bio-one, cat. no. 65010; 35 μL/well). Red blood cells (RBC) were lysed by addition of 100 μL RBC lysis buffer (10 mM KHCO$_3$ [Sigma P9144], 0.1 mM EDTA [Fluka 03620] and 0.15 mM NH$_4$CL [Sigma A5666]) and incubated on ice until RBC lysis was complete. After centrifugation for 3 minutes at 300×g, cells were incubated for 30 minutes at 4° C. with serial dilutions (0.014-30 μg/mL final antibody concentration in 3× serial dilutions) of Alexa-488 labeled bsIgG1-016-H5L2-LC90S-F405L-E430Gx010-H5L2-K409R-E430G or Alexa-488 labeled control IgG1 (IgG1-b12) and a directly labeled antibody to identify B cells (among a mixture of antibodies to further identify blood cell subsets):

For human blood B cells the following antibody was used

| Target protein | Clone | Label | Target cells | Company | Cat. no. |
|---|---|---|---|---|---|
| CD19 | HIB19 | BV711 | B cells | Biolegend | 302245 |

For cynomolgus monkey blood B cells the following antibody was used

| Target protein | Clone | Label | Target cells | Company | Cat. no. |
|---|---|---|---|---|---|
| CD19 | J3-119 | PE | B cells | Beckman Coulter | A07769 |

Cells were pelleted and washed twice in 150 μL FACS buffer and resuspended in 150 μL TO-PRO-3 (end concentration 0.2 μM; Molecular Probes, cat no. T3605). Samples were measured by flow cytometry using an LSRFortessa flow cytometer. Binding is expressed as geometric mean of A488 fluorescence intensity for viable TO-PRO-3$^-$/CD14$^-$/CD19$^+$ B-cells (human) or viable TO-PRO-3$^-$/CD14$^-$/CD19$^+$/CD20$^+$ B-cells (cynomolgus monkey). Log-transformed data were analyzed using best-fit values of a non-linear dose-response fit in GraphPad PRISM.

FIG. 19 shows the concentration dependent binding of bsIgG1-016-H5L2-LC90S-F405L-E430Gx010-H5L2-K409R-E430G to B cells in (A) human and (B) cynomolgus monkey blood, for one representative donor/animal. The average EC$_{50}$ values for binding to human and cynomolgus monkey B cells were in the same range ([0.85 μg/mL±0.284 based on binding to B cells in blood from 6 human donors] and [0.63 μg/mL±0.228 based on binding to B cells in blood from 4 animals], respectively), indicating that bsIgG1-016-H5L2-LC90S-F405L-E430Gx010-H5L2-K409R-E430G shows comparable binding to human and cynomolgus monkey CD37.

Cytotoxicity to Human or Cynomolgus Monkey B Cells

Cytotoxicity towards human or cynomolgus monkey B cells was determined in a whole blood cytotoxicity assay. Hirudin-treated human blood from healthy volunteers was derived from UMC Utrecht (Utrecht, The Netherlands), hirudin-treated blood from cynomolgus monkeys was derived from Covance (Munster, Germany). Blood was aliquoted to wells of a 96-well round-bottom plate, 35 µL/well.

Serial dilutions (0.0005-10 µg/mL final antibody concentration in 3× serial dilutions; final volume 100 µL/well) of bsIgG1-016-H5L2-LC90S-F405L-E430Gx010-H5L2-K409R-E430G or IgG1-b12 were added. In cytotoxicity assays using human whole blood, the monoclonal FcγR-interaction enhanced CD37 specific antibody IgG1-G28.1-5239D-I332E was included as reference. Samples were incubated at 37° C. for 4 hours. Thereafter, red blood cells were lysed as described above and samples were stained to identify B cells as described above. Cells were pelleted and washed twice in 150 µL FACS buffer and resuspended in 150 µL TO-PRO-3 (end concentration 0.2 µM; Molecular Probes, cat no. T3605). Samples were measured by flow cytometry using an LSRFortessa flow cytometer. After exclusion of doublets the percentage viable TO-PRO-3$^-$/CD14$^-$/CD19$^+$ B-cells (human) or viable TO-PRO-3$^-$/CD14$^-$/CD19$^+$/CD20$^+$ B cells (cynomolgus monkey) was determined. The percentage B-cell depletion was calculated as follows: % B cell depletion=100*[(% B-cells no Ab control-% B cells sample)/(% B cells no Ab control)]. Log-transformed data were analyzed using best-fit values of a non-linear dose-response fit in GraphPad PRISM.

FIG. 20 shows the concentration dependent cytotoxicity of bsIgG1-016-H5L2-LC90S-F405L-E430Gx010-H5L2-K409R-E430G to B cells in (A) human and (B) cynomolgus monkey blood, for one representative donor/animal.

Based on $EC_{50}$, the capacity of bsIgG1-016-H5L2-LC90S-F405L-E430Gx010-H5L2-K409R-E430G to induce cytotoxicity in human and cynomolgus monkey B cells was comparable: the average $EC_{50}$ for cytotoxicity to human B cells (in blood from 6 donors) was 0.077 µg/mL±0.039; the average $EC_{50}$ for cytotoxicity to cynomolgus monkey B cells (in blood from 4 animals) was 0.043 µg/mL±0.019.

FIG. 20A also shows the cytotoxicity of the FcγR-interaction enhanced monoclonal CD37 antibody IgG1-G28.1-5239D-I332E to human B cells for a representative responding donor, which showed lower cytotoxicity than bsIgG1-016-H5L2-LC90S-F405L-E430Gx010-H5L2-K409R-E430G. In B cells from 3 responding donors, a maximum B-cell depletion of 50% by IgG1-G28.1-5239D-I332E was measured, whereas in 3 other donors no cytotoxicity to B cells by this antibody was measured. BsIgG1-016-H5L2-LC90S-F405L-E430Gx010-H5L2-K409R-E430G induced cytotoxicity in 93-99% of B cells in 6/6 donors. Binding of IgG1-G28.1-S239D-I332E to CD37 expressed on Daudi cells was comparable to that of bsIgG1-016-H5L2-LC90S-F405L-E430Gx010-H5L2-K409R-E430G (data not shown).

Example 14: Potent CDC Activity by a Combination of a Bispecific CD37 Antibody with an Fc-Fc Interaction Enhancing Mutation with a CD20-Specific Antibody The capacity to induce CDC was tested for a combination of bsIgG1-016-H5L2-LC90S-F405L-E430Gx010-H5L2-K409R-E430G and an anti-CD20 antibody (IgG1-CD20-ofa; ofatumumab) on patient derived CLL tumor cells obtained from ConversantBio (Huntsville, Ala., USA). Patient derived PBMCs were resuspended in RPMI containing 0.2% BSA (bovine serum albumin) and plated into polystyrene 96-well round-bottom plates (Greiner bio-one Cat #650101) at a density of 0.1×10$^6$ cells/well (30 µL/well) and 50 µL of a concentration series of bsIgG1-016-H5L2-LC90S-F405L-E430Gx010-H5L2-K409R-E430G (0.0625-0.05 µg/mL) and IgG1-CD20-ofa (1-8 µg/mL) was added in 2-fold dilutions. BsIgG1-016-H5L2-LC90S-F405L-E430Gx010-H5L2-K409R-E430G and IgG1-CD20-ofa were combined at antibody concentrations that were based on relative potency (differences in EC50s) of each of the antibodies, by mixing two concentrations that would, on average, separately reach the same effect. IgG1-b12 was used as negative control.

After incubation (RT, 15 min while shaking), 20 µL of pooled normal human serum (NHS Cat #M0008 Sanquin, Amsterdam, The Netherlands) was added to each well as a source of complement and plates were incubated at 37° C. for 45 minutes. The reaction was stopped by cooling the plates on ice. After centrifugation for 3 minutes at 300×g, cells were washed twice with 150 µL FACS buffer and incubated for 30 minutes at 4° C. with an R-Phycoerythrin (PE) labeled mouse-anti-human IgG1-CD19 antibody (clone J3-119, Beckman Coulter, cat no. A07769, 1:50 diluted from stock) to determine the tumor B cells and TO-PRO-3 (end concentration 0.2 µM; Molecular Probes, cat no. T3605) for the identification of dead cells. Cells were pelleted and washed twice in 150 µL FACS buffer and measured by flow cytometry using an LSRFortessa flow cytometer. The percentage of viable cells was calculated as follows: % viable cells=100*(#TO-PRO-3 negative events)/(# total events).

Figure 21A:
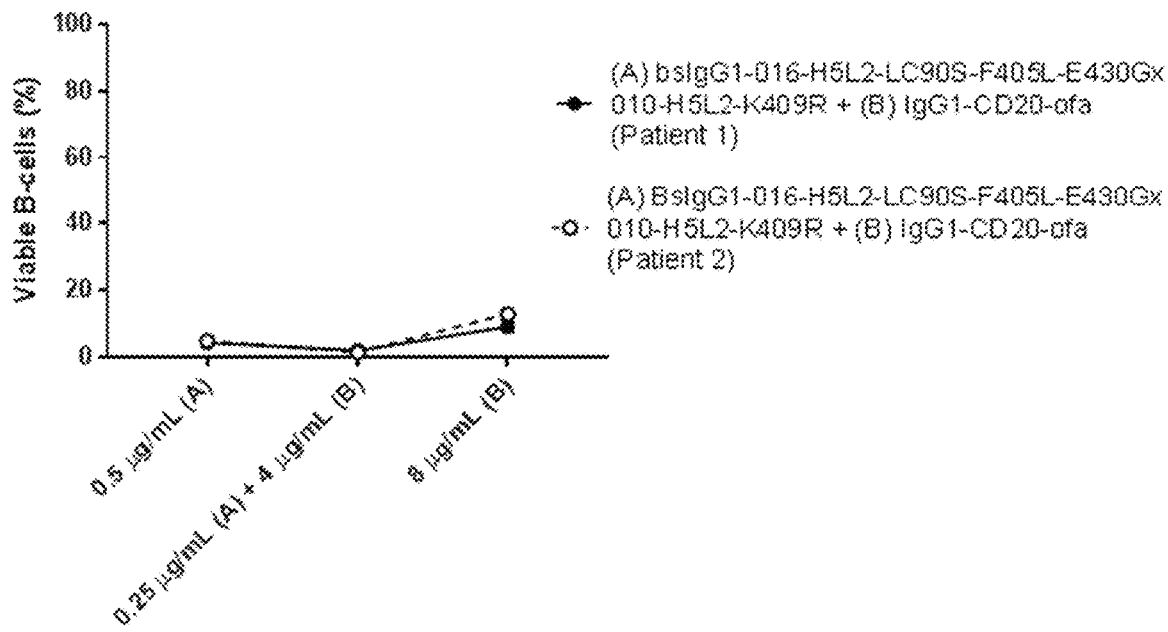
Figure 21B:
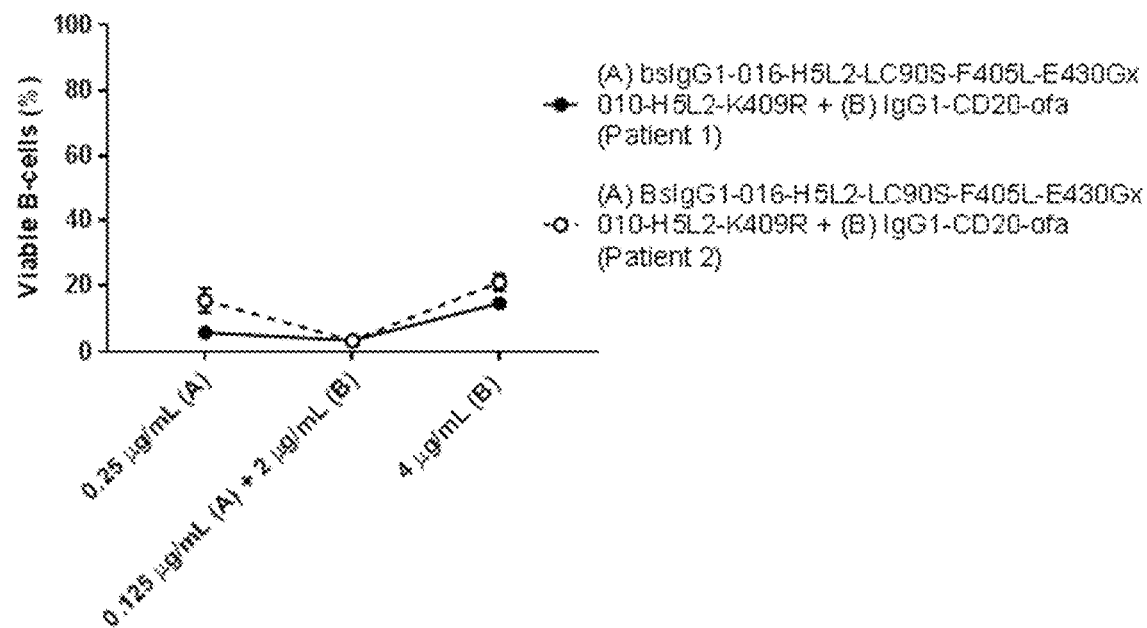
Figure 21C:
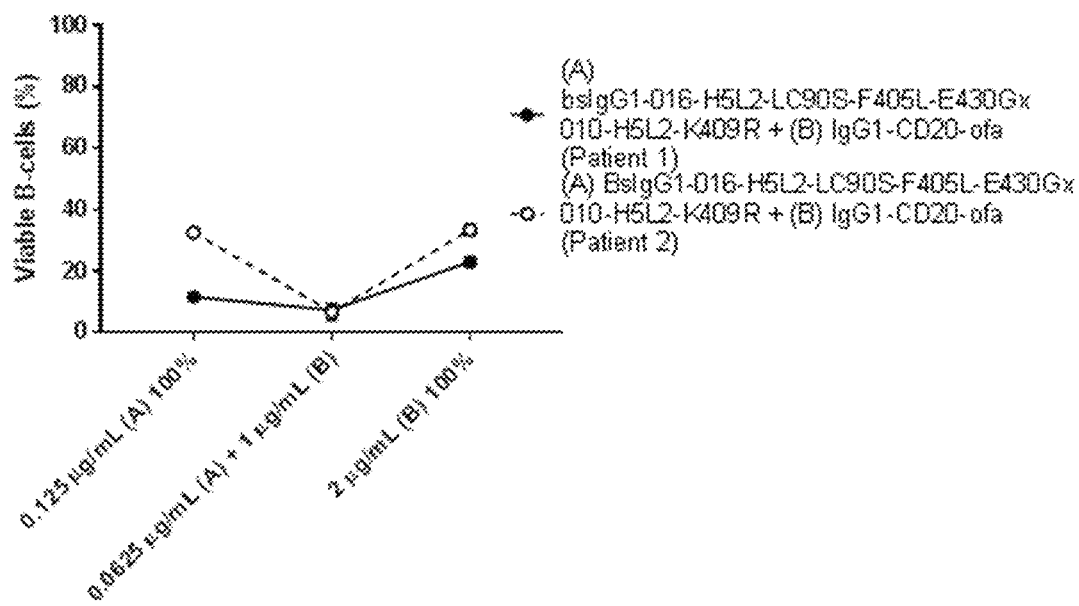
Figure 21D:
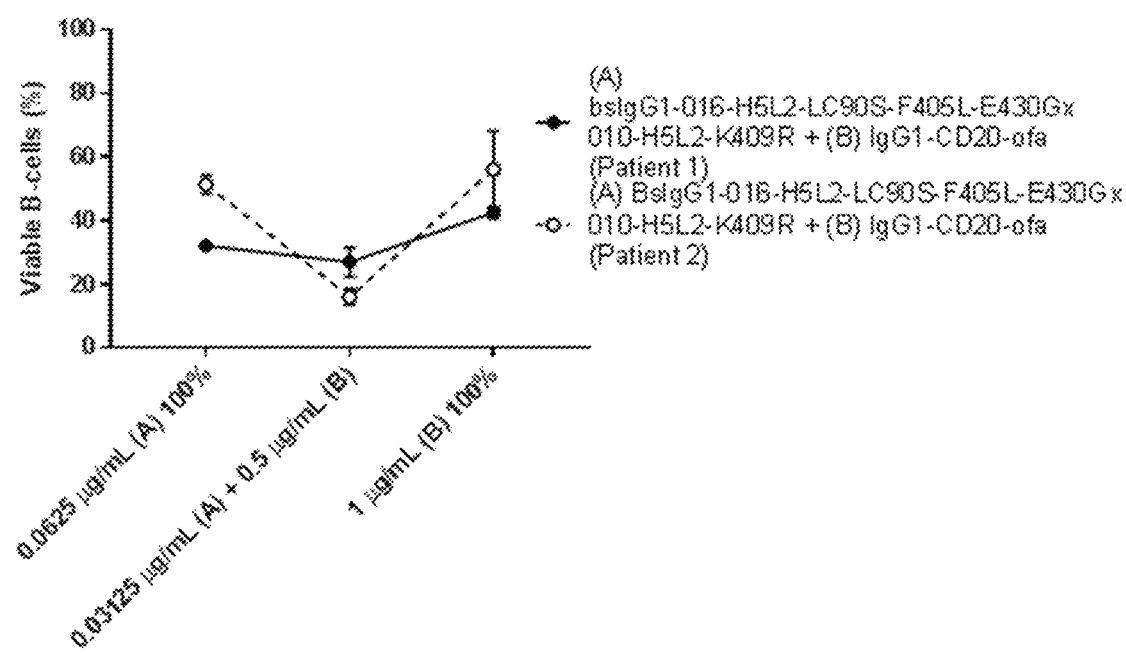

FIGS. 21A-D show that both bsIgG1-016-H5L2-LC90S-F405L-E430Gx010-H5L2-K409R-E430G and ofatumumab induced CDC in tumor cells derived from 2 CLL patients, with CDC activity increasing with increasing dose levels. Combining bsIgG1-016-H5L2-LC90S-F405L-E430Gx010-H5L2-K409R-E430G with ofatumumab resulted in enhanced CDC activity at all tested concentrations for both CLL patients tested, although these effects were less evident at higher antibody concentrations, where almost complete cell kill was induced by the single agents (FIGS. 21A and B). These results indicate that the addition of ofatumumab to bsIgG1-016-H5L2-LC90S-F405L-E430Gx010-H5L2-K409R-E430G can improve CDC-mediated tumor cell kill in malignant B cells obtained from CLL patients.

Example 15: Anti-Tumor Activity of a Bispecific CD37 Antibody with an Fc-Fc Interaction Enhancing Mutation in Xenograft Models of B Cell Malignancies Anti-Tumor Activity in a Subcutaneous JVM-3 Human Chronic B Cell Leukemia Xenograft Model JVM-3 cells (1×10$^7$) were inoculated into the right flank of CB17.SCID mice and antibody treatment (3 weekly doses of 0.1, 0.3, 1, 3 or 10 mg/kg, injected intravenously; IgG1-b12 was used as negative control, dosed at 10 mg/kg) was initiated when tumors reached a mean volume of approximately 158 mm$^3$. Tumor volumes were measured twice weekly in two dimensions using a caliper, and the volume was expressed in mm$^3$ using the formula: V=(L×W×W)/2, where V is tumor volume, L is tumor length (the longest tumor dimension) and W is tumor width (the longest tumor dimension perpendicular to L).

FIG. 22A shows the tumor volume per dose group over time, FIG. 22B shows the tumor volumes per mouse per dose group on day 25 when all groups were still complete. Three weekly doses of bsIgG1-016-H5L2-LC90S-F405L-E430Gx010-H5L2-K409R-E430G at 1, 3 or 10 mg/kg significantly reduced the JVM-3 cell tumor growth, whereas dosing at 0.1 or 0.3 mg/kg did not affect tumor growth (Mann Whitney test, p<0.01).

Anti-Tumor Activity in an Intravenous Daudi-Luc Burkitt's Lymphoma Xenograft Model On day 0, SCID mice (C.B-17/IcrHan®Hsd-Prkdcscid; Harlan) were intravenously injected with Daudi-luc cells (luciferase transfected Daudi cell, $2.5 \times 10^6$ cells/mouse). At day 14, 21 and 28, mice were injected intraperitoneally with 0.1, 0.3, 1, 3 or 10 mg/kg of bsIgG1-016-H5L2-LC90S-F405L-E430Gx010-H5L2-K409R-E430G. IgG1-b12 was used as negative control antibody, dosed at 10 mg/kg. Tumor growth was evaluated weekly (starting at day 2) by bioluminescence imaging (BLI). Mice were injected intraperitoneally with 100 μL firefly D-luciferin (30 mg/mL; Caliper LifeSciences, cat. no. 119222) and bioluminescence (radiance in $p/s/cm^2/sr$ [photons per second per $cm^2$ per square radian]) was measured under isoflurane anesthesia using a Biospace Bioluminescence Imaging System (PerkinElmer; mice were imaged from the dorsal site).

FIG. 23A shows luciferase activity (bioluminescence, as a measure of tumor volume) per dose group over time, FIG. 23B shows the luciferase activity per mouse per dose group on day 36 when all groups were still complete. Three weekly doses of bsIgG1-016-H5L2-LC90S-F405L-E430Gx010-H5L2-K409R-E430G at 0.1, 0.3, 1, 3 or 10 mg/kg significantly reduced the in vivo growth of Daudi-luc cells (One Way Anova, Uncorrected Fisher's LSD).

Example 16: Evaluation of Plasma Clearance of a Bispecific CD37 Antibody with an Fc-Fc Interaction Enhancing Mutation in SCID Mice 11-12 week old, female SCID mice (C.B-17/IcrHan®Hsd-Prkdcscid; Harlan) (3 mice per group) were injected intravenously (i.v.) injected with a single dose of 100 μg (5 mg/kg) or 500 μg (25 mg/kg) of bsIgG1-016-H5L2-LC90S-F405L-E430Gx010-H5L2-K409R-E430G or IgG1-b12. The experiment was set up to study antibody clearance in absence of target-mediated clearance as neither bsIgG1-016-H5L2-LC90S-F405L-E430Gx010-H5L2-K409R-E430G nor IgG1-b12 show cross-reactivity with mouse.

50-100 μL blood samples were collected from the saphenous vein at 10 minutes, 4 hours, 24 hours, 2 days, 7 or 8 days, 14 days and 21 days after antibody administration. Blood was collected into heparin containing vials and centrifuged for 5 minutes at 10,000 g. Plasma samples were diluted 1:50 for mice dosed with 5 mg/kg (20 μL sample in 980 μL PBSA (PBS supplemented with 0.2% bovine serum albumin (BSA)) and 1:20 for mice dosed with 25 mg/kg (20 μL sample in 380 μL PBSA) and stored at −20° C. until determination of mAb concentrations.

Figure 24A:
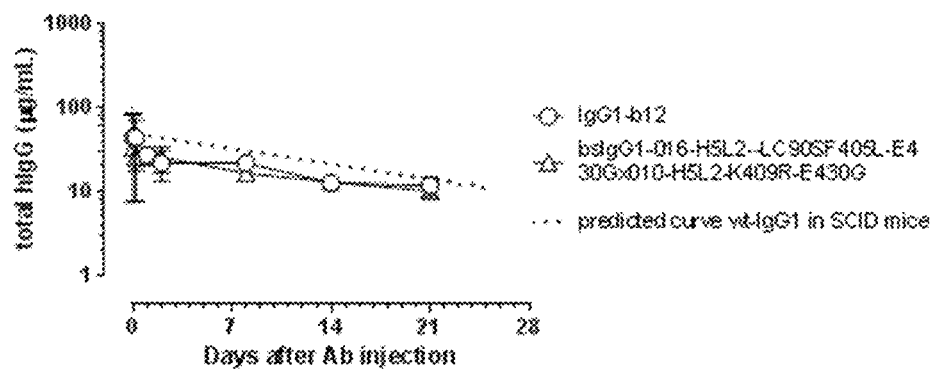
Figure 24B:
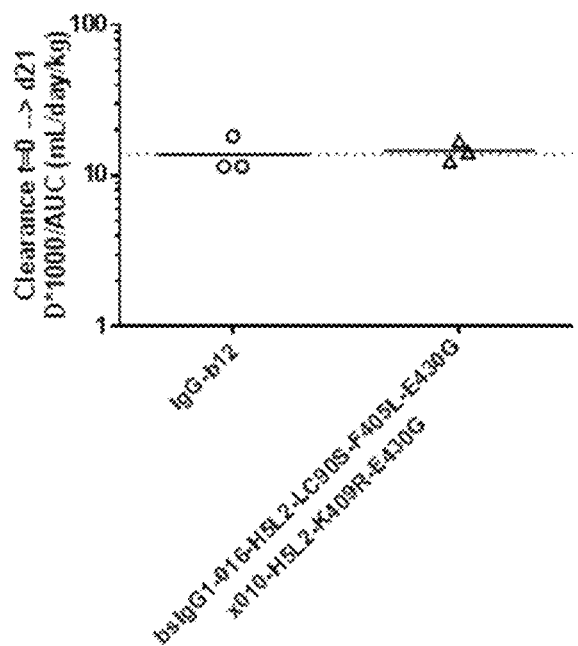
Figure 24C:
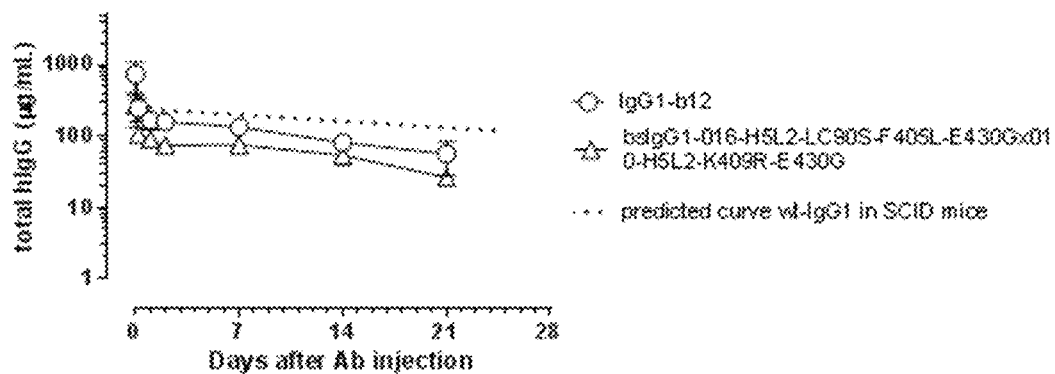
Figure 24D:
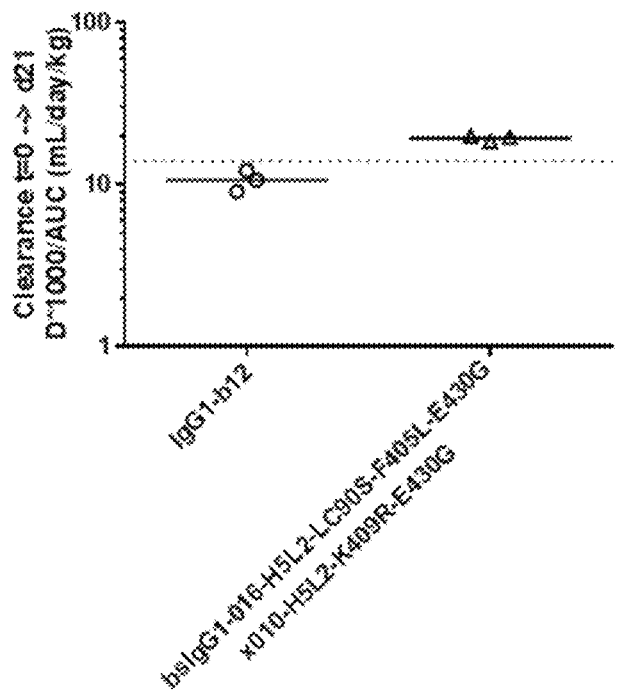

Human IgG concentrations were determined using a sandwich ELISA. Mouse mAb anti-human IgG-kappa clone MH16 (CLB Sanquin, The Netherlands; cat. no. M1268), coated in 100 μL overnight at 4° C. to 96-well Microlon ELISA plates (Greiner, Germany) at a concentration of 2 μg/mL, was used as capturing antibody. After blocking plates with PBSA for 1 hour at room temperature (RT), samples were added, serially diluted in PBSA, and incubated on a plate shaker for 1 hour at RT. Plates were washed three times with 300 μL PBST (PBS supplemented with 0.05% Tween 20) and subsequently incubated for 1 hour at RT with goat anti-human IgG immunoglobulin (Jackson, West Grace, Pa.; cat. no. 109-035-098; 1:10.000 in PBST supplemented with 0.2% BSA). Plates were washed again three times with 300 μL PBST before incubation with 2,2'-azinobis (3-ethylbenzthiazoline-6-sulfonic acid) (ABTS; Roche, Mannheim, Germany) protected from light. The reaction was stopped by adding 100 μL 2% oxalic acid. Absorbance was measured in a microplate reader (Biotek, Winooski, Vt.) at 405 nm. Human IgG concentration was calculated by using the injected material as a reference curve. As a plate control, purified human IgG1 (The binding site, cat. no. BP078) was included. Human IgG concentrations (in μg/mL) were plotted (FIGS. 24A and C) and the area under the curve (AUC) was calculated using Graphpad prism 6.0. IgG clearance until the last day of blood sampling (day 21) was determined by the formula D*1.000/AUC, in which D is the dose of injection (1 mg/kg) (FIGS. 24B and D).

There were no substantial differences between plasma clearance rates of bsIgG1-016-H5L2-LC90S-F405L-E430Gx010-H5L2-K409R-E430G and IgG1-b12, demonstrating that bsIgG1-016-H5L2-LC90S-F405L-E430Gx010-H5L2-K409R-E430G showed a comparable pharmacokinetic profile as wild type human IgG1 in absence of target binding.

Example 17: Determination of the Contribution of CD37 Amino Acid Residues to Binding of CD37 Antibodies Using Alanine Scanning Library Design A CD37 single residue alanine library was synthesized (Geneart) in which all amino acid (aa) residues in the extracellular domains of human CD37 (Uniprot P11049) were individually mutated to alanines except for positions already containing alanines or cysteines. Cysteines were not mutated to minimize the chance of structural disruption of the antigen. The library was cloned in the pMAC expression vector containing a CMV/TK-polyA expression cassette, an Amp resistance gene and a pBR322 replication origin.

Library Production and Screening

The wild type CD37 and alanine mutants were expressed individually in FreeStyle HEK293 cells according to the manufacturer's instructions (Thermo Scientific). One day post transfection the cells were harvested. Approximately 100,000 cells were incubated with 20 μL Alexa488 conjugated bsIgG1-b12-F405L-E430Gx010-H5L2-K409R-E430G (monovalent binding 010) or Alexa488 conjugated bsIgG1-016-H5L2-LC90S-F405L-E430Gxb12-K409R-E430G (monovalent binding 016) at a concentration of 3 μg/mL in FACS buffer (PBS+0.1% (w/v) bovine serum albumin (BSA)+0.02% (w/v) sodium azide). Cells were incubated for 1 hour at room temperature. Subsequently, cells were washed twice by adding 150 μL FACS buffer and removing the supernatant after centrifugation. Cells were resuspended in 20 μL fresh FACS buffer and stored at 4° C. until analysis by flow cytometry using an iQue screener (IntelliCyt). The entire experiment was performed 2 times.

Data Analysis

For every sample, the average antibody binding per cell was determined as the geometric mean of the fluorescence intensity (gMFI) for the ungated cell population. The gMFI is influenced by the affinity of the antibody for the CD37 mutant and the expression level of the CD37 mutant per cell. Since specific alanine mutations can impact the surface expression level of the mutant CD37, and to correct for expression differences for each CD37 mutant in general, data were normalized against the binding intensity of a non-competing CD37 specific control antibody (in this example antibodies monovalent binding 010 and monovalent binding 016 were non-competing antibodies and one antibody was used as control for the other antibody), using the following equation:

$$\text{Normalized } gMFI_{aa\ positition} = \text{Log}_{10}\left(\frac{gMFI_{Test\ Ab}}{gMFI_{Control\ Ab}}\right)$$

In which 'aa position' refers to either a particular alanine mutant position in CD37 or wild type (wt) CD37.

To express loss or gain of binding of the antibodies the standard score was determined according to the following calculation:

$$zscore(\text{fold change}) = \frac{\text{Normalized } gMFJ_{aa\ position} - \mu}{\sigma}$$

Where μ and σ are the mean and standard deviation (SD) of the Normalized gMFI of all mutants.

Gain of binding in most cases will be caused by loss of binding of the reference antibody to specific ala mutants. Using these calculations, amino acid positions for which, upon replacing the amino acid with alanine, there is no loss or gain of binding by a particular antibody will give a zscore of '0', gain of binding will result in 'zscore>0' and loss of binding will result in 'zscore<0'. To correct for sample variation, only CD37 amino acid residues where the zscore was lower than −1.5 were considered 'loss of binding mutants'. In case the gMFI of the control antibody for a particular CD37 mutant was lower than the mean gMFI−2.5×SD of the mean gMFI$_{Control\ Ab}$, data were excluded from analysis (as for those CD37 mutants it was assumed expression levels were not sufficient).

FIG. 25 shows the 'zscore (fold change)' of the CD37 antibodies to CD37 variants with ala mutations at positions 42 to 131 (according to SEQ ID No 94). The results indicate that:

binding of antibody 010 is at least dependent on aa Y182, D189, T191, I192, D194, K195, V196, I197 and P199 of human CD37, binding of antibody 016 is at least dependent on aa E124, F162, Q163, V164, L165 and H175 of human CD37.

In Summary

In summary, bispecific antibodies composed of two CD37-specific antibodies that do not compete for target binding with an Fc-Fc interaction enhancing mutation, showed the most favorable combination of CDC potency and ADCC potency in CD37-positive tumor cells. For both effector mechanisms, the bispecific antibodies with the Fc-Fc interaction enhancing mutation showed superior potency compared to the combination of two non-competing CD37 antibodies containing the Fc-Fc interaction enhancing mutation or to the single CD37 antibodies with the Fc-Fc interaction enhancing mutation.

Example 18: In Vitro Evaluation of CDC Activity of Mixtures of Novel Hexamerization-Enhanced CD37 Antibodies with Clinically Established CD20 Antibody Products on Raji Cells The CDC activity of mixtures of CD37 antibodies with an Fc-Fc interaction enhancing mutation, IgG1-37.3-E430G, IgG1-G28.1-E430G, IgG1-004-E430G, IgG1-005-E430G, IgG1-010-E430G and IgG1-016-E430G (the latter 4 being chimeric rabbit/human), plus the clinically established CD20-targeting monoclonal antibody products MabThera (rituximab; Roche, H01241308), Arzerra (ofatumumab; Novartis; C656294) and Gazyva (obinutuzumab, GA101; Roche, D287-41A GACD20) was tested in vitro using Burkitt's lymphoma Raji cells. Raji cells (ATCC, Cat No. CCL-86) were cultured in RPMI 1640 supplemented with 10% heat-inactivated FBS, 1 U/mL penicillin, 1 μg/mL streptomycin, and 4 mM L-glutamine. $0.1 \times 10^6$ Raji cells were pre-incubated with antibodies in a total volume of 80 μL RPMI/0.2% BSA per well for 15 min on a shaker at RT. Next, NHS was added to the pre-incubated cells to a final volume of 100 μL (final antibody concentrations 10 μg/mL; 20% NHS) and incubated for 45 minutes at 37° C. For all tested total antibody concentrations, different ratios of the two antibodies in the mixtures were tested (1:0-3:1-1:1-1:3-0:1). Plates were centrifuged and cells were resuspended in 30 μL PI (2 μg/mL). Killing was calculated as the fraction PI-positive cells (%) determined by flow cytometry on an iQue screener (Intellicyt). Data were analyzed and plotted using GraphPad Prism software.

The mixtures of the tested CD37 antibodies with an Fc-Fc interaction enhancing mutation and clinically established CD20 antibody products showed enhanced dose-dependent CDC activity compared to the same concentration of the single antibodies on Raji cells (FIG. 8). There was little difference in CDC activity at the different tested ratios of the two antibodies in the mixtures (1:3, 1:1 or 3:1). These data indicate that the mixture of a hexamerization-enhanced CD37 antibody with an Fc-Fc interaction enhancing mutation plus a clinically established CD20 antibody product, such as MabThera, Arzerra (type I CD20 antibodies) or Gazyva (type II CD20 antibody), may improve the therapeutic potential for patients with B cell malignancies, which frequently become refractory to standard CD20 targeted therapies alone.

What is claimed is:

1. An antibody which binds to human CD37 comprising:
   (a) a variable heavy chain (VH) region comprising the CDR1, CDR2, and CDR3 sequences set forth in SEQ ID NOs: 23, 24, and 25, respectively, and a variable light chain (VL) region comprising the CDR1, CDR2, and CDR3 sequences set forth in SEQ ID NO: 27, the sequence YAS, and SEQ ID NO: 31, respectively, or
   (b) a VH region comprising the CDR1, CDR2, and CDR3 sequences set forth in SEQ ID NOs: 16, 17, and 18, respectively, and a VL region comprising the CDR1, CDR2, and CDR3 sequences set forth in SEQ ID NO: 20, the sequence KAS, and SEQ ID NO: 21, respectively.

2. The antibody of claim 1, which comprises the VH region comprising the CDR1, CDR2, and CDR3 sequences set forth in SEQ ID NOs: 23, 24, and 25, respectively, and the VL region comprising the CDR1, CDR2, and CDR3 sequences set forth in SEQ ID NO: 27, the sequence YAS, and SEQ ID NO: 31, respectively.

3. The antibody of claim 1, which comprises the VH region comprising the CDR1, CDR2, and CDR3 sequences set forth in SEQ ID NOs: 16, 17, and 18, respectively, and the VL region comprising the CDR1, CDR2, and CDR3 sequences set forth in SEQ ID NO: 20, the sequence KAS, and SEQ ID NO: 21, respectively.

4. The antibody of claim 2, which comprises a VH region comprising the amino acid sequence set forth in SEQ ID NO: 22 and a VL region comprising the amino acid sequence set forth in SEQ ID NO: 29.

5. The antibody of claim 3, which comprises a VH region comprising the amino acid sequence set forth in SEQ ID NO: 15 and a VL region comprising the amino acid sequence set forth in SEQ ID NO: 19.

6. The antibody of claim 2, which comprises a human IgG1 heavy chain constant region.

7. The antibody of claim 3, which comprises a human IgG1 heavy chain constant region.

8. The antibody of claim 6, wherein the human IgG1 heavy chain constant region comprises a substitution of glutamic acid at position 430 for glycine, and wherein the amino acid residue is numbered according to the EU Index.

9. The antibody of claim 7, wherein the human IgG1 heavy chain constant region comprises a substitution of glutamic acid at position 430 for glycine, and wherein the amino acid residue is numbered according to the EU Index.

10. The antibody of claim 2, which comprises a kappa light chain constant region.

11. The antibody of claim 3, which comprises a kappa light chain constant region.

12. A bispecific antibody comprising a first binding arm and a second binding arm, wherein the first binding arm comprises a first antigen-binding region and the second binding arm comprises a second antigen-binding region, wherein both the first antigen-binding region and second antigen-binding region bind to human CD37, and wherein
   (a) the first antigen-binding region comprises a variable heavy chain (VH) region comprising the CDR1, CDR2, and CDR3 sequences set forth in SEQ ID NOs: 23, 24, and 25, respectively, and a variable light chain (VL) region comprising the CDR1, CDR2, and CDR3 sequences set forth in SEQ ID NO: 27, the sequence YAS, and SEQ ID NO: 31, respectively, and
   (b) the second antigen-binding region comprises a VH region comprising the CDR1, CDR2, and CDR3 sequences set forth in SEQ ID NOs: 16, 17, and 18, respectively, and a VL region comprising the CDR1, CDR2, and CDR3 sequences set forth in SEQ ID NO: 20, the sequence KAS, and SEQ ID NO: 21.

13. The bispecific antibody of claim 12, wherein:
   (a) the first antigen-binding region comprises a VH region comprising the amino acid sequence set forth in SEQ ID NO: 22 and a VL region comprising the amino acid sequence set forth in SEQ ID NO: 29, and
   (b) the second antigen-binding region comprises a VH region comprising the amino acid sequence set forth in SEQ ID NO: 15 and a VL region comprising the amino acid sequence set forth in SEQ ID NO: 19.

14. The bispecific antibody of claim 13, wherein the first binding arm comprises a first human IgG1 heavy chain constant region and the second binding arm comprises a second human IgG1 heavy chain constant region.

15. The bispecific antibody of claim 14, wherein both the first and second human IgG1 heavy chain constant regions comprise a substitution of glutamic acid at position 430 for glycine, and wherein the amino acid residue is numbered according to the EU Index.

16. The bispecific antibody of claim 14, wherein the first human IgG1 heavy chain constant region comprises a substitution of phenylalanine at position 405 for leucine, wherein the second human IgG1 heavy chain constant region comprises a substitution of lysine at position 409 for arginine, and wherein the amino acid residues are numbered according to the EU Index.

17. The bispecific antibody of claim 14, wherein the first human IgG1 heavy chain constant region comprises a substitution of lysine at position 409 for arginine, wherein the second human IgG1 heavy chain constant region comprises a substitution of phenylalanine at position 405 for leucine, and wherein the amino acid residues are numbered according to the EU Index.

18. The bispecific antibody of claim 13, wherein both the first binding arm and second binding arm comprise a human kappa light chain constant region.

19. A bispecific antibody comprising a first binding arm comprising a first heavy chain and a first light chain and a second binding arm comprising a second heavy chain and a second light chain, wherein both the first binding arm and second binding arm bind to human CD37, and wherein:

(a) the first heavy chain comprises a variable heavy chain (VH) region comprising the amino acid sequence set forth in SEQ ID NO: 22, and the first light chain comprises a variable light chain (VL) region comprising the amino acid sequence set forth in SEQ ID NO: 29, and (b) the second heavy chain comprises a VH region comprising the amino acid sequence set forth in SEQ ID NO: 15, and the second light chain comprises a VL region comprising the amino acid sequence set forth in SEQ ID NO: 19, wherein the first heavy chain and second heavy chain comprise heavy chain constant regions comprising the amino acid sequences set forth in SEQ ID NOs: 59 and 60, respectively, and wherein both the first light chain and second light chain comprise a light chain constant region comprising the amino acid sequence set forth in SEQ ID NO: 61.

20. A bispecific antibody comprising a first binding arm comprising a first heavy chain and a first light chain and a second binding arm comprising a second heavy chain and a second light chain, wherein both the first binding arm and second binding arm bind to human CD37, and wherein:

(a) the first heavy chain comprises a variable heavy chain (VH) region comprising the amino acid sequence set forth in SEQ ID NO: 22, and the first light chain comprises a variable light chain (VL) region comprising the amino acid sequence set forth in SEQ ID NO: 29, and (b) the second heavy chain comprises a VH region comprising the amino acid sequence set forth in SEQ ID NO: 15, and the second light chain comprises a VL region comprising the amino acid sequence set forth in SEQ ID NO: 19, wherein the first heavy chain and second heavy chain comprise heavy chain constant regions comprising the amino acid sequences set forth in SEQ ID NOs: 60 and 59, respectively, and wherein both the first light chain and second light chain comprise a light chain constant region comprising the amino acid sequence set forth in SEQ ID NO: 61.

* * * * *

SEQUENCE LISTING

<160> NUMBER OF SEQ ID NOS: 121

<210> SEQ ID NO 1
<211> LENGTH: 121
<212> TYPE: PRT
<213> ORGANISM: Artificial Sequence
<220> FEATURE:
<223> OTHER INFORMATION: Synthetic

<400> SEQUENCE: 1

-continued

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Thr Tyr
            20                  25                  30

Asp Met Ser Trp Val Arg Gln Ala Pro Gly Lys Gly Leu Glu Trp Val
        35                  40                  45

Ser Ile Ile Tyr Ser Ser Val Gly Ala Tyr Tyr Ala Ser Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Glu Tyr Gly Ala Ser Ser Asp Tyr Ile Phe Ser Leu Trp Gly
        100                 105                 110

Gln Gly Thr Leu Val Thr Val Ser Ser
        115                 120

<210> SEQ ID NO 2
<211> LENGTH: 8
<212> TYPE: PRT
<213> ORGANISM: oryctolagus cuniculus

<400> SEQUENCE: 2

Gly Phe Ser Leu Ser Thr Tyr Asp
1               5

<210> SEQ ID NO 3
<211> LENGTH: 7
<212> TYPE: PRT
<213> ORGANISM: oryctolagus cuniculus

<400> SEQUENCE: 3

Ile Tyr Ser Ser Val Gly Ala
1               5

<210> SEQ ID NO 4
<211> LENGTH: 15
<212> TYPE: PRT
<213> ORGANISM: oryctolagus cuniculus

<400> SEQUENCE: 4

Ala Arg Glu Tyr Gly Ala Ser Ser Asp Tyr Ile Phe Ser Leu
1               5                   10                  15

<210> SEQ ID NO 5
<211> LENGTH: 113
<212> TYPE: PRT
<213> ORGANISM: Artificial Sequence
<220> FEATURE:
<223> OTHER INFORMATION: Synthetic

<400> SEQUENCE: 5

Ala Gln Val Leu Thr Gln Ser Pro Ser Pro Leu Ser Ala Ser Val Gly
1               5                   10                  15

Asp Arg Val Thr Ile Thr Cys Gln Ala Ser Gln Ser Val Tyr Asn Ser
            20                  25                  30

Gln Asn Leu Ala Trp Tyr Gln Gln Lys Pro Gly Lys Ala Pro Lys Leu
        35                  40                  45

Leu Ile Tyr Glu Ala Ser Lys Leu Ala Ser Gly Val Pro Ser Arg Phe
    50                  55                  60
```

```
Lys Gly Ser Gly Ser Gly Thr Glu Phe Thr Leu Thr Ile Ser Ser Leu
 65                  70                  75                  80

Gln Pro Asp Asp Phe Ala Thr Tyr Tyr Cys Gln Gly Glu Phe Ser Cys
                 85                  90                  95

Ile Ser Ala Asp Cys Thr Ala Phe Gly Gly Gly Thr Lys Val Glu Ile
            100                 105                 110

Lys

<210> SEQ ID NO 6
<211> LENGTH: 8
<212> TYPE: PRT
<213> ORGANISM: oryctolagus cuniculus

<400> SEQUENCE: 6

Gln Ser Val Tyr Asn Ser Gln Asn
1               5

<210> SEQ ID NO 7
<211> LENGTH: 13
<212> TYPE: PRT
<213> ORGANISM: oryctolagus cuniculus

<400> SEQUENCE: 7

Gln Gly Glu Phe Ser Cys Ile Ser Ala Asp Cys Thr Ala
1               5                   10

<210> SEQ ID NO 8
<211> LENGTH: 117
<212> TYPE: PRT
<213> ORGANISM: Artificial Sequence
<220> FEATURE:
<223> OTHER INFORMATION: Synthetic

<400> SEQUENCE: 8

Glu Gln Ser Val Val Glu Ser Gly Gly Gly Leu Val Gln Pro Gly Gly
1               5                   10                  15

Ser Leu Arg Leu Ser Cys Thr Val Ser Gly Phe Ser Leu Ser Ser Asn
            20                  25                  30

Ala Met Asn Trp Val Arg Gln Ala Pro Gly Lys Gly Leu Glu Trp Ile
        35                  40                  45

Gly Leu Ile Tyr Ala Ser Gly Asn Thr Asp Tyr Ala Ser Trp Ala Lys
    50                  55                  60

Gly Arg Phe Thr Ile Ser Lys Thr Ser Thr Thr Val Tyr Leu Lys Ile
 65                 70                  75                  80

Thr Ser Pro Thr Ala Glu Asp Thr Ala Thr Tyr Phe Cys Ala Arg Glu
                85                  90                  95

Gly Ser Val Trp Gly Ala Ala Phe Asp Pro Trp Gly Gln Gly Thr Leu
            100                 105                 110

Val Thr Val Ser Ser
        115

<210> SEQ ID NO 9
<211> LENGTH: 8
<212> TYPE: PRT
<213> ORGANISM: oryctolagus cuniculus

<400> SEQUENCE: 9

Gly Phe Ser Leu Ser Ser Asn Ala
1               5
```

```
<210> SEQ ID NO 10
<211> LENGTH: 7
<212> TYPE: PRT
<213> ORGANISM: oryctolagus cuniculus

<400> SEQUENCE: 10

Ile Tyr Ala Ser Gly Asn Thr
1               5

<210> SEQ ID NO 11
<211> LENGTH: 13
<212> TYPE: PRT
<213> ORGANISM: oryctolagus cuniculus

<400> SEQUENCE: 11

Ala Arg Glu Gly Ser Val Trp Gly Ala Ala Phe Asp Pro
1               5                   10

<210> SEQ ID NO 12
<211> LENGTH: 110
<212> TYPE: PRT
<213> ORGANISM: Artificial Sequence
<220> FEATURE:
<223> OTHER INFORMATION: Synthetic

<400> SEQUENCE: 12

Ala Tyr Asp Met Thr Gln Ser Pro Ser Val Ser Ala Ser Val Gly
1               5                   10                  15

Asp Arg Val Thr Ile Thr Cys Gln Ala Ser Gln Ser Ile Ser Asn Trp
                20                  25                  30

Leu Ala Trp Tyr Gln Gln Lys Pro Gly Lys Ala Pro Lys Gln Leu Ile
            35                  40                  45

Tyr Ala Ala Ser Thr Leu Ala Ser Gly Val Pro Ser Arg Phe Lys Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ser Asn Ser Asn
                85                  90                  95

Ile Asp Asn Thr Phe Gly Gly Gly Thr Lys Val Glu Ile Lys
            100                 105                 110

<210> SEQ ID NO 13
<211> LENGTH: 6
<212> TYPE: PRT
<213> ORGANISM: oryctolagus cuniculus

<400> SEQUENCE: 13

Gln Ser Ile Ser Asn Trp
1               5

<210> SEQ ID NO 14
<211> LENGTH: 12
<212> TYPE: PRT
<213> ORGANISM: oryctolagus cuniculus

<400> SEQUENCE: 14

Gln Gln Gly Tyr Ser Asn Ser Asn Ile Asp Asn Thr
1               5                   10

<210> SEQ ID NO 15
<211> LENGTH: 119
<212> TYPE: PRT
<213> ORGANISM: Artificial Sequence
```

```
<220> FEATURE:
<223> OTHER INFORMATION: Synthetic

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Tyr Asn
            20                  25                  30

Ala Met Asn Trp Val Arg Gln Ala Pro Gly Lys Gly Leu Glu Trp Val
        35                  40                  45

Ser Ile Ile Phe Ala Ser Gly Arg Thr Asp Tyr Ala Ser Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Gly Ser Thr Trp Gly Asp Ala Leu Asp Pro Trp Gly Gln Gly
            100                 105                 110

Thr Leu Val Thr Val Ser Ser
        115

<210> SEQ ID NO 16
<211> LENGTH: 8
<212> TYPE: PRT
<213> ORGANISM: oryctolagus cuniculus

<400> SEQUENCE: 16

Gly Phe Ser Leu Ser Tyr Asn Ala
1               5

<210> SEQ ID NO 17
<211> LENGTH: 7
<212> TYPE: PRT
<213> ORGANISM: oryctolagus cuniculus

<400> SEQUENCE: 17

Ile Phe Ala Ser Gly Arg Thr
1               5

<210> SEQ ID NO 18
<211> LENGTH: 13
<212> TYPE: PRT
<213> ORGANISM: oryctolagus cuniculus

<400> SEQUENCE: 18

Ala Arg Glu Gly Ser Thr Trp Gly Asp Ala Leu Asp Pro
1               5                   10

<210> SEQ ID NO 19
<211> LENGTH: 110
<212> TYPE: PRT
<213> ORGANISM: Artificial Sequence
<220> FEATURE:
<223> OTHER INFORMATION: Synthetic

<400> SEQUENCE: 19

Ala Tyr Asp Met Thr Gln Ser Pro Ser Thr Leu Ser Ala Ser Val Gly
1               5                   10                  15

Asp Arg Val Thr Ile Thr Cys Gln Ala Ser Gln Asn Ile Ile Asp Tyr
            20                  25                  30

Leu Ala Trp Tyr Gln Gln Lys Pro Gly Lys Ala Pro Lys Leu Leu Ile
```

```
            35                  40                  45
His Lys Ala Ser Thr Leu Ala Ser Gly Val Pro Ser Arg Phe Lys Gly
         50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Gly Tyr Ser Asn Ser Asn
                 85                  90                  95

Ile Asp Asn Thr Phe Gly Gly Gly Thr Lys Val Glu Ile Lys
            100                 105                 110
```

<210> SEQ ID NO 20
<211> LENGTH: 6
<212> TYPE: PRT
<213> ORGANISM: oryctolagus cuniculus

<400> SEQUENCE: 20

```
Gln Asn Ile Ile Asp Tyr
1               5
```

<210> SEQ ID NO 21
<211> LENGTH: 12
<212> TYPE: PRT
<213> ORGANISM: oryctolagus cuniculus

<400> SEQUENCE: 21

```
Gln Gln Gly Tyr Ser Asn Ser Asn Ile Asp Asn Thr
1               5                   10
```

<210> SEQ ID NO 22
<211> LENGTH: 120
<212> TYPE: PRT
<213> ORGANISM: Artificial Sequence
<220> FEATURE:
<223> OTHER INFORMATION: Synthetic

<400> SEQUENCE: 22

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Asn Tyr
             20                  25                  30

Asn Met Gly Trp Val Arg Gln Ala Pro Gly Lys Gly Leu Glu Trp Val
         35                  40                  45

Ser Val Ile Asp Ala Ser Gly Thr Thr Tyr Tyr Ala Thr Trp Ala Lys
     50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Thr Tyr Tyr Cys Ala
                 85                  90                  95

Arg Glu Leu Leu Tyr Phe Gly Ser Ser Tyr Tyr Asp Leu Trp Gly Gln
            100                 105                 110

Gly Thr Leu Val Thr Val Ser Ser
        115                 120
```

<210> SEQ ID NO 23
<211> LENGTH: 8
<212> TYPE: PRT
<213> ORGANISM: oryctolagus cuniculus

<400> SEQUENCE: 23

```
Gly Phe Ser Leu Ser Asn Tyr Asn
```

```
<210> SEQ ID NO 24
<211> LENGTH: 7
<212> TYPE: PRT
<213> ORGANISM: oryctolagus cuniculus

<400> SEQUENCE: 24

Ile Asp Ala Ser Gly Thr Thr
1               5

<210> SEQ ID NO 25
<211> LENGTH: 14
<212> TYPE: PRT
<213> ORGANISM: oryctolagus cuniculus

<400> SEQUENCE: 25

Ala Arg Glu Leu Leu Tyr Phe Gly Ser Ser Tyr Tyr Asp Leu
1               5                   10

<210> SEQ ID NO 26
<211> LENGTH: 110
<212> TYPE: PRT
<213> ORGANISM: Artificial Sequence
<220> FEATURE:
<223> OTHER INFORMATION: Synthetic

<400> SEQUENCE: 26

Asp Val Val Met Thr Gln Ser Pro Ser Thr Leu Ser Ala Ser Val Gly
1               5                   10                  15

Asp Arg Val Thr Ile Thr Cys Gln Ala Ser Gln Asn Ile Asp Ser Asn
            20                  25                  30

Leu Ala Trp Tyr Gln Gln Lys Pro Gly Lys Ala Pro Lys Phe Leu Ile
        35                  40                  45

Tyr Tyr Ala Ser Asn Leu Pro Phe Gly Val Pro Ser Arg Phe Lys Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Cys Ala Asp Val Gly Ser Thr
                85                  90                  95

Tyr Val Ala Ala Phe Gly Gly Gly Thr Lys Val Glu Ile Lys
            100                 105                 110

<210> SEQ ID NO 27
<211> LENGTH: 6
<212> TYPE: PRT
<213> ORGANISM: oryctolagus cuniculus

<400> SEQUENCE: 27

Gln Asn Ile Asp Ser Asn
1               5

<210> SEQ ID NO 28
<211> LENGTH: 12
<212> TYPE: PRT
<213> ORGANISM: oryctolagus cuniculus

<400> SEQUENCE: 28

Gln Cys Ala Asp Val Gly Ser Thr Tyr Val Ala Ala
1               5                   10

<210> SEQ ID NO 29
```

```
<211> LENGTH: 110
<212> TYPE: PRT
<213> ORGANISM: Artificial Sequence
<220> FEATURE:
<223> OTHER INFORMATION: Synthetic

<400> SEQUENCE: 29

Asp Val Val Met Thr Gln Ser Pro Ser Thr Leu Ser Ala Ser Val Gly
 1               5                  10                  15

Asp Arg Val Thr Ile Thr Cys Gln Ala Ser Gln Asn Ile Asp Ser Asn
            20                  25                  30

Leu Ala Trp Tyr Gln Gln Lys Pro Gly Lys Ala Pro Lys Phe Leu Ile
        35                  40                  45

Tyr Tyr Ala Ser Asn Leu Pro Phe Gly Val Pro Ser Arg Phe Lys Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Ser Ala Asp Val Gly Ser Thr
                85                  90                  95

Tyr Val Ala Ala Phe Gly Gly Gly Thr Lys Val Glu Ile Lys
            100                 105                 110

<210> SEQ ID NO 30
<211> LENGTH: 6
<212> TYPE: PRT
<213> ORGANISM: oryctolagus cuniculus

<400> SEQUENCE: 30

Gln Asn Ile Asp Ser Asn
 1               5

<210> SEQ ID NO 31
<211> LENGTH: 12
<212> TYPE: PRT
<213> ORGANISM: oryctolagus cuniculus

<400> SEQUENCE: 31

Gln Ser Ala Asp Val Gly Ser Thr Tyr Val Ala Ala
 1               5                  10

<210> SEQ ID NO 32
<211> LENGTH: 127
<212> TYPE: PRT
<213> ORGANISM: Artificial Sequence
<220> FEATURE:
<223> OTHER INFORMATION: Synthetic

<400> SEQUENCE: 32

Gln Val Gln Leu Val Gln Ser Gly Ala Glu Val Lys Lys Pro Gly Ala
 1               5                  10                  15

Ser Val Lys Val Ser Cys Gln Ala Ser Gly Tyr Arg Phe Ser Asn Phe
            20                  25                  30

Val Ile His Trp Val Arg Gln Ala Pro Gly Gln Arg Phe Glu Trp Met
        35                  40                  45

Gly Trp Ile Asn Pro Tyr Asn Gly Asn Lys Glu Phe Ser Ala Lys Phe
50                  55                  60

Gln Asp Arg Val Thr Phe Thr Ala Asp Thr Ser Ala Asn Thr Ala Tyr
65                  70                  75                  80

Met Glu Leu Arg Ser Leu Arg Ser Ala Asp Thr Ala Val Tyr Tyr Cys
                85                  90                  95
```

Ala Arg Val Gly Pro Tyr Ser Trp Asp Asp Ser Pro Gln Asp Asn Tyr
            100                 105                 110

Tyr Met Asp Val Trp Gly Lys Gly Thr Thr Val Ile Val Ser Ser
        115                 120                 125

<210> SEQ ID NO 33
<211> LENGTH: 8
<212> TYPE: PRT
<213> ORGANISM: Artificial Sequence
<220> FEATURE:
<223> OTHER INFORMATION: Synthetic

<400> SEQUENCE: 33

Gly Tyr Arg Phe Ser Asn Phe Val
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic

<400> SEQUENCE: 34

Ile Asn Pro Tyr Asn Gly Asn Lys
1               5

<210> SEQ ID NO 35
<211> LENGTH: 20
<212> TYPE: PRT
<213> ORGANISM: Artificial Sequence
<220> FEATURE:
<223> OTHER INFORMATION: Synthetic

<400> SEQUENCE: 35

Ala Arg Val Gly Pro Tyr Ser Trp Asp Asp Ser Pro Gln Asp Asn Tyr
1               5                   10                  15

Tyr Met Asp Val
            20

<210> SEQ ID NO 36
<211> LENGTH: 108
<212> TYPE: PRT
<213> ORGANISM: Artificial Sequence
<220> FEATURE:
<223> OTHER INFORMATION: Synthetic

<400> SEQUENCE: 36

Glu Ile Val Leu Thr Gln Ser Pro Gly Thr Leu Ser Leu Ser Pro Gly
1               5                   10                  15

Glu Arg Ala Thr Phe Ser Cys Arg Ser Ser His Ser Ile Arg Ser Arg
            20                  25                  30

Arg Val Ala Trp Tyr Gln His Lys Pro Gly Gln Ala Pro Arg Leu Val
        35                  40                  45

Ile His Gly Val Ser Asn Arg Ala Ser Gly Ile Ser Asp Arg Phe Ser
    50                  55                  60

Gly Ser Gly Ser Gly Thr Asp Phe Thr Leu Thr Ile Thr Arg Val Glu
65                  70                  75                  80

Pro Glu Asp Phe Ala Leu Tyr Tyr Cys Gln Val Tyr Gly Ala Ser Ser
                85                  90                  95

Tyr Thr Phe Gly Gln Gly Thr Lys Leu Glu Arg Lys
            100                 105

<210> SEQ ID NO 37
<211> LENGTH: 7
<212> TYPE: PRT
<213> ORGANISM: Artificial Sequence
<220> FEATURE:
<223> OTHER INFORMATION: Synthetic

<400> SEQUENCE: 37

```
His Ser Ile Arg Ser Arg Arg
1               5
```

<210> SEQ ID NO 38
<211> LENGTH: 9
<212> TYPE: PRT
<213> ORGANISM: Artificial Sequence
<220> FEATURE:
<223> OTHER INFORMATION: Synthetic

<400> SEQUENCE: 38

```
Gln Val Tyr Gly Ala Ser Ser Tyr Thr
1               5
```

<210> SEQ ID NO 39
<211> LENGTH: 116
<212> TYPE: PRT
<213> ORGANISM: Artificial Sequence
<220> FEATURE:
<223> OTHER INFORMATION: Synthetic

<400> SEQUENCE: 39

```
Ala Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Asn Asn Gly Lys Ser Leu Glu Trp Ile
        35                  40                  45

Gly Asn Ile Asp Pro Tyr Tyr Gly Gly Thr Thr Tyr Asn Arg Lys Phe
    50                  55                  60

Lys Gly Lys Ala Thr Leu Thr Val Asp Lys Ser Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Arg Ser Val Gly Pro Met Asp Tyr Trp Gly Gln Gly Thr Ser Val
            100                 105                 110

Thr Val Ser Ser
        115
```

<210> SEQ ID NO 40
<211> LENGTH: 8
<212> TYPE: PRT
<213> ORGANISM: Artificial Sequence
<220> FEATURE:
<223> OTHER INFORMATION: Synthetic

<400> SEQUENCE: 40

```
Gly Tyr Ser Phe Thr Gly Tyr Asn
1               5
```

<210> SEQ ID NO 41
<211> LENGTH: 8
<212> TYPE: PRT
<213> ORGANISM: Artificial Sequence
<220> FEATURE:

<223> OTHER INFORMATION: Synthetic

<400> SEQUENCE: 41

Ile Asp Pro Tyr Tyr Gly Gly Thr
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic

<400> SEQUENCE: 42

Ala Arg Ser Val Gly Pro Met Asp Tyr
1               5

<210> SEQ ID NO 43
<211> LENGTH: 107
<212> TYPE: PRT
<213> ORGANISM: Artificial Sequence
<220> FEATURE:
<223> OTHER INFORMATION: Synthetic

<400> SEQUENCE: 43

Asp Ile Gln Met Thr Gln Ser Pro Ala Ser Leu Ser Ala Ser Val Gly
1               5                   10                  15

Glu Thr Val Thr Ile Thr Cys Arg Thr Ser Glu Asn Val Tyr Ser Tyr
            20                  25                  30

Leu Ala Trp Tyr Gln Gln Lys Gln Gly Lys Ser Pro Gln Leu Leu Val
        35                  40                  45

Ser Phe Ala Lys Thr Leu Ala Glu Gly Val Pro Ser Arg Phe Ser Gly
    50                  55                  60

Ser Gly Ser Gly Thr Gln Phe Ser Leu Lys Ile Ser Ser Leu Gln Pro
65                  70                  75                  80

Glu Asp Ser Gly Ser Tyr Phe Cys Gln His His Ser Asp Asn Pro Trp
                85                  90                  95

Thr Phe Gly Gly Gly Thr Glu Leu Glu Ile Lys
            100                 105

<210> SEQ ID NO 44
<211> LENGTH: 6
<212> TYPE: PRT
<213> ORGANISM: Artificial Sequence
<220> FEATURE:
<223> OTHER INFORMATION: Synthetic

<400> SEQUENCE: 44

Glu Asn Val Tyr Ser Tyr
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic

<400> SEQUENCE: 45

Gln His His Ser Asp Asn Pro Trp Thr
1               5

<210> SEQ ID NO 46

```
<211> LENGTH: 115
<212> TYPE: PRT
<213> ORGANISM: Artificial Sequence
<220> FEATURE:
<223> OTHER INFORMATION: Synthetic

<400> SEQUENCE: 46

Gln Val Gln Val Lys Glu Ser Gly Pro Gly Leu Val Ala Pro Ser Gln
1               5                   10                  15

Ser Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ala Leu Lys
    50                  55                  60

Ser Arg Leu Ser Ile Lys Lys Asp His Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ala
        115

<210> SEQ ID NO 47
<211> LENGTH: 8
<212> TYPE: PRT
<213> ORGANISM: Artificial Sequence
<220> FEATURE:
<223> OTHER INFORMATION: Synthetic

<400> SEQUENCE: 47

Gly Phe Ser Leu Thr Thr Ser Gly
1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic

<400> SEQUENCE: 48

Ile Trp Gly Asp Gly Ser Thr
1               5

<210> SEQ ID NO 49
<211> LENGTH: 9
<212> TYPE: PRT
<213> ORGANISM: Artificial Sequence
<220> FEATURE:
<223> OTHER INFORMATION: Synthetic

<400> SEQUENCE: 49

Ala Lys Gly Gly Tyr Ser Leu Ala His
1               5

<210> SEQ ID NO 50
<211> LENGTH: 107
<212> TYPE: PRT
<213> ORGANISM: Artificial Sequence
<220> FEATURE:
<223> OTHER INFORMATION: Synthetic
```

-continued

<400> SEQUENCE: 50

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Arg Ser Asn
            20                  25                  30

Leu Ala Trp Tyr Gln Gln Lys Gln Gly Lys Ser Pro Gln Leu Leu Val
        35                  40                  45

Asn Val Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Thr Tyr Tyr Cys Gln His Tyr Trp Gly Thr Thr Trp
                85                  90                  95

Thr Phe Gly Gly Gly Thr Lys Leu Glu Ile Lys
            100                 105

<210> SEQ ID NO 51
<211> LENGTH: 6
<212> TYPE: PRT
<213> ORGANISM: Artificial Sequence
<220> FEATURE:
<223> OTHER INFORMATION: Synthetic

<400> SEQUENCE: 51

Glu Asn Ile Arg Ser Asn
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic

<400> SEQUENCE: 52

Gln His Tyr Trp Gly Thr Thr Trp Thr
1               5

<210> SEQ ID NO 53
<211> LENGTH: 330
<212> TYPE: PRT
<213> ORGANISM: Homo Sapiens

<400> SEQUENCE: 53

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro

```
            115                 120                 125
Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 54
<211> LENGTH: 329
<212> TYPE: PRT
<213> ORGANISM: Artificial Sequence
<220> FEATURE:
<223> OTHER INFORMATION: Synthetic

<400> SEQUENCE: 54

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
```

-continued

```
            145                 150                 155                 160
Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 55
<211> LENGTH: 330
<212> TYPE: PRT
<213> ORGANISM: Artificial Sequence
<220> FEATURE:
<223> OTHER INFORMATION: Synthetic

<400> SEQUENCE: 55

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
```

```
            180                 185                 190
His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
                325                 330

<210> SEQ ID NO 56
<211> LENGTH: 330
<212> TYPE: PRT
<213> ORGANISM: Artificial Sequence
<220> FEATURE:
<223> OTHER INFORMATION: Synthetic

<400> SEQUENCE: 56

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
```

```
            210                 215                 220
Gln Pro Arg Arg Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 57
<211> LENGTH: 330
<212> TYPE: PRT
<213> ORGANISM: Artificial Sequence
<220> FEATURE:
<223> OTHER INFORMATION: Synthetic

<400> SEQUENCE: 57

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
```

```
                    245                 250                 255
Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Leu
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 58
<211> LENGTH: 330
<212> TYPE: PRT
<213> ORGANISM: Artificial Sequence
<220> FEATURE:
<223> OTHER INFORMATION: Synthetic

<400> SEQUENCE: 58

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
```

```
                275                 280                 285
Leu Tyr Ser Arg Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 59
<211> LENGTH: 330
<212> TYPE: PRT
<213> ORGANISM: Artificial Sequence
<220> FEATURE:
<223> OTHER INFORMATION: Synthetic

<400> SEQUENCE: 59

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Leu
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
```

Gln Lys Ser Leu Ser Leu Ser Pro Gly Lys
                325                 330

<210> SEQ ID NO 60
<211> LENGTH: 330
<212> TYPE: PRT
<213> ORGANISM: Artificial Sequence
<220> FEATURE:
<223> OTHER INFORMATION: Synthetic

<400> SEQUENCE: 60

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Gln Gly Asn
    290                 295                 300

Val Phe Ser Cys Ser Val Met His Gly Ala Leu His Asn His Tyr Thr
305                 310                 315                 320

Gln Lys Ser Leu Ser Leu Ser Pro Gly Lys
                325                 330

```
<210> SEQ ID NO 61
<211> LENGTH: 107
<212> TYPE: PRT
<213> ORGANISM: Homo Sapiens

<400> SEQUENCE: 61

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 62
<211> LENGTH: 281
<212> TYPE: PRT
<213> ORGANISM: Homo Sapiens

<400> SEQUENCE: 62

Met Ser Ala Gln Glu Ser Cys Leu Ser Leu Ile Lys Tyr Phe Leu Phe
1               5                   10                  15

Val Phe Asn Leu Phe Phe Phe Val Leu Gly Ser Leu Ile Phe Cys Phe
            20                  25                  30

Gly Ile Trp Ile Leu Ile Asp Lys Thr Ser Phe Val Ser Phe Val Gly
        35                  40                  45

Leu Ala Phe Val Pro Leu Gln Ile Trp Ser Lys Val Leu Ala Ile Ser
    50                  55                  60

Gly Ile Phe Thr Met Gly Ile Ala Leu Leu Gly Cys Val Gly Ala Leu
65                  70                  75                  80

Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
            100                 105                 110

Ala Gln Leu Glu Arg Ser Leu Arg Asp Val Val Glu Lys Thr Ile Gln
        115                 120                 125

Lys Tyr Gly Thr Asn Pro Glu Glu Thr Ala Ala Glu Glu Ser Trp Asp
    130                 135                 140

Tyr Val Gln Phe Gln Leu Arg Cys Cys Gly Trp His Tyr Pro Gln Asp
145                 150                 155                 160

Trp Phe Gln Val Leu Ile Leu Arg Gly Asn Gly Ser Glu Ala His Arg
                165                 170                 175

Val Pro Cys Ser Cys Tyr Asn Leu Ser Ala Thr Asn Asp Ser Thr Ile
            180                 185                 190

Leu Asp Lys Val Ile Leu Pro Gln Leu Ser Arg Leu Gly His Leu Ala
        195                 200                 205

Arg Ser Arg His Ser Ala Asp Ile Cys Ala Val Pro Ala Glu Ser His
    210                 215                 220

Ile Tyr Arg Glu Gly Cys Ala Gln Gly Leu Gln Lys Trp Leu His Asn
```

225                 230                 235                 240

Asn Leu Ile Ser Ile Val Gly Ile Cys Leu Gly Val Gly Leu Leu Glu
                245                 250                 255

Leu Gly Phe Met Thr Leu Ser Ile Phe Leu Cys Arg Asn Leu Asp His
            260                 265                 270

Val Tyr Asn Arg Leu Ala Arg Tyr Arg
        275                 280

<210> SEQ ID NO 63
<211> LENGTH: 281
<212> TYPE: PRT
<213> ORGANISM: Macaca fascicularis

<400> SEQUENCE: 63

Met Ser Ala Gln Glu Ser Cys Leu Ser Leu Ile Lys Tyr Phe Leu Phe
1               5                   10                  15

Val Phe Asn Leu Phe Phe Phe Val Leu Gly Ser Leu Ile Phe Cys Phe
            20                  25                  30

Gly Ile Trp Ile Leu Ile Asp Lys Thr Ser Phe Val Ser Phe Val Gly
        35                  40                  45

Leu Ala Phe Val Pro Leu Gln Ile Trp Ser Lys Val Leu Ala Ile Ser
    50                  55                  60

Gly Val Phe Thr Met Gly Leu Ala Leu Leu Gly Cys Val Gly Ala Leu
65                  70                  75                  80

Lys Glu Leu Arg Cys Leu Leu Gly Leu Tyr Phe Gly Met Leu Leu Leu
                85                  90                  95

Leu Phe Ala Thr Gln Ile Thr Leu Gly Ile Leu Ile Ser Thr Gln Arg
            100                 105                 110

Ala Gln Leu Glu Arg Ser Leu Gln Asp Ile Val Glu Lys Thr Ile Gln
        115                 120                 125

Lys Tyr His Thr Asn Pro Glu Glu Thr Ala Ala Glu Glu Ser Trp Asp
    130                 135                 140

Tyr Val Gln Phe Gln Leu Arg Cys Cys Gly Trp His Ser Pro Gln Asp
145                 150                 155                 160

Trp Phe Gln Val Leu Thr Leu Arg Gly Asn Gly Ser Glu Ala His Arg
                165                 170                 175

Val Pro Cys Ser Cys Tyr Asn Leu Ser Ala Thr Asn Asp Ser Thr Ile
            180                 185                 190

Leu Asp Lys Val Ile Leu Pro Gln Leu Ser Arg Leu Gly Gln Leu Ala
        195                 200                 205

Arg Ser Arg His Ser Thr Asp Ile Cys Ala Val Pro Ala Asn Ser His
    210                 215                 220

Ile Tyr Arg Glu Gly Cys Ala Arg Ser Leu Gln Lys Trp Leu His Asn
225                 230                 235                 240

Asn Leu Ile Ser Ile Val Gly Ile Cys Leu Gly Val Gly Leu Leu Glu
                245                 250                 255

Leu Gly Phe Met Thr Leu Ser Ile Phe Leu Cys Arg Asn Leu Asp His
            260                 265                 270

Val Tyr Asn Arg Leu Ala Arg Tyr Arg
        275                 280

<210> SEQ ID NO 64
<211> LENGTH: 390
<212> TYPE: PRT
<213> ORGANISM: Artificial Sequence
<220> FEATURE:

<223> OTHER INFORMATION: Synthetic

<400> SEQUENCE: 64

```
Met Trp Trp Arg Leu Trp Trp Leu Leu Leu Leu Leu Leu Leu Leu Trp
1               5                   10                  15
Pro Met Val Trp Ala Arg Ala Gln Leu Glu Arg Ser Leu Arg Asp Val
            20                  25                  30
Val Glu Lys Thr Ile Gln Lys Tyr Gly Thr Asn Pro Glu Glu Thr Ala
        35                  40                  45
Ala Glu Glu Ser Trp Asp Tyr Val Gln Phe Gln Leu Arg Cys Cys Gly
    50                  55                  60
Trp His Tyr Pro Gln Asp Trp Phe Gln Val Leu Ile Leu Arg Gly Asn
65                  70                  75                  80
Gly Ser Glu Ala His Arg Val Pro Cys Ser Cys Tyr Asn Leu Ser Ala
            85                  90                  95
Thr Asn Asp Ser Thr Ile Leu Asp Lys Val Ile Leu Pro Gln Leu Ser
            100                 105                 110
Arg Leu Gly His Leu Ala Arg Ser Arg His Ser Ala Asp Ile Cys Ala
        115                 120                 125
Val Pro Ala Glu Ser His Ile Tyr Arg Glu Gly Cys Ala Gln Gly Leu
130                 135                 140
Gln Lys Trp Leu His Asn Asn Pro Lys Ser Cys Asp Lys Thr His Thr
145                 150                 155                 160
Cys Pro Pro Cys Pro Ala Pro Glu Ala Glu Gly Ala Pro Ser Val Phe
            165                 170                 175
Leu Phe Pro Pro Lys Pro Lys Asp Thr Leu Met Ile Ser Arg Thr Pro
            180                 185                 190
Glu Val Thr Cys Val Val Val Asp Val Ser His Glu Asp Pro Glu Val
        195                 200                 205
Lys Phe Asn Trp Tyr Val Asp Gly Val Glu Val His Asn Ala Lys Thr
    210                 215                 220
Lys Pro Arg Glu Glu Gln Tyr Asn Ser Thr Tyr Arg Val Val Ser Val
225                 230                 235                 240
Leu Thr Val Leu His Gln Asp Trp Leu Asn Gly Lys Glu Tyr Lys Cys
            245                 250                 255
Lys Val Ser Asn Lys Ala Leu Pro Ala Pro Ile Glu Lys Thr Ile Ser
            260                 265                 270
Lys Ala Lys Gly Gln Pro Arg Glu Pro Gln Val Tyr Thr Leu Pro Pro
        275                 280                 285
Ser Arg Glu Glu Met Thr Lys Asn Gln Val Ser Leu Thr Cys Leu Val
290                 295                 300
Lys Gly Phe Tyr Pro Ser Asp Ile Ala Val Glu Trp Glu Ser Asn Gly
305                 310                 315                 320
Gln Pro Glu Asn Asn Tyr Lys Thr Ala Pro Pro Val Leu Asp Ser Asp
            325                 330                 335
Gly Ser Phe Phe Leu Tyr Ser Lys Leu Thr Val Asp Lys Ser Arg Trp
            340                 345                 350
Gln Gln Gly Asn Val Phe Ser Cys Ser Val Met His Glu Ala Leu His
        355                 360                 365
Asn His Tyr Thr Gln Lys Ser Leu Ser Leu Ser Pro Gly Lys His His
    370                 375                 380
His His His His
385                 390
```

```
<210> SEQ ID NO 65
<211> LENGTH: 390
<212> TYPE: PRT
<213> ORGANISM: Artificial Sequence
<220> FEATURE:
<223> OTHER INFORMATION: Synthetic

<400> SEQUENCE: 65

Met Trp Trp Arg Leu Trp Trp Leu Leu Leu Leu Leu Leu Leu Trp
1               5                   10                  15

Pro Met Val Trp Ala Arg Ala Gln Leu Glu Arg Ser Leu Gln Asp Ile
            20                  25                  30

Val Glu Lys Thr Ile Gln Lys Tyr His Thr Asn Pro Glu Glu Thr Ala
            35                  40                  45

Ala Glu Glu Ser Trp Asp Tyr Val Gln Phe Gln Leu Arg Cys Cys Gly
        50                  55                  60

Trp His Ser Pro Gln Asp Trp Phe Gln Val Leu Thr Leu Arg Gly Asn
65                  70                  75                  80

Gly Ser Glu Ala His Arg Val Pro Cys Ser Cys Tyr Asn Leu Ser Ala
                85                  90                  95

Thr Asn Asp Ser Thr Ile Leu Asp Lys Val Ile Leu Pro Gln Leu Ser
            100                 105                 110

Arg Leu Gly Gln Leu Ala Arg Ser Arg His Ser Thr Asp Ile Cys Ala
        115                 120                 125

Val Pro Ala Asn Ser His Ile Tyr Arg Glu Gly Cys Ala Arg Ser Leu
    130                 135                 140

Gln Lys Trp Leu His Asn Asn Pro Lys Ser Cys Asp Lys Thr His Thr
145                 150                 155                 160

Cys Pro Pro Cys Pro Ala Pro Glu Ala Glu Gly Ala Pro Ser Val Phe
                165                 170                 175

Leu Phe Pro Pro Lys Pro Lys Asp Thr Leu Met Ile Ser Arg Thr Pro
            180                 185                 190

Glu Val Thr Cys Val Val Val Asp Val Ser His Glu Asp Pro Glu Val
        195                 200                 205

Lys Phe Asn Trp Tyr Val Asp Gly Val Glu Val His Asn Ala Lys Thr
    210                 215                 220

Lys Pro Arg Glu Glu Gln Tyr Asn Ser Thr Tyr Arg Val Val Ser Val
225                 230                 235                 240

Leu Thr Val Leu His Gln Asp Trp Leu Asn Gly Lys Glu Tyr Lys Cys
                245                 250                 255

Lys Val Ser Asn Lys Ala Leu Pro Ala Pro Ile Glu Lys Thr Ile Ser
            260                 265                 270

Lys Ala Lys Gly Gln Pro Arg Glu Pro Gln Val Tyr Thr Leu Pro Pro
        275                 280                 285

Ser Arg Glu Glu Met Thr Lys Asn Gln Val Ser Leu Thr Cys Leu Val
    290                 295                 300

Lys Gly Phe Tyr Pro Ser Asp Ile Ala Val Glu Trp Glu Ser Asn Gly
305                 310                 315                 320

Gln Pro Glu Asn Asn Tyr Lys Thr Ala Pro Pro Val Leu Asp Ser Asp
                325                 330                 335

Gly Ser Phe Phe Leu Tyr Ser Lys Leu Thr Val Asp Lys Ser Arg Trp
            340                 345                 350

Gln Gln Gly Asn Val Phe Ser Cys Ser Val Met His Glu Ala Leu His
        355                 360                 365
```

```
Asn His Tyr Thr Gln Lys Ser Leu Ser Leu Ser Pro Gly Lys His His
    370                 375                 380

His His His His His His
385                 390

<210> SEQ ID NO 66
<211> LENGTH: 330
<212> TYPE: PRT
<213> ORGANISM: Artificial Sequence
<220> FEATURE:
<223> OTHER INFORMATION: Synthetic

<400> SEQUENCE: 66

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Arg Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Leu
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 67
<211> LENGTH: 330
<212> TYPE: PRT
<213> ORGANISM: Artificial Sequence
<220> FEATURE:
<223> OTHER INFORMATION: Synthetic

<400> SEQUENCE: 67

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Lys Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Leu
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 68
<211> LENGTH: 330
<212> TYPE: PRT
<213> ORGANISM: Artificial Sequence
<220> FEATURE:

<223> OTHER INFORMATION: Synthetic

<400> SEQUENCE: 68

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Arg Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Leu
        275                 280                 285
Leu Tyr Ser Lys Leu Thr Val Asp Lys Ser Arg Trp Gln Gln Gly Asn
    290                 295                 300
Val Phe Ser Cys Ser Val Met His Ser Ala Leu His Asn His Tyr Thr
305                 310                 315                 320
Gln Lys Ser Leu Ser Leu Ser Pro Gly Lys
                325                 330
```

<210> SEQ ID NO 69
<211> LENGTH: 330
<212> TYPE: PRT
<213> ORGANISM: Artificial Sequence
<220> FEATURE:
<223> OTHER INFORMATION: Synthetic

<400> SEQUENCE: 69

```
Ala Ser Thr Lys Gly Pro Ser Val Phe Pro Leu Ala Pro Ser Ser Lys
1               5                   10                  15
```

-continued

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Arg Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 70
<211> LENGTH: 330
<212> TYPE: PRT
<213> ORGANISM: Artificial Sequence
<220> FEATURE:
<223> OTHER INFORMATION: Synthetic

<400> SEQUENCE: 70

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Lys Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 71
<211> LENGTH: 330
<212> TYPE: PRT
<213> ORGANISM: Artificial Sequence
<220> FEATURE:
<223> OTHER INFORMATION: Synthetic

<400> SEQUENCE: 71

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

```
Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Arg Leu Thr Val Asp Lys Ser Arg Trp Gln Gln Gly Asn
290                 295                 300

Val Phe Ser Cys Ser Val Met His Ser Ala Leu His Asn His Tyr Thr
305                 310                 315                 320

Gln Lys Ser Leu Ser Leu Ser Pro Gly Lys
                325                 330

<210> SEQ ID NO 72
<211> LENGTH: 297
<212> TYPE: PRT
<213> ORGANISM: Homo Sapiens

<400> SEQUENCE: 72

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
```

```
            115                 120                 125
Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
                180                 185                 190

Ile Leu Ser Val Met Leu Ile Phe Ala Phe Phe Gln Glu Leu Val Ile
            195                 200                 205

Ala Gly Ile Val Glu Asn Glu Trp Lys Arg Thr Cys Ser Arg Pro Lys
        210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Pro Ile Gln Glu Glu Glu Glu
                260                 265                 270

Glu Glu Thr Glu Thr Asn Phe Pro Glu Pro Pro Gln Asp Gln Glu Ser
                275                 280                 285

Ser Pro Ile Glu Asn Asp Ser Ser Pro
            290                 295

<210> SEQ ID NO 73
<211> LENGTH: 297
<212> TYPE: PRT
<213> ORGANISM: Macaca fascicularis

<400> SEQUENCE: 73

Met Thr Thr Pro Arg Asn Ser Val Asn Gly Thr Phe Pro Ala Glu Pro
1               5                   10                  15

Met Lys Gly Pro Ile Ala Met Gln Pro Gly Pro Lys Pro Leu Leu Arg
            20                  25                  30

Arg Met Ser Ser Leu Val Gly Pro Thr Gln Ser Phe Phe Met Arg Glu
        35                  40                  45

Ser Lys Ala Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Val His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
                180                 185                 190
```

Ile Leu Ser Val Met Leu Ile Phe Ala Phe Gln Glu Leu Val Ile
            195                 200                 205

Ala Gly Ile Val Glu Asn Glu Trp Arg Arg Thr Cys Ser Arg Pro Lys
        210                 215                 220

Ser Ser Val Val Leu Leu Ser Ala Glu Glu Lys Lys Glu Gln Val Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu
        260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295

<210> SEQ ID NO 74
<211> LENGTH: 122
<212> TYPE: PRT
<213> ORGANISM: Artificial Sequence
<220> FEATURE:
<223> OTHER INFORMATION: Synthetic

<400> SEQUENCE: 74

Glu Val Gln Leu Val Glu Ser Gly Gly Gly Leu Val Gln Pro Asp Arg
1               5                   10                  15

Ser Leu Arg Leu Ser Cys Ala Ala Ser Gly Phe Thr Phe His Asp Tyr
            20                  25                  30

Ala Met His Trp Val Arg Gln Ala Pro Gly Lys Gly Leu Glu Trp Val
        35                  40                  45

Ser Thr Ile Ser Trp Asn Ser Gly Thr Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Gly Met Asp Val Trp
            100                 105                 110

Gly Gln Gly Thr Thr Val Thr Val Ser Ser
        115                 120

<210> SEQ ID NO 75
<211> LENGTH: 8
<212> TYPE: PRT
<213> ORGANISM: Artificial Sequence
<220> FEATURE:
<223> OTHER INFORMATION: Synthetic

<400> SEQUENCE: 75

Gly Phe Thr Phe His Asp Tyr Ala
1               5

<210> SEQ ID NO 76
<211> LENGTH: 8
<212> TYPE: PRT
<213> ORGANISM: Artificial Sequence
<220> FEATURE:
<223> OTHER INFORMATION: Synthetic

<400> SEQUENCE: 76

Ile Ser Trp Asn Ser Gly Thr Ile

```
1               5

<210> SEQ ID NO 77
<211> LENGTH: 15
<212> TYPE: PRT
<213> ORGANISM: Artificial Sequence
<220> FEATURE:
<223> OTHER INFORMATION: Synthetic

<400> SEQUENCE: 77

Ala Lys Asp Ile Gln Tyr Gly Asn Tyr Tyr Gly Met Asp Val
1               5                   10                  15

<210> SEQ ID NO 78
<211> LENGTH: 107
<212> TYPE: PRT
<213> ORGANISM: Artificial Sequence
<220> FEATURE:
<223> OTHER INFORMATION: Synthetic

<400> SEQUENCE: 78

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105

<210> SEQ ID NO 79
<211> LENGTH: 6
<212> TYPE: PRT
<213> ORGANISM: Artificial Sequence
<220> FEATURE:
<223> OTHER INFORMATION: Synthetic

<400> SEQUENCE: 79

Gln Ser Val Ser Ser Tyr
1               5

<210> SEQ ID NO 80
<211> LENGTH: 9
<212> TYPE: PRT
<213> ORGANISM: Artificial Sequence
<220> FEATURE:
<223> OTHER INFORMATION: Synthetic

<400> SEQUENCE: 80

Gln Gln Arg Ser Asn Trp Pro Ile Thr
1               5

<210> SEQ ID NO 81
<211> LENGTH: 125
<212> TYPE: PRT
<213> ORGANISM: Artificial Sequence
<220> FEATURE:
<223> OTHER INFORMATION: Synthetic
```

<400> SEQUENCE: 81

Glu Val Gln Leu Val Gln Ser Gly Gly Gly Leu Val His Pro Gly Gly
1               5                   10                  15

Ser Leu Arg Leu Ser Cys Thr Gly Ser Gly Phe Thr Phe Ser Tyr His
            20                  25                  30

Ala Met His Trp Val Arg Gln Ala Pro Gly Lys Gly Leu Glu Trp Val
        35                  40                  45

Ser Ile Ile Gly Thr Gly Gly Val Thr Tyr Tyr Ala Asp Ser Val Lys
    50                  55                  60

Gly Arg Phe Thr Ile Ser Arg Asp Asn Val Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Asp Tyr Tyr Gly Ala Gly Ser Phe Tyr Asp Gly Leu Tyr Gly Met
            100                 105                 110

Asp Val Trp Gly Gln Gly Thr Thr Val Thr Val Ser Ser
        115                 120                 125

<210> SEQ ID NO 82
<211> LENGTH: 8
<212> TYPE: PRT
<213> ORGANISM: Artificial Sequence
<220> FEATURE:
<223> OTHER INFORMATION: Synthetic

<400> SEQUENCE: 82

Gly Phe Thr Phe Ser Tyr His Ala
1               5

<210> SEQ ID NO 83
<211> LENGTH: 7
<212> TYPE: PRT
<213> ORGANISM: Artificial Sequence
<220> FEATURE:
<223> OTHER INFORMATION: Synthetic

<400> SEQUENCE: 83

Ile Gly Thr Gly Gly Val Thr
1               5

<210> SEQ ID NO 84
<211> LENGTH: 19
<212> TYPE: PRT
<213> ORGANISM: Artificial Sequence
<220> FEATURE:
<223> OTHER INFORMATION: Synthetic

<400> SEQUENCE: 84

Ala Arg Asp Tyr Tyr Gly Ala Gly Ser Phe Tyr Asp Gly Leu Tyr Gly
1               5                   10                  15

Met Asp Val

<210> SEQ ID NO 85
<211> LENGTH: 6
<212> TYPE: PRT
<213> ORGANISM: Artificial Sequence
<220> FEATURE:
<223> OTHER INFORMATION: Synthetic

<400> SEQUENCE: 85

Gln Ser Val Ser Ser Tyr

```
1               5
```

<210> SEQ ID NO 86
<211> LENGTH: 9
<212> TYPE: PRT
<213> ORGANISM: Artificial Sequence
<220> FEATURE:
<223> OTHER INFORMATION: Synthetic

<400> SEQUENCE: 86

```
Gln Gln Arg Ser Asp Trp Pro Leu Thr
1               5
```

<210> SEQ ID NO 87
<211> LENGTH: 122
<212> TYPE: PRT
<213> ORGANISM: Artificial Sequence
<220> FEATURE:
<223> OTHER INFORMATION: Synthetic

<400> SEQUENCE: 87

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asn Asp Tyr
            20                  25                  30

Ala Met His Trp Val Arg Gln Ala Pro Gly Lys Gly Leu Glu Trp Val
        35                  40                  45

Ser Thr Ile Ser Trp Asn Ser Gly Ser Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Gln Tyr Gly Asn Tyr Tyr Tyr Gly Met Asp Val Trp
            100                 105                 110

Gly Gln Gly Thr Thr Val Thr Val Ser Ser
        115                 120
```

<210> SEQ ID NO 88
<211> LENGTH: 8
<212> TYPE: PRT
<213> ORGANISM: Artificial Sequence
<220> FEATURE:
<223> OTHER INFORMATION: Synthetic

<400> SEQUENCE: 88

```
Gly Phe Thr Phe Asn Asp Tyr Ala
1               5
```

<210> SEQ ID NO 89
<211> LENGTH: 8
<212> TYPE: PRT
<213> ORGANISM: Artificial Sequence
<220> FEATURE:
<223> OTHER INFORMATION: Synthetic

<400> SEQUENCE: 89

```
Ile Ser Trp Asn Ser Gly Ser Ile
1               5
```

<210> SEQ ID NO 90
<211> LENGTH: 15
<212> TYPE: PRT

```
<213> ORGANISM: Artificial Sequence
<220> FEATURE:
<223> OTHER INFORMATION: Synthetic

<400> SEQUENCE: 90

Ala Lys Asp Ile Gln Tyr Gly Asn Tyr Tyr Tyr Gly Met Asp Val
1               5                   10                  15

<210> SEQ ID NO 91
<211> LENGTH: 107
<212> TYPE: PRT
<213> ORGANISM: Artificial Sequence
<220> FEATURE:
<223> OTHER INFORMATION: Synthetic

<400> SEQUENCE: 91

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105

<210> SEQ ID NO 92
<211> LENGTH: 6
<212> TYPE: PRT
<213> ORGANISM: Artificial Sequence
<220> FEATURE:
<223> OTHER INFORMATION: Synthetic

<400> SEQUENCE: 92

Gln Ser Val Ser Ser Tyr
1               5

<210> SEQ ID NO 93
<211> LENGTH: 9
<212> TYPE: PRT
<213> ORGANISM: Artificial Sequence
<220> FEATURE:
<223> OTHER INFORMATION: Synthetic

<400> SEQUENCE: 93

Gln Gln Arg Ser Asn Trp Pro Ile Thr
1               5

<210> SEQ ID NO 94
<211> LENGTH: 121
<212> TYPE: PRT
<213> ORGANISM: Artificial Sequence
<220> FEATURE:
<223> OTHER INFORMATION: Synthetic

<400> SEQUENCE: 94

Gln Val Gln Leu Gln Gln Pro Gly Ala Glu Leu Val Lys Pro Gly Ala
1               5                   10                  15
```

-continued

```
Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala
        115                 120

<210> SEQ ID NO 95
<211> LENGTH: 8
<212> TYPE: PRT
<213> ORGANISM: Artificial Sequence
<220> FEATURE:
<223> OTHER INFORMATION: Synthetic

<400> SEQUENCE: 95

Gly Tyr Thr Phe Thr Ser Tyr Asn
1               5

<210> SEQ ID NO 96
<211> LENGTH: 8
<212> TYPE: PRT
<213> ORGANISM: Artificial Sequence
<220> FEATURE:
<223> OTHER INFORMATION: Synthetic

<400> SEQUENCE: 96

Ile Tyr Pro Gly Asn Gly Asp Thr
1               5

<210> SEQ ID NO 97
<211> LENGTH: 14
<212> TYPE: PRT
<213> ORGANISM: Artificial Sequence
<220> FEATURE:
<223> OTHER INFORMATION: Synthetic

<400> SEQUENCE: 97

Ala Arg Ser Thr Tyr Tyr Gly Gly Asp Trp Tyr Phe Asn Val
1               5                   10

<210> SEQ ID NO 98
<211> LENGTH: 106
<212> TYPE: PRT
<213> ORGANISM: Artificial Sequence
<220> FEATURE:
<223> OTHER INFORMATION: Synthetic

<400> SEQUENCE: 98

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45
```

-continued

```
Ala Thr Ser Asn Leu Ala Ser Gly Val Pro Val Arg Phe Ser Gly Ser
 50                  55                  60
Gly Ser Gly Thr Ser Tyr Ser Leu Thr Ile Ser Arg Val Glu Ala Glu
 65                  70                  75                  80
Asp Ala Ala Thr Tyr Tyr Cys Gln Gln Trp Thr Ser Asn Pro Pro Thr
                 85                  90                  95
Phe Gly Gly Gly Thr Lys Leu Glu Ile Lys
             100                 105
```

<210> SEQ ID NO 99
<211> LENGTH: 5
<212> TYPE: PRT
<213> ORGANISM: Artificial Sequence
<220> FEATURE:
<223> OTHER INFORMATION: Synthetic

<400> SEQUENCE: 99

```
Ser Ser Val Ser Tyr
 1               5
```

<210> SEQ ID NO 100
<211> LENGTH: 9
<212> TYPE: PRT
<213> ORGANISM: Artificial Sequence
<220> FEATURE:
<223> OTHER INFORMATION: Synthetic

<400> SEQUENCE: 100

```
Gln Gln Trp Thr Ser Asn Pro Pro Thr
 1               5
```

<210> SEQ ID NO 101
<211> LENGTH: 119
<212> TYPE: PRT
<213> ORGANISM: Artificial Sequence
<220> FEATURE:
<223> OTHER INFORMATION: Synthetic

<400> SEQUENCE: 101

```
Gln Val Gln Leu Val Gln Ser Gly Ala Glu Val Lys Lys Pro Gly Ser
 1               5                  10                  15
Ser Val Lys Val Ser Cys Lys Ala Ser Gly Tyr Ala Phe Ser Tyr Ser
                 20                  25                  30
Trp Ile Asn Trp Val Arg Gln Ala Pro Gly Gln Gly Leu Glu Trp Met
             35                  40                  45
Gly Arg Ile Phe Pro Gly Asp Gly Asp Thr Asp Tyr Asn Gly Lys Phe
 50                  55                  60
Lys Gly Arg Val Thr Ile Thr Ala Asp Lys Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Asn Val Phe Asp Gly Tyr Trp Leu Val Tyr Trp Gly Gln Gly
             100                 105                 110
Thr Leu Val Thr Val Ser Ser
         115
```

<210> SEQ ID NO 102
<211> LENGTH: 8
<212> TYPE: PRT
<213> ORGANISM: Artificial Sequence
<220> FEATURE:
<223> OTHER INFORMATION: Synthetic

<400> SEQUENCE: 102

Gly Tyr Ala Phe Ser Tyr Ser Trp
1               5

<210> SEQ ID NO 103
<211> LENGTH: 8
<212> TYPE: PRT
<213> ORGANISM: Artificial Sequence
<220> FEATURE:
<223> OTHER INFORMATION: Synthetic

<400> SEQUENCE: 103

Ile Phe Pro Gly Asp Gly Asp Thr
1               5

<210> SEQ ID NO 104
<211> LENGTH: 12
<212> TYPE: PRT
<213> ORGANISM: Artificial Sequence
<220> FEATURE:
<223> OTHER INFORMATION: Synthetic

<400> SEQUENCE: 104

Ala Arg Asn Val Phe Asp Gly Tyr Trp Leu Val Tyr
1               5                   10

<210> SEQ ID NO 105
<211> LENGTH: 112
<212> TYPE: PRT
<213> ORGANISM: Artificial Sequence
<220> FEATURE:
<223> OTHER INFORMATION: Synthetic

<400> SEQUENCE: 105

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

<210> SEQ ID NO 106
<211> LENGTH: 11
<212> TYPE: PRT
<213> ORGANISM: Artificial Sequence
<220> FEATURE:
<223> OTHER INFORMATION: Synthetic

<400> SEQUENCE: 106

Lys Ser Leu Leu His Ser Asn Gly Ile Thr Tyr
1               5                   10

<210> SEQ ID NO 107
<211> LENGTH: 9

```
<212> TYPE: PRT
<213> ORGANISM: Artificial Sequence
<220> FEATURE:
<223> OTHER INFORMATION: Synthetic

<400> SEQUENCE: 107

Ala Gln Asn Leu Glu Leu Pro Tyr Thr
1               5

<210> SEQ ID NO 108
<211> LENGTH: 330
<212> TYPE: PRT
<213> ORGANISM: Artificial Sequence
<220> FEATURE:
<223> OTHER INFORMATION: Synthetic

<400> SEQUENCE: 108

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Asp Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Glu Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

Gln Lys Ser Leu Ser Leu Ser Pro Gly Lys
            325                 330

<210> SEQ ID NO 109
<211> LENGTH: 107
<212> TYPE: PRT
<213> ORGANISM: Artificial Sequence
<220> FEATURE:
<223> OTHER INFORMATION: Synthetic

<400> SEQUENCE: 109

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asp Trp Pro Leu
                85                  90                  95

Thr Phe Gly Gly Gly Thr Lys Val Glu Ile Lys
            100                 105

<210> SEQ ID NO 110
<211> LENGTH: 118
<212> TYPE: PRT
<213> ORGANISM: Artificial Sequence
<220> FEATURE:
<223> OTHER INFORMATION: Synthetic

<400> SEQUENCE: 110

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Thr Tyr Asp
            20                  25                  30

Met Ser Trp Val Arg Gln Ala Pro Gly Lys Gly Leu Glu Trp Ile Gly
        35                  40                  45

Ile Ile Tyr Ser Ser Val Gly Ala Tyr Tyr Ala Ser Trp Ala Lys Gly
    50                  55                  60

Arg Phe Thr Phe Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Glu Tyr
                85                  90                  95

Gly Ala Ser Ser Ser Asp Tyr Ile Phe Ser Leu Trp Gly Gln Gly Thr
            100                 105                 110

Leu Val Thr Val Ser Ser
        115

<210> SEQ ID NO 111
<211> LENGTH: 107
<212> TYPE: PRT
<213> ORGANISM: Artificial Sequence
<220> FEATURE:
<223> OTHER INFORMATION: Synthetic

<400> SEQUENCE: 111

-continued

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asp Trp Pro Leu
                85                  90                  95

Thr Phe Gly Gly Gly Thr Lys Val Glu Ile Lys
            100                 105

<210> SEQ ID NO 112
<211> LENGTH: 116
<212> TYPE: PRT
<213> ORGANISM: Artificial Sequence
<220> FEATURE:
<223> OTHER INFORMATION: Synthetic

<400> SEQUENCE: 112

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Asn Ala
            20                  25                  30

Met Asn Trp Val Arg Gln Ala Pro Gly Lys Gly Leu Glu Trp Ile Gly
        35                  40                  45

Leu Ile Tyr Ala Ser Gly Asn Thr Asp Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Glu Gly
                85                  90                  95

Ser Val Trp Gly Ala Ala Phe Asp Pro Trp Gly Pro Gly Thr Leu Val
            100                 105                 110

Thr Val Ser Ser
        115

<210> SEQ ID NO 113
<211> LENGTH: 110
<212> TYPE: PRT
<213> ORGANISM: Artificial Sequence
<220> FEATURE:
<223> OTHER INFORMATION: Synthetic

<400> SEQUENCE: 113

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Ser Asn Trp
            20                  25                  30

Leu Ala Trp Tyr Gln Gln Lys Pro Gly Gln Pro Pro Lys Gln Leu Ile
        35                  40                  45

Tyr Ala Ala Ser Thr Leu Ala Ser Gly Val Pro Ser Arg Phe Lys Gly
    50                  55                  60

Ser Gly Ser Gly Thr Gln Phe Thr Leu Thr Ile Ser Gly Val Glu Ser
65                  70                  75                  80

Ala Asp Ala Ala Thr Tyr Tyr Cys Gln Gln Gly Tyr Ser Asn Ser Asn
            85                  90                  95

Ile Asp Asn Thr Phe Gly Gly Gly Thr Glu Val Val Val Lys
            100                 105                 110

<210> SEQ ID NO 114
<211> LENGTH: 116
<212> TYPE: PRT
<213> ORGANISM: Artificial Sequence
<220> FEATURE:
<223> OTHER INFORMATION: Synthetic

<400> SEQUENCE: 114

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Tyr Asn Ala
            20                  25                  30

Met Asn Trp Val Arg Gln Ala Pro Gly Lys Gly Leu Glu Trp Ile Gly
        35                  40                  45

Ile Ile Phe Ala Ser Gly Arg Thr Asp Tyr Ala Ser Trp Ala Lys Gly
    50                  55                  60

Arg Phe Thr Ile Ser Lys Thr Ser Thr Thr Val Glu Leu Lys Ile Thr
65                  70                  75                  80

Ser Pro Thr Thr Glu Asp Thr Ala Thr Tyr Phe Cys Ala Arg Glu Gly
                85                  90                  95

Ser Thr Trp Gly Asp Ala Leu Asp Pro Trp Gly Pro Gly Thr Leu Val
            100                 105                 110

Thr Val Ser Ser
        115

<210> SEQ ID NO 115
<211> LENGTH: 110
<212> TYPE: PRT
<213> ORGANISM: Artificial Sequence
<220> FEATURE:
<223> OTHER INFORMATION: Synthetic

<400> SEQUENCE: 115

Ala Tyr Asp Met Thr Gln Thr Pro Ser Ser Val Glu Ala Ala Val Gly
1               5                   10                  15

Gly Thr Val Thr Ile Lys Cys Gln Ala Ser Gln Asn Ile Ile Asp Tyr
            20                  25                  30

Leu Ala Trp Tyr Gln Gln Lys Pro Gly Gln Pro Pro Gln Leu Leu Ile
        35                  40                  45

His Lys Ala Ser Thr Leu Ala Ser Gly Val Pro Ser Arg Phe Lys Gly
    50                  55                  60

Ser Gly Ser Gly Thr Gln Phe Thr Leu Thr Ile Ser Gly Val Gln Ser
65                  70                  75                  80

Asp Asp Ala Ala Thr Tyr Tyr Cys Gln Gln Gly Tyr Ser Asn Ser Asn
                85                  90                  95

Ile Asp Asn Thr Phe Gly Gly Gly Thr Glu Val Val Val Lys
            100                 105                 110

<210> SEQ ID NO 116
<211> LENGTH: 117
<212> TYPE: PRT
<213> ORGANISM: Artificial Sequence
<220> FEATURE:
<223> OTHER INFORMATION: Synthetic

<400> SEQUENCE: 116

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Asn Tyr Asn
                20                  25                  30

Met Gly Trp Val Arg Gln Ala Pro Gly Lys Gly Leu Glu Trp Ile Gly
            35                  40                  45

Val Ile Asp Ala Ser Gly Thr Thr Tyr Tyr Ala Thr Trp Ala Lys Gly
    50                  55                  60

Arg Phe Thr Cys Ser Lys Thr Ser Ser Thr Val Glu Leu Lys Met Thr
65                  70                  75                  80

Ser Leu Thr Thr Glu Asp Thr Ala Thr Tyr Phe Cys Ala Arg Glu Leu
                85                  90                  95

Leu Tyr Phe Gly Ser Ser Tyr Tyr Asp Leu Trp Gly Gln Gly Thr Leu
                100                 105                 110

Val Thr Val Ser Ser
            115

<210> SEQ ID NO 117
<211> LENGTH: 110
<212> TYPE: PRT
<213> ORGANISM: Artificial Sequence
<220> FEATURE:
<223> OTHER INFORMATION: Synthetic

<400> SEQUENCE: 117

Asp Val Val Met Thr Gln Thr Pro Ala Ser Val Ser Glu Pro Val Gly
1               5                   10                  15

Gly Thr Val Thr Ile Lys Cys Gln Ala Ser Gln Asn Ile Asp Ser Asn
                20                  25                  30

Leu Ala Trp Tyr Gln Gln Lys Pro Gly Gln Pro Pro Lys Phe Leu Ile
            35                  40                  45

Tyr Tyr Ala Ser Asn Leu Pro Phe Gly Val Ser Ser Arg Phe Lys Gly
    50                  55                  60

Ser Gly Ser Gly Thr Gln Phe Thr Leu Thr Ile Ser Asp Leu Glu Ser
65                  70                  75                  80

Ala Asp Ala Ala Thr Tyr Tyr Cys Gln Cys Ala Asp Val Gly Ser Thr
                85                  90                  95

Tyr Val Ala Ala Phe Gly Gly Gly Thr Glu Val Val Val Lys
                100                 105                 110

<210> SEQ ID NO 118
<211> LENGTH: 4
<212> TYPE: PRT
<213> ORGANISM: Artificial Sequence
<220> FEATURE:
<223> OTHER INFORMATION: Synthetic

<400> SEQUENCE: 118

Cys Pro Pro Cys
1

<210> SEQ ID NO 119
<211> LENGTH: 4
<212> TYPE: PRT
<213> ORGANISM: Artificial Sequence
<220> FEATURE:
<223> OTHER INFORMATION: Synthetic

```
<400> SEQUENCE: 119

Cys Pro Ser Cys
1

<210> SEQ ID NO 120
<211> LENGTH: 6
<212> TYPE: PRT
<213> ORGANISM: Artificial Sequence
<220> FEATURE:
<223> OTHER INFORMATION: Synthetic

<400> SEQUENCE: 120

Ala Gly Ile Tyr Ala Pro
1               5

<210> SEQ ID NO 121
<211> LENGTH: 13
<212> TYPE: PRT
<213> ORGANISM: Artificial Sequence
<220> FEATURE:
<223> OTHER INFORMATION: Synthetic

<400> SEQUENCE: 121

Met Glu Ser Leu Asn Phe Ile Arg Ala His Thr Pro Tyr
1               5                   10
```